(12) United States Patent
Brown et al.

(10) Patent No.: US 9,340,493 B2
(45) Date of Patent: *May 17, 2016

(54) HYDROXAMIC ACID DERIVATIVES USEFUL AS ANTIBACTERIAL AGENTS

(71) Applicant: Pfizer Inc., Groton, CT (US)

(72) Inventors: Matthew Frank Brown, Stonington, CT (US); Charles Francis Donovan, Colchester, CT (US); Edmund Lee Ellsworth, Vicksburg, MI (US); Denton Wade Hoyer, Niantic, CT (US); Timothy Allan Johnson, Vicksburg, MI (US); Manjinder Singh Lall, East Lyme, CT (US); Chris Limberakis, Pawatuck, CT (US); Sean Timothy Murphy, Oceanside, CA (US); Debra Ann Sherry, Chelsea, MI (US); Clarke Bentley Taylor, Ann Arbor, MI (US); Joseph Scott Warmus, Ledyard, CT (US)

(73) Assignee: Pfizer Inc., New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/223,061

(22) Filed: Mar. 24, 2014

(65) Prior Publication Data

US 2014/0206651 A1   Jul. 24, 2014

Related U.S. Application Data

(63) Continuation of application No. 13/119,484, filed as application No. PCT/IB2009/053809 on Sep. 1, 2009, now Pat. No. 8,722,686.

(60) Provisional application No. 61/098,249, filed on Sep. 19, 2008.

(51) Int. Cl.
*A61K 31/685* (2006.01)
*A61K 31/19* (2006.01)
(Continued)

(52) U.S. Cl.
CPC .......... *C07C 259/06* (2013.01); *C07D 207/267* (2013.01); *C07D 213/30* (2013.01); *C07D 213/38* (2013.01); *C07D 213/55* (2013.01); *C07D 231/12* (2013.01); *C07D 233/64* (2013.01); *C07D 237/04* (2013.01); *C07D 239/26* (2013.01); *C07D 249/04* (2013.01); *C07D 249/08* (2013.01); *C07D 257/04* (2013.01); *C07D 261/08* (2013.01); *C07D 261/10* (2013.01); *C07D 263/32* (2013.01); *C07D 271/06* (2013.01); *C07D 277/24* (2013.01); *C07D 277/28* (2013.01);
(Continued)

(58) Field of Classification Search
CPC .. C07D 233/64; C07D 213/55; C07D 307/54; C07D 261/08; C07D 239/26; C07D 277/30; C07C 259/06; A61K 31/685; A61K 31/19; A61K 31/415; A61K 31/44; A61K 31/34; A61K 31/42; A61K 31/425; A61K 31/535
USPC ........... 514/92, 575, 400, 357, 471, 374, 256, 514/365, 236.8; 544/335, 137; 546/337; 548/338.1, 247, 204, 119; 549/496
See application file for complete search history.

(56) References Cited

U.S. PATENT DOCUMENTS

| 4,769,461 A | 9/1988 | Musser et al. |
| 5,110,831 A | 5/1992 | Magolda et al. |

(Continued)

FOREIGN PATENT DOCUMENTS

| CN | 101016270 | 8/2007 |
| EP | 1437349 | 7/2004 |

(Continued)

OTHER PUBLICATIONS

Chinese Application No. 201280016114.4 Office Action and search report dated Aug. 26, 2014, 17 pages.

(Continued)

*Primary Examiner* — James O Wilson
*Assistant Examiner* — Ebenezer O Sackey
(74) *Attorney, Agent, or Firm* — Knobbe Martens Olson & Bear LLP

(57) ABSTRACT

The invention relates to a compound of formula (I):

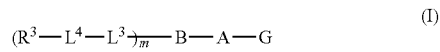

or a pharmaceutically acceptable salt thereof, thereof, wherein:
G is a group of formula (II):

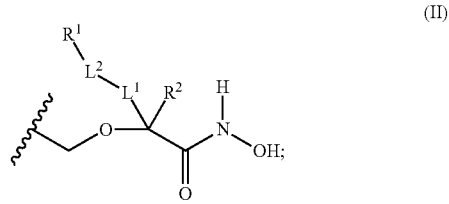

and pharmaceutically acceptable salts, prodrugs, hydrates, or solvates, thereof, wherein A, B, $L^1$-$L^4$, A, B, $R^1$-$R^4$, and m are as defined herein. The invention also relates to pharmaceutical compositions comprising the compounds of formula (I) and their use in treating a bacterial infection.

16 Claims, No Drawings

(51) Int. Cl.

| | | |
|---|---|---|
| A61K 31/415 | (2006.01) | |
| A61K 31/44 | (2006.01) | |
| A61K 31/34 | (2006.01) | |
| A61K 31/42 | (2006.01) | |
| A61K 31/425 | (2006.01) | |
| A61K 31/535 | (2006.01) | |
| C07D 233/64 | (2006.01) | |
| C07D 213/55 | (2006.01) | |
| C07D 307/54 | (2006.01) | |
| C07C 259/06 | (2006.01) | |
| C07D 207/267 | (2006.01) | |
| C07D 213/30 | (2006.01) | |
| C07D 213/38 | (2006.01) | |
| C07D 231/12 | (2006.01) | |
| C07D 237/04 | (2006.01) | |
| C07D 239/26 | (2006.01) | |
| C07D 249/04 | (2006.01) | |
| C07D 249/08 | (2006.01) | |
| C07D 257/04 | (2006.01) | |
| C07D 261/08 | (2006.01) | |
| C07D 261/10 | (2006.01) | |
| C07D 263/32 | (2006.01) | |
| C07D 271/06 | (2006.01) | |
| C07D 277/24 | (2006.01) | |
| C07D 277/28 | (2006.01) | |
| C07D 285/06 | (2006.01) | |
| C07D 307/14 | (2006.01) | |
| C07D 307/42 | (2006.01) | |
| C07D 309/10 | (2006.01) | |
| C07D 413/04 | (2006.01) | |
| C07D 413/12 | (2006.01) | |
| C07D 471/04 | (2006.01) | |
| C07F 9/653 | (2006.01) | |
| C07D 277/30 | (2006.01) | |

(52) U.S. Cl.
CPC ............ *C07D277/30* (2013.01); *C07D 285/06* (2013.01); *C07D 307/14* (2013.01); *C07D 307/42* (2013.01); *C07D 307/54* (2013.01); *C07D 309/10* (2013.01); *C07D 413/04* (2013.01); *C07D 413/12* (2013.01); *C07D 471/04* (2013.01); *C07F 9/653* (2013.01); *C07C 2101/04* (2013.01)

(56) References Cited

U.S. PATENT DOCUMENTS

| | | | |
|---|---|---|---|
| 6,673,965 | B1 | 1/2004 | Ward et al. |
| 8,722,686 | B2 * | 5/2014 | Brown et al. ................. 514/256 |
| 2005/0119305 | A1 | 6/2005 | Naka et al. |
| 2006/0247271 | A1 | 11/2006 | Bruton et al. |
| 2006/0276409 | A1 | 12/2006 | Hunter et al. |
| 2008/0085893 | A1 | 4/2008 | Yang et al. |
| 2008/0234297 | A1 | 9/2008 | Quian et al. |
| 2011/0178042 | A1 | 7/2011 | Brown et al. |
| 2012/0232083 | A1 | 9/2012 | Reilly et al. |
| 2012/0258948 | A1 | 10/2012 | Brown et al. |

FOREIGN PATENT DOCUMENTS

| | | |
|---|---|---|
| JP | 50-121218 | 9/1975 |
| JP | 2002-502815 | 1/2002 |
| JP | 2006-519772 | 8/2006 |
| WO | 0130747 | 5/2001 |
| WO | WO 02/074298 | 9/2002 |
| WO | 2004062601 | 7/2004 |
| WO | 2004067502 | 8/2004 |
| WO | 2006063281 | 6/2006 |
| WO | 2006118155 | 9/2006 |
| WO | 2006124897 | 11/2006 |
| WO | 2007069020 | 6/2007 |
| WO | 2007093904 | 8/2007 |
| WO | 2008045671 | 4/2008 |
| WO | 2008105515 | 9/2008 |
| WO | 2008115262 | 9/2008 |
| WO | 2009008905 | 1/2009 |
| WO | 2010017060 | 2/2010 |
| WO | 2010024356 | 3/2010 |
| WO | 2010031750 | 3/2010 |
| WO | 2010032147 | 3/2010 |
| WO | 2010100475 | 9/2010 |
| WO | 2011073845 | 6/2011 |
| WO | 2012120397 | 9/2012 |
| WO | 2012137094 | 10/2012 |
| WO | 2012137099 | 10/2012 |

OTHER PUBLICATIONS

Guangjian Du et al., "Synthesis and Antibacterial Activity of 3-(Morpholinopyridyl)-5-substituted Isoxazole Derivatives", Chinese Journal of Organic Chemistry, Dec. 31, 2009, pp. 1575-1581, 29(10).

Antinfective Therapy, Antiboitics and Antibacterial Drugs, "455710"(Vicuron Pharmaceuticals), Drug Data Report, Jul./Aug. 2007, p. 629, 29(7).

IUPAC. Compendium of Chemical Terminology, 2nd ed. (the "Gold Book"). Compiled by A. D. McNaught and A. Wilkinson. Blackwell Scientific Publications, Oxford (1997). XML on-line corrected version: http://goldbook.iupac.org (2006-) created by M. Nic, J. Jirat, B. Kosata; updates compiled by A. Jenkins. ISBN 0-9678550-9-8. doi:10.1351/goldbook. Last update: Feb. 24, 2014; version: 2.3.3.

Machine Translation of WO 2010/024356 published Mar. 4, 2010.

Product Label—ACTEMRA (toclizumab) Injection, for intravenous infusion; revised Apr. 2013, pp. 1-35.

Iupac, E.D., et al., "alkyl groups", Compendium of Chemical Terminology: IUPAC Recommendations; http://www.iupac.org/goldbook/A00228.pdf Jan. 1, 1997.

Kirsch, P., et al., "Super-Fluorinated Liquid Crystals: Towards the Limits of Polarity", European Journal Organic Chemistry, Jul. 2008, pp. 3479-3487, 2008(20).

Kwok, A., et al., "Helicobacter Pylori Eradication Therapy: Indications, efficacy and Safety", Expert Opinion Drug Safety, May 2008, pp. 271-281, 7(3).

International Patent Application No. PCT/IB2009/053809, PCT International Search Report (ISR), mailed Apr. 4, 2010, 7 pages.

International Patent Application No. PCT/IB2009/053809, PCT International Written Opinion, mailed Apr. 4, 2010, 7 pages.

International Patent Application No. PCT/IB2012/050812, PCT International Search Report ISR and Written Opinion mailed Apr. 23, 2012, 4 pages.

Qu, W., et al., "Quick Assembly of 1,4-Diphenyltriazoles as Probes Targeting β-Amyloid Aggregates in Alzheimer's Disease", Journal of Medicinal Chemistry, 2007, pp. 3380-3387, 50(14).

Raetz, Christian, H., et al., "Lipid A Modification Systems in Gram-Negative Bacteria", Annual Review Biochemistry, 2007, pp. 295-329, vol. 76.

Rice, Louis B., "Unmet Medical Needs in Antibacterial Therapy", Biochemical Pharmacology, Mar. 30, 2006, pp. 991-995, 71(7).

Wang, Y., et al., "A novel and efficient synthesis of terminal arylacetylenes via Sonogashira coupling reactions catalysed by MCM-41-supported bidentate phosphine palladium (0) complex", Journal of Chemical Research, Dec. 2007, pp. 728-732, 2007(12).

Apfel, Christian et al., "Hydroxamic Acid Derivatives as Potent Peptide Deformylase Inhibitors and Antibacterial Agents", Journal of Medicinal Medicinal Chemistry, Jun. 15, 2000, pp. 2324-2331, 43(12).

Brown, Matthew F., et al., "Potent Inhibitors of LpxC for the Treatment of Gram-Negative Infections", Journal of Medicinal Chemistry, Dec. 18, 2011, pp. 914-923, 55(18).

International Patent Application No. PCT/IB2012/051406 PCT International Search Report (ISR) and Written Opinion mailed Oct. 7, 2012, 5 pages.

(56) References Cited

OTHER PUBLICATIONS

Dube, Peter H., et al., "Protective Role of Interleukin-6 During Yersinia enterocolitica Infection Is Mediated through the Modulation of Inflammatory Cytokines", Infection and Immunity, Jun. 2004, pp. 3561-3570, 72(6).

Hennigan, Stephanie, et al., "Interleukin-6 Inhibitors in the Treatment of Rheumatoid Arthritis", Therapeutics and Clinical Risk Management, 2008, pp. 767-775, 4(4).

Imanishi, Jiro, "Expression of Cytokines in Bacterial and Viral Infections and Their Biochemical Aspects", The Japanese Biochemical Society, 2000, pp. 525-530, 127(4).

"455710(Antibiotics and Antibacterial Drugs)", Annual Drug Data Report, Jan. 1, 2007, p. 629, 29(7).

Barlaam, B., et al., "New Alpha-Substituted Succinate-Based Hydroxamic Acids As TNFALPHA Convertase . Inhibitors", Journal of Medicinal Chemistry, Jan. 1, 1999, pp. 4890-4908, 42(23).

Clements, J.M., et al., "Antimicrobial Activities and Characterization of Novel Inhibitors of LpxC", Antimicrobial Agents and Chemotherapy, American Society for Microbiology, Jun. 1, 2002, pp. 1793-1799, 46(6).

Conreaux, D., et I., "A practical procedure for the selective N-alkylation of 4-alkoxy-2-pyridones and its use in a sulfone-mediated synthesis of N-methyl-4-methoxy-2-pyridone", Tetrahedron Letters, 2005, pp. 7917-7920, 46(46).

English Translation of International Patent Application WO 2008/105515 publication date Sep. 4, 2008.

Gennadios, H.A., et al., "Mechanistic Inferences from the Binding of Ligands to LpxC, a Metal-Dependent Deacetylase", Biochemistry, 2006, pp. 7940-7948, 45(26).

Gipstein, E., et al., "Synthesis and Polymerization of Alkyl.α-(Alkylsulfonyl)acrylates1a", Journal of Organic Chemistry, 1980, pp. 1486-1489, 45(8).

International Patent Application No. PCT/IB2010/055596, publication No. WO 2011/073845,Search Report and Written Opinion mailed Mar. 23, 2011, 15 pages.

\* cited by examiner

HYDROXAMIC ACID DERIVATIVES USEFUL AS ANTIBACTERIAL AGENTS

This application is a continuation application under 35 U.S.C. §120 of U.S. Non-Provisional patent application Ser. No. 13/119,484, filed Mar. 17, 2011, which claims priority under 35 U.S.C. 371 of PCT/IB2009/053809, filed on Sep. 1, 2009 which claims the benefit of U.S. Provisional Patent Application No. 61/098,249, filed on Sep. 19, 2008, the disclosures of which are hereby incorporated by reference in their entirety.

FIELD OF THE INVENTION

This invention relates to novel hydroxamic acid derivatives that are useful for the treatment of a bacterial infection, such as a gram-negative infection, in mammals. The invention also relates to methods of using such compounds in the treatment of bacterial infections in mammals, and to pharmaceutical compositions containing such compounds.

BACKGROUND OF THE INVENTION

Infection by Gram-negative bacteria such as *Pseudomonas aeruginosa* and *Acinetobacter baumannii* is a major health problem, especially in the case of hospital-acquired infections. In addition, there is an increasing level of resistance to current antibiotic therapies, which severely limits treatment options. For example, in 2002, 33% of *Pseudomonas aeruginosa* infections from intensive care units were resistant to fluoroquinolones, while resistance to imipenem was 22% (CID 42: 657-68, 2006). In addition, multi-drug resistant (MDR) infections are also increasing; in the case of *Pseudomonas aeruginosa*, MDR increased from 4% in 1992 to 14% in 2002 (Biochem Pharm 71: 991, 2006).

Gram-negative bacteria are unique in that their outer membrane contains lipopolysaccharide (LPS), which is crucial for maintaining membrane integrity, and essential for bacterial viability (reviewed in Ann. Rev. Biochem 76: 295-329, 2007). The major lipid component of LPS is Lipid A, and inhibition of Lipid A biosynthesis is lethal to bacteria. Lipid A is synthesized on the cytoplasmic surface of the bacterial inner membrane via a pathway that consists of nine different enzymes. These enzymes are highly conserved in most gram-negative bacteria. LpxC is the enzyme that catalyzes the first committed step in the Lipid A biosynthetic pathway, the removal of the N-acetyl group of UDP-3-O—(R-3-hydroxymyristoyl)-N-acetylglucosamine. LpxC is a $Zn^{2+}$-dependent enzyme that has no mammalian homologue, making it a good target for the development of novel antibiotics. Several inhibitors of LpxC with low nM affinity have been reported (Biochemistry 45: 7940-48, 2006) and these compounds also have potent antibacterial activity against many gram-negative bacteria.

Thus, there is a great need for new antibiotics useful against Gram-negative organisms.

SUMMARY OF THE INVENTION

The present invention relates to compounds of formula (I):
A compound of formula (I):

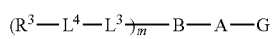

or a pharmaceutically acceptable salt thereof, thereof, wherein:
G is a group of formula (II)

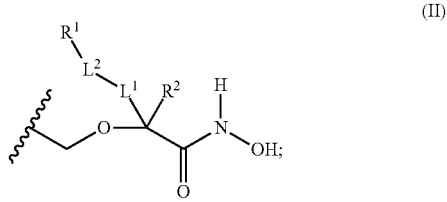

A is phenyl of formula (III)

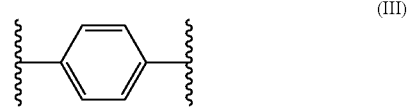 [SMILES: *c1ccc(*)cc1]

or a 6-membered heteroaryl of formula (IV)

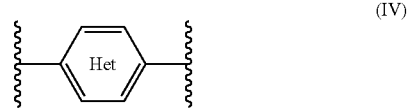

wherein said phenyl or said 6-membered heteroaryl of said A is optionally substituted by one to four $R^4$ groups;
B is $—(C_6-C_{10})$aryl or $—(C_1-C_9)$heteroaryl;
$L^1$ is either absent or a linker moiety selected from the group consisting of —C(O)— and —C(O)N($R^7$)—;
$L^2$ is absent or a —$(C_1-C_6)$alkylene- linker moiety; wherein said —$(C_1-C_6)$alkylene- linker moiety of said $L^2$ may optionally be substituted by one to three groups independently selected from the group consisting of -halo, —OH and —N($R^7$)$_2$;
$L^3$ is absent or a linker moiety selected from the group consisting of —C(O)—, —N($R^7$)—, —C(O)N($R^7$)—, —N($R^7$)C(O)—, —S(O)$_j$—, —N($R^7$)S(O)$_j$—, and —S(O)$_j$N($R^7$)—;
$L^4$ is absent or a —$(C_1-C_6)$alkylene- linker moiety; wherein said —$(C_1-C_6)$alkylene- linker moiety of said $L^4$ may optionally be substituted by one to three groups independently selected from the group consisting of -halo, —OH and —N($R^7$)$_2$;
$R^1$ is selected from the group consisting of —H, —OH, -halo, —$(C_1-C_6)$alkyl, -perfluorinated$(C_1-C_6)$alkyl, —O($C_1-C_6$)alkyl, —$(C_2-C_6)$alkenyl, —$(C_3-C_{10})$cycloalkyl, —$(C_2-C_9)$heterocycloalkyl, —$(C_6-C_{10})$aryl, and —$(C_1-C_9)$heteroaryl; wherein each of said —$(C_1-C_6)$alkyl, —O($C_1-C_6$)alkyl, —$(C_2-C_6)$alkenyl, —$(C_3-C_{10})$cycloalkyl, —$(C_2-C_9)$heterocycloalkyl, —$(C_6-C_{10})$aryl and —$(C_1-C_9)$heteroaryl of said $R^1$ is optionally substituted with one to three $R^5$ groups;
$R^2$ is selected from the group consisting of —H, —$(C_1-C_6)$alkyl, -perfluorinated$(C_1-C_6)$alkyl, —O($C_1-C_6$)alkyl, —$(C_2-C_6)$alkenyl, —$(C_3-C_{10})$cycloalkyl, —$(C_2-C_9)$heterocycloalkyl, —$(C_6-C_{10})$aryl, and —$(C_1-C_9)$heteroaryl; wherein each of said —$(C_1-C_6)$alkyl, —O($C_1-C_6$)alkyl, —$(C_2-C_6)$alkenyl, —$(C_3-C_{10})$cycloalkyl, —$(C_2-C_9)$heterocycloalkyl, —$(C_6-C_{10})$aryl and —$(C_1-C_9)$heteroaryl of said $R^2$ is optionally substituted with one to three groups selected from the group consisting of —OH, -halo, —N(R$^7$)$_2$, —N(R$^7$)C(O)R$^9$, —C(O)N(R$^7$)$_2$, —S(O)$_j$R$^8$, —N(R$^7$)S(O)$_j$R$^8$, —S(O)$_j$N(R$^7$)$_2$, -perfluorinated(C$_1$-C$_6$)alkyl, —O(C$_1$-C$_6$)alkyl, and —O(perfluorinated(C$_1$-C$_6$)alkyl);

R$^1$ and R$^2$ together with the carbon atom to which they are attached may form a 3- to 7-membered carbocyclic ring when both L$^1$ and L$^2$ are absent or a 4- to 7-membered heterocyclic ring when both L$^1$ and L$^2$ are absent; wherein each of said 3-to 7-membered carbocyclic ring or a 4- to 7-membered heterocyclic ring formed by the joinder of R$^1$ and R$^2$ is optionally substituted by one to three R$^5$ groups;

each R$^3$ is independently selected from the group consisting of —H, —OH, -halo, —S(O)$_j$R$^8$, —S(O)N(R$^7$)$_2$, —(C$_1$-C$_6$)alkyl, —O(C$_1$-C$_6$)alkyl, -perfluorinated(C$_1$-C$_6$)alkyl, —O(perfluorinated(C$_1$-C$_6$)alkyl), —(C$_2$-C$_6$)alkenyl, —(C$_3$-C$_{10}$)cycloalkyl, —(C$_2$-C$_9$)heterocycloalkyl, —(C$_6$-C$_{10}$)aryl, and —(C$_1$-C$_9$)heteroaryl; wherein each of said —(C$_1$-C$_6$)alkyl, —O(C$_1$-C$_6$)alkyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl of said R$^3$ is optionally independently substituted with one to three R$^6$ groups;

each R$^4$ is independently selected from the group consisting of —OH, -halo, —CN, —C(O)R$^9$, —N(R$^7$)$_2$, —N(R$^7$)C(O)R$^9$, —C(O)N(R$^7$)$_2$, —S(O)$_j$R$^8$, —N(R$^7$)S(O)$_j$R$^8$, —S(O)$_j$N(R$^7$)$_2$, —OP(O)(OH)$_2$, —(C$_1$-C$_6$)alkyl, —(C$_1$-C$_6$)alkyl, perfluorinated(C$_1$-C$_6$)alkyl, —O(C$_1$-C$_6$)alkyl, —O(perfluorinated(C$_1$-C$_6$)alkyl), —(C$_2$-C$_6$)alkenyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl; wherein each of said —(C$_1$-C$_6$)alkyl, —O(C$_1$-C$_6$)alkyl, —(C$_2$-C$_6$)alkenyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl of said R$^4$ is optionally independently substituted with one to three groups selected from the group consisting of —OH, -halo, —(C$_1$-C$_6$)alkyl, —O(C$_1$-C$_6$)alkyl, —(C$_6$-C$_{10}$)aryl, and —(C$_1$-C$_9$)heteroaryl;

each R$^5$ is independently selected from the group consisting of —OH, -halo, —CN, —N(R$^7$)$_2$, —N(R$^7$)C(O)R$^9$, —C(O)N(R$^7$)$_2$, —S(O)$_j$R$^8$, —N(R$^7$)S(O)$_j$R$^8$, —S(O)$_j$N(R$^7$)$_2$, —OP(O)(OH)$_2$, —(C$_1$-C$_6$)alkyl, perfluorinated(C$_1$-C$_6$)alkyl, —O(C$_1$-C$_6$)alkyl, —O(perfluorinated(C$_1$-C$_6$)alkyl), —(C$_2$-C$_6$)alkenyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl; wherein each of said —(C$_1$-C$_6$)alkyl, —O(C$_1$-C$_6$)alkyl, —(C$_2$-C$_6$)alkenyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl of said R$^5$ is optionally independently substituted with one to three groups selected from the group consisting of —OH, -halo, —(C$_1$-C$_6$)alkyl, —O(C$_1$-C$_6$)alkyl, —(C$_6$-C$_{10}$)aryl, and —(C$_1$-C$_9$)heteroaryl;

each R$^6$ is independently selected from the group consisting of —OH, -halo, —CN, —N(R$^7$)$_2$, —N(R$^7$)C(O)R$^9$, —C(O)N(R$^7$)$_2$, —S(O)$_j$R$^8$, —N(R$^7$)S(O)$_j$R$^8$, —S(O)N(R$^7$)$_2$, —CF$_3$, —(C$_1$-C$_6$)alkyl, —O(C$_1$-C$_6$)alkyl, -perfluorinated (C$_1$-C$_6$)alkyl, —O(perfluorinated(C$_1$-C$_6$)alkyl), —(C$_2$-C$_6$)alkenyl, —(C$_3$-C$_{10}$)cycloalkyl, —(C$_2$-C$_9$)heterocycloalkyl, —(C$_6$-C$_{10}$)aryl, —(C$_1$-C$_9$)heteroaryl, —(C$_1$-C$_6$)alkylene-OH, —(C$_1$-C$_6$)alkylene-halo, —(C$_1$-C$_6$)alkylene-N(R$^7$)$_2$, —(C$_1$-C$_6$)alkylene-N(R$^7$)C(O)R$^8$, —(C$_1$-C$_6$)alkylene-S(O)$_j$R$^8$, —(C$_1$-C$_6$)alkylene-perfluorinated(C$_1$-C$_6$)alkyl, —(C$_1$-C$_6$)alkylene-O(C$_1$-C$_6$)alkyl, —(C$_1$-C$_6$)alkylene-O(perfluorinated(C$_1$-C$_6$)alkyl), —(C$_1$-C$_6$)alkylene-(C$_3$-C$_{10}$)cycloalkyl, —(C$_1$-C$_6$)alkylene-(C$_2$-C$_9$)heterocycloalkyl, —(C$_1$-C$_6$)alkylene-(C$_1$-C$_6$)alkyl, —(C$_1$-C$_6$)alkylene-(C$_6$-C$_{10}$)aryl, —(C$_1$-C$_6$)alkylene-(C$_1$-C$_9$)heteroaryl; wherein each of said —(C$_1$-C$_6$)alkyl, —O(C$_1$-C$_6$)alkyl, —(C$_2$-C$_6$)alkenyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl of said R$^6$ is optionally independently substituted with one to three groups independently selected from the group consisting of —OH, -halo, —(C$_1$-C$_6$)alkyl, —O(C$_1$-C$_6$)alkyl, —(C$_3$-C$_{10}$)cycloalkyl, —(C$_2$-C$_9$)heterocycloalkyl, —(C$_6$-C$_{10}$)aryl and —(C$_1$-C$_9$)heteroaryl;

each R$^7$, R$^8$, and R$^9$ is independently selected from the group consisting of —H, —(C$_1$-C$_6$)alkyl, —(C$_3$-C$_{10}$)cycloalkyl, —(C$_2$-C$_9$)heterocycloalkyl, —(C$_6$-C$_{10}$)aryl, and —(C$_1$-C$_9$)heteroaryl;

j is 0, 1 or 2; and m is 0, 1 or 2.

The invention also relates to compositions comprising the compounds of formula (I) and pharmaceutically acceptable salts thereof.

The invention still further relates to methods of making the compounds of formula (I) and pharmaceutically acceptable salts thereof.

The invention also relates to methods of treating a bacterial infection in a mammal, comprising administering an effective amount of a compound of formula (I) and pharmaceutically acceptable salts thereof, to said mammal.

DETAILED DESCRIPTION OF THE INVENTION

As noted above, the present invention relates to a compound of formula (I) and pharmaceutically acceptable salts thereof.

In one embodiment, the invention relates to a compound of formula (I) or a pharmaceutically acceptable salt thereof, wherein A is phenyl optionally substituted by one to four R$^4$ groups.

In another embodiment, the invention relates to a compound of formula (I) or a pharmaceutically acceptable salt thereof, wherein A is phenyl.

In another embodiment, the invention relates to a compound of formula (I) or a pharmaceutically acceptable salt thereof, wherein A is 6-membered heteroaryl optionally substituted by one to four R$^4$ groups.

In another embodiment, the invention relates to a compound of formula (I) or a pharmaceutically acceptable salt thereof, wherein A is selected from the group consisting of -pyridyl, -pyridazinyl, -pyrimidinyl, and -pryazinyl.

In one embodiment, the invention relates to a compound of formula (I) or a pharmaceutically acceptable salt thereof, wherein B is —(C$_6$-C$_{10}$)aryl.

In another embodiment, the invention relates to a compound of formula (I) or a pharmaceutically acceptable salt thereof, wherein B is phenyl.

In another embodiment, the invention relates to a compound of formula (I) or a pharmaceutically acceptable salt thereof, wherein B is a —(C$_1$-C$_9$)heteroaryl.

In another embodiment, the invention relates to a compound of formula (I) or a pharmaceutically acceptable salt thereof, wherein B is selected from the group consisting of -pyridyl, -pyridazinyl, -pyrimidinyl, and -pryazinyl.

In one embodiment, the invention relates to a compound of formula (I) or a pharmaceutically acceptable salt thereof, wherein L$^1$ is absent.

In another embodiment, the invention relates to a compound of formula (I) or a pharmaceutically acceptable salt thereof, wherein L$^1$ is a linker moiety selected from the group consisting of —C(O)— and —C(O)N(R$^7$)—.

In another embodiment, the invention relates to a compound of formula (I) or a pharmaceutically acceptable salt thereof, wherein L$^1$ is —C(O)—.

In another embodiment, the invention relates to a compound of formula (I) or a pharmaceutically acceptable salt thereof, wherein $L^1$ —C(O)N($R^7$)—.

In one embodiment, the invention relates to a compound of formula (I) or a pharmaceutically acceptable salt thereof, wherein $L^2$ is absent.

In another embodiment, the invention relates to a compound of formula (I) or a pharmaceutically acceptable salt thereof, wherein $L^2$ is a —($C_1$-$C_6$)alkylene- linker moiety; wherein said —($C_1$-$C_6$)alkylene- linker moiety of said $L^2$ may optionally be substituted by one to three groups independently selected from the group consisting of -halo, —OH and —N($R^7$)$_2$.

In one embodiment, the invention relates to a compound of formula (I) or a pharmaceutically acceptable salt thereof, wherein $L^3$ is absent.

In another embodiment, the invention relates to a compound of formula (I) or a pharmaceutically acceptable salt thereof, wherein $L^3$ is a linker moiety selected from the group consisting of —C(O)—, —N($R^7$)—, —C(O)N($R^7$)—, —N($R^7$)C(O)—, —S(O)$_j$—, —N($R^7$)S(O)$_j$—, and —S(O)$_j$N($R^7$)—.

In another embodiment, the invention relates to a compound of formula (I) or a pharmaceutically acceptable salt thereof, wherein $L^3$ is —C(O)—.

In another embodiment, the invention relates to a compound of formula (I) or a pharmaceutically acceptable salt thereof, wherein $L^3$ is —N($R^7$)—.

In another embodiment, the invention relates to a compound of formula (I) or a pharmaceutically acceptable salt thereof, wherein $L^3$ is —C(O)N($R^7$)—.

In another embodiment, the invention relates to a compound of formula (I) or a pharmaceutically acceptable salt thereof, wherein $L^3$ is —N($R^7$)C(O)—.

In another embodiment, the invention relates to a compound of formula (I) or a pharmaceutically acceptable salt thereof, wherein $L^3$ is —S(O)$_j$—.

In another embodiment, the invention relates to a compound of formula (I) or a pharmaceutically acceptable salt thereof, wherein $L^3$ is —N($R^7$)S(O)$_j$—.

In another embodiment, the invention relates to a compound of formula (I) or a pharmaceutically acceptable salt thereof, wherein $L^3$ is —S(O)$_j$N($R^7$)—.

In one embodiment, the invention relates to a compound of formula (I) or a pharmaceutically acceptable salt thereof, wherein $L^4$ is absent.

In another embodiment, the invention relates to a compound of formula (I) or a pharmaceutically acceptable salt thereof, wherein $L^4$ is a —($C_1$-$C_6$)alkylene- linker moiety; wherein said —($C_1$-$C_6$)alkylene- linker moiety of said $L^4$ may optionally be substituted by one to three groups independently selected from the group consisting of -halo, —OH and —N($R^7$)$_2$.

In one embodiment, the invention relates to a compound of formula (I) or a pharmaceutically acceptable salt thereof, wherein $R^1$ is selected from the group consisting of —H, —OH and -halo.

In another embodiment, the invention relates to a compound of formula (I) or a pharmaceutically acceptable salt thereof, wherein $R^1$ is selected from the group consisting of —($C_1$-$C_6$)alkyl, -perfluorinated($C_1$-$C_6$)alkyl, —O($C_1$-$C_6$)alkyl and —($C_2$-$C_6$)alkenyl; wherein each of said —($C_1$-$C_6$)alkyl, —O($C_1$-$C_6$)alkyl, and —($C_2$-$C_6$)alkenyl of said $R^1$ is optionally substituted with one to three $R^5$ groups.

In another embodiment, the invention relates to a compound of formula (I) or a pharmaceutically acceptable salt thereof, wherein $R^1$ is selected from the group consisting of —($C_3$-$C_{10}$)cycloalkyl and —($C_2$-$C_9$)heterocycloalkyl; wherein each of said —($C_3$-$C_{10}$)cycloalkyl and —($C_2$-$C_9$)heterocycloalkyl of said $R^1$ is optionally substituted with one to three $R^4$ groups.

In another embodiment, the invention relates to a compound of formula (I) or a pharmaceutically acceptable salt thereof, wherein $R^1$ is selected from the group consisting of —($C_6$-$C_{10}$)aryl, and —($C_1$-$C_9$)heteroaryl; wherein each of said —($C_6$-$C_{10}$)aryl and —($C_1$-$C_9$)heteroaryl of said $R^1$ is optionally substituted with one to three $R^4$ groups.

In one embodiment, the invention relates to a compound of formula (I) or a pharmaceutically acceptable salt thereof, wherein $R^2$ is selected from the group consisting of —H, —($C_1$-$C_6$)alkyl, -perfluorinated($C_1$-$C_6$)alkyl, —O($C_1$-$C_6$)alkyl, and —($C_2$-$C_6$)alkenyl; wherein each of said —($C_1$-$C_6$)alkyl, —O($C_1$-$C_6$)alkyl, and —($C_2$-$C_6$)alkenyl of said $R^2$ is optionally substituted with one to three groups selected from the group consisting of —OH, -halo, —N($R^7$)$_2$, —N($R^7$)C(O)$R^9$, —C(O)N($R^7$)$_2$, —S(O)$_j$$R^8$, —N($R^7$)S(O)$_j$$R^8$, —S(O)$_j$N($R^7$)$_2$, -perfluorinated($C_1$-$C_6$)alkyl, —O($C_1$-$C_6$)alkyl, and —O(perfluorinated($C_1$-$C_6$)alkyl).

In another embodiment, the invention relates to a compound of formula (I) or a pharmaceutically acceptable salt thereof, wherein $R^2$ is selected from the group consisting of —($C_3$-$C_{10}$)cycloalkyl and —($C_2$-$C_9$)heterocycloalkyl; wherein each of said —($C_3$-$C_{10}$)cycloalkyl and —($C_2$-$C_9$)heterocycloalkyl of said $R^2$ is optionally substituted with one to three groups selected from the group consisting of —OH, -halo, —N($R^7$)$_2$, —N($R^7$)C(O)$R^9$, —C(O)N($R^7$)$_2$, —S(O)$_j$$R^8$, —N($R^7$)S(O)$_j$$R^8$, —S(O)$_j$N($R^7$)$_2$, -perfluorinated($C_1$-$C_6$)alkyl, —O($C_1$-$C_6$)alkyl, and —O(perfluorinated($C_1$-$C_6$)alkyl).

In another embodiment, the invention relates to a compound of formula (I) or a pharmaceutically acceptable salt thereof, wherein $R^2$ is selected from the group consisting of —($C_6$-$C_{10}$)aryl and —($C_1$-$C_9$)heteroaryl; wherein each of said —($C_6$-$C_{10}$)aryl and —($C_1$-$C_9$)heteroaryl of said $R^2$ is optionally substituted with one to three groups selected from the group consisting of —OH, -halo, —N($R^7$)$_2$, —N($R^7$)C(O)$R^9$, —C(O)N($R^7$)$_2$, —S(O)$_j$$R^8$, —N($R^7$)S(O)$_j$$R^8$, —S(O)$_j$N($R^7$)$_2$, -perfluorinated($C_1$-$C_6$)alkyl, —O($C_1$-$C_6$)alkyl, and —O(perfluorinated($C_1$-$C_6$)alkyl).

In another embodiment, the invention relates to a compound of formula (I) or a pharmaceutically acceptable salt thereof, wherein $R^1$ and $R^2$ together with the carbon atom to which they are attached forms a 3- to 7-membered carbocyclic ring when both $L^1$ and $L^2$ are absent or a 4- to 7-membered heterocyclic ring when both $L^1$ and $L^2$ are absent; wherein each of said 3- to 7-membered carbocyclic ring or a 4- to 7-membered heterocyclic ring formed by the joinder of $R^1$ and $R^2$ is optionally substituted by one to three $R^5$ groups.

In one embodiment, the invention relates to a compound of formula (I) or a pharmaceutically acceptable salt thereof, wherein each $R^3$ is independently selected from the group consisting of —H, —OH, and -halo.

In another embodiment, the invention relates to a compound of formula (I) or a pharmaceutically acceptable salt thereof, wherein each $R^3$ is independently selected from the group consisting of —($C_1$-$C_6$)alkyl, —O($C_1$-$C_6$)alkyl, -perfluorinated($C_1$-$C_6$)alkyl, —O(perfluorinated($C_1$-$C_6$)alkyl), and —($C_2$-$C_6$)alkenyl; wherein each of said —($C_1$-$C_6$)alkyl, —O($C_1$-$C_6$)alkyl and —($C_2$-$C_6$)alkenyl of said $R^3$ is optionally independently substituted with one to three $R^6$ groups.

In another embodiment, the invention relates to a compound of formula (I) or a pharmaceutically acceptable salt thereof, wherein each $R^3$ is independently selected from the group consisting of —($C_3$-$C_{10}$)cycloalkyl and —($C_2$-$C_9$)heterocycloalkyl; wherein each of said —($C_3$-$C_{10}$)cycloalkyl and —($C_2$-$C_9$)heterocycloalkyl of said $R^3$ is optionally independently substituted with one to three $R^6$ groups.

In another embodiment, the invention relates to a compound of formula (I) or a pharmaceutically acceptable salt thereof, wherein each $R^3$ is independently selected from the group consisting of —($C_6$-$C_{10}$)aryl and —($C_1$-$C_9$)heteroaryl; wherein each of said —($C_6$-$C_{10}$)aryl and —($C_1$-$C_9$)heteroaryl of said $R^3$ is optionally independently substituted with one to three $R^6$ groups.

In one embodiment, the invention relates to a compound of formula (I) or a pharmaceutically acceptable salt thereof, wherein $L^1$ is absent; $L^2$ is a —($C_1$-$C_6$)alkylene- linker moiety; $R^1$ is selected from the group consisting of —($C_1$-$C_6$)alkyl, —($C_3$-$C_{10}$)cycloalkyl, —($C_2$-$C_9$)heterocycloalkyl, —($C_6$-$C_{10}$)aryl, and —($C_1$-$C_9$)heteroaryl; and $R^2$ is a —($C_1$-$C_6$)alkyl; wherein said —($C_1$-$C_6$)alkylene- linker moiety of said $L^2$ is optionally substituted by —OH; and wherein said —($C_1$-$C_6$)alkyl, —($C_3$-$C_{10}$)cycloalkyl, —($C_2$-$C_9$)heterocycloalkyl, —($C_6$-$C_{10}$)aryl, and —($C_1$-$C_9$)heteroaryl of said $R^1$ is optionally independently substituted with one to three groups $R^5$ groups.

In another embodiment, the invention relates to a compound of formula (I) or a pharmaceutically acceptable salt thereof, wherein said —($C_1$-$C_6$)alkyl, —($C_3$-$C_{10}$)cycloalkyl, —($C_2$-$C_9$)heterocycloalkyl, —($C_6$-$C_{10}$)aryl, and —($C_1$-$C_9$)heteroaryl of said $R^1$ is substituted with one to three groups selected from the group consisting of —OH, -halo, —N($R^7$)$_2$, —N($R^7$)C(O)$R^9$, —C(O)N($R^7$)$_2$, —S(O)$R^8$, —N($R^7$)S(O)$_j$$R^8$, —S(O)$_j$N($R^7$)$_2$, —OP(O)(OH)$_2$, —($C_1$-$C_6$)alkyl, —O($C_1$-$C_6$)alkyl, —($C_3$-$C_{10}$)cycloalkyl, —($C_2$-$C_9$)heterocycloalkyl, —($C_6$-$C_{10}$)aryl and —($C_1$-$C_9$)heteroaryl.

In another embodiment, the invention relates to a compound of formula (I) or a pharmaceutically acceptable salt thereof, wherein said —($C_1$-$C_6$)alkyl, —($C_3$-$C_{10}$)cycloalkyl, —($C_2$-$C_9$)heterocycloalkyl, —($C_6$-$C_{10}$)aryl, and —($C_1$-$C_9$)heteroaryl of said $R^1$ is substituted with —OP(OH)$_2$.

In another embodiment, the invention relates to a compound of formula (I) or a pharmaceutically acceptable salt thereof, wherein $L^3$ is absent; $L^4$ is a —($C_1$-$C_6$)alkylene- linker moiety; m is 0 or 1; and $R^3$ is independently selected from the group consisting of —H, —OH, -halo, —S(O)$_j$$R^8$, —S(O)N($R^7$)$_2$, —($C_1$-$C_6$)alkyl, —O($C_1$-$C_6$)alkyl, -perfluorinated($C_1$-$C_6$)alkyl, —O(perfluorinated($C_1$-$C_6$)alkyl), —($C_2$-$C_6$)alkenyl, —($C_3$-$C_{10}$)cycloalkyl, —($C_2$-$C_9$)heterocycloalkyl, —($C_6$-$C_{10}$)aryl, and —($C_1$-$C_9$)heteroaryl; wherein said —($C_1$-$C_6$)alkyl, —O($C_1$-$C_6$)alkyl, —($C_3$-$C_{10}$)cycloalkyl, —($C_2$-$C_9$)heterocycloalkyl, —($C_6$-$C_{10}$)aryl and —($C_1$-$C_9$)heteroaryl of said $R^3$ is optionally independently substituted with one to three $R^6$ groups.

In another embodiment, the invention relates to a compound of formula (I) or a pharmaceutically acceptable salt thereof, wherein m is 1; and $R^3$ is selected from the group consisting of —($C_1$-$C_6$)alkyl, —O($C_1$-$C_6$)alkyl, —($C_3$-$C_{10}$)cycloalkyl, —($C_2$-$C_9$)heterocycloalkyl, —($C_6$-$C_{10}$)aryl, and —($C_1$-$C_9$)heteroaryl; wherein said —($C_1$-$C_6$)alkyl, —O($C_1$-$C_6$)alkyl, —($C_3$-$C_{10}$)cycloalkyl, —($C_2$-$C_9$)heterocycloalkyl, —($C_6$-$C_{10}$)aryl and —($C_1$-$C_9$)heteroaryl of said $R^3$ is substituted by —OP(O)(OH)$_2$.

In another embodiment, the invention relates to a compound of formula (I) or a pharmaceutically acceptable salt thereof, wherein the A is phenyl and B is phenyl.

In another embodiment, the invention relates to a compound of formula (I) or a pharmaceutically acceptable salt thereof, wherein $L^3$ and $L^4$ are both absent.

In another embodiment, the invention relates to a compound of formula (I) or a pharmaceutically acceptable salt thereof, wherein A is phenyl, B is phenyl, $L^3$ is absent and $L^4$ is absent.

In another embodiment, the invention relates to a compound of formula (I) or a pharmaceutically acceptable salt thereof, wherein m is 1.

In another embodiment, the invention relates to a compound of formula (I) or a pharmaceutically acceptable salt thereof, wherein A is phenyl, B is phenyl, $L^3$ is absent, $L^4$ is absent., m is 1, and $R^3$ is selected from the group consisting of —H, —OH, -halo, —S(O)$_j$$R^8$, and —S(O)$_j$N($R^7$)$_2$.

In another embodiment, the invention relates to a compound of formula (I) or a pharmaceutically acceptable salt thereof, wherein A is phenyl, B is phenyl, $L^3$ is absent, $L^4$ is absent., m is 1, and $R^3$ is —H.

In another embodiment, the invention relates to a compound of formula (I) or a pharmaceutically acceptable salt thereof, wherein A is phenyl, B is phenyl, $L^3$ is absent, $L^4$ is absent., m is 1, and $R^3$ is selected from the group consisting of —($C_1$-$C_6$)alkyl, —O($C_1$-$C_6$)alkyl, -perfluorinated($C_1$-$C_6$)alkyl, —O(perfluorinated($C_1$-$C_6$)alkyl), and —($C_2$-$C_6$)alkenyl, wherein each of said —($C_1$-$C_6$)alkyl, and —O($C_1$-$C_6$)alkyl of said $R^3$ is optionally independently substituted with one to three $R^6$ groups.

In another embodiment, the invention relates to a compound of formula (I) or a pharmaceutically acceptable salt thereof, wherein A is phenyl, B is phenyl, $L^3$ is absent, $L^4$ is absent., m is 1, and $R^3$ is —($C_1$-$C_6$)alkyl.

In another embodiment, the invention relates to a compound of formula (I) or a pharmaceutically acceptable salt thereof, wherein A is phenyl, B is phenyl, $L^3$ is absent, $L^4$ is absent., m is 1, and $R^3$ is selected from the group consisting of —($C_3$-$C_{10}$)cycloalkyl, —($C_2$-$C_9$)heterocycloalkyl, wherein each of said —($C_3$-$C_{10}$)cycloalkyl and —($C_2$-$C_9$)heterocycloalkyl of said $R^3$ is optionally independently substituted with one to three $R^6$ groups.

In another embodiment, the invention relates to a compound of formula (I) or a pharmaceutically acceptable salt thereof, wherein A is phenyl, B is phenyl, $L^3$ is absent, $L^4$ is absent., m is 1, and $R^3$ is selected from the group consisting of —($C_3$-$C_{10}$)cycloalkyl, —($C_2$-$C_9$)heterocycloalkyl, wherein each of said —($C_3$-$C_{10}$)cycloalkyl and —($C_2$-$C_9$)heterocycloalkyl of said $R^3$ is selected from the group consisting of —($C_6$-$C_{10}$)aryl, and —($C_1$-$C_9$)heteroaryl; wherein each of said —($C_6$-$C_{10}$)aryl and —($C_1$-$C_9$)heteroaryl of said $R^3$ is optionally independently substituted with one to three $R^6$ groups.

In another embodiment, the invention relates to a compound of formula (I) or a pharmaceutically acceptable salt thereof, wherein A is phenyl, B is phenyl, $L^3$ is absent, $L^4$ is absent, m is 1, and $R^3$ is —P(O)(OH)$_2$.

In another embodiment, the invention relates to a compound of formula (I) wherein G is a group of formula (V):

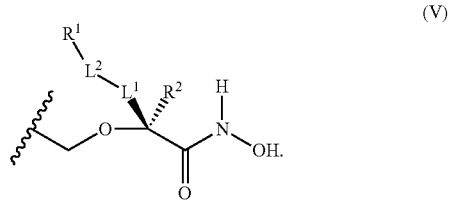

(V)

In one embodiment, the invention relates to a compound of formula (I) selected from the group consisting of any one of compounds 1 to 93 as exemplified in Examples 1 to 93 of the subject application or a pharmaceutically acceptable salt.

In another embodiment, the invention relates to a compound of formula (I) selected from the group consisting of any one of compounds 1 to 20 as exemplified in Examples 1 to 20 of the subject application or a pharmaceutically acceptable salt.

In another embodiment, the invention relates to a compound of formula (I) selected from the group consisting of any one of compounds 21 to 40 as exemplified in Examples 21 to 40 of the subject application or a pharmaceutically acceptable salt.

In another embodiment, the invention relates to a compound of formula (I) selected from the group consisting of any one of compounds 41 to 60 as exemplified in Examples 41 to 60 of the subject application or a pharmaceutically acceptable salt.

In another embodiment, the invention relates to a compound of formula (I) selected from the group consisting of any one of compounds 61 to 80 as exemplified in Examples 61 to 80 of the subject application or a pharmaceutically acceptable salt.

In another embodiment, the invention relates to a compound of formula (I) selected from the group consisting of any one of compounds 81 to 93 as exemplified in Examples 81 to 93 of the subject application or a pharmaceutically acceptable salt.

As used herein, the phrase "the compounds of the invention" includes the compounds of formula (I) and pharmaceutically acceptable salts. It will also be understood that the phrase "compound formula (I) and pharmaceutically acceptable salt(s) thereof" also encompasses the pharmaceutically acceptable, prodrugs, hydrates, and solvates of the compound of formula (I) and pharmaceutically acceptable salts thereof.

As used herein, the term "$(C_1-C_6)$alkyl," as well as the alkyl moieties of other groups referred to herein (e.g., $(C_1-C_6)$ alkoxy), refers to linear or branched (e.g., methyl, ethyl, n-propyl, isopropyl, n-butyl, iso-butyl, secondary-butyl, tertiary-butyl) radicals of 1 to 6 carbon atoms; optionally substituted by 1 to 5 suitable substituents as defined above such as fluoro, chloro, trifluoromethyl, —$(C_1-C_6)$alkoxy, —$(C_6-C_{10})$aryloxy, -trifluoromethoxy, -difluoromethoxy or —$(C_1-C_6)$alkyl. The phrase "each of said $(C_1-C_6)$alkyl" as used herein refers to any of the preceding alkyl moieties within a group such as alkoxy, alkenyl or alkylamino. Preferred alkyls include $(C_1-C_6)$alkyl, more preferred are $(C_1-C_4)$alkyl, and most preferred are methyl and ethyl.

As used herein, the term "$(C_2-C_6)$alkenyl" means straight or branched chain unsaturated radicals of 2 to 6 carbon atoms, including, but not limited to ethenyl, 1-propenyl, 2-propenyl (allyl), iso-propenyl, 2-methyl-1-propenyl, 1-butenyl, 2-butenyl, and the like; optionally substituted by 1 to 5 suitable substituents as defined above such as fluoro, chloro, trifluoromethyl, —$(C_1-C_6)$alkoxy, —$(C_6-C_{10})$aryloxy, trifluoromethoxy, difluoromethoxy or —$(C_1-C_6)$alkyl. When the compounds of formula (I) contain a —$(C_2-C_6)$alkenyl group, the compound may exist as the pure E (entgegen) form, the pure Z (zusammen) form, or any mixture thereof.

Unless otherwise specified, the —$(C_1-C_6)$alkyls and —$(C_2-C_6)$alkenyl can be independently straight-chain or branch-chain.

As used herein, the term "$(C_1-C_6)$alkylene" refers to linear or branched methylene, ethylene, propylene, butylene, pentylene and hexylene linkers.

As used herein, the term "$(C_3-C_{10})$cycloalkyl" refers to a mono-carbocyclic ring having from 3 to 10 carbon atoms (e.g., cyclopropyl, cyclobutyl, cyclopentyl, cyclohexyl, cycloheptyl, cyclooctyl, cyclononyl); optionally substituted by 1 to 5 suitable substituents as defined above such as, e.g., fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term "halo" includes fluoro, chloro, bromo or iodo.

As used herein, the term "$(C_6-C_{10})$aryl" means aromatic radicals such as phenyl, naphthyl, tetrahydronaphthyl, indanyl and the like; optionally substituted by 1 to 5 suitable substituents as defined above.

As used herein the term "6-membered heteroaryl" refers to an aromatic heterocyclic group with one to four heteroatoms selected from O, S, and N in the ring. Non-limiting examples of 6-membered heteroaryls include -pyridyl, -pyridazinyl, -pyrimidinyl, or -pryazinyl.

As used herein, the term "$(C_1-C_9)$heteroaryl" refers to an aromatic heterocyclic group usually with one heteroatom selected from O, S and N in the ring. In addition to said heteroatom, the aromatic group may optionally have up to four additional heteroatoms atoms in the ring. For example, heteroaryl group includes pyridyl, pyrazinyl, pyrimidinyl, pyridazinyl, thienyl, furyl, imidazolyl, pyrrolyl, oxazolyl (e.g., 1,3-oxazolyl, 1,2-oxazolyl), thiazolyl (e.g., 1,2-thiazolyl, 1,3-thiazolyl), pyrazolyl, tetrazolyl, triazolyl (e.g., 1,2,3-triazolyl, 1,2,4-triazolyl), oxadiazolyl (e.g., 1,2,3-oxadiazolyl), thiadiazolyl (e.g., 1,3,4-thiadiazolyl), quinolyl, isoquinolyl, benzothienyl, benzofuryl, indolyl, and the like; optionally substituted by 1 to 5 suitable substituents as defined above such as, e.g., fluoro, chloro, trifluoromethyl, $(C_1-C_6)$alkoxy, $(C_6-C_{10})$aryloxy, trifluoromethoxy, difluoromethoxy or $(C_1-C_6)$alkyl.

As used herein, the term heteroatom refers to an atom or group selected from N, O, S(O)$_j$ or NR$^7$, where j and R$^7$ are as defined above.

The term "$(C_2-C_9)$heterocycloalkyl" as used herein refers to a cyclic group containing 2-9 carbon atoms and 1 to 4 hetero atoms. Examples of such rings include azetidinyl, tetrahydrofuranyl, imidazolidinyl, pyrrolidinyl, piperidinyl, piperazinyl, oxazolidinyl, thiazolidinyl, pyrazolidinyl, thiomorpholinyl, tetrahydrothiazinyl, tetrahydro-thiadiazinyl, morpholinyl, oxetanyl, tetrahydrodiazinyl, oxazinyl, oxathiazinyl, indolinyl, isoindolinyl, quinuclidinyl, chromanyl, isochromanyl, benzoxazinyl, and the like. Examples of said monocyclic saturated or partially saturated ring systems are tetrahydrofuran-2-yl, tetrahydrofuran-3-yl, imidazolidin-1-yl, imidazolidin-2-yl, imidazolidin-4-yl, pyrrolidin-1-yl, pyrrolidin-2-yl, pyrrolidin-3-yl, piperidin-1-yl, piperidin-2-yl, piperidin-3-yl, piperazin-1-yl, piperazin-2-yl, piperazin-3-yl, 1,3-oxazolidin-3-yl, isothiazolidine, 1,3-thiazolidin-3-yl, 1,2-pyrazolidin-2-yl, 1,3-pyrazolidin-1-yl, thiomorpholin-yl, 1,2-tetrahydrothiazin-2-yl, 1,3-tetrahydrothiazin-3-yl, tetrahydrothiadiazin-yl, morpholin-yl, 1,2-tetrahydrodiazin-2-yl, 1,3-tetrahydrodiazin-1-yl, 1,4-oxazin-2-yl, 1,2,5-oxathiazin-4-yl and the like; optionally containing 1 or 2 double bonds and optionally substituted by 1 to 5 suitable substituents as defined above such as fluoro, chloro, trifluoromethyl, $(C_1-C_6)$alkoxy, $(C_6-C_{10})$aryloxy, trifluoromethoxy, difluoromethoxy or $(C_1-C_6)$alkyl.

The phrase "pharmaceutically acceptable salt(s)", as used herein, unless otherwise indicated, includes salts of acidic or basic groups which may be present in the compounds of the present invention. The compounds of the present invention that are basic in nature are capable of forming a wide variety of salts with various inorganic and organic acids. The acids that may be used to prepare pharmaceutically acceptable acid addition salts of such basic compounds of are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. The compounds of the present invention that include a basic moiety, such as an amino group, may form pharmaceutically acceptable salts with various amino acids, in addition to the acids mentioned above.

The invention also relates to base addition salts of the compounds of the invention. The chemical bases that may be used as reagents to prepare pharmaceutically acceptable base salts of those compounds of the compounds of the invention that are acidic in nature are those that form non-toxic base salts with such compounds. Such non-toxic base salts include, but are not limited to those derived from such pharmacologically acceptable cations such as alkali metal cations (e.g., potassium and sodium) and alkaline earth metal cations (e.g., calcium and magnesium), ammonium or water-soluble amine addition salts such as N-methylglucamine-(meglumine), and the lower alkanolammonium and other base salts of pharmaceutically acceptable organic amines.

Suitable base salts are formed from bases which form non-toxic salts. Non-limiting examples of suitable base salts include the aluminum, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, 2002). Methods for making pharmaceutically acceptable salts of compounds of the invention are known to one of skill in the art.

The compounds of the invention may also exist in unsolvated and solvated forms. Thus, it will be understood that the compounds of the invention (and pharmaceutically acceptable salts thereof) also include hydrates and solvates of said compounds of the invention (and pharmaceutically acceptable salts thereof) as discussed below.

The term "solvate" is used herein to describe a noncovalent or easily reversible combination between solvent and solute, or dispersion means and disperse phase. It will be understood that the solvate can be in the form of a solid, slurry (e.g., a suspension or dispersion), or solution. Non-limiting examples of solvents include ethanol, methanol, propanol, acetonitrile, dimethyl ether, diethyl ether, tetrahydrofuan, methylene chloride, and water. The term 'hydrate' is employed when said solvent is water.

A currently accepted classification system for organic hydrates is one that defines isolated site, channel, or metal-ion coordinated hydrates—see Polymorphism in Pharmaceutical Solids by K. R. Morris (Ed. H. G. Brittain, Marcel Dekker, 1995). Isolated site hydrates are ones in which the water molecules are isolated from direct contact with each other by intervening organic molecules. In channel hydrates, the water molecules lie in lattice channels where they are next to other water molecules. In metal-ion coordinated hydrates, the water molecules are bonded to the metal ion.

When the solvent or water is tightly bound, the complex will have a well-defined stoichiometry independent of humidity. When, however, the solvent or water is weakly bound, as in channel solvates and hygroscopic compounds, the water/solvent content will be dependent on humidity and drying conditions. In such cases, non-stoichiometry will be the norm.

Compounds of the invention containing one or more asymmetric carbon atoms can exist as two or more stereoisomers. The compounds of this invention include all stereoisomers (e.g., cis and trans isomers) and all optical isomers of compounds of the invention (e.g., R and S enantiomers), as well as racemic, diastereomeric and other mixtures of such isomers, and mixtures of one or more thereof. Also included are acid addition or base salts wherein the counterion is optically active, for example, d-lactate or l-lysine, or racemic, for example, dl-tartrate or dl-arginine.

When any racemate crystallizes, crystals of two different types are possible. The first type is the racemic compound (true racemate) wherein one homogeneous form of crystal is produced containing both enantiomers in equimolar amounts. The second type is the racemic mixture or conglomerate wherein two forms of crystal are produced in equimolar amounts each comprising a single enantiomer. While both of the crystal forms present in a racemic mixture have identical physical properties, they may have different physical properties compared to the true racemate. Racemic mixtures may be separated by conventional techniques known to those skilled in the art—see, for example, Stereochemistry of Organic Compounds by E. L. Eliel and S. H. Wilen (Wiley, 1994).

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC). For example, chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of an alcoholic solvent such as isopropanol, typically from 2% to 20%, and from 0 to 5% by volume of an alkylamine, typically 0.1% diethylamine. Concentration of the eluate affords the enriched mixture.

Alternatively, the racemate (or a racemic precursor) may be reacted with a suitable optically active compound, for example, an alcohol, or, in the case where the compound of the invention contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

The present invention also includes atropisomers of the present invention. Atropisomers refer to compounds of the invention that can be separated into rotationally restricted isomers.

The compounds of this invention may contain olefin-like double bonds. When such bonds are present, the compounds of the invention exist as cis and trans configurations and as mixtures thereof. Cis/trans isomers may be separated by conventional techniques well known to those skilled in the art, for example, chromatography and fractional crystallization.

Where a compound of the invention contains an alkenyl or alkenylene group, geometric cis/trans (or Z/E) isomers are possible. Where structural isomers are interconvertible via a low energy barrier, tautomeric isomerism ('tautomerism')

can occur. This can take the form of proton tautomerism in compounds of the invention containing, for example, an imino, keto, or oxime group, or so-called valence tautomerism in compounds which contain an aromatic moiety. It follows that a single compound may exhibit more than one type of isomerism. All such tautomeric forms are included within the scope of the present invention. Tautomers exist as mixtures of a tautomeric set in solution. In solid form, usually one tautomer predominates. Even though one tautomer may be described, the present invention includes all tautomers of the present compounds.

The invention also relates to prodrugs of the compounds of the invention. Thus certain derivatives of compounds of the invention which may have little or no pharmacological activity themselves can, when administered into or onto the body, be converted into compounds of the invention having the desired activity, for example, by hydrolytic cleavage. Such derivatives are referred to as "prodrugs". Further information on the use of prodrugs may be found in Pro-drugs as Novel Delivery Systems, Vol. 14, ACS Symposium Series (T. Higuchi and W. Stella) and Bioreversible Carriers in Drug Design, Pergamon Press, 1987 (Ed. E. B. Roche, American Pharmaceutical Association).

By way of example, compounds of the compounds of the invention having free amino, amido, hydroxy or carboxylic groups can be converted into prodrugs. Prodrugs include compounds wherein an amino acid residue, or a polypeptide chain of two or more (e.g., two, three or four) amino acid residues which are covalently joined through peptide bonds to free amino, hydroxy or carboxylic acid groups of compounds of the invention. The amino acid residues include the 20 naturally occur Amino acids commonly designated by three letter symbols and also include, 4-hydroxyproline, hydroxylysine, demosine, isodemosine, 3-methylhistidine, norvalin, beta-alanine, gamma-aminobutyric acid, citrulline, homocysteine, homoserine, ornithine and methionine sulfone. Prodrugs also include compounds wherein carbonates, carbamates, amides and alkyl esters are covalently bonded to the above substituents of the compounds of the invention through the carbonyl carbon prodrug sidechain.

Prodrugs in accordance with the invention can, for example, be produced by replacing appropriate functionalities present in the compounds of the invention with certain moieties known to those skilled in the art as 'pro-moieties' as described, for example, in Design of Prodrugs by H. Bundgaard (Elsevier, 1985).

Some non-limiting examples of prodrugs in accordance with the invention include (i) where the compound of the invention contains a carboxylic acid functionality (—COOH), an ester thereof, for example, a compound wherein the hydrogen of the carboxylic acid functionality of the compound of formula (I) is replaced by $(C_1-C_6)$alkyl;

(ii) where the compound of the invention contains an alcohol functionality (—OH), an ether thereof, for example, a compound wherein the hydrogen of the alcohol functionality of the compound of the invention is replaced by $(C_1-C_6)$ alkanoyloxymethyl, —P(O)(OH)$_2$, or polyethylene glycol (PEG);

(iii) where the compound of the invention contains a primary or secondary amino functionality (—NH$_2$ or —NHR$^7$ where R≠H), an amide thereof, for example, a compound wherein, as the case may be, one or both hydrogen atoms of the amino functionality of the compound of the invention is/are replaced by $(C_1-C_6)$alkanoyl; and (iv) where the compound of the invention contains an amino functionality (e.g, —N(R$^7$)$_2$ the amino functionality may be oxidized to form an N-oxide or a quaternary ammonium salt such as:

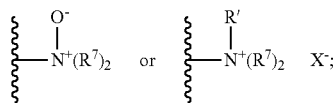

wherein R$^7$ is as defined above for the compound of formula (I), R' is .[DEFINE], and X is a counteranion.

Further examples of replacement groups in accordance with the foregoing examples and examples of other prodrug types may be found in the aforementioned references.

Moreover, certain compounds of the invention may themselves act as prodrugs of other compounds of the invention.

This invention also encompasses compositions containing prodrugs of compounds of the compounds of the invention (e.g., pharmaceutical compositions).

Also included within the scope of the invention are metabolites of compounds of the invention, that is, compounds formed in vivo upon administration of the drug. Some examples of metabolites in accordance with the invention include:

(i) where the compound of the invention contains a methyl group, an hydroxymethyl derivative thereof (e.g., —CH$_3$->— CH$_2$OH):

(ii) where the compound of the invention contains an alkoxy group, an hydroxy derivative thereof (e.g., —OR$^7$-> —OH);

(iii) where the compound of the invention contains a tertiary amino group, a secondary amino derivative thereof (e.g., —N(R$^7$)$_2$->—NHR$^7$ or —NH$_2$);

(iv) where the compound of the invention contains a secondary amino group, a primary derivative thereof (e.g., —NHR$^7$->—NH$_2$);

(v) where the compound of the invention contains a phenyl moiety, a phenol derivative thereof (e.g., -Ph->-PhOH); and (vi) where the compound of the invention contains an amide group, a carboxylic acid derivative thereof (e.g., —CONH$_2$->COOH);

wherein R$^7$ is as defined above for the compound of formula (I).

This invention also encompasses compounds of the invention containing protective groups. One skilled in the art will also appreciate that compounds of the invention can also be prepared with certain protecting groups that are useful for purification or storage and can be removed before administration to a patient. The protection and deprotection of functional groups is described in "Protective Groups in Organic Chemistry", edited by J. W. F. McOmie, Plenum Press (1973) and "Protective Groups in Organic Synthesis", 3rd edition, T. W. Greene and P. G. M. Wuts, Wiley-Interscience (1999).

The present invention also includes isotopically-labeled compounds, which are identical to those recited in formula I, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorous, fluorine and chlorine, such as, but not limited to, $^2$H, $^3$H, $^{13}$C, $^{14}$C, $^{15}$N, $^{18}$O, $^{17}$O, $^{31}$P, $^{32}$P, $^{35}$S, $^{18}$F, and $^{36}$Cl, respectively. Compounds of the present invention, prodrugs thereof, and pharmaceutically acceptable salts of said compounds or of said prodrugs which contain the aforementioned isotopes and/or other isotopes of other atoms are within the scope of this invention. Certain isotopically-labeled compounds of the present invention, for example those into which radioactive isotopes such as $^3$H and $^{14}$C are incorporated, are useful in drug and/or substrate tissue distribution assays. Tritiated, i.e., $^3$H, and carbon-14, i.e., $^{14}$C, isotopes are particularly preferred for their ease of preparation and detectability. Further, substitution with heavier isotopes such as deuterium, i.e., $^2$H, can afford certain therapeutic advantages resulting from greater metabolic stability, for example increased in vivo half-life or reduced dosage requirements and, hence, may be preferred in some circumstances. Isotopically-labeled compounds of this invention and prodrugs thereof can generally be prepared by carrying out the procedures disclosed in the Schemes and/or in the Examples below, by substituting a readily available isotopically-labeled reagent for a non-isotopically-labeled reagent.

In one embodiment, the invention relates to compositions comprising a compound of the invention and at least one additional ingredient (hereinafter "the compositions of the invention"). It will be understood that the compositions of the invention will encompass any combination of the compound of the invention and the at least one additional ingredient. Non-limiting examples of the at least one additional ingredient include impurities (e.g., intermediates present in the unrefined compounds of the invention), active ingredients as discussed herein (e.g., an additional anti-bacterial agent), pharmaceutically acceptable excipients, or one or more solvents (e.g., a pharmaceutically acceptable carrier as discussed herein).

The term "solvent" as it relates to the compositions of the invention includes organic solvents (e.g., methanol, ethanol, isopropanol, ethyl acetate, methylene chloride, and tetrahydrofuran) and water. The one or more solvents may be present in a non-stoichiometric amount, e.g., as a trace impurity, or in sufficient excess to dissolve the compound of the invention. Alternatively, the one or more solvents may be present in a stoichiometric amount, e.g., 0.5:1, 1:1, or 2:1 molar ratio, based on the amount of compound of the invention.

In one embodiment, the at least one additional ingredient that is present in the composition of the invention is an organic solvent.

In another embodiment, the at least one additional ingredient that is present in the composition of the invention is water.

In one embodiment, the at least one additional ingredient that is present in the composition of the invention is a pharmaceutically acceptable carrier.

In another embodiment, the at least one additional ingredient that is present in the composition of the invention is a pharmaceutically acceptable excipient.

In one embodiment, the composition of the invention is a solution.

In another embodiment, the composition of the invention is a suspension.

In another embodiment, the composition of the invention is a solid.

In another embodiment, the composition of the invention comprises an amount of the compound of the invention effective for treating abnormal cell growth.

In yet another embodiment, the invention relates to a composition comprising an effective amount of the compound of the invention, and a pharmaceutically acceptable carrier.

In another embodiment, the invention relates to a composition comprising a therapeutically effective amount of the compound the invention as defined above, a pharmaceutically acceptable carrier and, optionally, at least one additional medicinal or pharmaceutical agent.

The compounds of the invention can be prepared by the general procedures described below and discussed in detail in the Examples section. Schemes 1 and 2 below depict general non-limiting methods for making the compounds of formula (I) and intermediates useful for making compounds of formula (I). Other methods for making the compounds of formula (I) and intermediates useful for making compounds of formula (I) can be found in the Examples section. Unless otherwise indicated, all substituent and linker groups are as defined above. For sake of simplicity, the groups A and B are depicted as phenyl rings, and the linkers $L^1$ and $L^2$ are absent. However, it will be understood that compounds of formula (I) where one or both of A and B is not phenyl, or/and one or both of $L^1$ and $L^2$ are present can be prepared by these same methods or slight variations which are well understood in the art.

One method for making the compounds of formula (I) is depicted in Scheme 1 below.

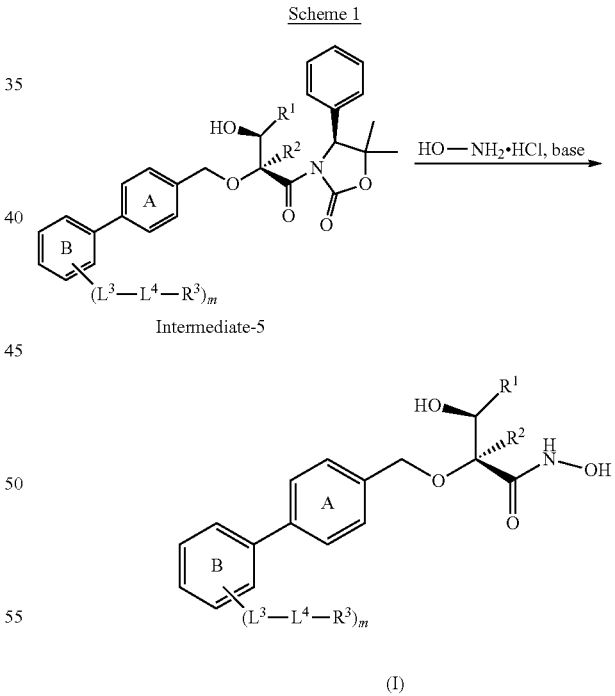

As depicted in Scheme 1, the oxazolidinoyl Intermediate-5 can be reacted with hydroxylamine hydrochloride in the presence of a suitable base such as lithium methoxide or methylmagnesium bromide (Example 16) to provide the compound of formula (I).

Intermediate-5 can be prepared according to the general procedure depicted in Scheme 2 below.

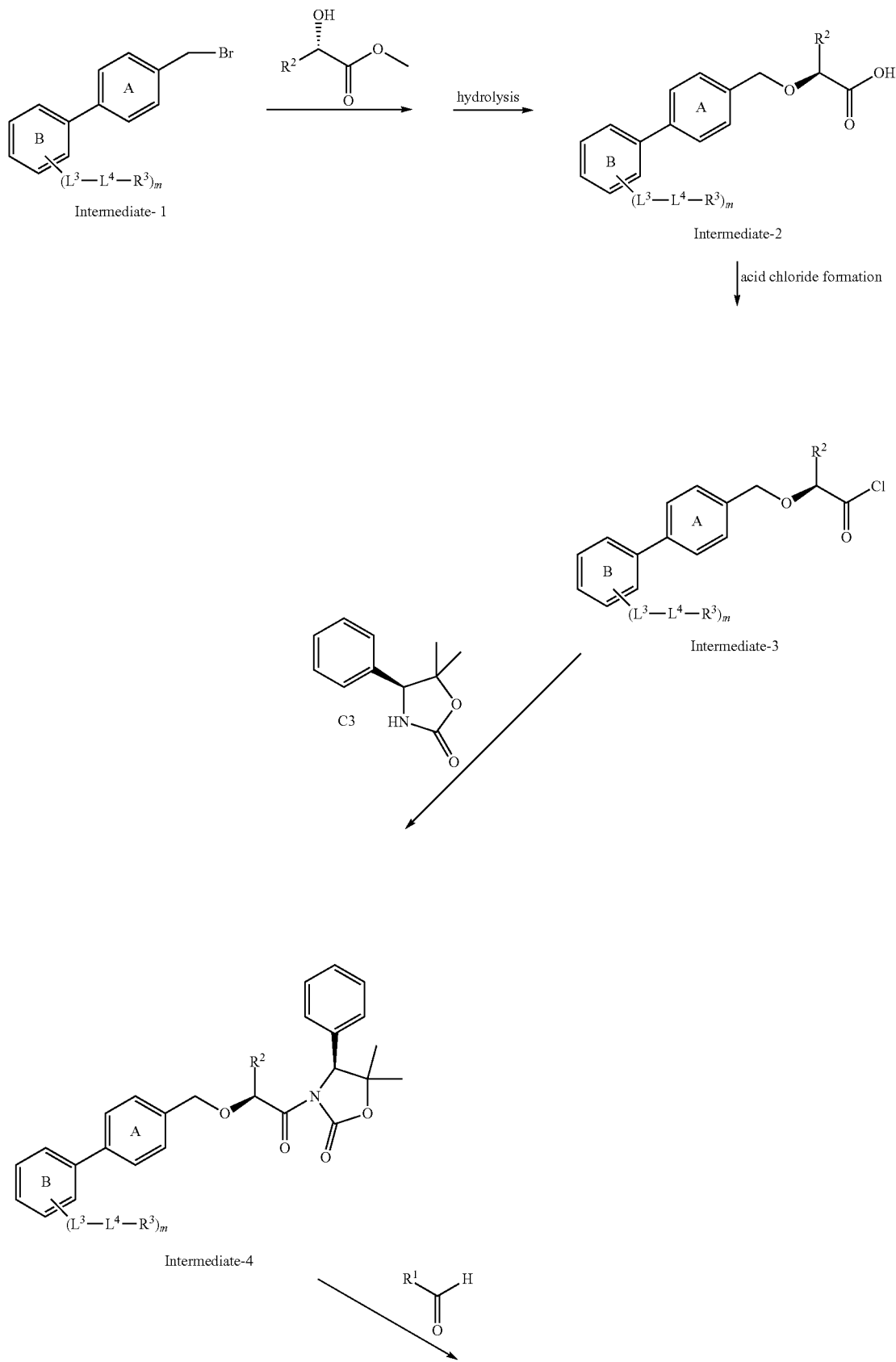

19

-continued

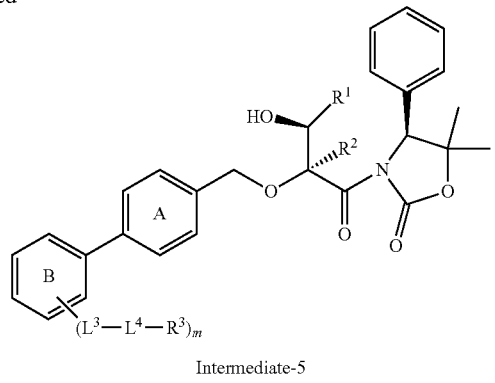
Intermediate-5

As depicted in Scheme 2, Intermediate-1 can be reacted with an alpha-hydroxy ester (such as the (S)-2-hydroxyester shown) followed by hydrolysis to form Intermediate-2 followed by formation of the acid chloride with a suitable chlorinating agent such as thionyl chloride, to provide Intermediate-3. Intermediate-3 is then allowed to react with the compound C3 (see Example 1) to provide Intermediate-4.

20

Intermediate-4 is then allowed to react with a suitable base such as lithium diisopropylamide, followed by treatment with chlorotitanium triisopropoxide; further reaction with aldehyde $R^1CHO$ provides Intermediate-5.

Another method for making the compounds of formula (I) is depicted in Scheme 2a below.

Scheme 2a

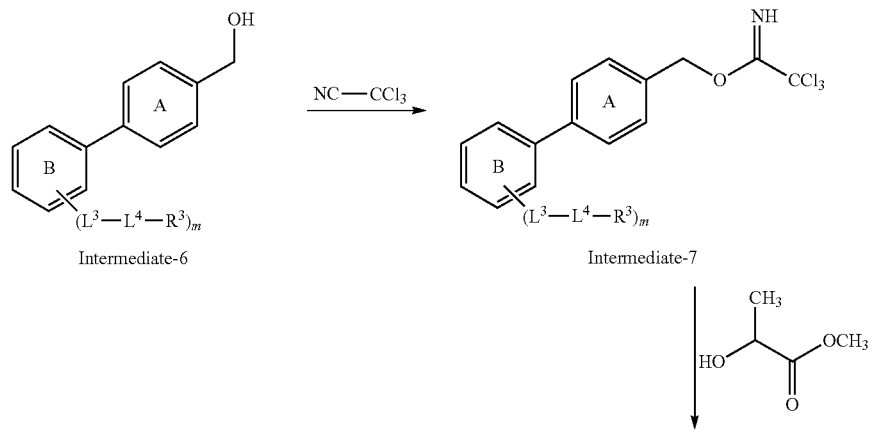

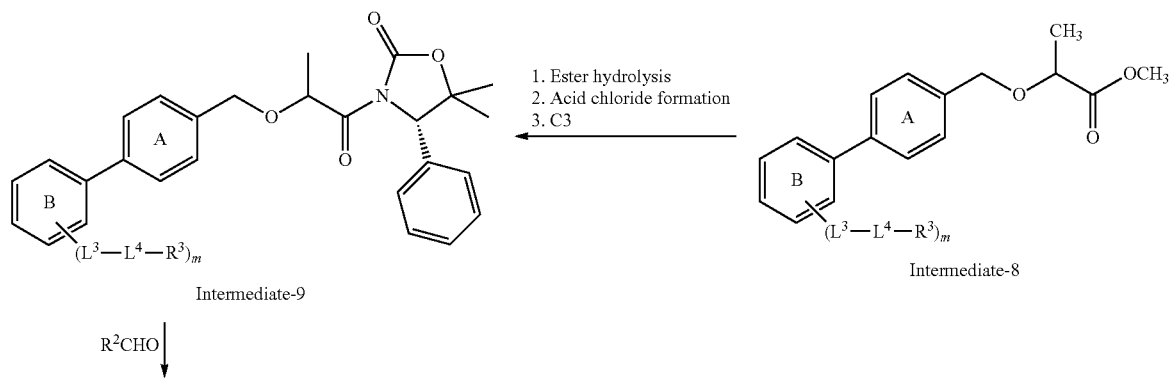

$R^2CHO$

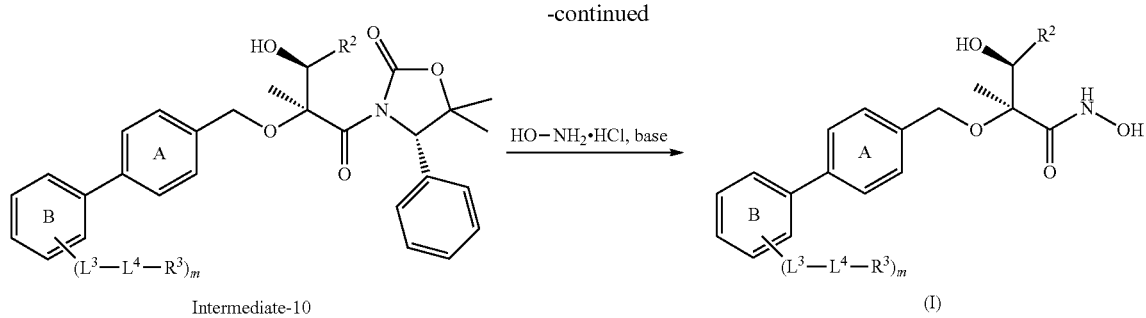

Intermediate-10 → (I)

In Scheme 2a, a biphenyl alcohol as shown is allowed to react with trichloroacetonitrile to form Intermediate-7. Intermediate-7 is then allowed to react with methyl 2-hydroxypropanoate to form Intermediate-8. Intermediate-8 is then subjected to ester hydrolysis followed by conversion of the resulting carboxylic acid to its acid chloride, and finally reaction with C3 to provide Intermediate-9. Reaction of intermediate-9 with the aldehyde $R^2CHO$, as outlined for Scheme 2, provides Intermediate-10. Intermediate-10 is then reacted with hydroxylamine hydrochloride in the presence of a suitable base to provide the compound of formula (I).

Intermediate-8 depicted in Scheme 2a can also be made by the methods depicted below in Scheme 2b.

Scheme 2b

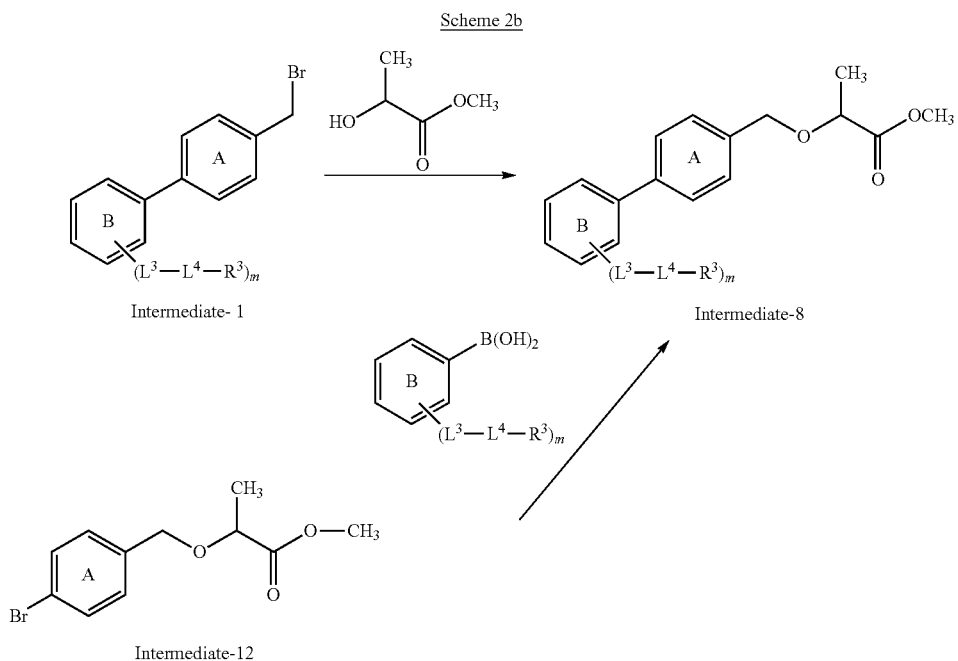

In Scheme 2b, a 4-(bromomethyl)biphenyl derivative (Intermediate-1) is allowed to react with methyl 2-hydroxypropanoate to form Intermediate-8. In the other embodiment depicted in Scheme 2b, Intermediate-12 is allowed to undergo a coupling reaction with an arylboronic acid to provide Intermediate-8.

Scheme 2c shows another non-limiting method for making compounds of formula (I).

Scheme 2c

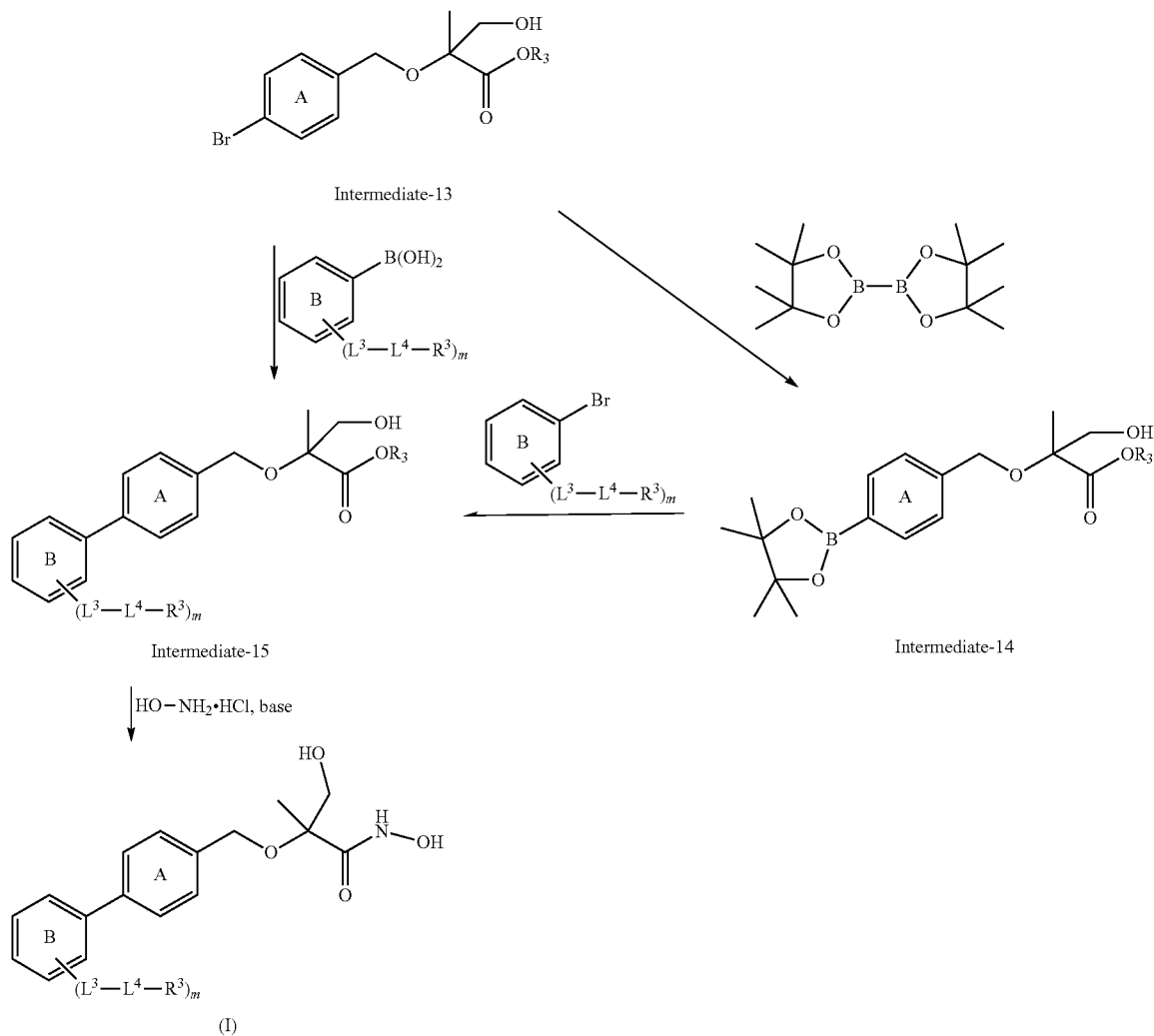

As depicted in one embodiment in Scheme 2c, Intermediate-13 is allowed to react with an arylboronic acid, under conditions conducive to such coupling reactions, such as catalysis with various palladium complexes, to provide Intermediate-15. Alternatively, Intermediate-13 is allowed to react with 4,4,4',4',5,5,5',5'-octamethyl-2,2'-bi-1,3,2-dioxaborolane (pinacol diborane) under palladium catalysis to provide Intermediate-14. Intermediate-14 is then allowed to react with an arylbromide in a coupling reaction to provide Intermediate-15, as shown. Intermediate-15 is then reacted with hydroxylamine hydrochloride in the presence of a suitable base to provide the compound of formula (I).

Scheme 2d depicts an alternative method for making Intermediate-15 depicted in Scheme 2c including heterocyclic analogs.

Scheme 2d

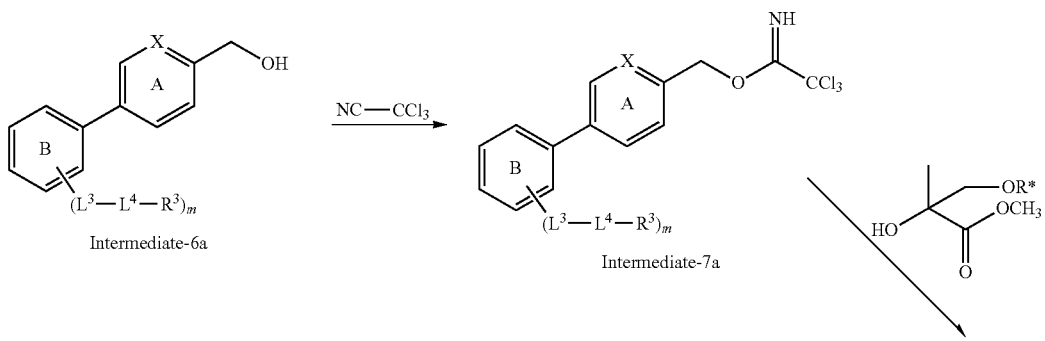

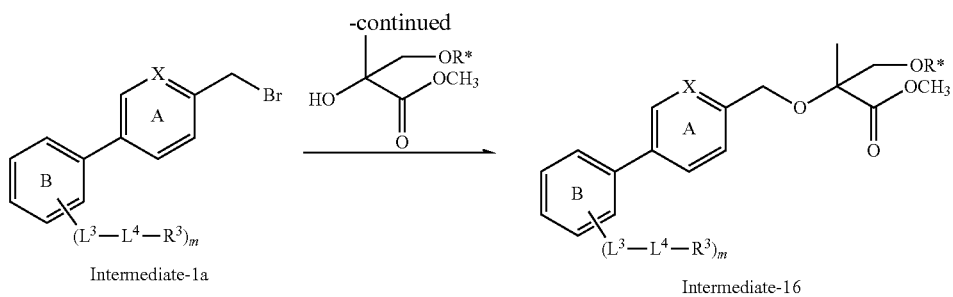

Intermediate-1a

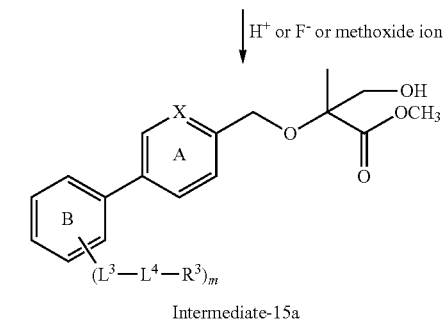

Intermediate-15a

As depicted in one embodiment in Scheme 2d, Intermediate-6a (where X is CH or N) is allowed to react with trichloroacetonitrile to form Intermediate-7a. Intermediate-7a is then allowed to react with the 3-hydroxy derivative of methyl 2-hydroxy-2-methylpropanoate as shown (where R*=tert-butyldimethylsilyl or pivaloyl) to form Intermediate-16. In the other embodiment in Scheme 2d, Intermediate-1a (where X is CH or N) is allowed to react with the 3-hydroxy derivative of methyl 2-hydroxy-2-methylpropanoate as shown to form Intermediate-16. Intermediate-16 is then deprotected to provide Intermediate-15a.

Scheme 2e depicts another method of making the compounds of formula (I).

Scheme 2e

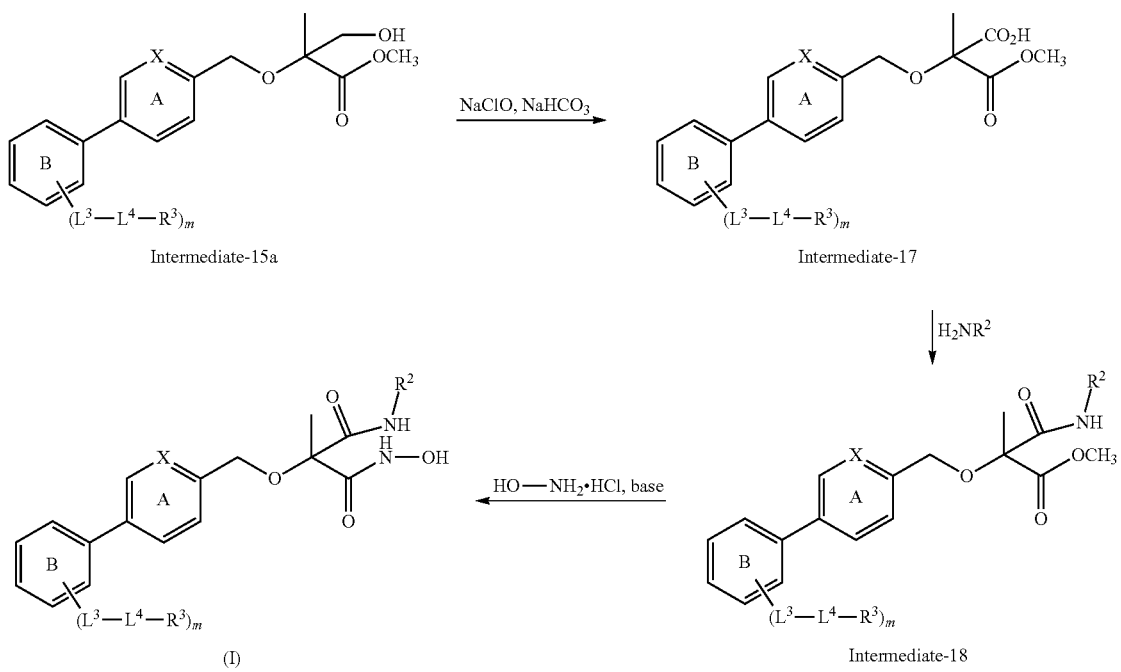

As shown in Scheme 2e, Intermediate-15a is allowed to react with sodium hypochlorite/sodium bicarbonate to provide Intermediate-17. Intermediate-17 is then reacted with an alkylamine under standard conditions for amide formation to provide Intermediate-18, which is further reacted with hydroxylamine hydrochloride to provide the compound of formula (I).

Another method for making the compounds of formula (I) is depicted below in Scheme 2f.

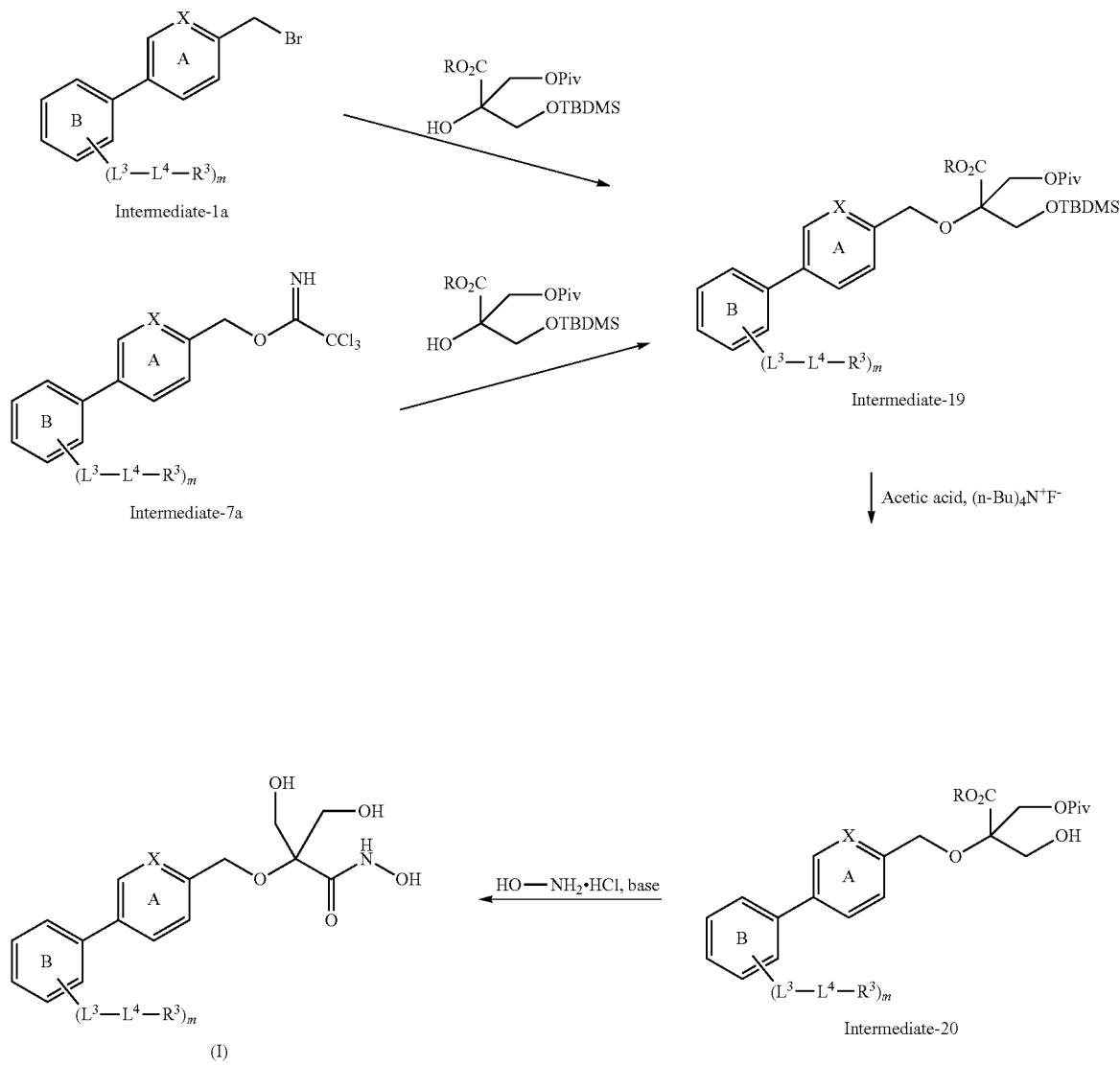

Scheme 2f

As shown in Scheme 2f, Intermediate-1a or Intermediate-7a (where X is CH or N) is allowed to react with the reagent shown (where Piv=pivaloyl and TBDMS=tert-butyldimethylsilyl) to provide Intermedate-19. Intermediate-19 is then allowed to react with acetic acid and tetra-n-butylammonium fluoride to provide Intermediate-20. Reaction of Intermediate-20 with hydroxylamine hydrochloride in the presence of base provides the compound of formula (I).

Another method for making the compounds of formula (I) is depicted below in Scheme 2g.

Scheme 2g

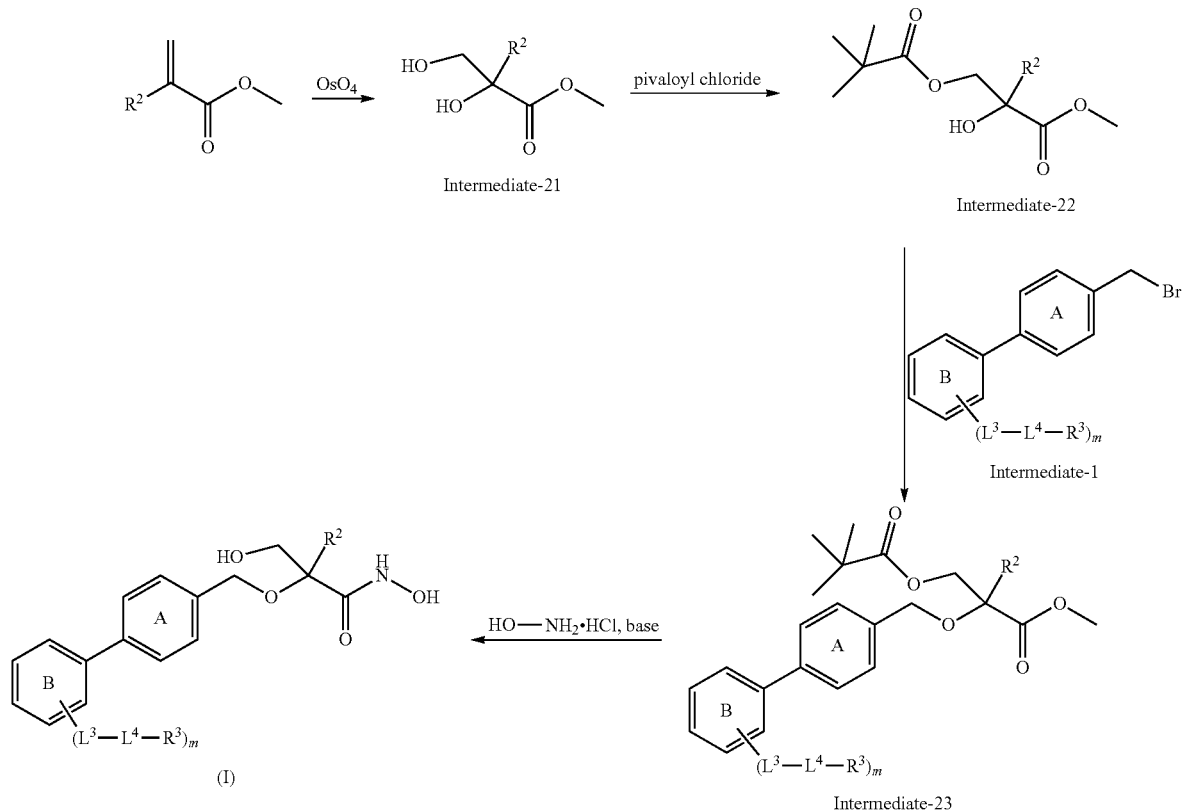

As depicted in Scheme 2g, an acrylate derivative is allowed to react with a suitable oxidizing agent such as osmium tetroxide to form Intermediate-21. Intermediate-21 is then reacted with pivaloyl chloride to form Intermediate-22 which is further reacted with Intermediate-1 to form Intermediate-23. Reaction of Intermediate-23 with hydroxylamine hydrochloride in the presence of a suitable base provides the compound of formula (I).

As noted above, the compounds of the invention are useful for a treating bacterial infection in a mammal comprising administering to said mammal an amount of a compound of formula (I) that is effective in treating said bacterial infection.

In a preferred embodiment, the bacterial infection is a gram-negative infection. Accordingly, in another embodiment, the compounds of the invention are useful for a treating a gram-negative infection in a mammal comprising administering to said mammal an amount of a compound of formula (I) this is effective in treating said bacteria gram-negative infection.

Non limiting examples of gram-negative bacteriae amenable to treatment by the compounds of the invention, and pharmaceutically acceptable salts thereof, include *Acinetobacter baumannii, Acinetobacter* spp., *Alloiococcus otitidis, Bacillus subtilis, Bacteroides fragilis, Citrobacter diversus, Citrobacter freundii, Clostridium perfringens, Enterobacter aerogenes, Enterobacter cloacae, Escherichia coli, Haemophilus influenzae* β-lactamase negative, *Haemophilus influenzae* β-lactamase positive, *Klebsiella oxytoca, Klebsiella pneurnoniae* (including those encoding extended-spectrum β-lactamases (hereinafter "ESBLs"), *Legionella pneumophila, Listeria monocytogenes,* methicillin-resistant staphylococci, *Moraxella catarrhalis* β-lactamase-negative, *Moraxella catarrhalis* β-positive, *Morganella morganii,* multi-resistant enterococci, *Neisseria meningitidis, Prevotella* spp. and members of the Enterobacteriaceae that express ESBLs and AmpC-type beta-lactamases that confer resistance to currently available cephalosporins, cephamycins and beta-lactam/beta-lactamase inhibitor combinations, *Proteus mirabilis, Pseudomonas aeruginosa, Salmonella/Shigella, Serratia marcescens,* and *Stenotrophomonas maltophilia.*

In another embodiment, the gram negative organism is selected from the group consisting of *Acinetobacter baumannii, Acinetobacter* spp. *Enterobacter aerogenes, Enterobacter cloacae, Escherichia coli, Klebsiella oxytoca, Klebsiella pneurnoniae* (including ESBLs), and *Pseudomonas aeruginosa.*

In another embodiment, the gram negative organism is *Pseudomonas aeruginosa.*

Non-limiting examples of gram-negative infections include the types of conditions that arise from the above-listed gram-negative organisms including nosocomial pneumonia, urinary tract infections, systemic infections (bacteremia and sepsis), skin and soft tissue infections, surgical infections, intraabdominal infections, lung infections in patients with cystic fibrosis, patients suffering from lung infections, endocarditis, diabetic foot infections, osteomyelitis, and central nervous system infections.

In Vitro Assays $IC_{50}$ assay, LpxC enzyme from *P. aeruginosa*: $IC_{50}$ determination in the LpxC enzyme assay was carried out in a similar manner to that described by S. A. Hyland et al., *J. Bacteriology* 1997, 179, 2029-2037. [See also T. Kline et al., J. Medicinal Chemistry 2002, 45, 3112-3129.] Briefly, Pseudomonas aeruginosa LpxC enzyme (0.5 nM) purified from E. coli-overexpressing bacteria was incubated at 25° C. in a final volume of 25 ul containing 0.5 uM UDP-3-O—(R-3-hydroxydecanoyl)-N—[$^3$H-acetyl]glucosamine (B. D. Maxwell and J. C. Bronstein, J. Labeled Compounds and Radiopharmaceuticals 2005, 48, 1049-1054), 1 mg/ml BSA, and 50 mM sodium phosphate buffer, pH 8.0 in the presence and absence of inhibitor compound. At the end of 20 min, 90 ul of a pre-mixed 3% suspension of activated charcoal in 100 mM sodium acetate, pH 7.5, was added to stop the enzyme reaction. The contents of the well were transferred to a filter plate and filtered, and an aliquot of the filtrate was quantitated by liquid scintillation spectrometry. A no-enzyme control was subtracted in order to eliminate background counts.

MIC determinations: The in vitro antibacterial activity of compounds described in the Examples was evaluated by minimum inhibitory concentration (MIC) testing according to Clinical and Laboratory Standards Institute (CLSI, formerly NCCLS) guidelines. See: Clinical and Laboratory Standards Institute. Methods for Dilution Antimicrobial Susceptibility Tests for Bacteria that Grow Aerobically; Approved Standard-Seventh Edition. CLSI document M7-A7 [ISBN 1-56238-587-9]. Clinical and Laboratory Standards Institute, 940 West Valley Road, Suite 1400, Wayne, Pa. 19087-1898 USA, 2006; also Clinical and Laboratory Standards Institute. Performance Standards for Antimicrobial Susceptibility Testing; Eighteenth Informational Supplement. CLSI document M100-S18 [ISBN1-56238-653-0]. Clinical and Laboratory Standards Institute.

The following bacterial strains were used:

Pseudomonas aeruginosa PA0280: lacks efflux pumps MexAB-oprM, MexXY and MexZ

P. aeruginosa UI-18: Wild-type;

Acinetobacter baumanii/haemolyticus: Multidrug-resistant clinical isolate;

Enterobacter aerogenes: Quinolone-resistant isolate, expresses extended-spectrum beta-lactamases (ESBL), clinical isolate;

Escherichia coli EC-1: VOGEL;

Klebsiella pneumoniae: Ciprofloxacin-resistant isolate, expresses extended-spectrum beta-lactamases (ESBL), clinical isolate;

Staphylococcus aureus ATCC 29213: CLSI quality control reference strain; and

Serratia marcescens: Multidrug-resistant clinical isolate.

The results of the in vitro assays are shown in Table 3 in the Examples section of the application.

Administration of the compounds of the present invention (hereinafter the "active compound(s)") can be effected by any method that enables delivery of the compounds to the site of action. These methods include oral routes, intraduodenal routes, parenteral injection (including intravenous, subcutaneous, intramuscular, intravascular or infusion), topical, and rectal administration.

The amount of the active compound administered (e.g., the pharmaceutically effective amount) will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to about 7 g/day, preferably about 0.2 to about 2.5 g/day. In some instances, dosage levels below the lower limit of the aforesaid range may be more than adequate, while in other cases still larger doses may be employed without causing any harmful side effect, provided that such larger doses are first divided into several small doses for administration throughout the day.

The pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compounds in sterile aqueous solutions, for example, aqueous propylene glycol or dextrose solutions. Such dosage forms can be suitably buffered, if desired.

Suitable pharmaceutical carriers include inert diluents or fillers, water and various organic solvents. The pharmaceutical compositions may, if desired, contain additional ingredients such as flavorings, binders, excipients and the like. Thus for oral administration, tablets containing various excipients, such as citric acid may be employed together with various disintegrants such as starch, alginic acid and certain complex silicates and with binding agents such as sucrose, gelatin and acacia. Additionally, lubricating agents such as magnesium stearate, sodium lauryl sulfate and talc are often useful for tableting purposes. Solid compositions of a similar type may also be employed in soft and hard filled gelatin capsules. Preferred materials, therefore, include lactose or milk sugar and high molecular weight polyethylene glycols. When aqueous suspensions or elixirs are desired for oral administration the active compound therein may be combined with various sweetening or flavoring agents, coloring matters or dyes and, if desired, emulsifying agents or suspending agents, together with diluents such as water, ethanol, propylene glycol, glycerin, or combinations thereof.

Methods of preparing various pharmaceutical compositions with a specific amount of active compound are known, or will be apparent, to those skilled in this art. For examples, see Remington's Pharmaceutical Sciences, Mack Publishing Company, Easter, Pa., 15th Edition (1975).

The compounds of the invention may be administered in combination with one or more additional medicinal or pharmaceutical agents ("the additional active agent"). Such use of compounds of the invention in combination with an additional active agent may be for simultaneous, separate or sequential use.

In one embodiment, the additional active agent is an antibacterial agent.

In another embodiment, the additional agent is an antibacterial agent selected from the group consisting of an aminoglycoside, an ansamycin, a β-lactam, a β-lactam/β-lactamase inhibitor combination, a carbapenem, a dihydrofolate reductase inhibitor, a glycopeptide, a ketolide, a lipopeptide, a lincosamide, a macrolide, an oxazolidinone, a polymyxin, a quinolone or fluoroquinolone, a phenylpropanoid, a phosphonate, sulfonamide, a sulopenem and a tetracycline.

In another embodiment, the additional agent is an antibacterial agent, wherein said antibacterial agent is a β-lactam.

Non-limiting examples of aminoglycosides include streptomycin, gentamycin, kanamycin and amikacin.

A Non-limiting example of an ansamycins is rifamycin.

Non-limiting examples of β-lactams include penicillins (e.g., amoxicillin and ampicillin) and cephalosporins (e.g., cefipime, cefditoren pivoxil (Spectracef®), ceftazidime (Ceptaz®), cephalothin, cefaclor and cefixime)).

Non-limiting examples of β-lactamase inhibitors that can be used in combination with a β-lactam include sulbactam, clavulanic acid, tazobactam and piperacillin-tazobactam (Zosyn®).

Non-limiting examples of carbapenems include ertapenem (Invanz®), imipenem-cilastatin (Primaxin®) and meropenem (Merrem®).

A non-limiting example of a dihydrofolate reductase inhibitor is iclaprim.

Non-limiting examples of glycopeptides include vancomycin (Vancocin®), dalbavancin (Pfizer), oritavancin (Targenta Therapeutics), telavancin (Theravance), ramoplanin (Pfizer and Oscient), and teicoplanin (Targocid®).

A non-limiting example of a ketolide is telithromycin (Ketek®).

A non-limiting example of a lipopeptide is daptomycin (Cubicin®).

Non-limiting examples of lincosamides include clindamycin and lincomycin.

Non-limiting examples of macrolides include azithromycin, erythromycin, and clarithromycin.

Non-limiting examples of oxazolidinones include linezolid (Zyvox®); ranbezolid (RBX 7644); DA 7867; AZD-2563; the compounds disclosed in U.S. Pat. No. 7,141,588; and the compounds disclosed in U.S. Patent Application Publication Nos. 20040176610 and 20060030609.

Non-limiting examples of polymyxins include polymyxin B sulfate and colistin.

Non-limiting examples of quinolones and fluoroquinolones include norfloxacin, ciprofloxacin, levofloxacin (Levaquin®), gemifloxacin (Factive®), moxifloxacin (Avelox®), nalidixic acid and enoxacin.

A non-limiting example of a phenylpropanoid is chloramphenicol.

A non-limiting example of a phosphonate is fosfomycin.

A non-limiting example of a sulfonamide is sulfapyridine.

Non-limiting examples of sulopenems include ((5R,6S)-6-[(1R)-1-hydroxyethyl]-7-oxo-3-[(1R,3S)-tetrahydro-1-oxido-3-thienylthio]-4-thia-1-azabicyclo[3.2.0]hept-2-ene-2-carboxylic acid) and prodrug forms of sulopenem such as those disclosed in Pfizer's US Patent Application Publication No. 20080009474 and U.S. application Ser. No. 11/769,849.

Non-limiting examples of tetracyclines include chlortetracycline, and doxycycline, tigecycline (Tygacil®).

Other non-limiting examples of additional antibacterial agents can be found in Chemical Reviews 105(2): 391-394 (2005); and Bush et al., Current Opinion in Microbiology 7:466-476 (2004); the entire contents of each of the foregoing references being incorporated herein in their entirety.

In one embodiment, the one or more additional active agents, when used, are administered prior to administration of the compounds of the invention. In another embodiment, the one or more additional active agents, when used, are administered after administration of the compounds of the invention. In another embodiment, the one or more additional active agents, when used, are administered at about the same time as administration of the compounds of the invention.

The additional active agent may be administered by any route useful to administer said additional active agent.

In one embodiment, the one or more additional active agents are present in the pharmaceutical composition of the invention. Accordingly, in another embodiment, the invention relates to a method of treating a patient with a pharmaceutical composition of the invention further comprising one or more additional active agents.

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

All patents, applications, publications, test methods, literature, and other materials cited herein are hereby incorporated by reference in their entireties.

EXAMPLES

Experimental Procedures

Experiments were generally carried out under inert atmosphere (nitrogen or argon), particularly in cases where oxygen- or moisture-sensitive reagents or intermediates were employed. Commercial solvents and reagents were generally used without further purification. Nuclear magnetic resonance (NMR) data are reported in part per million (ppm, δ) referenced to the deuterium lock signal from the solvent used.

The stereochemistry of the penultimate intermediate (compound C13) in Example 6 below was determined by X-ray crystallographic analysis of a single crystal. The stereochemistry of all similar compounds described below was assigned by analogy to Example 6.

Example 1

Preparation of (2S,3S)-2-(biphenyl-4-ylmethoxy)-N, 3-dihydroxy-2-methylpentanamide (1)

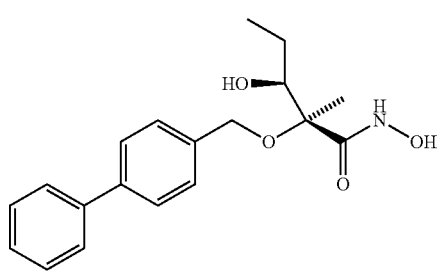

Compound 1 was prepared by the procedures depicted in Schemes 1 and 2 and described in detail below.

Step 1. Preparation of (4S)-5,5-dimethyl-4-phenyl-1,3-oxazolidin-2-one (C3)

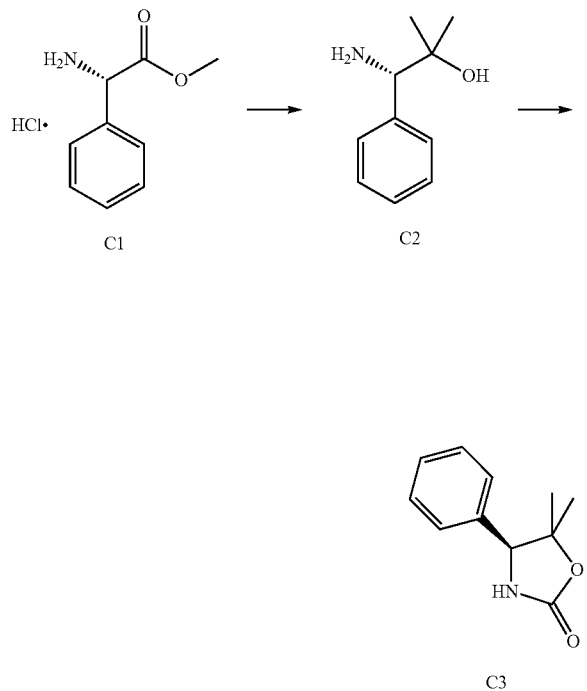

A. Preparation of (1S)-1-amino-2-methyl-1-phenylpropan-2-ol (C2). Methyl (2S)-amino(phenyl)acetate hydrochloride (C1) (20.0 g, 99.2 mmol) was added portion-wise to a solution of methylmagnesium bromide in toluene/tetrahydrofuran (1.4 M, 425 mL, 595 mmol) over a 15 minute period, and then stirred under nitrogen at 25° C. overnight. The solution was quenched with saturated aqueous ammonium chloride solution and the mixture was filtered through a pad of Celite. The layers were separated, and the aqueous layer was made basic by addition of aqueous ammonia and extracted with ethyl acetate (2×). The combined organic extracts were concentrated to provide C2 as a thick yellow oil. Yield: 14.3 g, 87%. MS (APCI) m/z 166.2 (M+1). $^1$H NMR (400 MHz, CDCl$_3$) δ 1.02 (3H, s), 1.18 (3H, s), 2.10-2.35 (3H, br s), 3.80 (1H, s), 7.20-7.34 (5H, m). The crude material was used in the next step without further purification.

B. A solution of C2 (38.8 g, 235 mmol) in dichloromethane (1000 mL) was treated with carbonyldiimidazole (45.6 g, 281 mmol) and heated at reflux for 2 hours. The reaction mixture was cooled to 25° C., quenched with 1 N hydrochloric acid (560 mL), and extracted with dichloromethane (3×). The combined organic extracts were dried over sodium sulfate and concentrated, and the resultant residue was purified by trituration with 4:1 hexanes:ethyl acetate, followed by chromatography on silica gel (gradient: 9:1 hexanes:ethyl acetate to 1:1 hexanes:ethyl acetate) to provide C3 as a white solid. Yield: 24.7 g, 55%. MS (APCI) m/z 192.2 (M+1). $^1$H NMR (400 MHz, CDCl$_3$) δ 0.91 (3H, s), 1.58 (3H, s), 4.62 (1H, s), 5.53-5.60 (1H, br s), 7.20-7.39 (5H, m).

Step 2. Preparation of (4S)-3-[(2S)-2-(biphenyl-4-ylmethoxy)propanoyl]-5,5-dimethyl-4-phenyl-1,3-oxazolidin-2-one (C7).

Compound C7 was prepared according to the procedure depicted below in Scheme 3.

Scheme 3

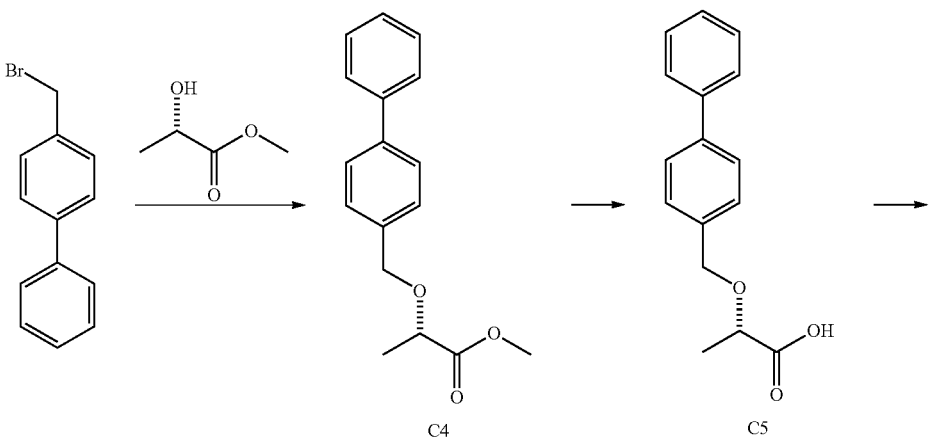

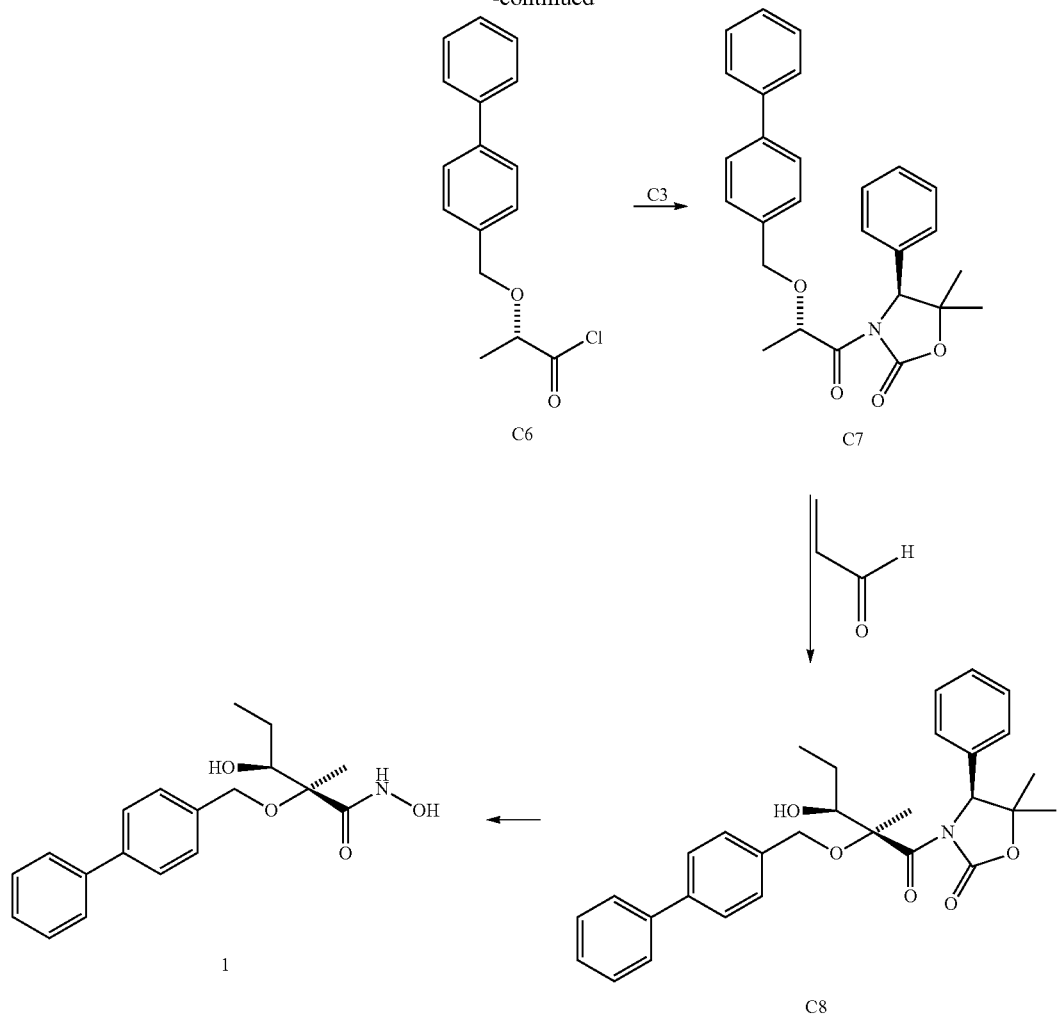

A. Preparation of methyl (2S)-2-(biphenyl-4-ylmethoxy) propanoate (C4). A mixture of 4-(bromomethyl)biphenyl (49.9 g, 202 mmol), and sodium hydride (60% dispersion in mineral oil, 8.45 g, 211 mmol) in dimethylformamide/tetrahydrofuran (400 mL/600 mL) was held at −20° C. and treated drop-wise with methyl (S)-2-hydroxypropanoate (20.0 g, 192 mmol). The mixture was stirred at −20° C. for 30 minutes, then 25° C. for 30 minutes, then 50° C. for 1 hour. The mixture was then carefully quenched with a mixture of water (1000 mL) and hexanes (500 mL). The organic layer was collected, and the aqueous layer was re-extracted with 1:1 hexanes:diethyl ether. The combined organic fractions were washed with water (2×) and saturated aqueous sodium chloride solution, and then dried over sodium sulfate. The crude material was then concentrated, and purified by chromatography on silica gel (gradient: 95:5 hexanes:ethyl acetate to 80:20 hexanes:ethyl acetate) to provide C4 as a clear oil. Yield: 44.4 g, 85%. $^1$H NMR (400 MHz, CDCl$_3$) δ 1.43 (3H, d, J=7.0 Hz), 3.74 (3H, s), 4.07 (1H, q, J=6.8 Hz), 4.46 (1H, d, J=11.5 Hz), 4.70 (1H, d, J=11.7 Hz), 7.32 (1H, t, J=7.3 Hz), 7.40 (4H, m), 7.55 (4H, m).

B. Preparation of (2S)-2-(biphenyl-4-ylmethoxy)propanoic acid (C5). A 1 M aqueous solution of lithium hydroxide (492 mL) was added to a solution of C4 (44.4 g, 164 mmol) in tetrahydrofuran (1000 mL), and the mixture was stirred vigorously at 25° C. for 18 hours. The crude mixture was concentrated to remove most of the tetrahydrofuran, and then diluted with water (1000 mL). The pH was adjusted to 2 with 3 M hydrochloric acid, and the product was extracted with ethyl acetate (3×). The combined organic extracts were washed with saturated aqueous sodium chloride solution, dried over sodium sulfate, and concentrated to provide C5 as a white solid. Yield: 42.0 g, 100%. MS (APCI) m/z 255.4 (M−1). $^1$H NMR (400 MHz, CDCl$_3$) δ 1.50 (3H, d, J=7.1 Hz), 4.13 (1H, q, J=6.8 Hz), 4.54 (1H, d, J=11.5 Hz), 4.74 (1H, d, J=11.7 Hz), 7.33 (1H, m), 7.42 (4H, m), 7.56 (4H, m), 10.60-10.90 (1H, br s).

C. Preparation of (2S)-2-(biphenyl-4-ylmethoxy)propanoyl chloride (C6). An anhydrous solution of C5 (20.00 g, 78.03 mmol) in thionyl chloride (110 mL) was heated to 65° for 1 hour. The reaction mixture was concentrated under reduced pressure. The resultant residue was dissolved in anhydrous dichloromethane and concentrated under reduced pressure. The concentration from dichloromethane was repeated twice to provide C6 as a yellow solid. The product was used in Step D below without purification, assuming quantitative conversion. $^1$H NMR (400 MHz, CDCl$_3$) δ 1.55 (3H, d, J=6.8 Hz), 4.28 (1H, q, J=7.0 Hz), 4.47 (1H, d, J=11.5 Hz), 4.76 (1H, d, J=11.3 Hz), 7.32 (1H, m), 7.43 (4H, m), 7.54 (4H, m).

D. A butyllithium solution (9.7 M in hexanes, 7.64 mL, 74 mmol) was added drop-wise to a solution of C3 (13.5 g, 70.6 mmol) in tetrahydrofuran (800 mL) at −78° C., and the mixture was stirred for 30 minutes at −78° C. A solution of C6 (21.3 g, 78 mmol) in tetrahydrofuran (50 mL) was then added slowly, and the reaction was stirred at −78° C. for 30 minutes and then at 25° C. for about 3 hours. The reaction mixture was then poured into phosphate buffer (pH 7) and extracted with ethyl acetate (2×). The organic extract was washed with aqueous sodium bicarbonate solution, saturated aqueous sodium chloride solution, dried over sodium sulfate and concentrated to a minimal volume. The resultant residue was then precipitated by addition of 1 liter of hexanes. The solid white product was collected by filtration, and the filtrate was concentrated. The resultant residue was purified by silica gel chromatography (gradient: 9:1 hexanes:ethyl acetate to 6:4 hexanes:ethyl acetate), to provide C7 as a white solid. Yield: 22.8 g, 75 LCMS m/z 430.3 (M+1). $^1$H NMR (400 MHz, DMSO-$d_6$) δ 0.85 (3H, s), 1.35 (3H, d, J=6.6 Hz), 1.57 (3H, s), 4.36 (2H, apparent s, actual AB quartet, J=12.3 Hz), 5.21 (1H, s), 5.21 (1H, q, J=6.6 Hz), 7.23 (2H, m), 7.36 (8H, m), 7.61 (4H, m).

Step 3. Preparation of (4S)-3-[(2S,3S)-2-(biphenyl-4-yl-methoxy)-3-hydroxy-2-methylpentanoyl]-5,5-dimethyl-4-phenyl-1,3-oxazolidin-2-one (C8). A solution of C7 (300 mg, 0.70 mmol) in tetrahydrofuran (3 mL) was slowly added to a solution of lithium diisopropylamide (LDA) in heptane/tetrahydrofuran/ethylbenzene (2 M, 0.38 mL, 0.76 mmol) at −78° C., and the resultant solution was stirred at −78° C. for 30 minutes. Chlorotitanium triisopropoxide (1 M, 2.8 mL) was then added slowly, and the resulting mixture was stirred at −40° C. for 1 hour. The reaction was cooled to −78° C., and propionaldehyde (49 mg, 0.84 mmol) was added slowly. This mixture was then warmed to −40° C., and stirred at −40° C. for 2 hours. The reaction mixture was quenched with saturated aqueous ammonium chloride solution (1 mL), diluted with 10 mL of tetrahydrofuran, and treated with Celite for 1 hour. The resultant slurry was filtered and concentrated. The resultant residue was purified by silica gel chromatography (gradient: 95:5 hexanes:ethyl acetate to 65:35 hexanes:ethyl acetate) to provide C8 as a white solid. Yield: 230 mg, 68%. MS (APCI) m/z 488.2 (M+1). $^1$H NMR (400 MHz, CDCl$_3$) δ 0.99-0.85 (6H, m), 1.53 (3H, s), 1.58-1.36 (2H, m), 1.70 (3H, s), 4.28 (1H, d, J=9.6 Hz), 4.49 (2H, s), 5.13 (1H, s), 7.16-7.14 (2H, m), 7.35-7.28 (4H, m), 7.42-7.37 (4H, m), 7.56-7.48 (4H, m).

Step 4. Preparation of compound 1. A solution of lithium methoxide in methanol (1 M, 6.15 mL) was added to hydroxylamine hydrochloride (214 mg). The mixture was sonicated for several seconds and stirred for 15 minutes. Compound C8 (150 mg, 0.308 mmol) was then added, and the reaction mixture was stirred at 25° C. for 5 hours. The mixture was treated with acetic acid (0.176 mL, 10 equivalents) and stirred for an additional 15 minutes. The resultant solution was then concentrated, and the resultant residue was purified by chromatography (gradient: 90:10 water:acetonitrile to 30:70 water:acetonitrile, C-18 silica cartridge) to provide 1 as a white solid. Yield: 50 mg, 49%. LCMS (APCI) m/z 328.2 (M−1). $^1$H NMR (400 MHz, DMSO-$d_6$) δ 0.88 (3H, t, J=7.2 Hz), 1.28 (1H, m), 1.31 (3H, s), 1.47 (1H, m), 3.53 (1H, dd, J=10.3, 1.8 Hz), 4.43 (1H, d, J=12.1 Hz), 4.55 (1H, d, J=11.7 Hz), 4.85 (1H, v br s), 7.32 (1H, m), 7.42 (4H, m), 7.60 (4H, m), 8.70 (1H, v br s), 10.3 (1H, v br s).

Example 2

Preparation of (2S,3S)-2-(biphenyl-4-ylmethoxy)-N, 3-dihydroxy-2-methylbutanamide (2a) and (2S,3R)-2-(biphenyl-4-ylmethoxy)-N,3-dihydroxy-2-methylbutanamide (2b)

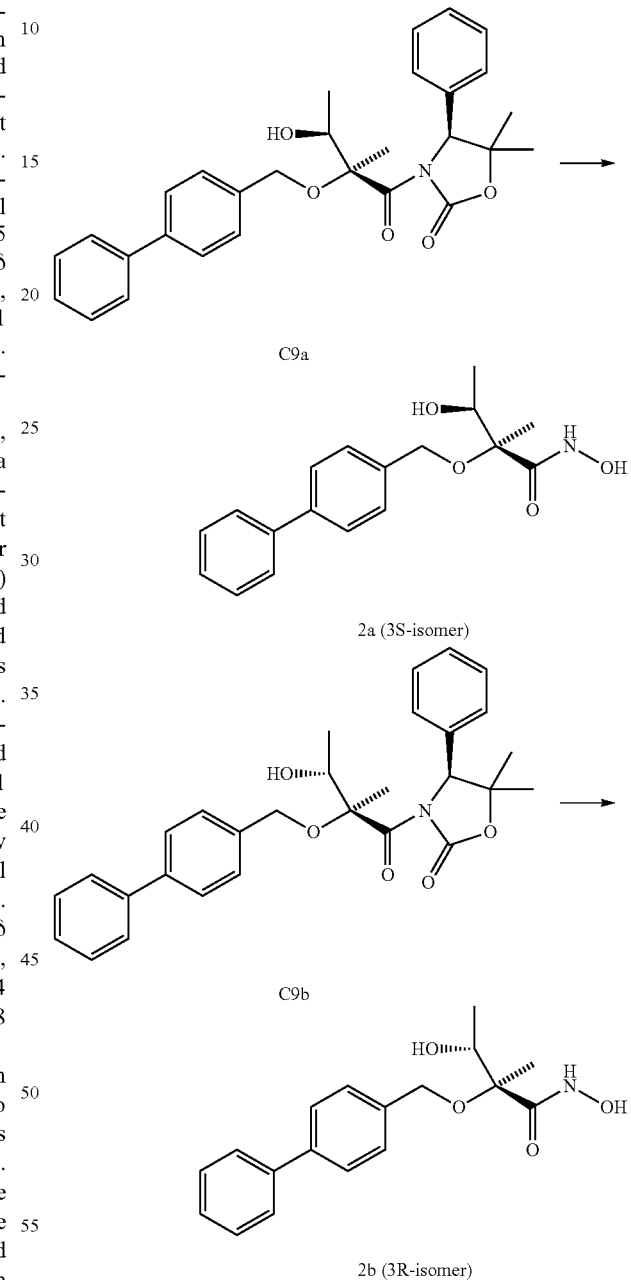

C9a 2a (3S-isomer)

C9b 2b (3R-isomer)

Step 1. Preparation of (4S)-3-[(2S,3S)-2-(biphenyl-4-yl-methoxy)-3-hydroxy-2-methylbutanoyl]-5,5-dimethyl-4-phenyl-1,3-oxazolidin-2-one (C9a) and (4S)-3-[(2S,3R)-2-(biphenyl-4-ylmethoxy)-3-hydroxy-2-methylbutanoyl]-5,5-dimethyl-4-phenyl-1,3-oxazolidin-2-one (C9b). Compounds C9a and C9b were synthesized according to the general procedure described in Example 1 for the preparation of C8 except that acetaldehyde was used instead of propionaldehyde. The resultant two diastereomers were separated by silica gel chromatography to provide C9a (3S isomer) and C9b (3R isomer) as white solids. Yield: 3S=80 mg, 14%, 3R=140 mg, 26%. MS (APCI) m/z 469.4 (M+1, derivatized with H₂NCH₂CH₂CH₂CH₂CH₂N(CH(CH₃)₂)₂).

Step 2. Compound 2a was synthesized according to the general procedure for the synthesis of 1 in Example 1 except that compound C9a was used instead of compound C8 to provide 2a as a white solid. Yield: 35 mg, 66%. LCMS (APCI) m/z 316.3 (M+1). ¹H NMR (400 MHz, DMSO-d₆) δ 1.07 (3H, d, J=6.4 Hz), 1.34 (3H, s), 3.89 (1H, dq, J=6.2, 6.0 Hz), 4.46 (1H, d, J=12.0 Hz), 4.59 (1H, d, J=12.0 Hz), 7.35 (1H, m), 7.46 (4H, m), 7.63 (4H, m), 8.72 (1H, s), 10.32 (1H, s).

Compound 2b was synthesized by a procedure similar to that described above for making 2a except that C9b was used instead of C9a. Yield: 22 mg, 24%. LCMS (APCI) m/z 316.3 (M+1). ¹H NMR (400 MHz, DMSO-d₆) δ 1.07 (3H, d, J=6.4 Hz), 1.34 (3H, s), 3.88 (1H, apparent quint, J=5.9 Hz), 4.47 (1H, d, J=12 Hz), 4.59 (1H, d, J=12 Hz), 4.82 (1H, d, J=5.5 Hz), 7.35 (1H, m), 7.46 (4H, m), 7.63 (4H, m), 8.72 (1H, s), 10.32 (1H, s).

Example 3

Preparation of (2S,3S)-2-(biphenyl-4-ylmethoxy)-N,3-dihydroxy-2,4-dimethylpentanamide (3)

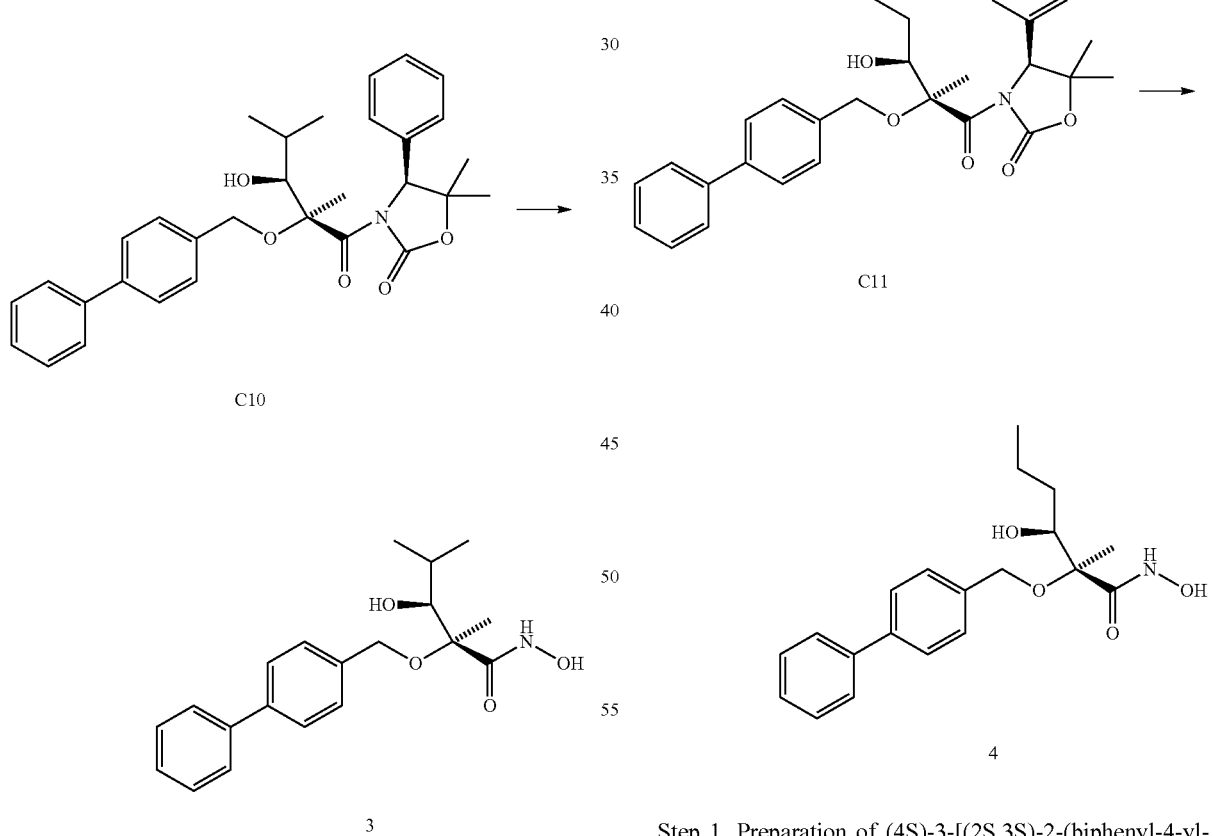

Step 1. Preparation of (4S)-3-[(2S,3S)-2-(biphenyl-4-ylmethoxy)-3-hydroxy-2,4-dimethylpentanoyl]-5,5-dimethyl-4-phenyl-1,3-oxazolidin-2-one (C10). Compound C10 was synthesized according to the general procedure for the synthesis of C8 in Example 1, except that 2-methyl-1-propionaldehyde was used instead of propionaldehyde to provide C10 as a white solid. Yield: 190 mg, 54%. MS (APCI) m/z 502.2 (M+1). ¹H NMR (400 MHz, CDCl₃) δ 0.88 (3H, d, J=6.8 Hz), 0.97 (6H, m), 1.53 (3H, s), 1.73 (1H, m), 1.80 (3H, s), 4.40 (3H, m), 5.17 (1H, s), 7.16 (2H, m), 7.35 (8H, m), 7.50 (4H, m).

Step 2. Compound 3 was synthesized according to the general procedure for the synthesis of 1 in Example 1 except that compound C10 was used instead of compound C8 to provide 3 as a white solid. Yield: 40 mg, 34%. LCMS (APCI) m/z 344.3 (M+1). ¹H NMR (400 MHz, CDCl₃) δ 0.89 (3H, d, J=6.6 Hz), 0.96 (3H, d, J=6.8 Hz), 1.51 (3H, s), 1.86 (1H, m), 3.56 (1H, d, J=4.1 Hz), 4.42 (1H, d, J=10.9 Hz), 4.58 (1H, d, J=10.7 Hz), 7.30 (3H, m), 7.39 (1H, t, J=7.5 Hz), 7.39 (1H, m), 7.56 (1H, m), 7.53 (4H, d, J=8.2 Hz), 9.35 (1H, br s).

Example 4

Preparation of Prophetic Compound (2S,3S)-2-(biphenyl-4-ylmethoxy)-N,3-dihydroxy-2-methylhexanamide (4)

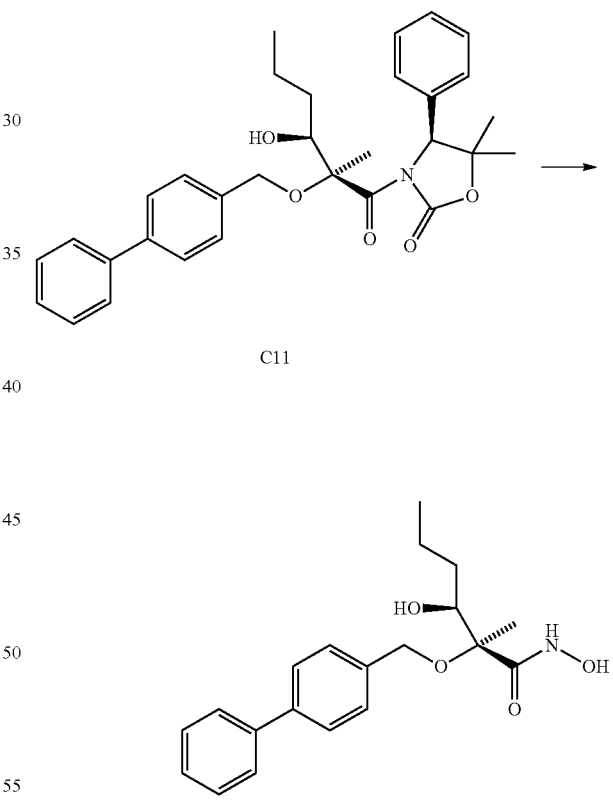

Step 1. Preparation of (4S)-3-[(2S,3S)-2-(biphenyl-4-ylmethoxy)-3-hydroxy-2-methylhexanoyl]-5,5-dimethyl-4-phenyl-1,3-oxazolidin-2-one (C11). Compound C11 was synthesized according to the general procedure for the synthesis of C8 in Example 1 except that butyraldehyde was used instead of propionaldehyde to provide C11 as a white solid. Yield: 80 mg, 14%. MS (APCI) m/z 497.3 (M+1, derivatized with H₂NCH₂CH₂CH₂CH₂CH₂N(CH(CH₃)₂)₂).

Step 2. Prophetic compound 4 can be synthesized according to the general procedure for the synthesis of 1 in Example 1 except that compound C11 would be used instead of compound C8.

Example 5

Preparation of (2S,3S)-2-(biphenyl-4-ylmethoxy)-N,3-dihydroxy-2-methylheptanamide (5)

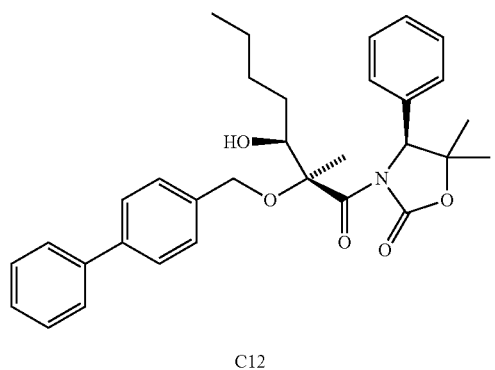

C12

Step 1. Preparation of (4S)-3-[(2S,3S)-2-(biphenyl-4-yl-methoxy)-3-hydroxy-2-methylheptanoyl]-5,5-dimethyl-4-phenyl-1,3-oxazolidin-2-one (C12). Compound C12 was synthesized according to the general procedure for the synthesis of C8 in Example 1 except that valeraldehyde was used instead of propionaldehyde to provide C12 as a white solid. Yield: 200 mg, 33%. MS (APCI) m/z 511.4 (M+1, derivatized with $H_2NCH_2CH_2CH_2CH_2CH_2N(CH(CH_3)_2)_2$).

Step 2. Compound 5 was synthesized according to the general procedure for the synthesis of 1 in Example 1 except that compound C12 was used instead of compound C8 to provide 5 as a white solid. Yield: 52 mg, 38%. LCMS (APCI) m/z 358.3 (M+1). $^1$H NMR (400 MHz, DMSO-$d_6$) δ 0.85 (3H, t, J=7.1 Hz), 1.23-1.45 (9H, m), 3.65 (1H, m), 4.46 (1H, d, J=12.0 Hz), 4.59 (1H, d, J=12.0 Hz), 4.81 (1H, d, J=6.4 Hz), 7.35 (1H, m), 7.46 (4H, m), 7.65 (4H, m), 8.70 (1H, s), 10.32 (1H, s).

Example 6

Preparation of (2S,3S)-2-(biphenyl-4-ylmethoxy)-N,3-dihydroxy-2,5-dimethylhexanamide (6)

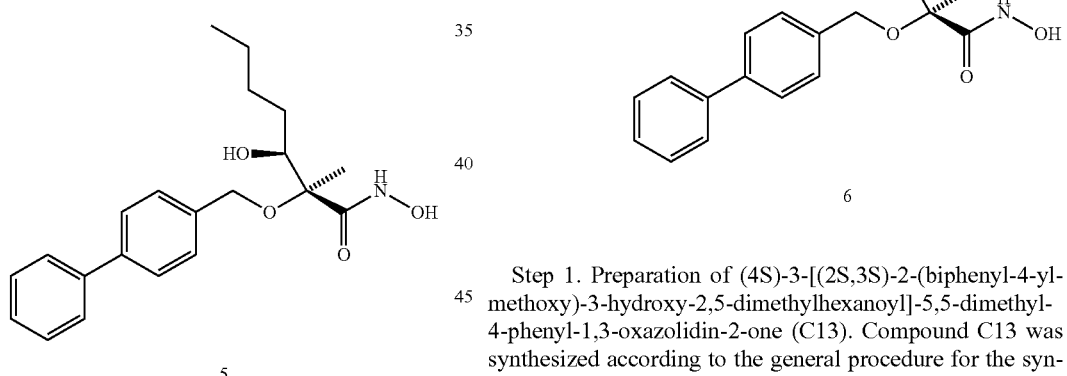

Step 1. Preparation of (4S)-3-[(2S,3S)-2-(biphenyl-4-yl-methoxy)-3-hydroxy-2,5-dimethylhexanoyl]-5,5-dimethyl-4-phenyl-1,3-oxazolidin-2-one (C13). Compound C13 was synthesized according to the general procedure for the synthesis of C8 in Example 1 except that 3-methylbutyraldehyde was used instead of propionaldehyde to provide C13 as a white solid. Yield: 150 mg, 25%. MS (APCI) m/z 511.4 (M+1, derivatized with $H_2NCH_2CH_2CH_2CH_2CH_2N(CH(CH_3)_2)_2$). A small amount of C13 was dissolved in ethyl acetate; hexane was allowed to diffuse in slowly, providing a crystal appropriate for structure determination. An X-ray crystal structure analysis confirmed the stereochemistry of C13 to be that indicated above.

Step 2. Compound 6 was synthesized according to the general procedure for the synthesis of 1 in Example 1 except that compound C13 was used instead of compound C8 to provide 6 as a white solid. Yield: 43 mg, 41%. LCMS (APCI) m/z 358.3 (M+1). $^1$H NMR (400 MHz, DMSO-$d_6$) δ 0.80 (3H, d, J=6.2 Hz), 0.86 (3H, d, J=6.6 Hz), 1.11 (1H, m), 1.32 (3H, s), 1.36 (1H, m), 1.73 (1H, m), 3.73 (1H, ddd, J=10.5, 6.4, 1.7 Hz), 4.45 (1H, d, J=12.1 Hz), 4.57 (1H, d, J=12.1 Hz), 4.75 (1H, d, J=6.2 Hz), 7.32 (1H, m), 7.42 (4H, m), 7.61 (4H, m), 8.68 (1H, s), 10.27 (1H, br s).

Example 7

Preparation of (2S,3S)-2-(biphenyl-4-ylmethoxy)-N, 3-dihydroxy-2-methyl-5,5,5-trifluoropentanamide (7)

Example 8

Preparation of (2S,3S)-2-(biphenyl-4-ylmethoxy)-5-ethoxy-N,3-dihydroxy-2-methylpentanamide (8)

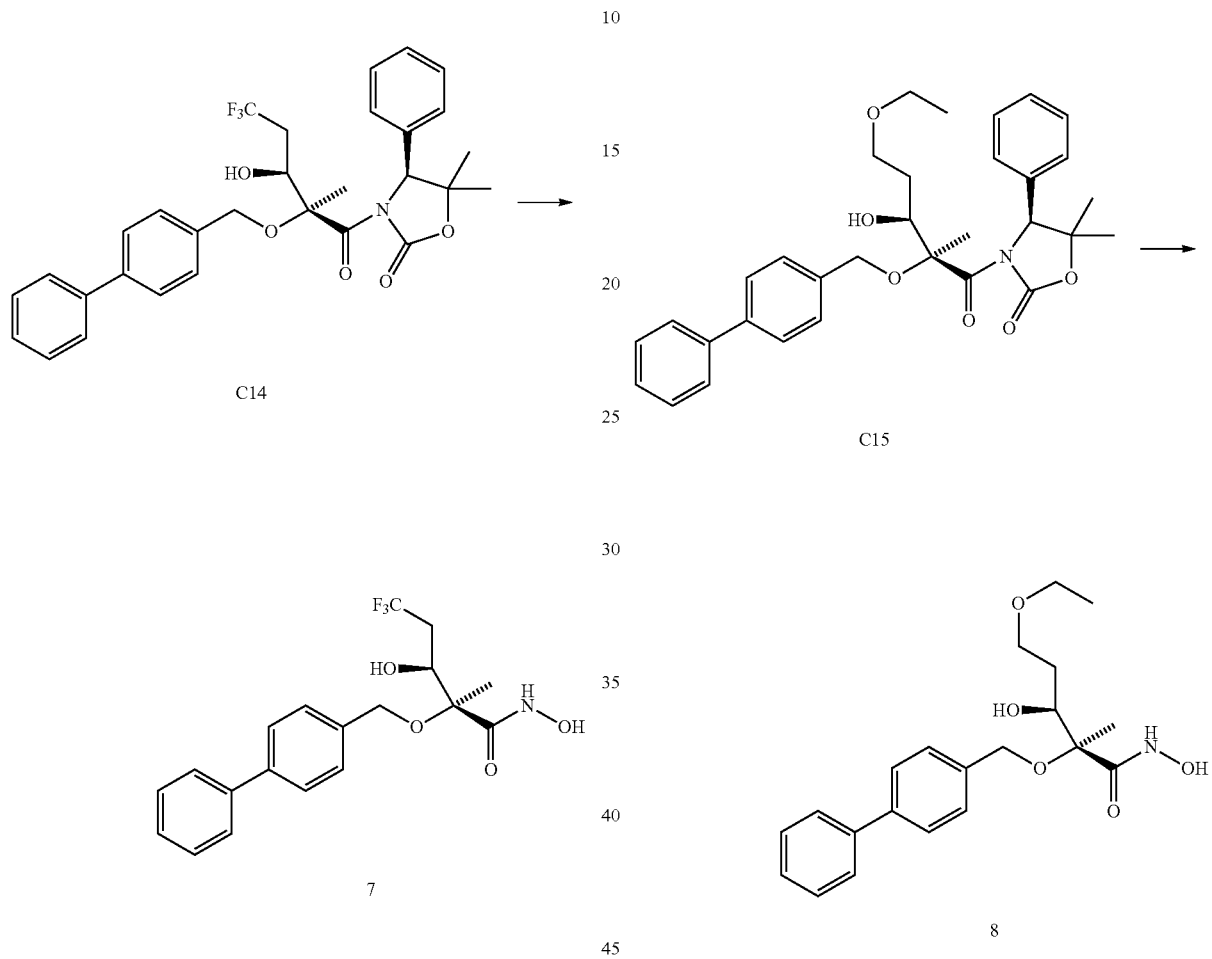

Step 1. Preparation of (4S)-3-[(2S,3S)-2-(biphenyl-4-ylmethoxy)-5,5,5-trifluoro-3-hydroxy-2-methylpentanoyl]-5,5-dimethyl-4-phenyl-1,3-oxazolidin-2-one (C14). Compound C14 was synthesized according to the general procedure for the synthesis of C8 in Example 1 except that 3,3,3-trifluoropropionaldehyde was used instead of propionaldehyde to provide C14 as a white solid. Yield: 300 mg, 48%. MS (APCI) m/z 537.4 (M+1, derivatized with $H_2NCH_2CH_2CH_2CH_2CH_2N(CH(CH_3)_2)_2$).

Step 2. Compound 7 was synthesized according to the general procedure for the synthesis of 1 in Example 1 except that compound C14 was used instead of compound C8 to provide 7 as a white solid. Yield: 90 mg, 42%. LCMS (APCI) m/z 382.1 (M−1). $^1$H NMR (400 MHz, DMSO-$d_6$) δ 1.39 (3H, s), 2.33 (2H, m), 4.09 (1H, m), 4.47 (1H, d, J=12.0 Hz), 4.60 (1H, d, J=11.9 Hz), 5.56 (1H, d, J=7.2 Hz), 7.35 (1H, m), 7.46 (4H, m), 7.64 (4H, m), 8.81 (1H, s), 10.59 (1H, br s).

Step 1. Preparation of (4S)-3-[(2S,3S)-2-(biphenyl-4-ylmethoxy)-5-ethoxy-3-hydroxy-2-methylpentanoyl]-5,5-dimethyl-4-phenyl-1,3-oxazolidin-2-one (C15). Compound C15 was synthesized according to the general procedure for the synthesis of C8 in Example 1 except that 3-ethoxypropionaldehyde was used instead of propionaldehyde to provide C15 as a white solid. Yield: 160 mg, 26%. MS (APCI) m/z 532.2 (M+1).

Step 2. Compound 8 was synthesized according to the general procedure for the synthesis of 1 in Example 1 except that compound C15 was used instead of compound C8 to provide 8 as a white solid. Yield: 32 mg, 29%. LCMS (APCI) m/z 374.3 (M+1). $^1$H NMR (400 MHz, DMSO-$d_6$) δ 1.08 (3H, t, J=6.9 Hz), 1.36 (3H, s), 1.56 (1H, m), 1.72 (1H, m), 3.38-3.45 (4H, m), 3.79 (1H, m), 4.47 (1H, d, J=12.0 Hz), 4.59 (1H, d, J=12.0 Hz), 4.88 (1H, d, J=6.2 Hz), 7.35 (1H, m), 7.46 (4H, m), 7.63 (4H, m), 8.72 (1H, s), 10.36 (1H, s).

Example 9

Preparation of (2S,3S)-2-(biphenyl-4-ylmethoxy)-N,3-dihydroxy-3-(1H-imidazol-4-yl)-2-methylpropanamide (9)

Example 10

Preparation of (2S,3S)-2-(biphenyl-4-ylmethoxy)-N,3-dihydroxy-2-methyl-3-(1-methyl-1H-imidazol-2-yl)propanamide (10)

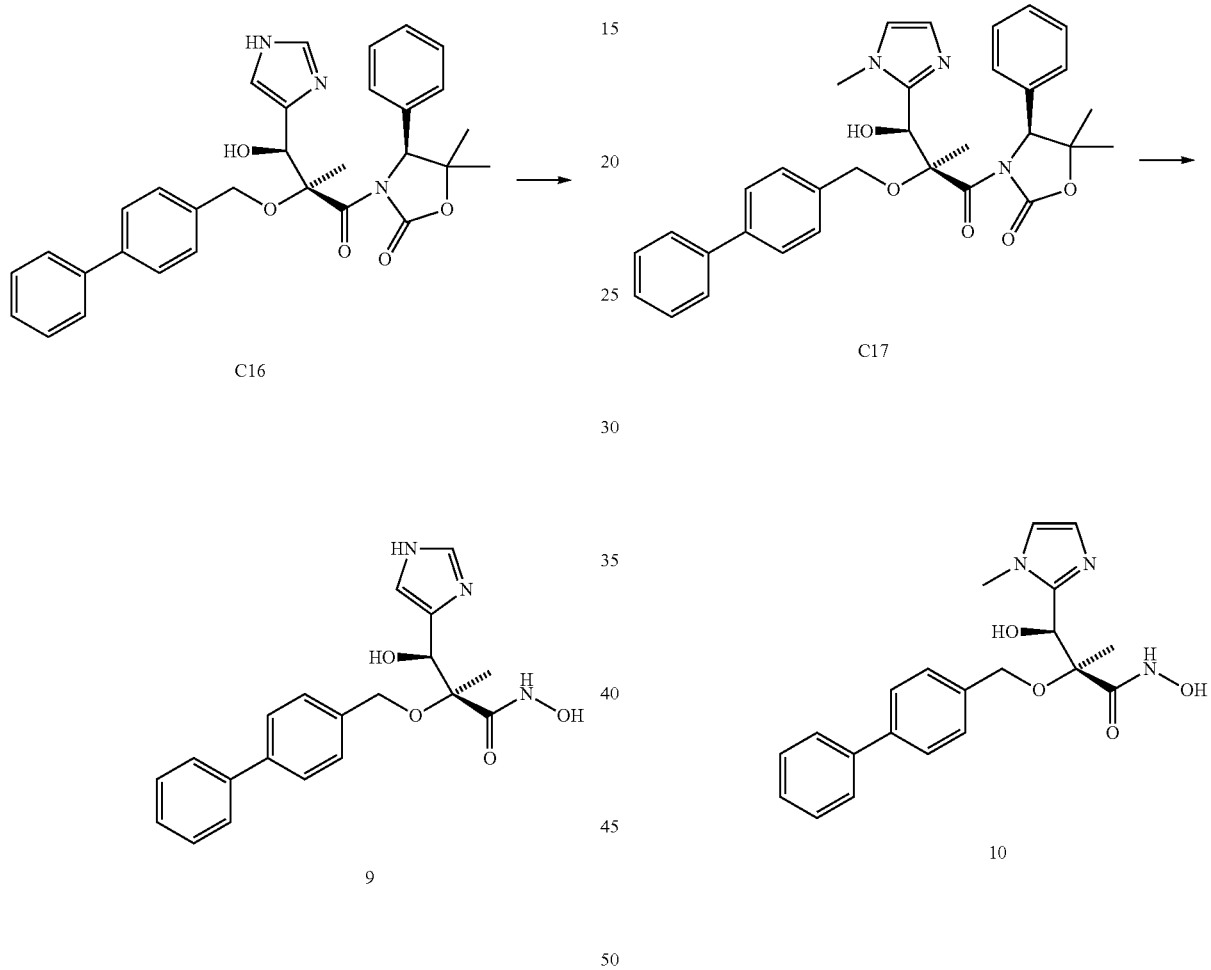

Step 1. Preparation of (4S)-3-[(2S,3S)-2-(biphenyl-4-ylmethoxy)-3-hydroxy-3-(1H-imidazol-4-yl)-2-methylpropanoyl]-5,5-dimethyl-4-phenyl-1,3-oxazolidin-2-one (C16). Compound C16 was synthesized according to the general procedure for the synthesis of C8 in Example 1 except that 1H-imidazole-4-carbaldehyde was used instead of propionaldehyde to provide C16 as a white solid. Yield: 160 mg, 26%. LCMS (APCI) m/z 526.2 (M+1).

Step 2. Compound 9 was synthesized according to the general procedure for the synthesis of 1 in Example 1 except that compound C16 was used instead of compound C8 to provide 9 as a white solid. Yield: 6 mg, 14%. LCMS (APCI) m/z 368.3 (M+1). $^1$H NMR (400 MHz, DMSO-$d_6$) δ 1.29 (3H, s), 4.52 (2H, br s), 4.90 (1H, m), 6.92 (1H, m), 7.32-7.62 (10H, m), 8.74 (1H, br s), 10.43 (1H, br s), 11.84 (1H, br s).

Step 1. Preparation of (4S)-3-[(2S,3S)-2-(biphenyl-4-ylmethoxy)-3-hydroxy-2-methyl-3-(1-methyl-1H-imidazol-2-yl)propanoyl]-5,5-dimethyl-4-phenyl-1,3-oxazolidin-2-one (C17). Compound C17 was synthesized according to the general procedure for the synthesis of C8 in Example 1 except that 1-methyl-1H-imidazole-2-carbaldehyde was used instead of propionaldehyde to provide C17 as a white solid. Yield: 190 mg, 30%. LCMS (APCI) m/z 540.3 (M+1).

Step 2. Compound 10 was synthesized according to the general procedure for the synthesis of 1 in Example 1 except that compound C17 was used instead of compound C8 to provide 10 as a white solid. Yield: 100 mg, 75%. LCMS (APCI) m/z 382.3 (M+1). $^1$H NMR (400 MHz, DMSO-$d_6$) δ 1.34 (3H, s), 3.52 (3H, s), 4.33 (2H, AB quartet, J=11.7 Hz), 4.99 (1H, d, J=4.9 Hz), 5.38 (1H, d, J=5.5 Hz), 6.78 (1H, s), 6.96 (1H, s), 7.29 (3H, m), 7.40 (2H, m), 7.54 (2H, d, J=7.8 Hz), 7.59 (2H, d, J=7.4 Hz), 8.82 (1H, br s), 10.68 (1H, br s).

Example 11

Preparation of (2S,3S)-2-(biphenyl-4-ylmethoxy)-N,3-dihydroxy-2-methyl-3-phenylpropanamide (11)

that compound C18 was used instead of compound C8 to provide 11 as a white solid. Yield: 59 mg, 36%. LCMS (APCI) m/z 378.3 (M+1).

Example 12

Preparation of (2S,3S)-2-(biphenyl-4-ylmethoxy)-N,3-dihydroxy-2-methyl-3-pyridin-3-ylpropanamide (12)

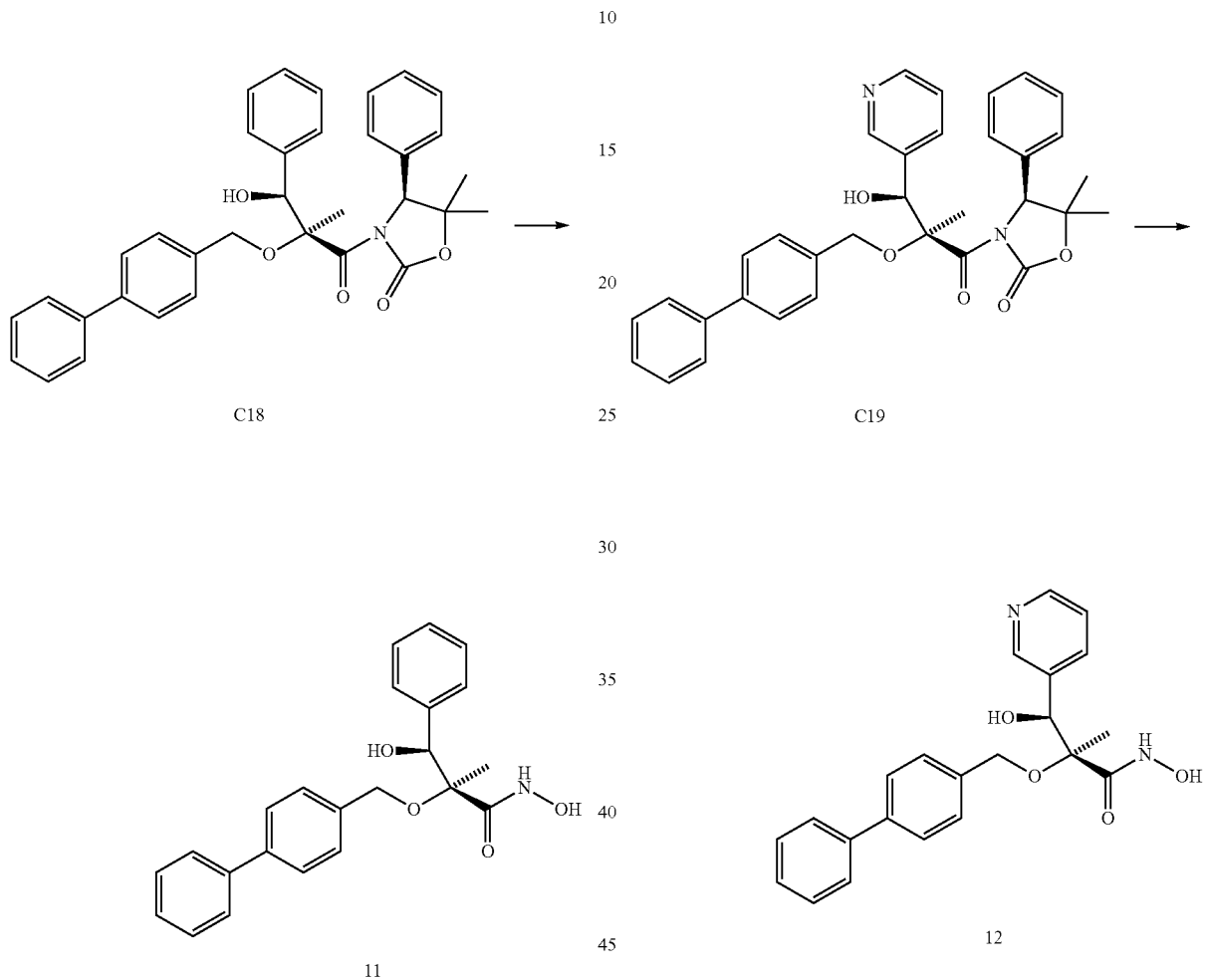

Step 1. Preparation of (4S)-3-[(2S,3S)-2-(biphenyl-4-ylmethoxy)-3-hydroxy-2-methyl-3-phenylpropanoyl]-5,5-dimethyl-4-phenyl-1,3-oxazolidin-2-one (C18). Compound C18 was synthesized according to the general procedure for the synthesis of C8 in Example 1 except that benzaldehyde was used instead of propionaldehyde to provide C18 as a white solid. Yield: 230 mg, 37%. MS (APCI) m/z 531.3 (M+1, derivatized with $H_2NCH_2CH_2CH_2CH_2CH_2N(CH(CH_3)_2)_2$).

Step 2. Compound 11 was synthesized according to the general procedure for the synthesis of 1 in Example 1 except Step 1. Preparation of (4S)-3-[(2S,3S)-2-(biphenyl-4-ylmethoxy)-3-hydroxy-2-methyl-3-pyridin-3-ylpropanoyl]-5,5-dimethyl-4-phenyl-1,3-oxazolidin-2-one (C19). Compound C19 was synthesized according to the general procedure for the synthesis of C8 in Example 1 except that nicotinaldehyde was used instead of propionaldehyde to provide C19 as a white solid. Yield: 290 mg, 46%. LCMS (APCI) m/z 537.3 (M+1).

Step 2. Compound 12 was synthesized according to the general procedure for the synthesis of 1 in Example 1 except that compound C19 was used instead of compound C8 to provide 12 as a white solid. Yield: 31 mg, 15%. LCMS (APCI) m/z 379.2 (M+1). $^1$H NMR (400 MHz, DMSO-$d_6$) δ 1.25 (3H, s), 4.48 (2H, AB quartet, J=12.0 Hz), 5.00 (1H, s), 5.80 (1H, br s), 7.29-7.47 (6H, m), 7.63 (4H, m), 7.72 (1H, apparent dt, J=7.8, 1.8 Hz), 8.41 (1H, dd, J=4.7, 1.8 Hz), 8.52 (1H, d, J=1.9 Hz), 8.81 (1H, br s), 10.55 (1H, br s).

Example 13

Preparation of (2S,3S)-2-(biphenyl-4-ylmethoxy)-3-(2-furyl)-N,3-dihydroxy-2-methylpropanamide (13)

that compound C20 was used instead of compound C8 to provide 13. Yield: 16 mg, 11%. LCMS (APCI) m/z 366.1 (M−1).

Example 14

Preparation of (2S,3S)-2-(biphenyl-4-ylmethoxy)-N,3-dihydroxy-3-[5-(hydroxymethyl)-2-furyl]-2-methylpropanamide (14)

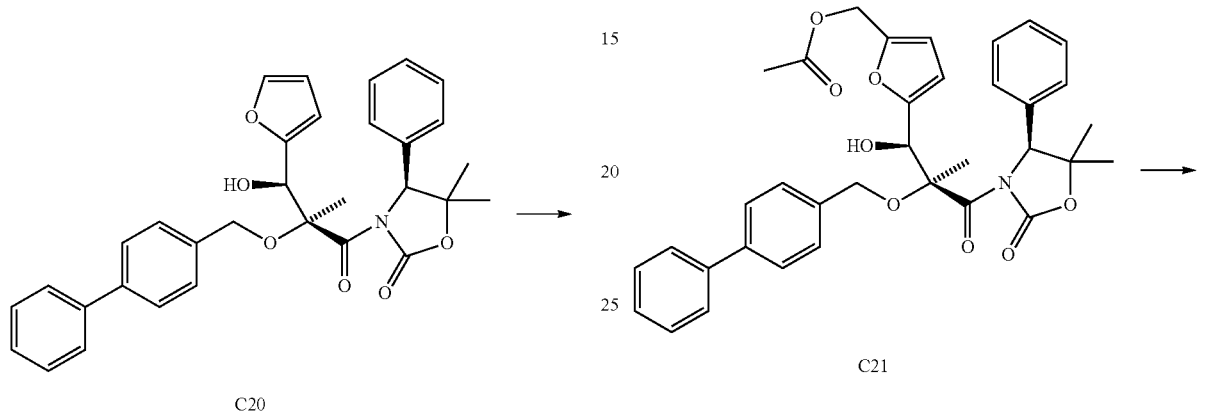

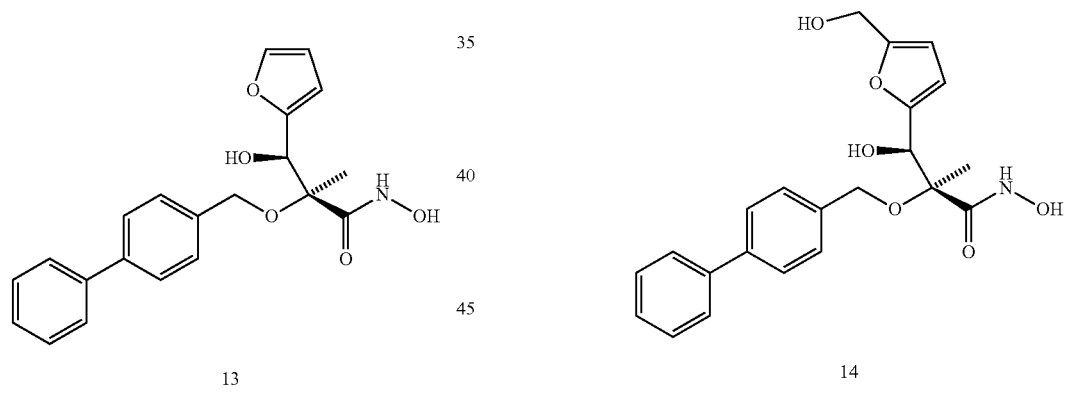

Step 1. Preparation of (4S)-3-[(2S,3S)-2-(biphenyl-4-ylmethoxy)-3-(2-furyl)-3-hydroxy-2-methylpropanoyl]-5,5-dimethyl-4-phenyl-1,3-oxazolidin-2-one (C20). Compound C20 was synthesized according to the general procedure for the synthesis of C8 in Example 1 except that furan-2-carbaldehyde was used instead of propionaldehyde to provide C20 as a white solid. Yield: 370 mg, 61%. MS (APCI) m/z 521.4 (M+1, derivatized with H$_2$NCH$_2$CH$_2$CH$_2$CH$_2$CH$_2$N(CH(CH$_3$)$_2$)$_2$).

Step 2. Compound 13 was synthesized according to the general procedure for the synthesis of 1 in Example 1 except Step 1. Preparation of (5-{(1S,2S)-2-(biphenyl-4-ylmethoxy)-3-[(4S)-5,5-dimethyl-2-oxo-4-phenyl-1,3-oxazolidin-3-yl]-1-hydroxy-2-methyl-3-oxopropyl}-2-furyl)methyl acetate (C21). Compound C21 was synthesized according to the general procedure for the synthesis of C8 in Example 1 except that (5-formyl-2-furyl)methyl acetate was used instead of propionaldehyde to provide C21 as a white solid. Yield: 470 mg, 68%. MS (APCI) m/z 593.5 (M+1, derivatized with H$_2$NCH$_2$CH$_2$CH$_2$CH$_2$CH$_2$N(CH(CH$_3$)$_2$)$_2$).

Step 2. Compound 14 was synthesized according to the general procedure for the synthesis of 1 in Example 1 except that compound C21 was used instead of compound C8 to provide 14 as a white solid. Yield: 52 mg, 17%. LCMS (APCI) m/z 396.2 (M−1). $^1$H NMR (400 MHz, DMSO-d$_6$) δ 1.36 (3H, s), 4.31 (2H, s), 4.47 (1H, d, J=12.0 Hz), 4.53 (1H, d, J=12.0 Hz), 4.90 (1H, s), 5.11 (1H, br s), 5.75 (1H, br s), 6.18 (1H, m), 6.21 (1H, m), 7.29-7.43 (5H, m), 7.54-7.63 (4H, m).

Example 15

Preparation of (2S,3S)-2-(biphenyl-4-ylmethoxy)-3-cyclopropyl-N,3-dihydroxy-2-methylpropanamide (15)

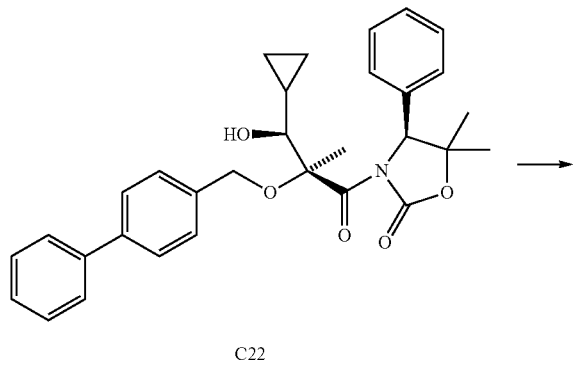

C22

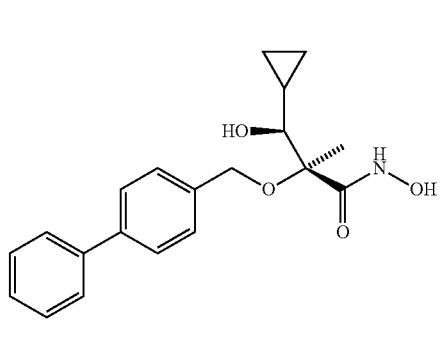

15

Step 1. Preparation of (4S)-3-[(2S,3S)-2-(biphenyl-4-ylmethoxy)-3-cyclopropyl-3-hydroxy-2-methylpropanoyl]-5,5-dimethyl-4-phenyl-1,3-oxazolidin-2-one (C22). Compound C22 was synthesized according to the general procedure for the synthesis of C8 in Example 1 except that cyclopropanecarbaldehyde was used instead of propionaldehyde to provide C22 as a white solid. Yield: 420 mg, 72%. MS (APCI) m/z 495.4 (M+1, derivatized with $H_2NCH_2CH_2CH_2CH_2CH_2N(CH(CH_3)_2)_2$).

Step 2. Compound 15 was synthesized according to the general procedure for the synthesis of 1 in Example 1 except that compound C22 was used instead of compound C8 to provide 15 as a white solid. Yield: 55 mg, 19%. LCMS (APCI) m/z 342.3 (M+1). $^1$H NMR (400 MHz, DMSO-$d_6$) δ 0.25 (2H, m), 0.36 (2H, m), 1.01 (1H, dt, J=7.1, 5.1 Hz), 1.41 (3H, s), 3.23 (1H, d, J=6.8 Hz), 4.48 (1H, d, J=12.0 Hz), 4.61

(1H, d, J=12.1 Hz), 4.84 (1H, br s), 7.35 (1H, m), 7.45 (4H, m), 7.64 (4H, m), 8.69 (1H, br s), 10.27 (1H, s).

Example 16

Preparation of (2S,3R)-2-(biphenyl-4-ylmethoxy)-N,3-dihydroxy-3-isoxazol-5-yl-2-methylpropanamide (16)

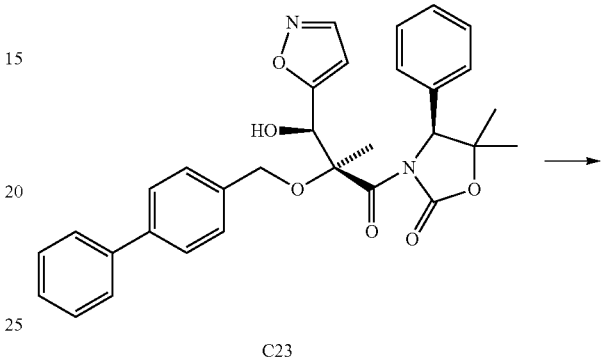

C23

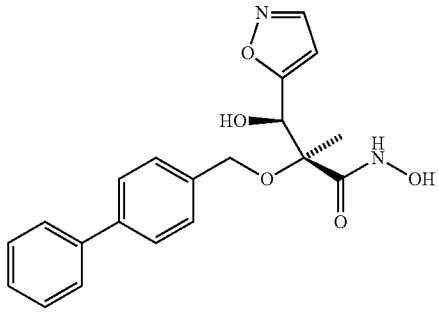

16

Step 1. Preparation of (4S)-3-[(2S,3R)-2-(biphenyl-4-ylmethoxy)-3-hydroxy-3-isoxazol-5-yl-2-methylpropanoyl]-5,5-dimethyl-4-phenyl-1,3-oxazolidin-2-one (C23). Compound C23 was synthesized according to the general procedure for the synthesis of C8 in Example 1 except that isoxazole-5-carbaldehyde was used instead of propionaldehyde to provide C23 as a white solid. Yield: 340 mg, 56%. LCMS (APCI) m/z 527.3 (M+1).

Step 2. A mixture of hydroxylamine hydrochloride (132 mg, 1.90 mmol) in anhydrous methanol (5 mL) was treated with a solution of methylmagnesium bromide (1.4 M, 2.70 mL, 3.8 mmol) and stirred and sonicated until complete dissolution occurred. The solution was then added to a solution of compound C23 (250 mg, 0.48 mmol) in anhydrous methanol (25 mL). The mixture was stirred at 25° C. for 2 hours and then quenched with sodium phosphate buffer (pH=7). The mixture was concentrated onto silica gel and purified by flash chromatography (gradient, ethyl acetate to 8:2 ethyl acetate:ethanol) to provide 16 as a white solid. Yield: 30 mg, 17%. LCMS (APCI) m/z 367.1 (M−1). $^1$H NMR (400 MHz, DMSO-$d_6$) δ 1.40 (3H, s), 4.51 (1H, d, J=12.0 Hz), 4.58 (1H, d, J=12.0 Hz), 5.18 (1H, s), 6.36 (1H, d, J=1.4 Hz), 7.33-7.38 (3H, m), 7.43-7.47 (2H, m), 7.58-7.66 (4H, m), 8.47 (1H, d, J=1.8 Hz), 8.85 (1H, br s).

Step 2. Compound 17 was synthesized according to the general procedure for the synthesis of 1 in Example 1 except that compound C24 was used instead of compound C8 to provide 17.

Example 17

Preparation of (2S,3S)-2-(biphenyl-4-ylmethoxy)-N,3-dihydroxy-2-methyl-3-pyridin-2-ylpropanamide (17)

Example 18

Preparation of prophetic compound (2S,3S)-2-(biphenyl-4-ylmethoxy)-N,3-dihydroxy-2-methyl-3-pyrimidin-5-ylpropanamide (18)

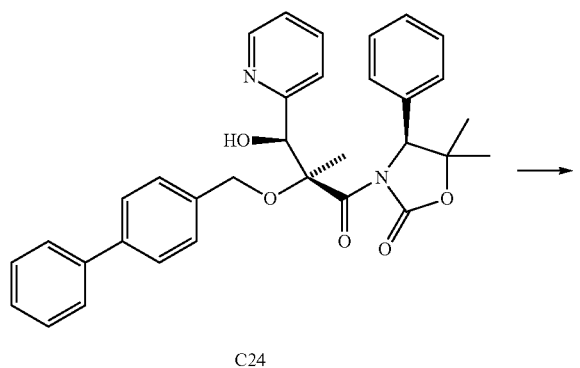

C24

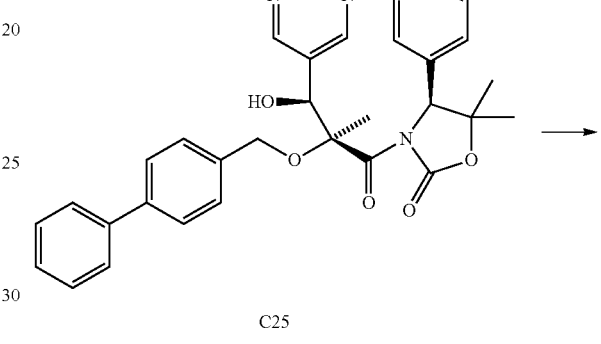

C25

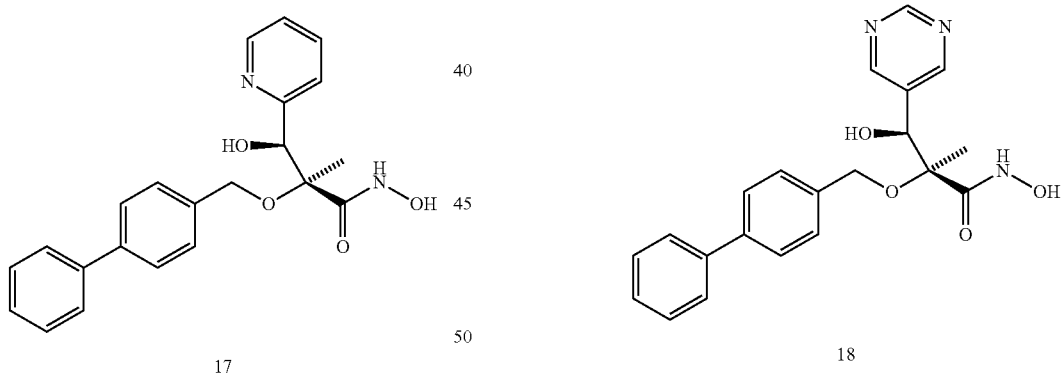

17

18

Step 1. Preparation of (4S)-3-[(2S,3S)-2-(biphenyl-4-ylmethoxy)-3-hydroxy-2-methyl-3-pyridin-2-ylpropanoyl]-5,5-dimethyl-4-phenyl-1,3-oxazolidin-2-one (C24). [NB 511557x31] Compound C24 was synthesized according to the general procedure for the synthesis of C8 in Example 1 except that picolinaldehyde was used instead of propionaldehyde to provide C24 as a white solid. Yield: 180 mg, 29%. MS (APCI) m/z 537.3 (M+1).

Step 1. Preparation of (4S)-3-[(2S,3S)-2-(biphenyl-4-ylmethoxy)-3-hydroxy-2-methyl-3-pyrimidin-5-ylpropanoyl]-5,5-dimethyl-4-phenyl-1,3-oxazolidin-2-one (C25). Compound C25 was synthesized according to the general procedure for the synthesis of C8 in Example 1 except that pyrimidine-5-carbaldehyde was used instead of propionaldehyde to provide C25 as a white solid. Yield: 250 mg, 40%. LCMS (APCI) m/z 538.3 (M+1).

Step 2. Prophetic compound 18 can be synthesized according to the general procedure for the synthesis of 1 in Example 1 except that compound C25 would be used instead of compound C8.

Example 19

Preparation of (2S,3S)-2-(biphenyl-4-ylmethoxy)-N,3-dihydroxy-2-methyl-3-(1-methyl-1H-1,2,3-triazol-5-yl)propanamide (19)

Example 20

Preparation of (2S,3R)-2-(biphenyl-4-ylmethoxy)-N,3-dihydroxy-2-methyl-3-(1,3-thiazol-2-yl)propanamide (20)

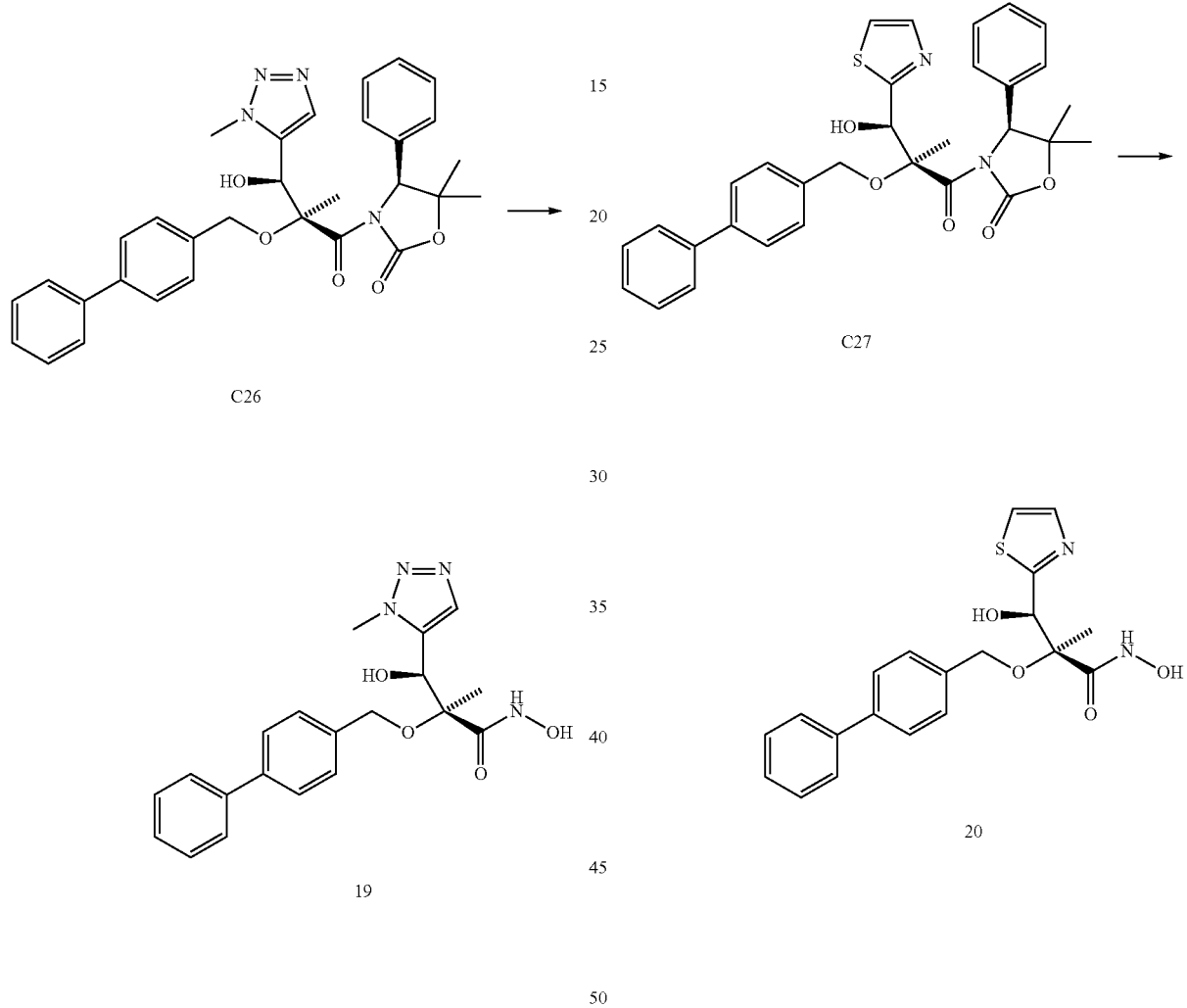

Step 1. Preparation of (4S)-3-[(2S,3S)-2-(biphenyl-4-ylmethoxy)-3-hydroxy-2-methyl-3-(1-methyl-1H-1,2,3-triazol-5-yl)propanoyl]-5,5-dimethyl-4-phenyl-1,3-oxazolidin-2-one (C26). Compound C26 was synthesized according to the general procedure for the synthesis of C8 in Example 1 except that 1-methyl-1H-1,2,3-triazole-5-carbaldehyde was used instead of propionaldehyde to provide C26 as a white solid. Yield: 290 mg, 46%. LCMS (APCI) m/z 541.3 (M+1).

Step 2. Compound 19 was synthesized according to the general procedure for the synthesis of 1 in Example 1 except that compound C26 was used instead of compound C8 to provide 19 as a white solid. Yield: 126 mg, 61%. LCMS (APCI) m/z 383.3 (M+1). $^1$H NMR (400 MHz, DMSO-$d_6$) δ 1.40 (3H, s), 3.90 (3H, s), 4.46 (1H, d, J=12.0 Hz), 4.53 (1H, d, J=12.0 Hz), 5.14 (1H, br s), 6.19 (1H, br s), 7.39 (5H, m), 7.62 (5H, m), 8.87 (1H, br s), 10.75 (1H, s).

Step 1. Preparation of (4S)-3-[(2S,3R)-2-(biphenyl-4-ylmethoxy)-3-hydroxy-2-methyl-3-(1,3-thiazol-2-yl)propanoyl]-5,5-dimethyl-4-phenyl-1,3-oxazolidin-2-one (C27). Compound C27 was synthesized according to the general procedure for the synthesis of C8 in Example 1 except that thiazole-2-carbaldehyde was used instead of propionaldehyde to provide C27 as a white solid. Yield: 190 mg, 30%. MS (APCI) m/z 543.2 (M+1).

Step 2. Compound 20 was synthesized according to the general procedure for the synthesis of 1 in Example 1 except that compound C27 was used instead of compound C8 to provide 20 as a white solid. Yield: 32 mg, 24%. LCMS (APCI) m/z 385.2 (M+1). $^1$H NMR (400 MHz, DMSO-$d_6$) δ 1.40 (3H, s), 4.59 (2H, AB quartet, J=11.9 Hz), 5.25 (1H, d, J=5.9 Hz), 6.49 (1H, d, J=5.5 Hz), 7.37 (5H, m), 7.55 (2H, d, J=8.2 Hz), 7.61 (3H, m), 7.71 (1H, d, J=3.1 Hz), 8.76 (1H, s), 10.35 (1H, s).

Example 21

Preparation of (2S,3R)-2-(biphenyl-4-ylmethoxy)-N,3-dihydroxy-2-methyl-3-(1,3-thiazol-5-yl)propanamide (21)

Example 22

Preparation of (2S,3S)-2-(biphenyl-4-ylmethoxy)-3-(3-furyl)-N,3-dihydroxy-2-methylpropanamide (22)

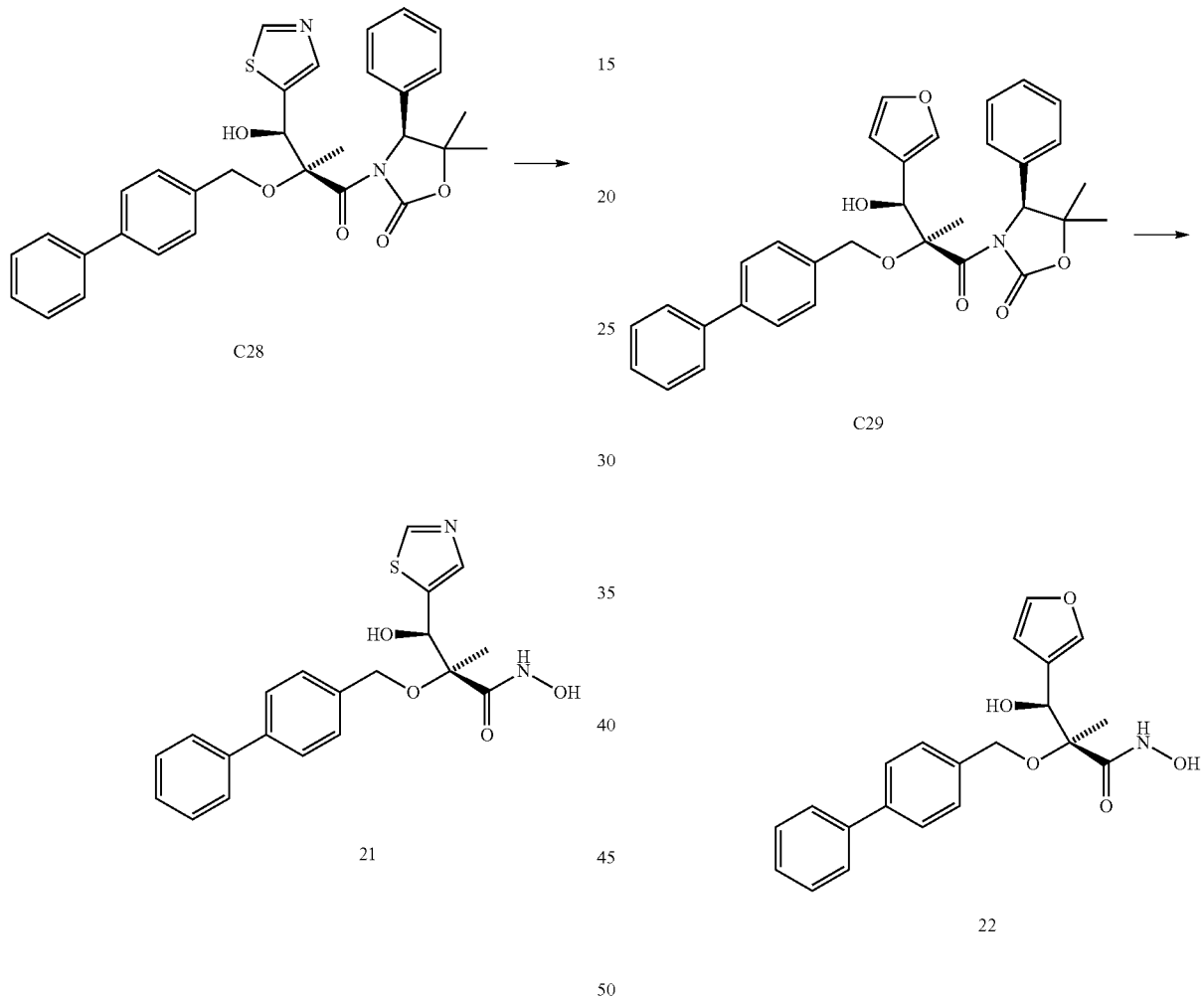

Step 1. Preparation of (4S)-3-[(2S,3R)-2-(biphenyl-4-ylmethoxy)-3-hydroxy-2-methyl-3-(1,3-thiazol-5-yl)propanoyl]-5,5-dimethyl-4-phenyl-1,3-oxazolidin-2-one (C28). Compound C28 was synthesized according to the general procedure for the synthesis of C8 in Example 1 except that 1,3-thiazole-5-carbaldehyde was used instead of propionaldehyde to provide C28 as a white solid. Yield: 300 mg, 48%. LCMS (APCI) m/z 543.3 (M+1).

Step 2. Compound 21 was synthesized according to the general procedure for the synthesis of 1 in Example 1 except that compound C28 was used instead of compound C8 to provide 21 as a white solid. Yield: 74 mg, 35%. LCMS (APCI) m/z 385.2 (M+1). $^1$H NMR (400 MHz, DMSO-$d_6$) δ

1.32 (3H, s), 4.48 (1H, d, J=12.0 Hz), 4.61 (1H, d, J=12.0 Hz), 5.26 (1H, s), 7.35 (1H, m), 7.46 (4H, m), 7.62 (6H, m), 8.95 (1H, s), 10.57 (1H, s).

Step 1. Preparation of (4S)-3-[(2S,3S)-2-(biphenyl-4-ylmethoxy)-3-(3-furyl)-3-hydroxy-2-methylpropanoyl]-5,5-dimethyl-4-phenyl-1,3-oxazolidin-2-one (C29). Compound C29 was synthesized according to the general procedure for the synthesis of C8 in Example 1 except that furan-3-carbaldehyde was used instead of propionaldehyde to provide C29 as a white solid. Yield: 160 mg, 26%. MS (APCI) m/z 526.3 (M+1).

Step 2. Compound 22 was synthesized according to the general procedure for the synthesis of 1 in Example 1 except that compound C29 was used instead of compound C8 to provide 22 as a white solid. Yield: 20 mg, 18%. LCMS (APCI) m/z 366.1 (M−1).

Example 23

Preparation of (2S,3S)-2-(biphenyl-4-ylmethoxy)-N,3-dihydroxy-2-methyl-3-(5-methylisoxazol-3-yl)propanamide (23)

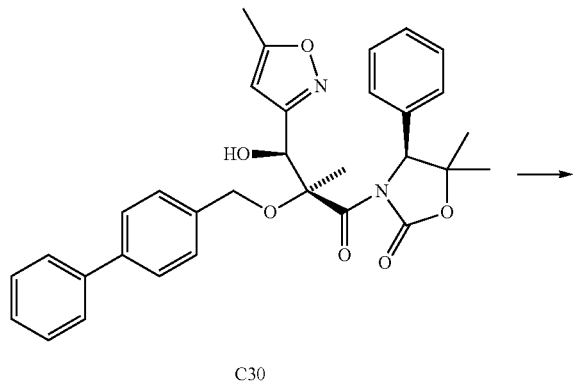

C30

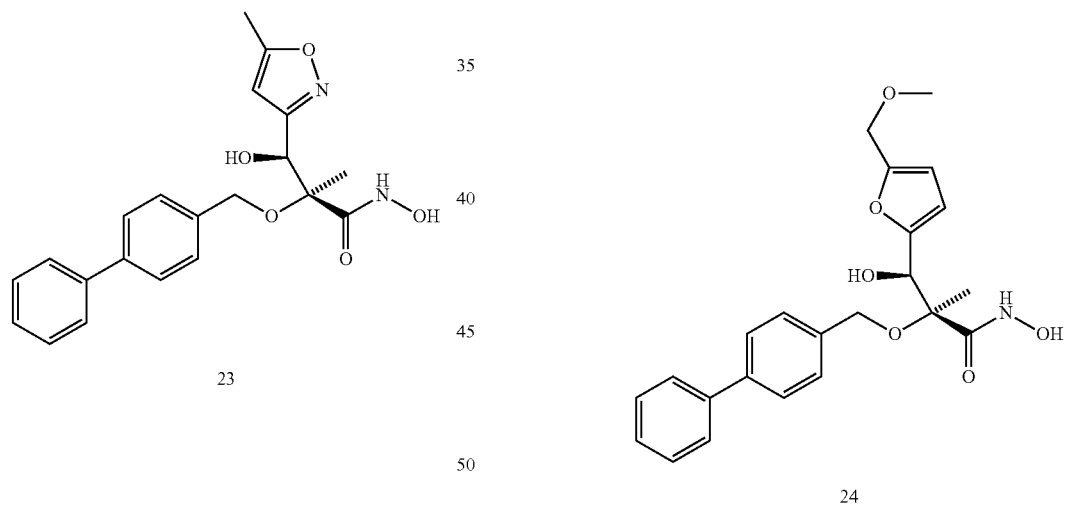

23 that compound C30 was used instead of compound C8 to provide 23 as a white solid. Yield: 63 mg, 38%. MS (APCI) m/z 383.2 (M+1).

Example 24

Preparation of (2S,3S)-2-(biphenyl-4-ylmethoxy)-N,3-dihydroxy-3-[5-(methoxymethyl)-2-furyl]-2-methylpropanamide (24)

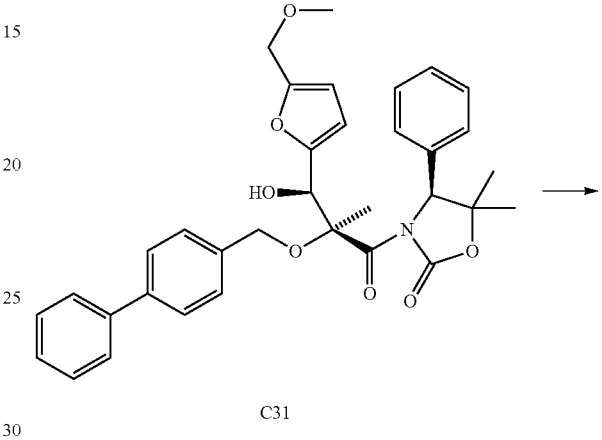

C31

24

Step 1. Preparation of (4S)-3-[(2S,3S)-2-(biphenyl-4-ylmethoxy)-3-hydroxy-2-methyl-3-(5-methylisoxazol-3-yl)propanoyl]-5,5-dimethyl-4-phenyl-1,3-oxazolidin-2-one (C30). Compound C30 was synthesized according to the general procedure for the synthesis of C8 in Example 1 except that 5-methylisoxazole-3-carbaldehyde was used instead of propionaldehyde to provide C30 as a white solid. Yield: 650 mg, 34%. MS (APCI) m/z 541.3 (M+1).

Step 2. Compound 23 was synthesized according to the general procedure for the synthesis of 1 in Example 1 except Step 1. Preparation of (4S)-3-{(2S,3S)-2-(biphenyl-4-ylmethoxy)-3-hydroxy-3-[5-(methoxymethyl)-2-furyl]-2-methylpropanoyl}-5,5-dimethyl-4-phenyl-1,3-oxazolidin-2-one (C31). Compound C31 was synthesized according to the general procedure for the synthesis of C8 in Example 1 except that 5-(methoxymethyl)furan-2-carbaldehyde was used instead of propionaldehyde to provide C31 as a white solid. Yield: 340 mg, 51%. MS (APCI) m/z 570.4 (M+1).

Step 2. Compound 24 was synthesized according to the general procedure for the synthesis of 1 in Example 1 except that compound C31 was used instead of compound C8 to provide 24 as a white solid. Yield: 50 mg, 20%. MS (APCI) m/z 412.2 (M+1).

Example 25

Preparation of (2S,3S)-2-(biphenyl-4-ylmethoxy)-N,3-dihydroxy-3-imidazo[1,2-a]pyridin-2-yl-2-methylpropanamide (25)

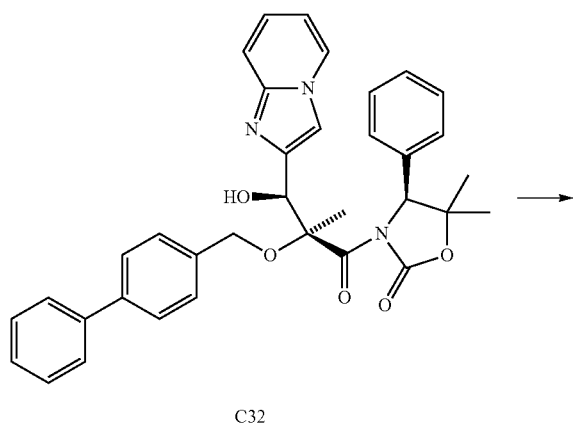

Step 1. Preparation of (4S)-3-[(2S,3S)-2-(biphenyl-4-ylmethoxy)-3-hydroxy-3-imidazo[1,2-a]pyridin-2-yl-2-methylpropanoyl]-5,5-dimethyl-4-phenyl-1,3-oxazolidin-2-one (C32). Compound C32 was synthesized according to the general procedure for the synthesis of C8 in Example 1 except that imidazo[1,2-a]pyridine-2-carbaldehyde was used instead of propionaldehyde to provide C32 as a white solid. Yield: 300 mg, 45%. LCMS (APCI) m/z 576.2 (M+1). $^1$H NMR (400 MHz, DMSO-$d_6$) δ 0.86 (3H, s), 1.64 (6H, m), 4.39 (1H, d, J=12.1 Hz), 4.53 (1H, d, J=12.3 Hz), 5.29 (1H, s), 5.58 (1H, d, J=7.4 Hz), 6.07 (1H, d, J=7.0 Hz), 6.83 (1H, td, J=6.8, 1.2 Hz), 7.18 (3H, m), 7.35 (6H, m), 7.43 (2H, t, J=7.6 Hz), 7.43 (1H, m), 7.55 (2H, d, J=8.4 Hz), 7.62 (2H, dd, J=8.4, 1.2 Hz), 7.79 (1H, s), 8.52 (1H, dt, J=6.8, 1.2 Hz).

Step 2. Compound 25 was synthesized according to the general procedure for the synthesis of 16 in Example 16 except that compound C32 was used instead of compound C23, and the methanol solution containing C32 was cooled to −40° C. to provide 25 as a white solid. Yield: 100 mg, 46%. LCMS (APCI) m/z 418.3 (M+1).

Example 26

Preparation of (2S,3S)-N,3-dihydroxy-3-imidazo[1,2-a]pyridin-2-yl-2-methyl-2-[(4'-propylbiphenyl-4-yl)methoxy]propanamide (26)

Step 1. Preparation of 4-(bromomethyl)-4'-propylbiphenyl (C34). Compound C34 was prepared according to the procedure depicted in Scheme 4 and described in detail below.

Scheme 4

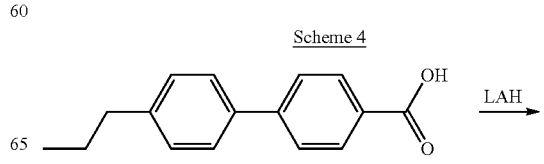

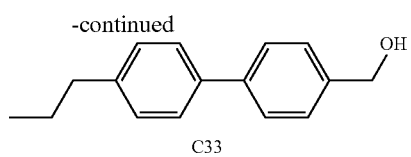

C33

↓ CBr₄ P(Ph)₃

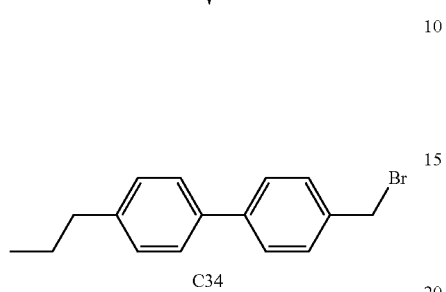

C34

A. Preparation of (4'-propylbiphenyl-4-yl)methanol (C33). A solution of lithium aluminum hydride (LAH) in tetrahydrofuran (1 M, 125 mL) was treated drop-wise with a solution of 4'-propylbiphenyl-4-carboxylic acid (20 g, 83.2 mmol) in tetrahydrofuran (100 mL) and stirred at 25° C. for about 18 hours. The reaction mixture was then diluted with diethyl ether (40 mL) and quenched in this order with 5 mL water, 5 mL of 10% sodium hydroxide, and 10 mL water. The mixture was stirred vigorously for 30 minutes and filtered through a sintered glass funnel. The aluminum salts were extracted with diethyl ether (5×), and the combined organic phases were dried over sodium sulfate and concentrated to provide C33 as a white solid. Yield: 17.7 g, 94%. ¹H NMR (400 MHz, CDCl₃) δ 0.91 (3H, t, J=7.4 Hz), 1.62 (2H, apparent dq, J=15.0, 7.4 Hz), 2.56 (2H, t, J=7.8 Hz), 4.66 (2H, s), 7.18 (2H, d, J=8.4 Hz), 7.35 (2H, d, J=8.4 Hz), 7.44 (2H, d, J=8.4 Hz), 7.51 (2H, d, J=8.2 Hz).

B. Preparation of 4-(bromomethyl)-4'-propylbiphenyl (C34). A solution of C33 (22.2 g, 98 mmol) in diethyl ether (400 mL) was treated with a solution of carbon tetrabromide (39.0 g, 118 mmol) in diethyl ether (100 mL). The solution was then slowly treated with solid triphenylphosphine (30.8 g, 118 mmol) and stirred for 2 hours. The precipitate was allowed to settle, the solution was filtered through a sintered glass filter, and the precipitate was washed repeatedly with diethyl ether. The combined filtrates were concentrated, and the resultant residue was purified by silica gel chromatography (gradient: hexanes to 80:20 hexanes:ethyl acetate) to provide C34 as an off-white solid. Yield: 23.2 g, 82%. ¹H NMR (400 MHz, CDCl₃) δ 0.96 (3H, t, J=7.3 Hz), 1.67 (2H, apparent dq, J=15.0, 7.4 Hz), 2.63 (2H, t, J=7.9 Hz), 4.53 (2H, s), 7.24 (2H, d, J=7.8 Hz), 7.43 (2H, m), 7.49 (2H, d, J=8.4 Hz), 7.54 (2H, d, J=8.4 Hz).

Step 2. Preparation of (4S)-3-{(2S,3S)-3-hydroxy-3-imidazo[1,2-a]pyridin-2-yl-2-methyl-2-[(4'-propylbiphenyl-4-yl)methoxy]propanoyl}-5,5-dimethyl-4-phenyl-1,3-oxazolidin-2-one (C35). Compound C35 was synthesized according to the general procedure for the synthesis of C8 in Example 1 except that imidazo[1,2-a]pyridine-2-carbaldehyde was used instead of propionaldehyde and C34 was used instead of 4-(bromomethyl)biphenyl to provide C35 as a white solid. Yield: 230 mg, 35%.

Step 3. Compound 26 was synthesized according to the general procedure for the synthesis of 16 in Example 16 except that compound C35 was used instead of compound C23 to provide 26 as a white solid. Yield: 2.4 mg, 1.4%. MS (APCI) m/z 460.4 (M+1).

Example 27

Preparation of (2S,3S)-2-(biphenyl-4-ylmethoxy)-3-(2,5-dimethyl-1,3-oxazol-4-yl)-N,3-dihydroxy-2-methylpropanamide (27)

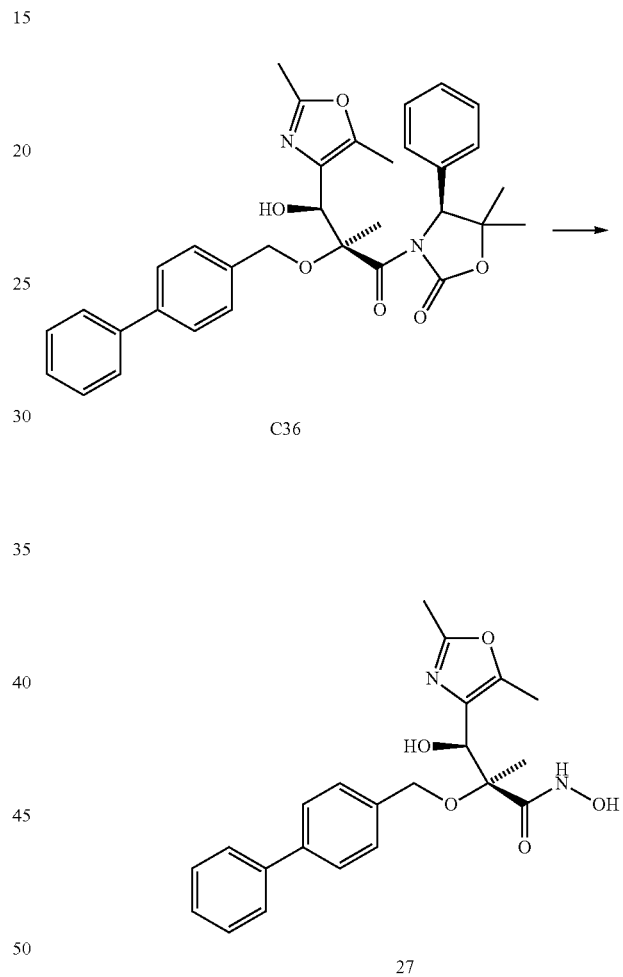

Step 1. Preparation of (4S)-3-[(2S,3S)-2-(biphenyl-4-ylmethoxy)-3-(2,5-dimethyl-1,3-oxazol-4-yl)-3-hydroxy-2-methylpropanoyl]-5,5-dimethyl-4-phenyl-1,3-oxazolidin-2-one (C36). Compound C36 was synthesized according to the general procedure for the synthesis of C8 in Example 1 except that 2,5-dimethyloxazole-4-carbaldehyde was used instead of propionaldehyde to provide C36 as a white solid. Yield: 400 mg, 62%. MS (APCI) m/z 555.5 (M+1).

Step 2. Compound 27 was synthesized according to the general procedure for the synthesis of 16 in Example 16 except that compound C36 was used instead of compound C23 to provide 27 as a white solid. Yield: 20 mg, 7%. LCMS (APCI) m/z 397.3 (M+1). ¹H NMR (400 MHz, DMSO-d₆) δ 1.34 (3H, s), 2.16 (3H, s), 2.28 (3H, s), 4.37 (1H, d, J=11.7

Hz), 4.48 (1H, d, J=11.7 Hz), 4.79 (1H, s), 5.26 (1H, brs), 7.37 (5H, m), 7.56 (2H, d, J=8.2 Hz), 7.61 (2H, m), 8.74 (1H, br s), 10.43 (1H, br s).

Example 28

Preparation of (2S,3S)-2-(biphenyl-4-ylmethoxy)-N,3-dihydroxy-2-methyl-3-(5-phenylisoxazol-3-yl)propanamide (28)

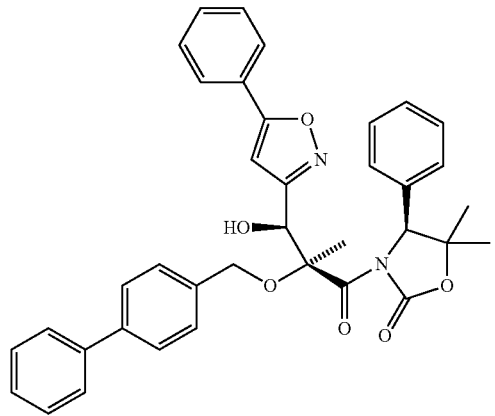

C37

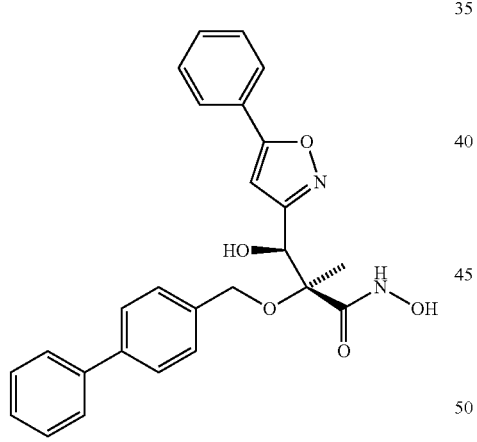

28

Step 1. Preparation of (4S)-3-[(2S,3S)-2-(biphenyl-4-ylmethoxy)-3-hydroxy-2-methyl-3-(5-phenylisoxazol-3-yl)propanoyl]-5,5-dimethyl-4-phenyl-1,3-oxazolidin-2-one (C37). Compound C37 was synthesized according to the general procedure for the synthesis of C8 in Example 1 except that 5-phenylisoxazole-3-carbaldehyde was used instead of propionaldehyde to provide C37 as a white solid. Yield: 520 mg, 74%. MS (APCI) m/z 603.5 (M+1).

Step 2. Compound 28 was synthesized according to the general procedure for the synthesis of 16 in Example 16 except that compound C37 was used instead of compound C23 to provide 28 as a white solid. Yield: 120 mg, 31%. LCMS (APCI) m/z 445.3 (M+1). $^1$H NMR (400 MHz, DMSO-$d_6$) δ 1.46 (3H, s), 4.60 (2H, AB quartet, J=12.0 Hz), 5.10 (1H, s), 6.14 (1H, br s), 6.86 (1H, s), 7.35 (1H, apparent dt, J=7.4, 1.6 Hz), 7.47 (7H, m), 7.61 (4H, m), 7.80 (2H, dd, J=7.9, 1.7 Hz), 8.84 (1H, br s).

Example 29

Preparation of prophetic compound (2S,3S)-2-(biphenyl-4-ylmethoxy)-3-[5-(2-furyl)isoxazol-3-yl]-N,3-dihydroxy-2-methylpropanamide (29)

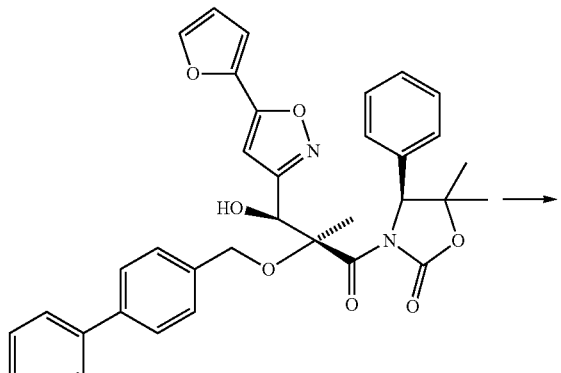

C38

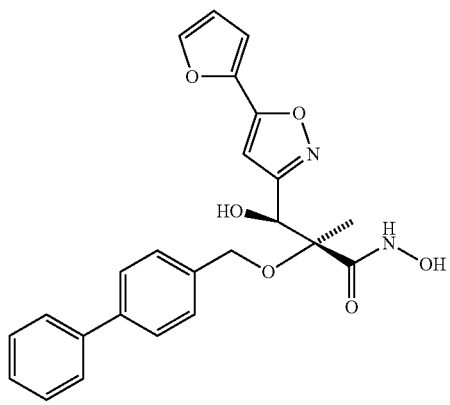

29

Step 1. Preparation of (4S)-3-{(2S,3S)-2-(biphenyl-4-ylmethoxy)-3-[5-(2-furyl)isoxazol-3-yl]-3-hydroxy-2-methylpropanoyl}-5,5-dimethyl-4-phenyl-1,3-oxazolidin-2-one (C38). Compound C38 was synthesized according to the general procedure for the synthesis of C8 in Example 1 except that 5-(furan-2-yl)isoxazole-3-carbaldehyde was used instead of propionaldehyde to provide C38 as a white solid. Yield: 150 mg, 22%. MS (APCI) m/z 593.5 (M+1).

Step 2. Prophetic compound 29 can be synthesized according to the general procedure for the synthesis of 16 in Example 16 except that compound C38 would be used instead of compound C23.

Example 30

Preparation of (2S,3S)-N,3-dihydroxy-2-methyl-3-(5-methylisoxazol-3-yl)-2-[(4'-propylbiphenyl-4-yl)methoxy]propanamide (30)

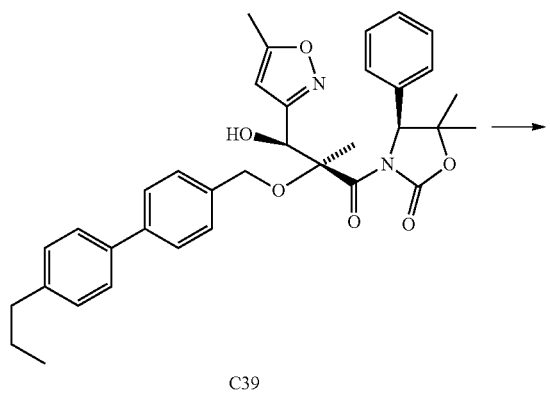

C39

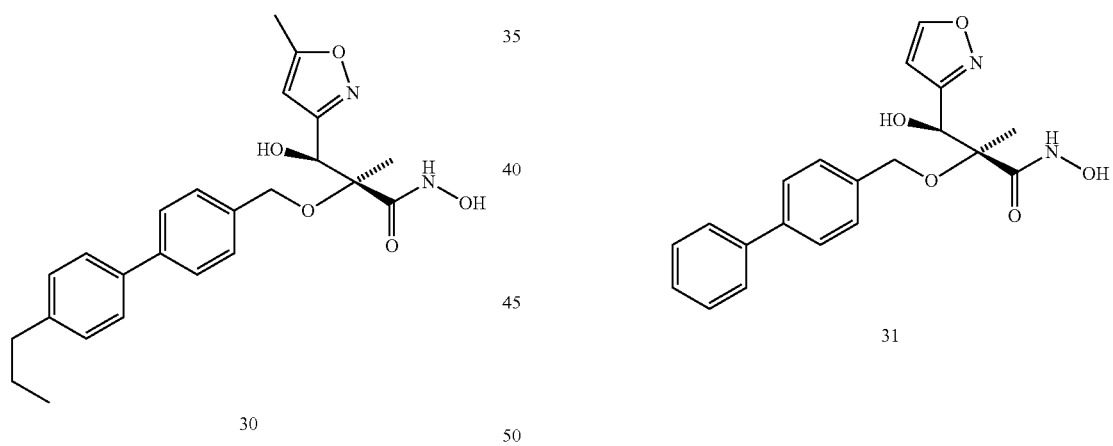

30

Step 1. Preparation of (4S)-3-{(2S,3S)-3-hydroxy-2-methyl-3-(5-methylisoxazol-3-yl)-2-[(4'-propylbiphenyl-4-yl)methoxy]propanoyl}-5,5-dimethyl-4-phenyl-1,3-oxazolidin-2-one (C39). Compound C39 was synthesized according to the general procedure for the synthesis of C8 in Example 1 except that 5-methylisoxazole-3-carbaldehyde was used instead of propionaldehyde and C34 was used instead of 4-(bromomethyl)biphenyl to provide C39 as a white solid. Yield: 250 mg, 41%. MS (APCI) m/z 583.5 (M+1).

Step 2. Compound 30 was synthesized according to the general procedure for the synthesis of 16 in Example 16 except that compound C39 was used instead of compound C23 to provide 30 as a white solid. Yield: 81 mg, 45%. LCMS (APCI) m/z 425.3 (M+1). $^1$H NMR (400 MHz, DMSO-$d_6$) δ 0.90 (3H, t, J=7.3 Hz), 1.37 (3H, s), 1.61 (2H, apparent sext, J=7.4 Hz), 2.35 (3H, d, J=0.8 Hz), 2.58 (2H, t, J=7.6 Hz), 4.52 (2H, AB quartet, J=12.0 Hz), 4.99 (1H, d, J=5.7 Hz), 5.96 (1H, d, J=5.8 Hz), 6.11 (1H, d, J=1.0 Hz), 7.26 (2H, d, J=8.4 Hz), 7.39 (2H, d, J=8.2 Hz), 7.56 (4H, apparent t, J=8.3 Hz), 8.81 (1H, s), 10.48 (1H, s).

Example 31

Preparation of (2S,3S)-2-(biphenyl-4-ylmethoxy)-N,3-dihydroxy-3-isoxazol-3-yl-2-methylpropanamide (31)

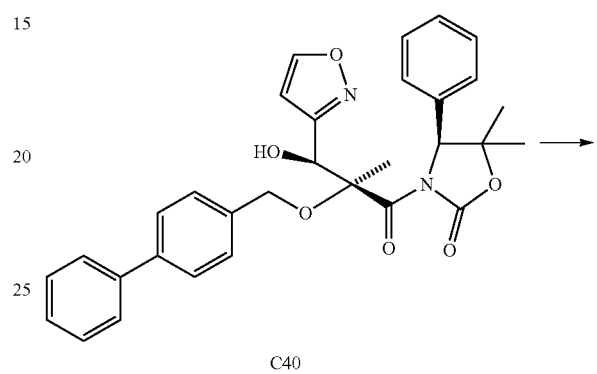

C40

31

Step 1. Preparation of (4S)-3-[(2S,3S)-2-(biphenyl-4-ylmethoxy)-3-hydroxy-3-isoxazol-3-yl-2-methylpropanoyl]-5,5-dimethyl-4-phenyl-1,3-oxazolidin-2-one (C40. Compound C40 was synthesized according to the general procedure for the synthesis of C8 in Example 1 except that isoxazole-3-carbaldehyde was used instead of propionaldehyde to provide C40 as a white solid. Yield: 150 mg, 25%. LCMS (APCI) m/z 527.3 (M+1).

Step 2. Compound 31 was synthesized according to the general procedure for the synthesis of 16 in Example 16 except that compound C40 was used instead of compound C23 to provide 31 as a white solid. Yield: 59 mg, 56%. MS (APCI) m/z 369.4 (M+1). $^1$H NMR (400 MHz, DMSO-$d_6$) δ 1.34 (3H, s), 4.50 (1H, d, J=12.0 Hz), 4.50 (1H, d, J=12.0 Hz), 5.05 (1H, d, J=5.7 Hz), 6.00 (1H, d, J=5.7 Hz), 6.41 (1H, d, J=1.6 Hz), 7.30 (1H, m), 7.39 (4H, m), 7.57 (4H, m), 8.73 (1H, d, J=1.6 Hz), 8.78 (1H, d, J=1.4 Hz), 10.45 (1H, s).

Example 32

Preparation of (2S,3S)-N,3-dihydroxy-2-methyl-3-(5-methylisoxazol-3-yl)-2-{[4-(5-methylpyridin-2-yl)benzyl]oxy}propanamide (32)

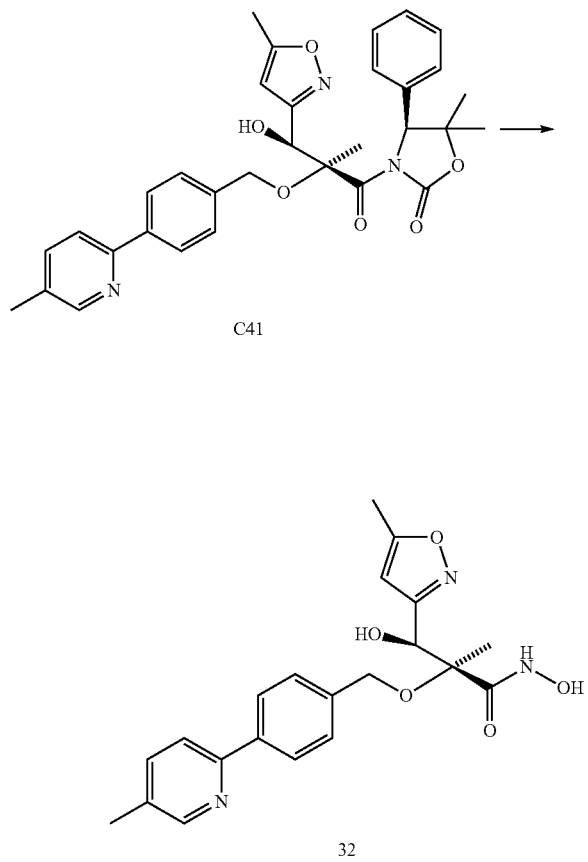

Step 1. Preparation of (4S)-3-{2-[(4-bromobenzyl)oxy]propanoyl}-5,5-dimethyl-4-phenyl-1,3-oxazolidin-2-one (C45). Compound C45 was prepared by the method depicted in Scheme 5 and described in detail below.

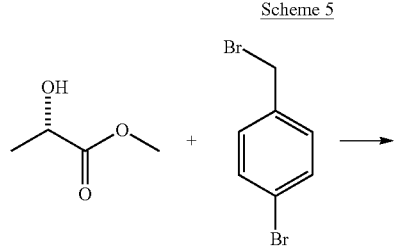

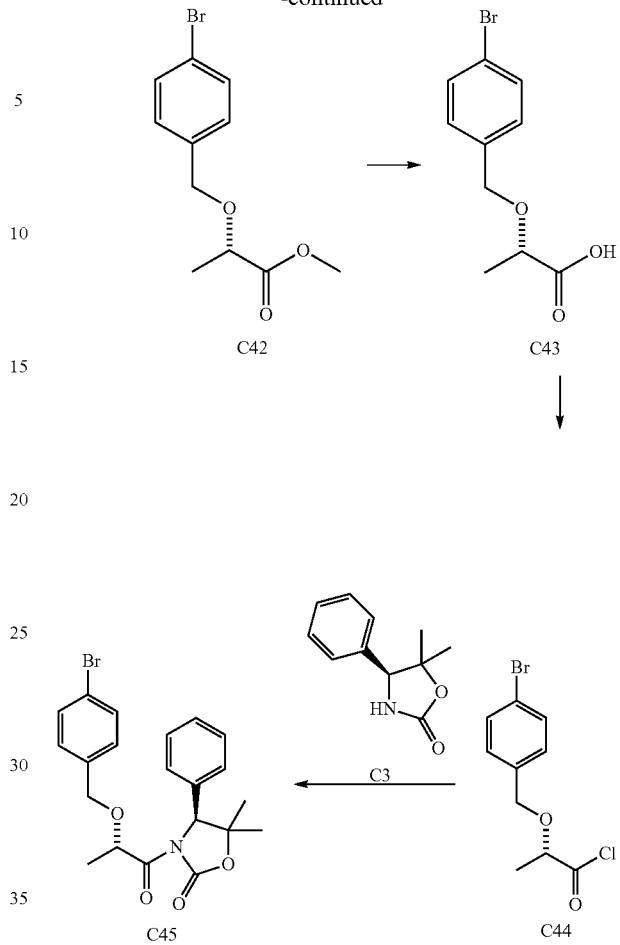

A. Preparation of methyl (S)-2-(4-bromobenzyloxy)propanoate (C42). A mixture of 1-bromo-4-(bromomethyl)benzene (50.4 g, 202 mmol) and sodium hydride (60% in mineral oil, 8.45 g, 211 mmol) in dimethylformamide/tetrahydrofuran (400 mL/600 mL) was cooled to −20° C. and treated drop-wise with methyl (S)-2-hydroxypropanoate (20.0 g, 192.1 mmol). The mixture was stirred at −20° C. for an additional 30 minutes followed by 30 minutes of mixing at 25° C. and 1 hour of mixing at 50° C. The mixture was then quenched with a mixture of water (1000 mL) and hexanes (500 mL). The resultant organic layer was collected and the aqueous layer was extracted with 1:1 hexanes:diethyl ether. The combined organic fractions were washed with water (2×) and saturated aqueous sodium chloride solution, dried over sodium sulfate, and concentrated to provide C42. Yield: 52.0 g, 99%. $^1$H NMR (400 MHz, CDCl$_3$) δ 1.45 (3H, d, J=6.8 Hz), 3.77 (3H, s), 4.06 (1H, q, J=6.8 Hz), 4.41 (1H, d, J=11.9 Hz), 4.64 (1H, d, J=11.7 Hz), 7.24 (2H, m), 7.48 (2H, m).

B. Preparation of (S)-2-(4-bromobenzyloxy)propanoic acid (C43). A solution of C42 (52.0 g, 190 mmol) in tetrahydrofuran (1.5 L) was treated with an aqueous solution of lithium hydroxide (1 M, 570 mL) and stirred vigorously at 25° C. for three days. The reaction mixture was then concentrated, diluted with water, and the pH adjusted to 2 with 3 M hydrochloric acid. The mixture was then extracted with ethyl acetate (3×), and the combined extracts were dried over sodium sulfate and concentrated under reduced pressure. The resultant residue was purified by chromatography on silica gel (gradient: dichloromethane to 9:1 dichloromethane:

methanol) to provide C43 as a white solid. Yield: 43.4 g, 88%. ¹H NMR (400 MHz, DMSO-d₆) δ 1.32 (3H, d, J=6.8 Hz), 4.00 (1H, q, J=6.8 Hz), 4.40 (1H, d, J=12.1 Hz), 4.55 (1H, d, J=12.1 Hz), 7.29 (2H, m), 7.52 (2H, m), 12.71 (1H, br s).

C. Preparation of (2S)-2-[(4-bromobenzyl)oxy]propanoyl chloride C44. A solution of C43 in thionyl chloride (244 mL) was heated at 65° for 1 hour then concentrated. The resultant residue was taken up in dichloromethane and concentrated to remove residual hydrogen chloride. This process was repeated two more times and the resultant residue (C44) was used below in Step D without further purification.

D. Preparation of (4S)-3-{(2S)-2-[(4-bromobenzyl)oxy]propanoyl}-5,5-dimethyl-4-phenyl-1,3-oxazolidin-2-one (C45). A solution of C3 (29.10 g, 152.2 mmol) in tetrahydrofuran (760 mL) was cooled to −78° C. under a nitrogen atmosphere and treated drop-wise with a solution of butyllithium in hexanes (9.71 M, 16.4 mL, 159 mmol). The mixture was stirred at −78° C. for an additional 30 minutes. The mixture was then treated with a solution of C44 (46.5 g, 167 mmol) in tetrahydrofuran (20 mL) and stirred at −78° C. for an additional 30 minutes followed by mixing at about 25° C. for about 3 hours. The reaction was then poured into phosphate buffer (pH 7) and extracted with dichloromethane (2×). The combined organic extracts were washed with aqueous sodium bicarbonate solution followed by saturated aqueous sodium chloride solution. The organics were then dried over sodium sulfate, concentrated to about 50 mL, and treated with heptane to induce precipitation. The resultant mixture was filtered, and the filtrate was concentrated onto silica gel. The resultant residue was purified by silica gel chromatography (gradient: 9:1 heptane:ethyl acetate to 6:4 heptane:ethyl acetate) to provide C45 as a white solid. Yield: 47.37 g, 72%. ¹H NMR (400 MHz, DMSO-d₆) δ 0.88 (3H, s), 1.36 (3H, d, J=6.4 Hz), 1.60 (3H, s), 4.33 (2H, AB quartet, J=11.9 Hz), 5.21 (2H, m), 7.22 (4H, m), 7.36 (3H, m), 7.53 (2H, d, J=8.2 Hz).

Step 2. Preparation of (4S)-5,5-dimethyl-3-[(2S)-2-{[4-(5-methylpyridin-2-yl)benzyl]oxy}propanoyl]-4-phenyl-1,3-oxazolidin-2-one (C46). Compound C46 was prepared according to methods depicted in Scheme 6 (Method A) or Scheme 7 (Method B) and described in detail below.

Method A

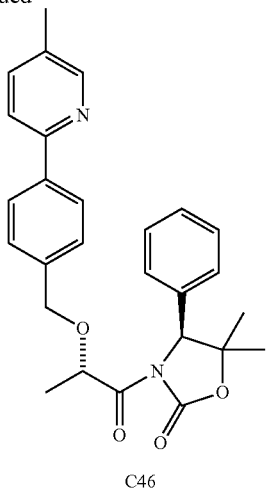

C46

A solution of C45 (3.00 g, 6.94 mmol), 2-(5-methylpyridin-2-yl)-6-phenyl-1,3,6,2-dioxazaborocane, which may be prepared using the method of Hodgson and Salingue, *Tetrahedron Letters* 2004, 45, 685-687, (3.92 g, 13.9 mmol), triphenylphosphine (365 mg, 1.39 mmol), copper iodide (530 mg, 2.78 mmol), and cesium carbonate (4.60 g, 13.9 mmol), in tetrahydrofuran (140 mL) was evacuated until vigorous bubbling was observed, then nitrogen gas was introduced. The degassing procedure was repeated twice and tetrakis(triphenylphosphine)palladium(0) (400 mg, 0.35 mmol) was added. The reaction mixture was heated at reflux for 18 hours. The mixture was filtered through a plug of Celite, which was then washed with copious amounts of tetrahydrofuran. The combined filtrates were concentrated onto silica gel and purified by chromatography (gradient: 9:1 heptane:ethyl acetate to 1:1 heptane:ethyl acetate) to provide C46 as a white solid. Yield: 2.13 g, 69%. MS (APCI) m/z 445.3 (M+1).

Method B

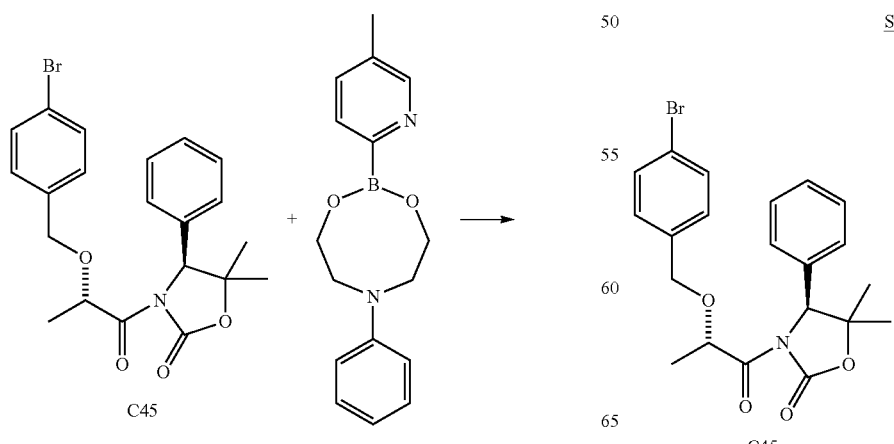

Scheme 6

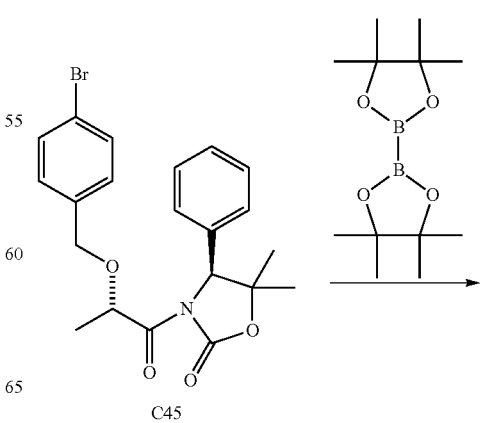

Scheme 7

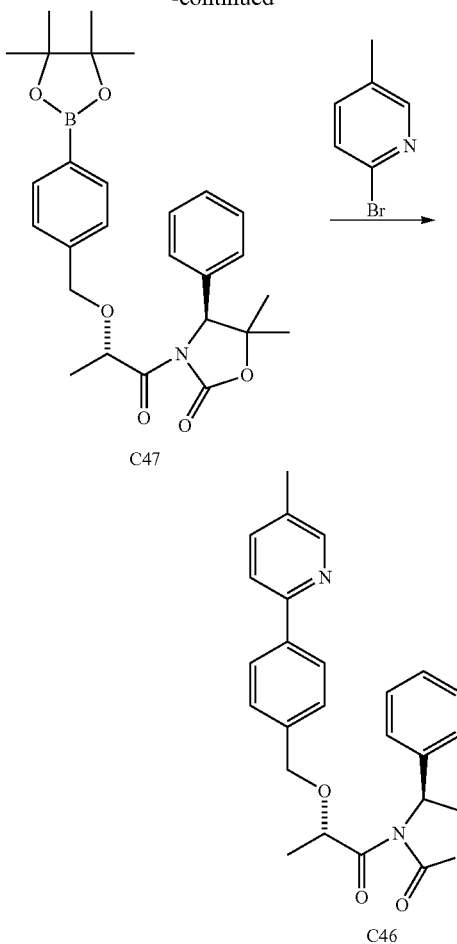

C47

C46

A. A solution of C45 (5.00 g, 11.57 mmol), pinacol diborane (3.82 g, 15.0 mmol), and potassium acetate (3.41 g, 34.7 mmol), in anhydrous dioxane (230 mL) was subjected to vacuum until boiling occurred, and the vacuum was then filled with nitrogen gas. The gas replacement was repeated twice. The reaction mixture was then treated with 1,1'-[bis(diphenylphosphino)ferrocene]dichloropalladium(II) (0.94 g, 1.16 mmol) and heated at reflux for 18 hours. The mixture was filtered through a Celite plug and then concentrated onto silica. The resultant residue was then purified by chromatography (gradient: 9:1 heptane:ethyl acetate to 6:4 heptane:ethyl acetate) to provide (4S)-5,5-dimethyl-4-phenyl-3-[(2S)-2-{[4-(4,4,5,5-tetramethyl-1,3,2-dioxaborolan-2-yl)benzyl]oxy}propanoyl]-1,3-oxazolidin-2-one (C47) as a white solid. Yield: 4.43 g, 80%. MS (APCI) m/z 480.3 (M+1). $^1$H NMR (400 MHz, DMSO-d$_6$) δ 0.88 (3H, s), 1.29 (12H, s), 1.37 (3H, d, J=6.6 Hz), 1.60 (3H, s), 4.38 (2H, AB quartet, J=12.5 Hz), 5.23 (2H, m), 7.24 (2H, m), 7.27 (2H, d, J=8.2 Hz), 7.36 (3H, m), 7.65 (2H, d, J=8.0 Hz).

B. A solution of C47 (1.0 g, 2.09 mmol), 2-bromo-5-methylpyridine (435 mg, 2.50 mmol), and sodium carbonate (670 mg, 6.26 mmol) in toluene/isopropanol/water (20 mL/20 mL/5 mL) was subjected to a vacuum (until boiling occurred), and then nitrogen was introduced to the system. The vacuum/gas sequence was repeated twice. The mixture was then treated with 1,1'-[bis(diphenylphosphino)ferrocene]dichloropalladium(II) (170 mg, 0.21 mmol) and heated at 90° C. for 5 hours. The reaction mixture was then concentrated onto silica gel, and the resultant residue was purified by chromatography (gradient: 9:1 heptane:ethyl acetate to 1:1 heptane:ethyl acetate) to provide C46 as a white solid. Yield: 120 mg, 13%. MS (APCI) m/z 445.3 (M+1).

Step 3. Preparation of (4S)-3-[(2S,3S)-3-hydroxy-2-methyl-3-(5-methylisoxazol-3-yl)-2-{[4-(5-methylpyridin-2-yl)benzyl]oxy}propanoyl]-5,5-dimethyl-4-phenyl-1,3-oxazolidin-2-one (C41). Compound C41 was synthesized according to the general procedure for the synthesis of C8 in Example 1 except that 5-methylisoxazole-3-carbaldehyde was used instead of propionaldehyde and C46 was used instead of C7 to provide C41 as a white solid. Yield: 220 mg, 35%. LCMS (APCI) m/z 556.3 (M+1).

Step 4. Compound 32 was synthesized according to the general procedure for the synthesis of 16 in Example 16 except that compound C41 was used instead of compound C23 to provide 32 as a white solid. Yield: 55 mg, 35%. MS (APCI) m/z 398.4 (M+1). $^1$H NMR (400 MHz, DMSO-d$_6$) δ 1.33 (3H, s), 2.27 (3H, s), 2.30 (3H, d, J=1.0 Hz), 4.47 (1H, d, J=12.0 Hz), 4.52 (1H, d, J=12.0 Hz), 4.94 (1H, d, J=5.3 Hz), 5.91 (1H, d, J=5.7 Hz), 6.07 (1H, d, J=1.0 Hz), 7.36 (2H, d, J=8.4 Hz), 7.63 (1H, m), 7.79 (1H, d, J=8.2 Hz), 7.94 (2H, d, J=8.4 Hz), 8.43 (1H, d, J=2.1 Hz), 8.77 (1H, s), 10.44 (1H, br s).

Example 33

Preparation of (2S,3R)-2-(biphenyl-4-ylmethoxy)-N,3-dihydroxy-2-methyl-3-(1,3-oxazol-2-yl)propanamide (33)

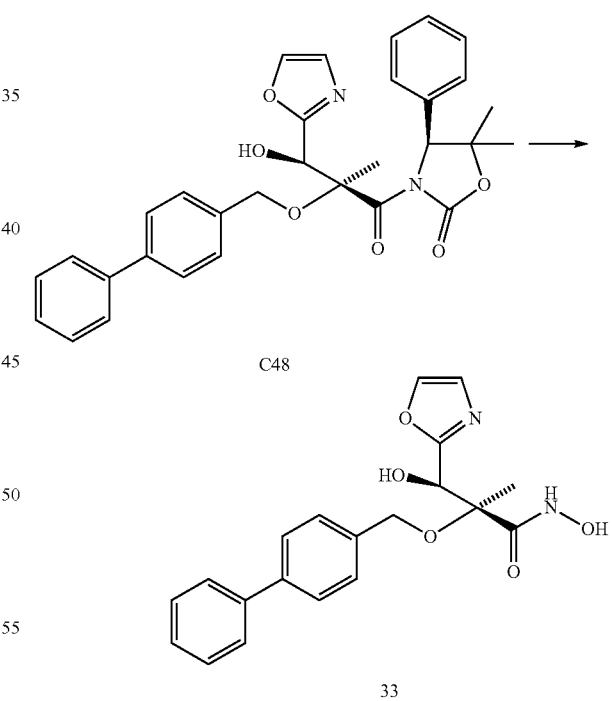

C48

33

Step 1. Preparation of (4S)-3-[(2S,3R)-2-(biphenyl-4-ylmethoxy)-3-hydroxy-2-methyl-3-(1,3-oxazol-2-yl)propanoyl]-5,5-dimethyl-4-phenyl-1,3-oxazolidin-2-one (C48). Compound C48 was synthesized according to the general procedure for the synthesis of C8 in Example 1 except that 1,3-oxazole-2-carbaldehyde was used instead of propionaldehyde to provide C48 as a white solid. Yield: 250 mg, 41%. MS (APCI) m/z 527.4 (M+1).

Step 2. Compound 33 was synthesized according to the general procedure for the synthesis of 16 in Example 16 except that compound C48 was used instead of compound C23 to provide 33 as a white solid. Yield: 45 mg, 26%. LCMS (APCI) m/z 369.2 (M+1). $^1$H NMR (400 MHz, DMSO-$d_6$) δ 1.47 (3H, s), 4.43 (1H, d, J=12.0 Hz), 4.51 (1H, d, J=12.0 Hz), 5.15 (1H, br s), 6.14 (1H, br s), 7.18 (1H, d, J=0.8 Hz), 7.28 (2H, d, J=8.4 Hz), 7.34 (1H, m), 7.44 (2H, apparent t, J=7.6 Hz), 7.56 (2H, d, J=8.2 Hz), 7.63 (2H, dd, J=8.3, 1.3 Hz), 8.05 (1H, s), 8.86 (1H, br s), 10.61 (1H, br s).

Example 34

Preparation of (2S,3S)-2-(biphenyl-4-ylmethoxy)-N,3-dihydroxy-3-[5-(hydroxymethyl)isoxazol-3-yl]-2-methylpropanamide (34)

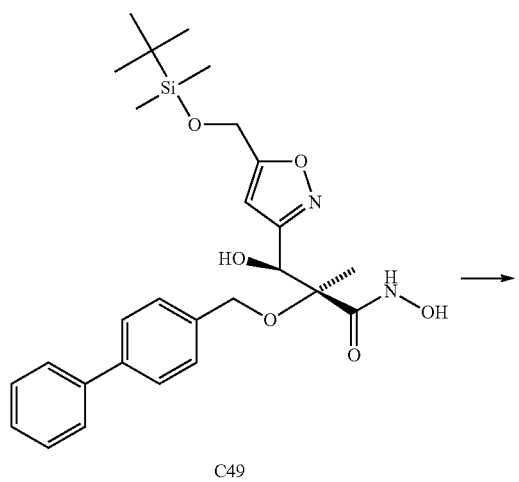

Step 1. Preparation of 5-[(tert-butyldimethylsilyloxy)methyl]isoxazole-3-carbaldehyde (C51). Compound C51 was prepared by the method depicted in Scheme 8 and described in detail below.

Scheme 8

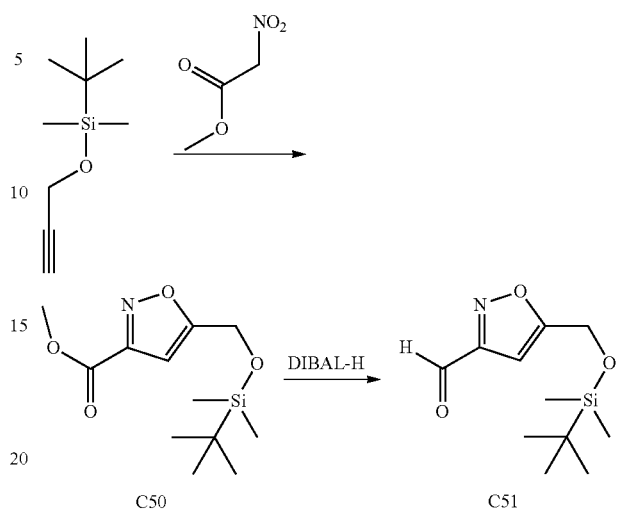

A. Preparation of methyl 5-[(tert-butyldimethylsilyloxy)methyl]isoxazole-3-carboxylate (C50). A solution of O-tert-butyldimethylsilylpropyn-3-ol (16 g, 94 mmol) and methyl nitroacetate (11.20 g, 94 mmol) in tetrahydrofuran (400 mL) was treated with 1,4-phenylene diisocyanate (38 g) followed by addition of ten drops of triethylamine. The reaction mixture was then stirred for eight days at about 25° C. A few drops of water were then added and the crude mixture was stirred for about 3 hours and filtered through a plug of Celite. The filtrate was concentrated, and the resultant residue was purified by silica gel chromatography (gradient; 10:90 ethyl acetate:heptane to 40:60 ethyl acetate:heptane) to provide C50 as a white solid. Yield: 11.56 g, 45%. $^1$H NMR (400 MHz, CDCl$_3$) δ 0.10 (6H, s), 0.90 (9H, s), 3.96 (3H, s), 4.80 (2H, s), 6.59 (1H, s).

B. A solution of C50 (14.15 g, 52.14 mmol) in anhydrous dichloromethane (175 mL) was cooled to −78° C. under nitrogen atmosphere and slowly treated over 5 minutes with a solution of diisobutylaluminum hydride (DIBAL-H) in toluene (1 M, 63 mL). The reaction mixture was stirred at −78° C. for 24 hours and then quenched with ice. The resultant biphasic mixture was allowed to warm to about 25° C. and treated with a saturated aqueous solution of potassium sodium tartrate tetrahydrate (175 mL). The layers were separated and the aqueous layer was back-extracted with methylene chloride. The combined organic extracts were then washed with saturated aqueous sodium chloride solution, dried over sodium sulfate, and concentrated onto silica gel. The resultant residue was purified by silica gel chromatography (gradient: 95:5 heptane:ethyl acetate to 80:20 heptane:ethyl acetate) to provide C51 as a clear oil. Yield: 7.86 g, 62%. $^1$H NMR (400 MHz, DMSO-$d_6$) δ 0.05 (6H, s), 0.83 (9H, s), 4.83 (2H, s), 6.74 (1H, s), 10.04 (1H, s).

Step 2. Preparation of (4S)-3-{(2S,3S)-2-(biphenyl-4-ylmethoxy)-3-{5-[(tert-butyldimethylsilyloxy)methyl]isoxazol-3-yl}-3-hydroxy-2-methylpropanoyl}-5,5-dimethyl-4-phenyl-1,3-oxazolidin-2-one (C52). Compound C52 was synthesized according to the general procedure for the synthesis of C8 in Example 1 except that C51 was used instead of propionaldehyde to provide C52 as a white solid. Yield: 440 mg, 56%. MS (APCI) m/z 671.7 (M+1).

Step 3. Preparation of (2S,3S)-2-(biphenyl-4-ylmethoxy)-3-{5-[(tert-butyldimethylsilyloxy)methyl]isoxazol-3-yl}-N,3-dihydroxy-2-methylpropanamide (C49).

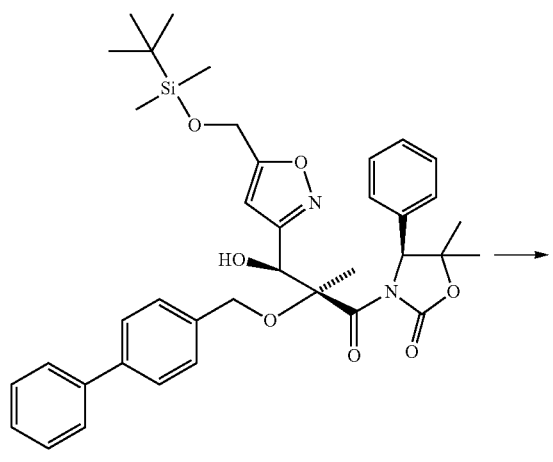

C52

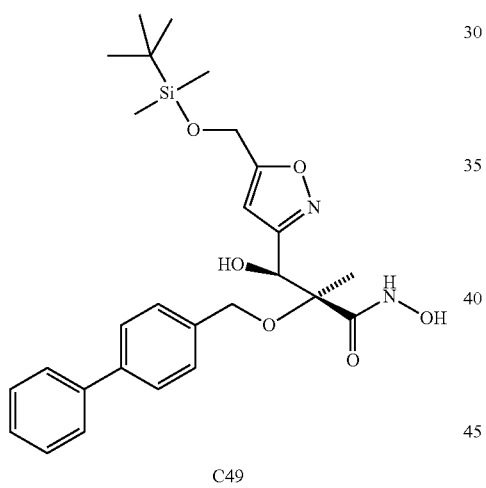

C49

Compound C49 was synthesized according to the general procedure for the synthesis of 16 in Example 16 except that compound C52 was used instead of compound C23 to provide C49 as a white solid. Yield: 140 mg, 38%. MS (APCI) m/z 513.5 (M+1).

Step 4. A solution of compound C49 (550 mg, 1.07 mmol) in tetrahydrofuran (55 mL) was treated with a solution of tetrabutylammonium fluoride (1 M, 2.15 mL) under a nitrogen atmosphere and stirred at about 25° C. for 2 hours. The reaction mixture was then treated with acetic acid (0.125 mL) and concentrated. The resultant residue was purified by silica gel chromatography (gradient: dichloromethane to 9:1 dichloromethane:methanol) to provide 34 as a white solid. Yield: (330 mg, 77%. MS (APCI) m/z 399.3 (M+1). $^1$H NMR (400 MHz, DMSO-$d_6$) δ 1.38 (3H, s), 4.49-4.59 (4H, m), 5.03 (1H, d, J=5.8 Hz), 5.59 (1H, t, J=6.0 Hz), 6.02 (1H, d, J=5.7 Hz), 6.27 (1H, s), 7.35 (1H, m), 7.47 (4H, m), 7.63 (4H, m), 8.83 (1H, s), 10.51 (1H, s).

Example 35

Preparation of (2S,3S)-2-[(4'-fluorobiphenyl-4-yl)methoxy]-N,3-dihydroxy-3-[5-(hydroxymethyl)isoxazol-3-yl]-2-methylpropanamide (35)

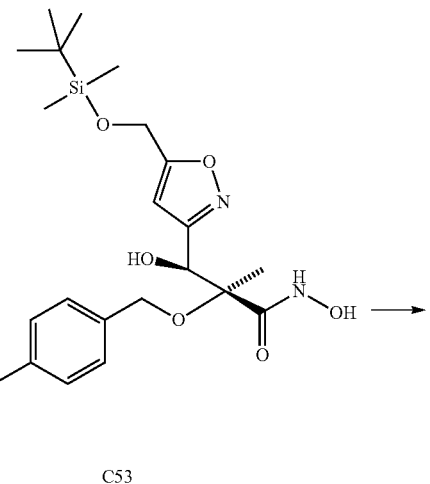

C53

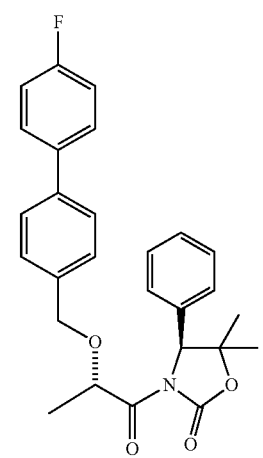

35

Step 1. Preparation of (4S)-3-{(2S)-2-[(4'-fluorobiphenyl-4-yl)methoxy]propanoyl}-5,5-dimethyl-4-phenyl-1,3-oxazolidin-2-one (C54).

C54

A mixture of 4-fluorophenylboronic acid (570 mg, 3.85 mmol), compound C45 (1.5 g, 3.47 mmol), and cesium carbonate (2.26 g, 6.94 mmol), in toluene (35 mL) was degassed with nitrogen for 2 minutes. Tetrakis(triphenylphosphine)palladium(O) (400 mg, 0.35 mmol) was then added and the mixture was again degassed for 2 minutes. The reaction mixture was then heated at 90° C. for about 2 hours. The mixture was then filtered through a plug of silica gel, eluting with copious amounts of ethyl acetate. The combined filtrates were concentrated onto silica gel and purified by chromatography (gradient: 9:1 heptane:ethyl acetate to 6:4 heptane:ethyl acetate) to provide C54 as a white solid. Yield: 680 mg, 44%. MS (APCI) m/z 448.3 (M+1). $^1$H NMR (400 MHz, CDCl$_3$) δ 0.96 (3H, s), 1.47 (3H, d, J=6.6 Hz), 1.57 (3H, s), 4.30 (1H, d, J=11.3 Hz), 4.46 (1H, d, J=11.3 Hz), 5.05 (1H, s), 5.26 (1H, q, J=6.6 Hz), 7.08 (4H, m), 7.34 (5H, m), 7.45 (4H, m).

Step 2. Preparation of (4S)-3-{(2S,3S)-3-{5-[(tert-butyldimethylsilyloxy)methyl]isoxazol-3-yl}-2-[(4'-fluorobiphenyl-4-yl)methoxy]-3-hydroxy-2-methylpropanoyl}-5,5-dimethyl-4-phenyl-1,3-oxazolidin-2-one (C55). Compound C55 was synthesized according to the general procedure for the synthesis of C8 in Example 1 except that C51 was used instead of propionaldehyde and C54 was used instead of C7 to provide C55 as a white solid. Yield: 220 mg, 42%): MS (APCI) m/z 689.5 (M+1).

Step 3. Preparation of (2S,3S)-3-{5-[(tert-butyldimethylsilyloxy)methyl]isoxazol-3-yl}-2-[(4'-fluorobiphenyl-4-yl)methoxy]-N,3-dihydroxy-2-methylpropanamide (C53).

Compound C53 was synthesized according to the general procedure for the synthesis of 16 in Example 16 except that compound C55 was used instead of compound C23 to provide C53 as a white solid. Yield: 100 mg, 48%. MS (APCI) m/z 531.3 (M+1).

Step 4. A solution of compound C53 (240 mg, 0.45 mmol) in tetrahydrofuran (1 mL) was treated with 24 mL of a solution prepared from hydrofluoric acid (48% aqueous, 1.5 mL), water (0.5 mL), and acetonitrile (27 mL). The reaction mixture was stirred at 25° C. for 1 hour, treated with tetrahydrofuran (20 mL), and concentrated onto silica gel. The resultant residue was then purified by chromatography (gradient: dichloromethane to 8:2 dichloromethane:methanol) to provide 35 as a white solid. Yield: 123 mg, 65%. LCMS (APCI) m/z 417.3 (M+1). $^1$H NMR (400 MHz, DMSO-d$_6$) δ 1.39 (3H, s), 4.49-4.59 (4H, m), 5.04 (1H, d, J=5.8 Hz), 5.59 (1H, t, J=6.0 Hz), 6.02 (1H, d, J=5.7 Hz), 6.27 (1H, s), 7.28 (2H, apparent t, J=8.9 Hz), 7.42 (2H, d, J=8.4 Hz), 7.59 (2H, d, J=8.2 Hz), 7.70 (2H, dd, J=9.0, 5.5 Hz), 8.84 (1H, m), 10.52 (1H, s).

Example 36

Preparation of (2S,3S)-2-[(4'-ethylbiphenyl-4-yl)methoxy]-N,3-dihydroxy-4-[5-(hydroxymethyl)isoxazol-3-yl]-2-methylpropanamide (36)

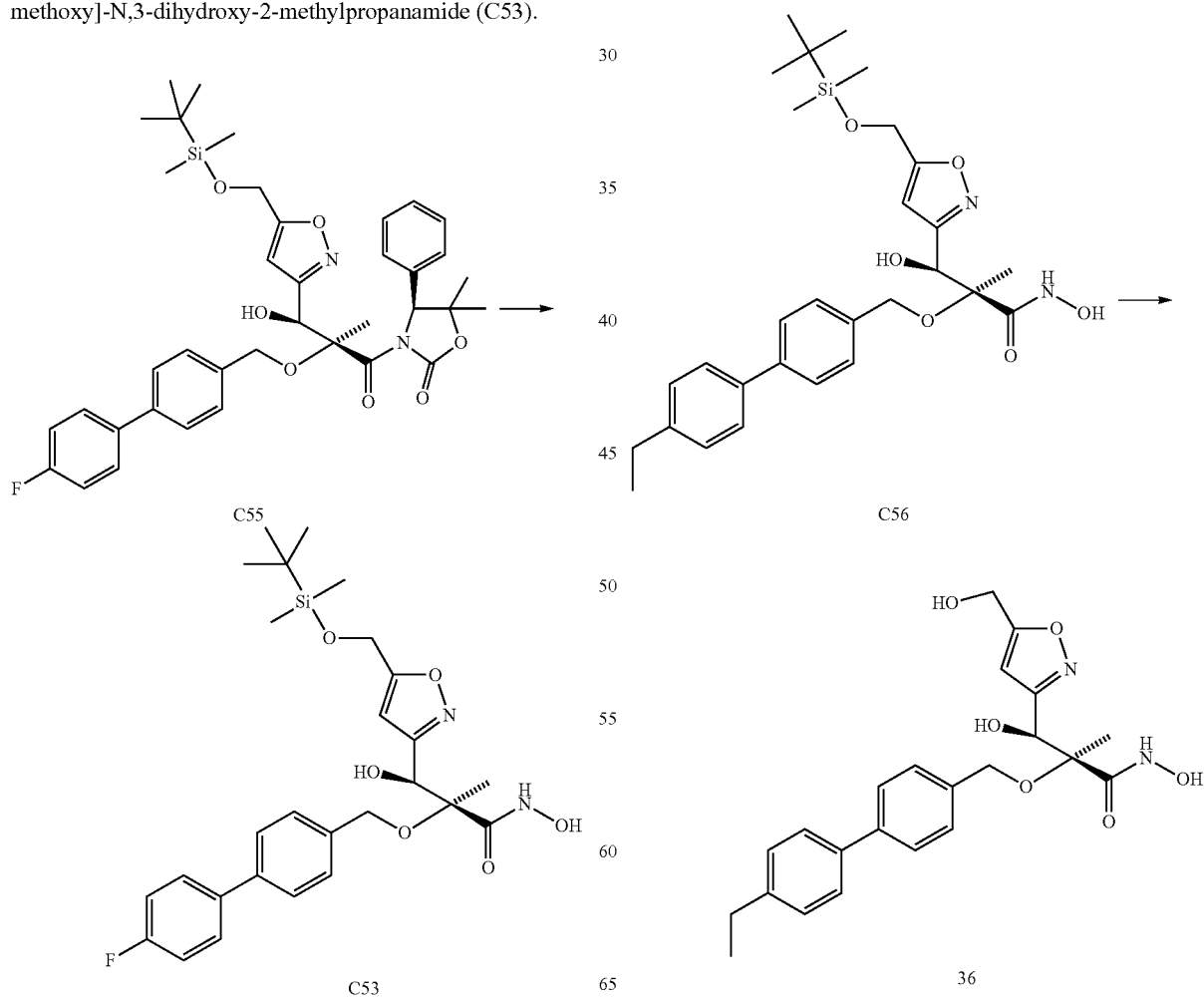

Step 1. Preparation of (4S)-3-{(2S)-2-[(4'-ethylbiphenyl-4-yl)methoxy]propanoyl}-5,5-dimethyl-4-phenyl-1,3-oxazolidin-2-one (C57).

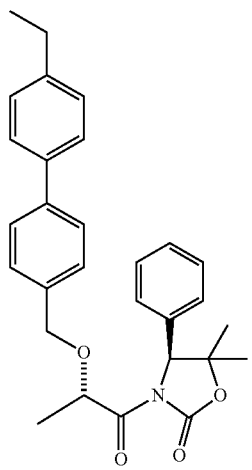

C57

Compound C57 was synthesized in a manner similar to that described for making compound C54 in Example 35 except that 4-ethylphenylboronic acid was used instead of 4-fluorophenylboronic acid to provide C57 as a white solid. Yield: 1.22 g, 77%. $^1$H NMR (400 MHz, CDCl$_3$) δ 0.95 (3H, s), 1.22 (3H, t, J=7.7 Hz), 1.46 (3H, d, J=6.6 Hz), 1.56 (3H, s), 2.63 (2H, q, J=7.6 Hz), 4.29 (1H, d, J=11.3 Hz), 4.45 (1H, d, J=11.3 Hz), 5.05 (1H, s), 5.26 (1H, q, J=6.5 Hz), 7.11 (2H, m), 7.22 (2H, m), 7.30 (5H, m), 7.44 (2H, d, J=8.2 Hz), 7.47 (2H, d, J=8.4 Hz).

Step 2. Preparation of (4S)-3-{(2S,3S)-3-{5-[(tert-butyldimethylsilyloxy)methyl]isoxazol-3-yl}-2-[(4'-ethylbiphenyl-4-yl)methoxy]-3-hydroxy-2-methylpropanoyl}-5,5-dimethyl-4-phenyl-1,3-oxazolidin-2-one (C58). Compound C58 was synthesized according to the general procedure for the synthesis of C8 in Example 1 except that C51 was used instead of propionaldehyde and C57 was used instead of C7 to provide C58 as a white solid. Yield: 280 mg, 37%. MS (APCI) m/z 699.6 (M+1).

Step 3. Preparation of (2S,3S)-3-{5-[(tert-butyldimethylsilyloxy)methyl]isoxazol-3-yl}-2-[(4'-ethylbiphenyl-4-yl)methoxy]-N,3-dihydroxy-2-methylpropanamide (C56).

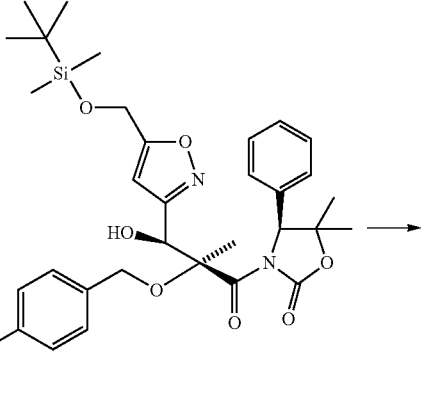

C58

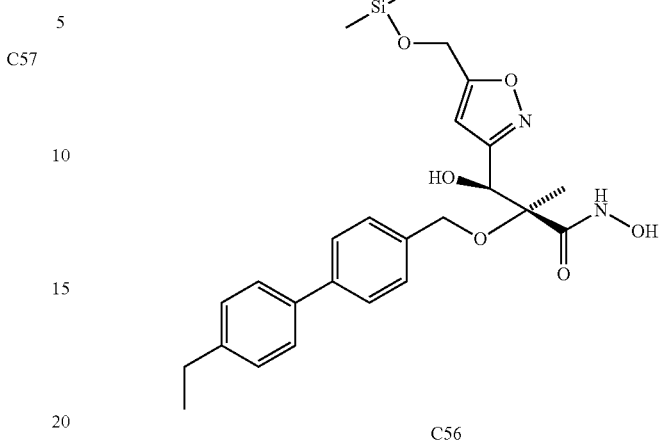

C56

Compound C56 was synthesized according to the general procedure for the synthesis of 16 in Example 16 except that compound C58 was used instead of compound C23 to provide C56 as a white solid. Yield: 180 mg, 83%. MS (APCI) m/z 541.5 (M+1).

Step 4. Compound 36 was synthesized in a manner similar to that described for making compound 34 in Example 34 except that compound C56 was used instead of compound C49 to provide 36 as a white solid. Yield: 65 mg, 46%. MS (APCI) m/z 427.3 (M+1). $^1$H NMR (400 MHz, DMSO-d$_6$) δ 1.20 (3H, t, J=7.6 Hz), 1.38 (3H, s), 2.63 (2H, q, J=7.6 Hz), 4.53 (4H, m), 5.03 (1H, d, J=5.8 Hz), 5.59 (1H, t, J=6.0 Hz), 6.01 (1H, d, J=5.8 Hz), 6.27 (1H, s), 7.28 (2H, d, J=8.4 Hz), 7.39 (2H, d, J=8.4 Hz), 7.56 (4H, m), 8.83 (1H, s), 10.50 (1H, s).

Example 37

Preparation of (2S,3S)-N,3-dihydroxy-3-[5-(hydroxymethyl)isoxazol-3-yl]-2-methyl-2-[(4'-methylbiphenyl-4-yl)methoxy]propanamide (37)

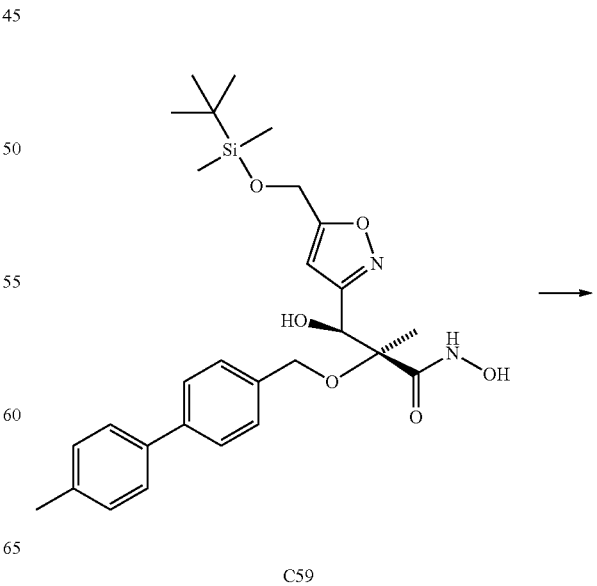

C59

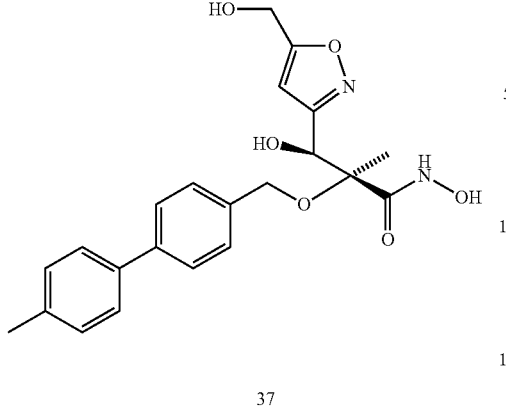

37

Step 1. Preparation of (4S)-5,5-dimethyl-3-{(2S)-2-[(4'-methylbiphenyl-4-yl)methoxy]propanoyl}-4-phenyl-1,3-oxazolidin-2-one (C60).

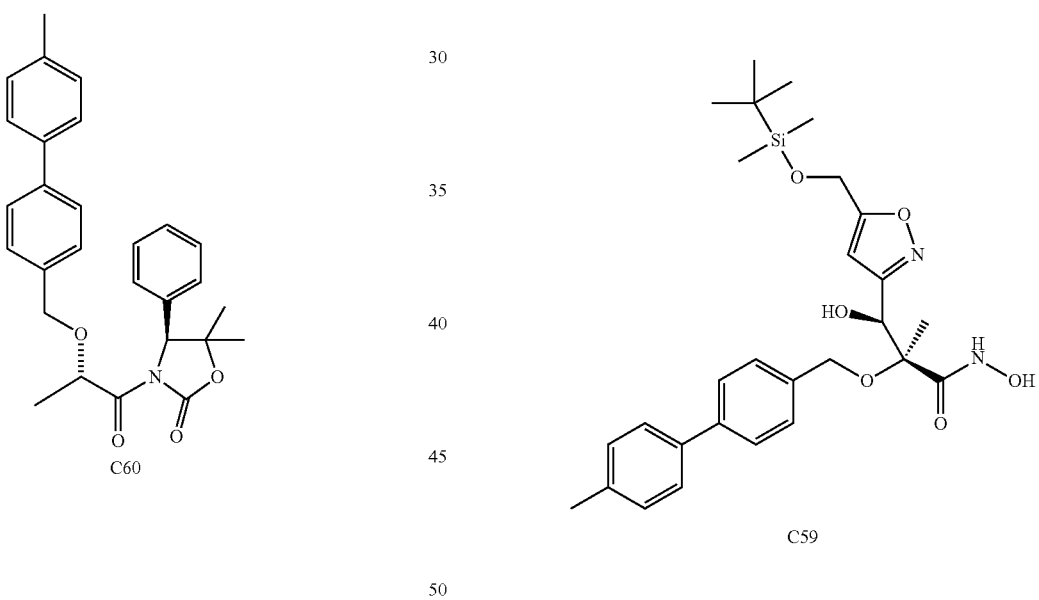

C60

Compound C60 was synthesized in a manner similar to that described for making compound C54 in Example 35 except that 4-methylphenylboronic acid was used instead of 4-fluorophenylboronic acid to provide C60 as a white solid. Yield: 580 mg, 57%. $^1$H NMR (400 MHz, DMSO-d$_6$) δ 0.89 (3H, s), 1.38 (3H, d, J=6.6 Hz), 1.61 (3H, s), 2.34 (3H, s), 4.38 (2H, AB quartet, J=11.7 Hz), 5.23 (2H, m), 7.27 (4H, d, J=8.0 Hz), 7.34 (3H, m), 7.40 (2H, m), 7.57 (2H, d, J=8 Hz), 7.61 (2H, d, J=8 Hz).

Step 2. Preparation of (4S)-3-{(2S,3S)-3-{5-[(tert-butyldimethylsilyloxy)methyl]isoxazol-3-yl}-3-hydroxy-2-methyl-2-[(4'-methylbiphenyl-4-yl)methoxy]propanoyl}-5,5-dimethyl-4-phenyl-1,3-oxazolidin-2-one (C61). Compound C61 was synthesized according to the general procedure for the synthesis of C8 in Example 1 except that C51 was used instead of propionaldehyde and C60 was used instead of C7 to provide C61 as a white solid. Yield: 280 mg, 37%. MS (APCI) m/z 685.5 (M+1).

Step 3. Preparation of (2S,3S)-3-{5-[(tert-butyldimethylsilyloxy)methyl]isoxazol-3-yl}-N,3-dihydroxy-2-methyl-2-[(4'-methylbiphenyl-4-yl)methoxy]propanamide (C59).

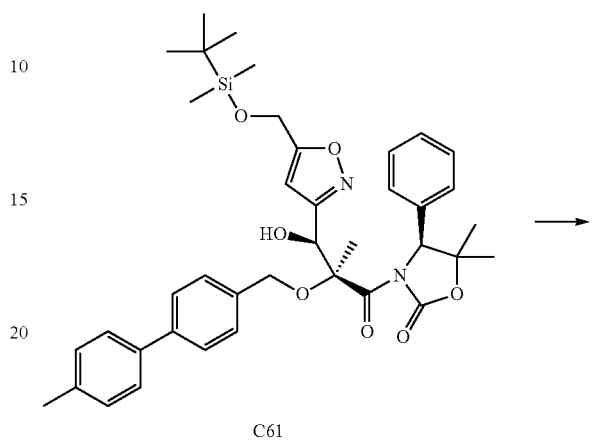

C61

C59

Compound C59 was synthesized according to the general procedure for the synthesis of 16 in Example 16 except that compound C61 was used instead of compound C23 to provide C59 as a white solid. Yield: 110 mg, 48%. MS (APCI) m/z 527.4 (M+1).

Step 4. Compound 37 was synthesized according to the general procedure for the synthesis of 34 in Example 34 except that compound C59 was used instead of compound C49 to provide 37 as a white solid. Yield: 160 mg, 79%. LCMS (APCI) m/z 413.3 (M+1). $^1$H NMR (400 MHz, DMSO-d$_6$) δ 1.39 (3H, s), 2.34 (3H, s), 4.54 (4H, m), 5.04 (1H, d, J=5.7 Hz), 5.59 (1H, t, J=6.0 Hz), 6.02 (1H, d, J=5.8

Hz), 6.27 (1H, s), 7.26 (2H, d, J=7.8 Hz), 7.40 (2H, d, J=8.4 Hz), 7.55 (2H, d, J=8.2 Hz), 7.58 (2H, d, J=8.4 Hz), 8.84 (1H, s), 10.51 (1H, s).

Example 38

Preparation of (2S,3S)-2-[(4'-fluorobiphenyl-4-yl)methoxy]-N,3-dihydroxy-2-methyl-3-(5-methylisoxazol-3-yl)propanamide (38)

except that compound C62 was used instead of compound C23 to provide 38 as a white solid. Yield: 8 mg, 10%. MS (APCI) m/z 401.3 (M+1).

Example 39

Preparation of (2S,3S)-N,3-dihydroxy-2-methyl-2-[(4'-methylbiphenyl-4-yl)methoxy]-3-(5-methylisoxazol-3-yl)propanamide (39)

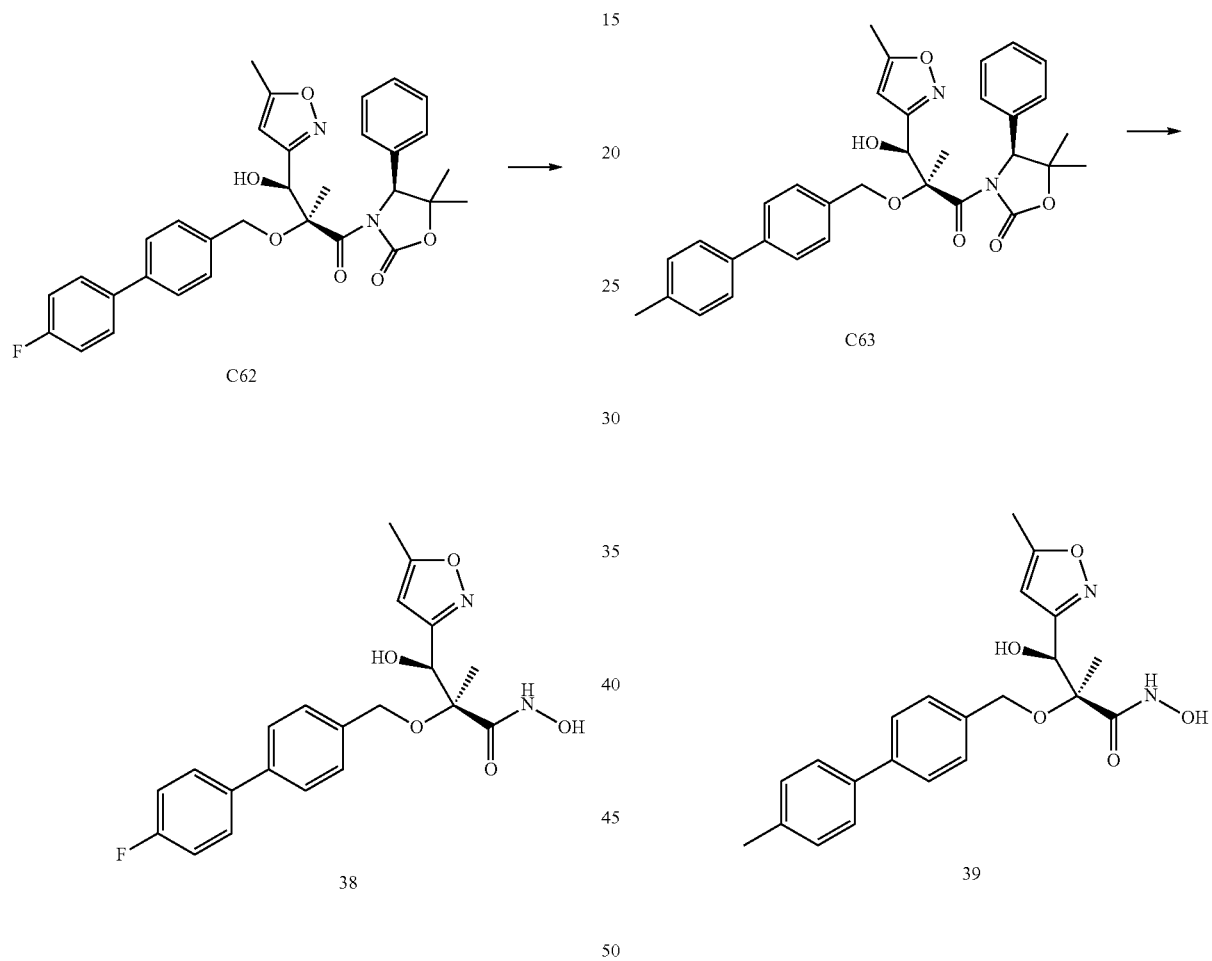

Step 1. Preparation of (4S)-3-[(2S,3S)-2-[(4'-fluorobiphenyl-4-yl)methoxy]-3-hydroxy-2-methyl-3-(5-methylisoxazol-3-yl)propanoyl]-5,5-dimethyl-4-phenyl-1,3-oxazolidin-2-one (C62). Compound C62 was synthesized according to the general procedure for the synthesis of C8 in Example 1 except that 5-methylisoxazole-3-carbaldehyde was used instead of propionaldehyde and C54 was used instead of C7 to provide C62 as a white solid. Yield: 100 mg, 24%. MS (APCI) m/z 559.4 (M+1).

Step 2. Compound 38 was synthesized according to the general procedure for the synthesis of 16 in Example 16

Step 1. Preparation of (4S)-3-[(2S,3S)-3-hydroxy-2-methyl-2-[(4'-methyl biphenyl-4-yl)methoxy]-3-(5-methylisoxazol-3-yl)propanoyl]-5,5-dimethyl-4-phenyl-1,3-oxazolidin-2-one (C63). Compound C63 was synthesized according to the general procedure for the synthesis of C8 in Example 1 except that 5-methylisoxazole-3-carbaldehyde was used instead of propionaldehyde and C60 was used instead of C7 to provide C63 as a white solid. Yield: 200 mg, 36%. MS (APCI) m/z 555.4 (M+1).

Step 2. Compound 39 was synthesized according to the general procedure for the synthesis of 16 in Example 16 except that compound C63 was used instead of compound C23 to provide 39 as a white solid. Yield: 24 mg, 17%. LCMS (APCI) m/z 397.3 (M+1).

Example 40

Preparation of (2S,3S)-N,3-dihydroxy-3-[5-(hydroxymethyl)isoxazol-3-yl]-2-methyl-2-{[4-(5-methylpyridin-2-yl)benzyl]oxy}propanamide (40)

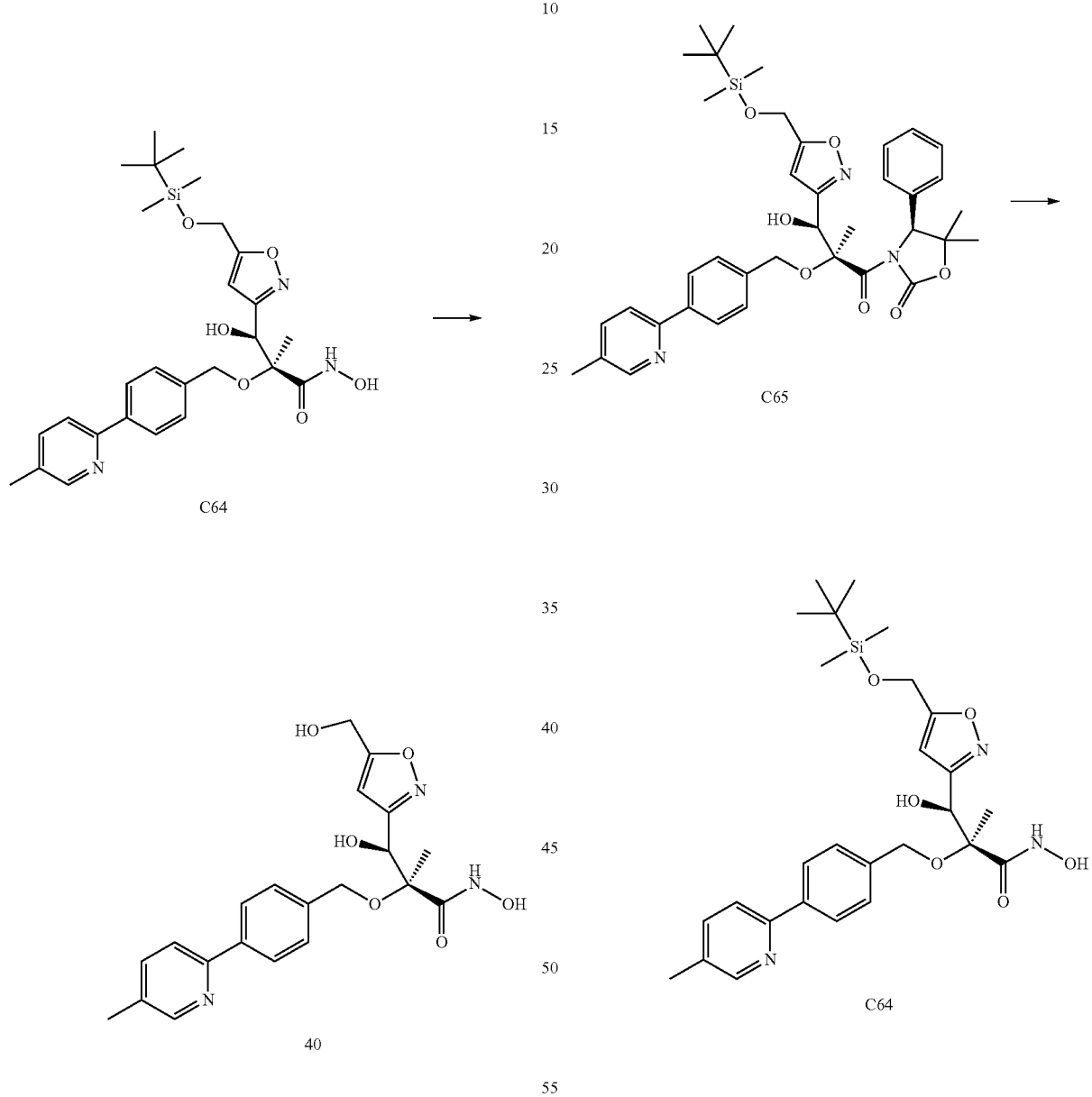

Step 1. Preparation of (4S)-3-[(2S,3S)-3-{5-[(tert-butyldimethylsilyloxy)methyl]isoxazol-3-yl}-3-hydroxy-2-methyl-2-{[4-(5-methylpyridin-2-yl)benzyl]oxy}propanoyl]-5,5-dimethyl-4-phenyl-1,3-oxazolidin-2-one (C65). Compound C65 was synthesized according to the general procedure for the synthesis of C8 in Example 1 except that C51 was used instead of propionaldehyde and C46 was used instead of C7 to provide C65 as a white solid. Yield: 220 mg, 49%. LCMS (APCI) m/z 686.3 (M+1).

Step 2. Preparation of (2S,3S)-3-{5-[(tert-butyldimethylsilyloxy)methyl]isoxazol-3-yl}-N,3-dihydroxy-2-methyl-2-{[4-(5-methylpyridin-2-yl)benzyl]oxy}propanamide (C64).

Compound C64 was synthesized according to the general procedure for the synthesis of 16 in Example 16 except that compound C65 was used instead of compound C23 to provide C64 as a white solid. Yield: 20 mg, 12%. MS (APCI) m/z 528.4 (M+1).

Step 3. Compound 40 was synthesized according to the general procedure for the synthesis of 34 in Example 34 except that compound C64 was used instead of compound C49 to provide 40 as a white solid. Yield: 16 mg, 100%. LCMS (APCI) m/z 414.3 (M+1).

Example 41

Preparation of (2S,3S)-N,3-dihydroxy-3-[5-(hydroxymethyl)isoxazol-3-yl]-2-methyl-2-({4-[5-(trifluoromethyl)pyridin-2-yl]benzyl}oxy)propanamide (41)

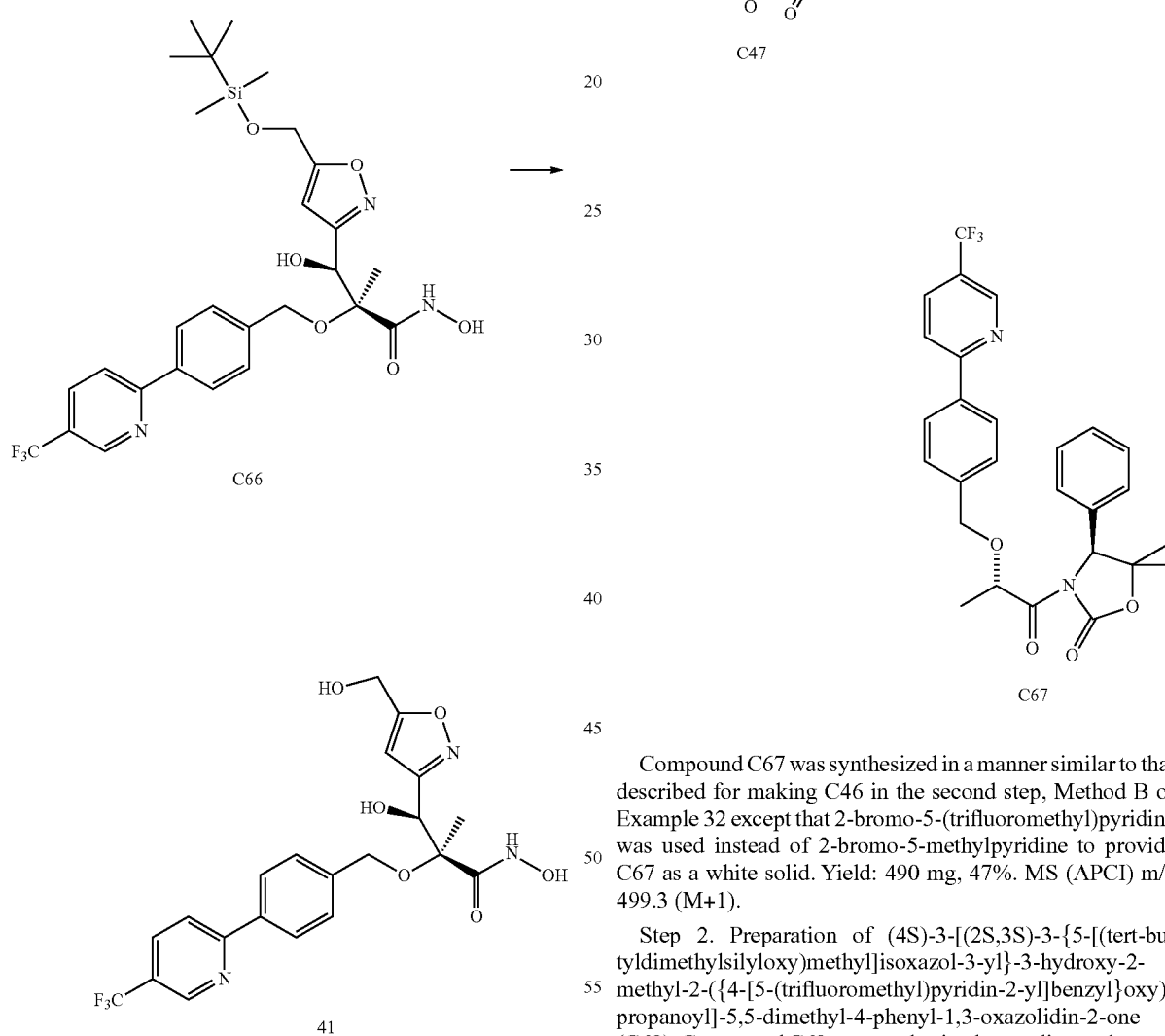

Step 1. Preparation of (4S)-5,5-dimethyl-4-phenyl-3-[(2S)-2-({4-[5-(trifluoromethyl)pyridin-2-yl]benzyl}oxy)propanoyl]-1,3-oxazolidin-2-one (C67).

Compound C67 was synthesized in a manner similar to that described for making C46 in the second step, Method B of Example 32 except that 2-bromo-5-(trifluoromethyl)pyridine was used instead of 2-bromo-5-methylpyridine to provide C67 as a white solid. Yield: 490 mg, 47%. MS (APCI) m/z 499.3 (M+1).

Step 2. Preparation of (4S)-3-[(2S,3S)-3-{5-[(tert-butyldimethylsilyloxy)methyl]isoxazol-3-yl}-3-hydroxy-2-methyl-2-({4-[5-(trifluoromethyl)pyridin-2-yl]benzyl}oxy)propanoyl]-5,5-dimethyl-4-phenyl-1,3-oxazolidin-2-one (C68). Compound C68 was synthesized according to the general procedure for the synthesis of C8 in Example 1 except that C51 was used instead of propionaldehyde and C67 was used instead of C7 to provide C68 as an inseparable mixture of starting material and product. The mixture was used without further purification. MS (APCI) m/z 740.5 (M+1).

Step 3. Preparation of (2S,3S)-3-{5-[(tert-butyldimethylsilyloxy)methyl]isoxazol-3-yl}-N,3-dihydroxy-2-methyl-2-({4-[5-(trifluoromethyl)pyridin-2-yl]benzyl}oxy)propanamide (C66).

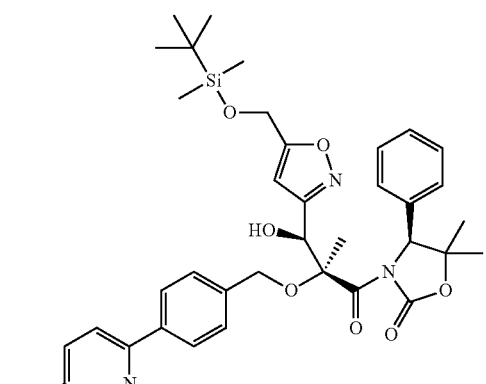

C68

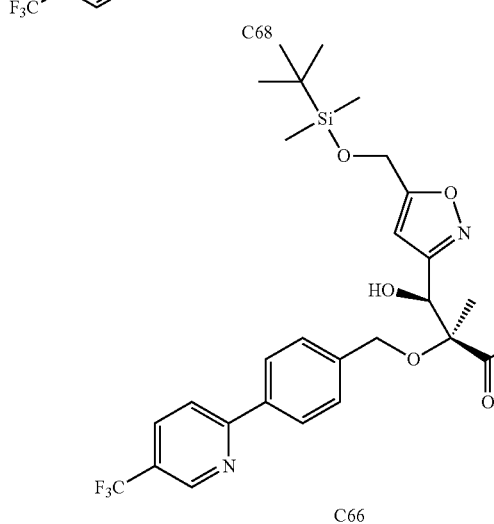

C66

Compound C66 was synthesized according to the general procedure for the synthesis of 16 in Example 16 except that compound C68 was used instead of compound C23 to provide C66 as a white solid. Yield: 50 mg, 32%. MS (APCI) m/z 582.3 (M+1).

Step 4. Compound 41 was synthesized according to the general procedure for the synthesis of 34 in Example 34 except that compound C66 was used instead of compound C49 to provide 41 as a white solid. Yield: 11 mg, 28%. LCMS (APCI) m/z 468.2 (M+1).

Example 42

Preparation of (2S,3S)-N,3-dihydroxy-3-[5-(hydroxymethyl)isoxazol-3-yl]-2-methyl-2-{[4'-(trifluoromethyl)biphenyl-4-yl]methoxy}propanamide (42)

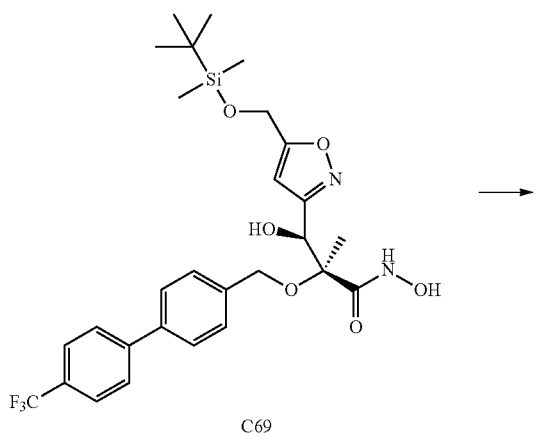

C69

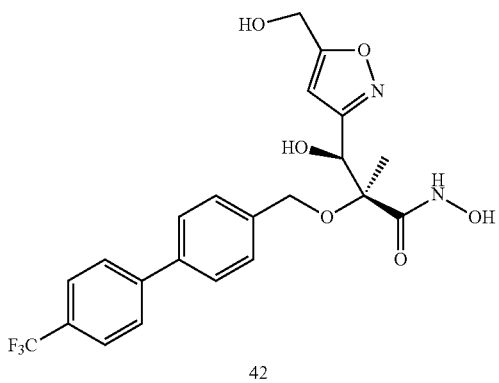

42

Step 1. Preparation of (4S)-5,5-dimethyl-4-phenyl-3-[(2S)-2-{[4'-(trifluoromethyl)biphenyl-4-yl]methoxy}propanoyl]-1,3-oxazolidin-2-one (C70).

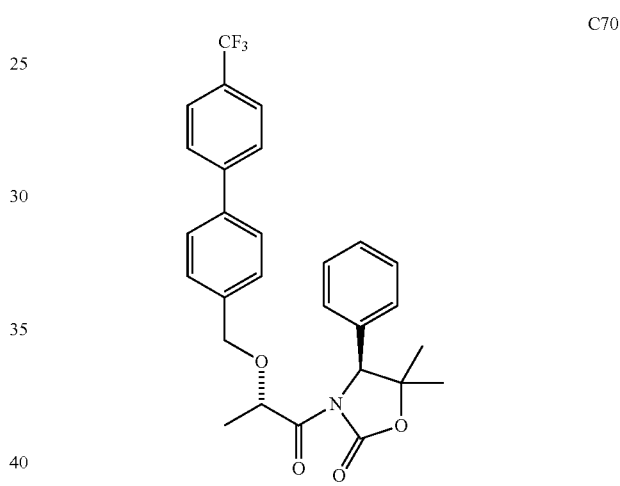

C70

Compound C70 was synthesized in a manner similar to that described for making compound C54 in Example 35 except that 4-(trifluoromethyl)phenylboronic acid was used instead of 4-fluorophenylboronic acid to provide C70 as a white solid. Yield: 1.76 g, 51%. MS (APCI) m/z 498.3 (M+1). $^1$H NMR (400 MHz, DMSO-$d_6$) δ 0.89 (3H, s), 1.39 (3H, d, J=6.4 Hz), 1.61 (3H, s), 4.42 (2H, s), 5.24 (2H, m), 7.27 (2H, m), 7.40 (5H, m), 7.72 (2H, d, J=8.4 Hz), 7.81 (2H, d, J=8.2 Hz), 7.89 (2H, d, J=8.2 Hz).

Step 2. Preparation of (4S)-3-[(2S,3S)-3-{5-[(tert-butyldimethylsilyloxy)methyl]isoxazol-3-yl}-3-hydroxy-2-methyl-2-{[4'-(trifluoromethyl)biphenyl-4-yl]methoxy}propanoyl]-5,5-dimethyl-4-phenyl-1,3-oxazolidin-2-one (C71). Compound C71 was synthesized according to the general procedure for the synthesis of C8 in Example 1 except that C51 was used instead of propionaldehyde and C70 was used instead of C7 to provide C71 as a white solid. Yield: 530 mg, 33%. MS (APCI) m/z 739.6 (M+1).

Step 3. Preparation of (2S,3S)-3-{5-[(tert-butyldimethylsilyloxy)methyl]isoxazol-3-yl}-N,3-dihydroxy-2-methyl-2-{[4'-(trifluoromethyl)biphenyl-4-yl]methoxy}propanamide (C69).

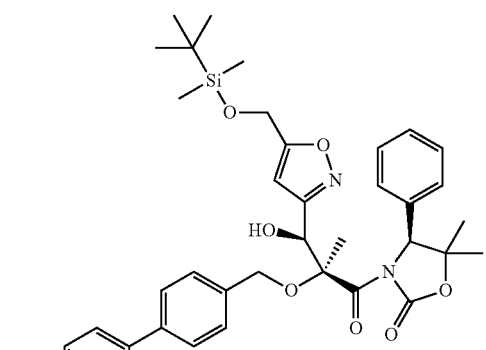

C71

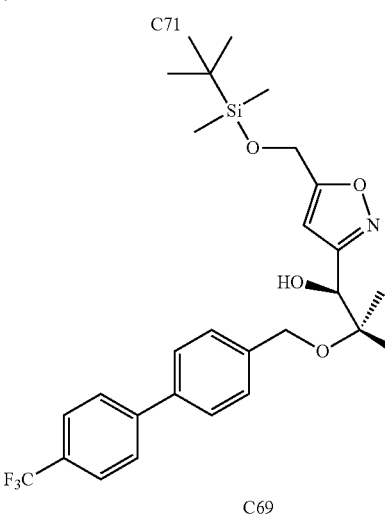

C69

Compound C69 was synthesized according to the general procedure for the synthesis of 16 in Example 16 except that compound C71 was used instead of compound C23 to provide C69 as a white solid. Yield: 40 mg, 10%. MS (APCI) m/z 581.4 (M+1).

Step 4. Compound 42 was synthesized according to the general procedure for the synthesis of 34 in Example 34 except that compound C69 was used instead of compound C49 to provide 42 as a white solid. Yield: 22 mg, 69%. LCMS (APCI) m/z 467.2 (M+1).

Example 43

Preparation of (2S,3S)-2-(biphenyl-4-ylmethoxy)-N,3-dihydroxy-2-methyl-3-[5-(methylsulfonyl)isoxazol-3-yl]propanamide (43)

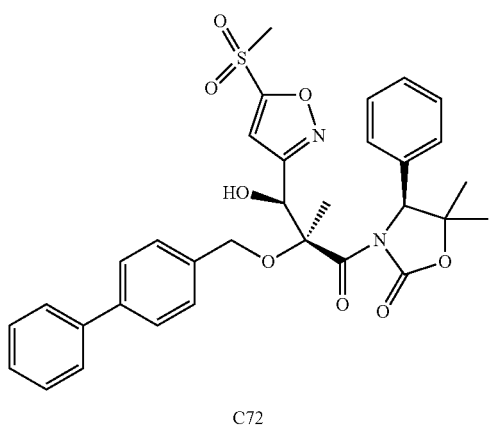

C72

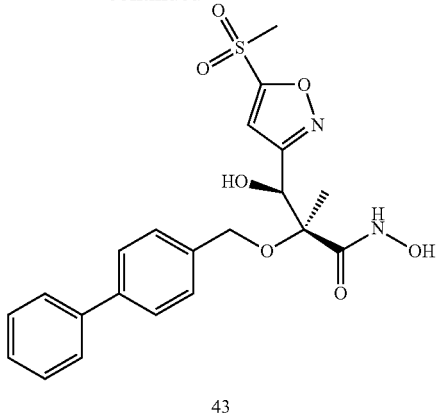

43

Step 1. Preparation of 5-(methylthio)isoxazole-3-carbaldehyde (C73). Compound C74 was prepared according to the procedure depicted in Scheme 9 and described in detail below.

Scheme 9

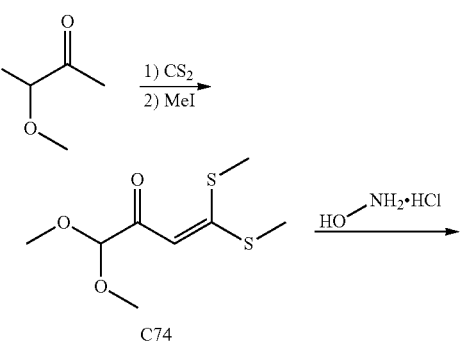

C74

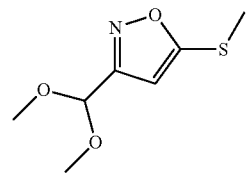

C75

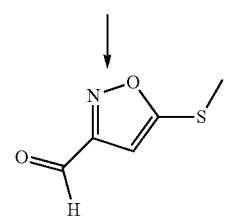

C73

A. Preparation of 1,1-dimethoxy-4,4-bis(methylthio)but-3-ene-2-one (C74). A suspension of sodium hydride (60% dispersion in mineral oil, 6.77 g, 169 mmol) in tetrahydrofuran (200 mL) under an atmosphere of nitrogen gas was cooled to 0° C., treated with a solution of carbon disulfide (5.1 mL, 84.7 mmol) in tetrahydrofuran (200 mL), and stirred for 20 minutes. The reaction mixture was then treated with a solution of pyruvaldehyde dimethyl acetal (10 g, 84.7 mmol) in tetrahydrofuran (200 mL) over 30 minutes at 0° C. followed by stirred at 25° C. for 7 hours. The reaction mixture was then cooled to 0° C., treated with a solution of methyl iodide (13.2 mL, 212 mmol) in tetrahydrofuran (200 mL), and stirred for another 6 hours. The reaction mixture was then poured into an aqueous solution of ammonium chloride (400 mL) and extracted with dichloromethane (3×300 mL). The combined organic extracts were then washed with water (3×200 mL), dried over sodium sulfate, and concentrated under reduced pressure. The resultant residue was purified by silica gel chromatography (isocratic; heptane:ethyl acetate 9:1, visualized with ceric ammonium molybdate stain) to provide C74 as a clear oil. Yield: 10.26 g, 55%. $^1$H NMR (400 MHz, CDCl$_3$) δ 2.50 (6H, s), 3.43 (6H, s), 4.57 (1H, s), 6.39 (1H, s).

B. Preparation of 3-(dimethoxymethyl)-5-(methylthio) isoxazole (C75). A suspension of C74 (10.26 g, 46.15 mmol), hydroxylamine hydrochloride (4.81 g, 69.2 mmol), and potassium hydroxide (3.90 g, 69.2 mmol) in ethanol (230 mL) was heated at reflux for about 18 hours. The reaction mixture was then concentrated under reduced pressure, diluted with water, and extracted with dichloromethane (3×). The combined extracts were washed with water (2×), dried over sodium sulfate, and concentrated. The resultant residue was purified by silica gel chromatography (gradient: 9:1 heptane: ethyl acetate to 6:4 heptane:ethyl acetate) to provide C75 as a clear oil. Yield: 2.54 g, 29%. $^1$H NMR (400 MHz, CDCl$_3$) δ 2.59 (3H, s), 3.43 (6H, s), 5.43 (1H, s), 6.14 (1H, s).

C. A solution of C75 (1.37 g, 7.24 mmol) in ethanol (10 mL) was treated with 1 N hydrochloric acid (20 mL) and heated at 60° C. for about 18 hours. The resultant solution was then cooled, neutralized with saturated aqueous sodium bicarbonate solution, and extracted with ethyl acetate (3×). The combined organic extracts were then dried over sodium sulfate and concentrated. The resultant residue was purified by silica gel chromatography (gradient: 95:5 heptane:ethyl acetate to 80:20 heptane:ethyl acetate) to provide C73 as a clear oil. Yield: 600 mg, 58%. $^1$H NMR (400 MHz, CDCl$_3$) δ 2.64 (3H, s), 6.45 (1H, s), 10.10 (1H, s).

Step 2. Preparation of (4S)-3-{(2S,3S)-2-(biphenyl-4-yl-methoxy)-3-hydroxy-2-methyl-3-[5-(methylthio)isoxazol-3-yl]propanoyl}-5,5-dimethyl-4-phenyl-1,3-oxazolidin-2-one (C76).

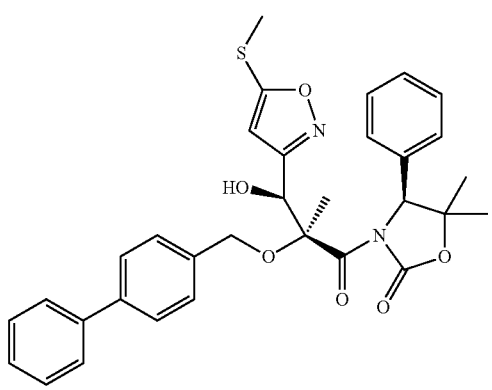

C76

Compound C76 was synthesized according to the general procedure for the synthesis of C8 in Example 1 except that C73 was used instead of propionaldehyde to provide C76 as a white solid. Yield: 460 mg, 38%. MS (APCI) m/z 573.3 (M+1).

Step 3. Preparation of (4S)-3-{(2S,3S)-2-(biphenyl-4-yl-methoxy)-3-hydroxy-2-methyl-3-[5-(methylsulfonyl)isox-azol-3-yl]propanoyl}-5,5-dimethyl-4-phenyl-1,3-oxazolidin-2-one (C72). A solution of C76 (460 mg, 0.80 mmol) in dichloromethane (32 mL) was treated with meta-chloroperbenzoic acid (<80%, 695 mg, 3 mmol) and stirred at 25° C. for 18 hours. The resultant solution was then treated with aqueous sodium bisulfite solution (20% w/v, 150 mL) and extracted into dichloromethane (3×). The combined organic extracts were washed with saturated aqueous sodium bicarbonate solution and saturated aqueous sodium chloride solution. The organic solution was dried over sodium sulfate, and concentrated under reduced pressure. The resultant residue was purified by silica gel chromatography (gradient: 9:1 heptane:ethyl acetate to 1:1 heptane:ethyl acetate) to provide C72 as a white solid. Yield: 330 mg, 68%. LCMS (APCI) m/z 605.2 (M+1).

Step 4. Compound 43 was synthesized according to the general procedure for the synthesis of 1 in Example 1 except that C72 was used instead of C8 to provide 43 as a white solid (107 mg, 44%): MS (APCI) m/z 447.2 (M+1). $^1$H NMR (400 MHz, DMSO-d$_6$) δ 1.44 (3H, s), 3.50 (3H, s), 4.55 (1H, d, J=12.0 Hz), 4.64 (1H, d, J=12.0 Hz), 5.14 (1H, d, J=5.8 Hz), 6.38 (1H, d, J=5.8 Hz), 7.12 (1H, s), 7.37 (1H, m), 7.45 (4H, m), 7.63 (4H, m), 8.87 (1H, d, J=1.6 Hz), 10.61 (1H, s).

Example 44

Preparation of (2S,3S)-2-[(4'-fluorobiphenyl-4-yl) methoxy]-N,3-dihydroxy-2-methyl-3-[5-(methylsulfinyl)isoxazol-3-yl]propanamide (44)

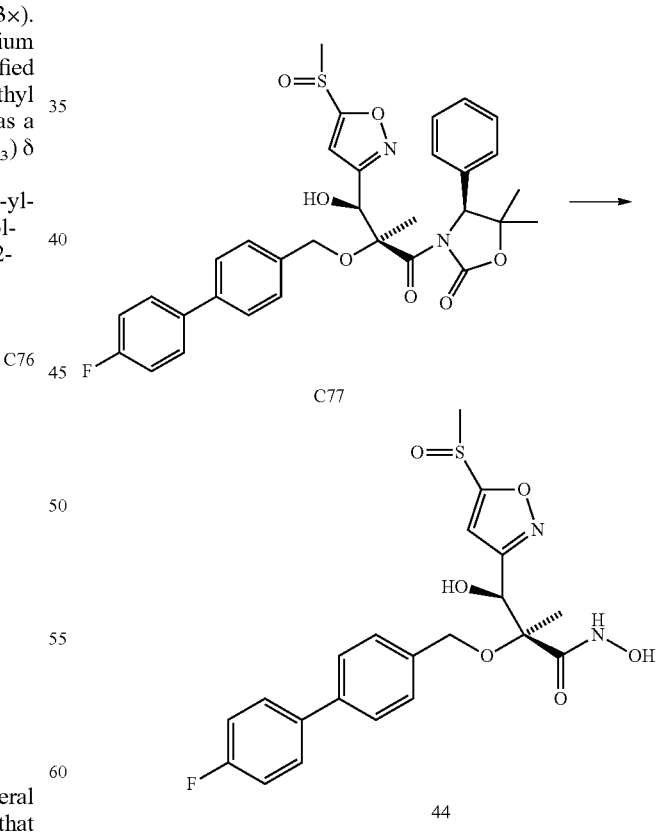

Step 1. Preparation of (4S)-3-{(2S,3S)-2-[(4'-fluorobiphenyl-4-yl)methoxy]-3-hydroxy-2-methyl-3-[5-(methylthio) isoxazol-3-yl]propanoyl}-5,5-dimethyl-4-phenyl-1,3-oxazolidin-2-one (C78).

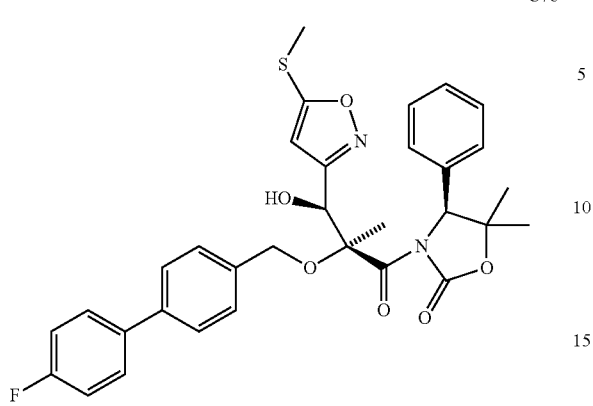

C78

Compound C78 was synthesized according to the general procedure for the synthesis of C8 in Example 1 except that C73 was used instead of propionaldehyde and C54 was used instead of C7 to provide C78 as a white solid. Yield: 690 mg, 37%. MS (APCI) m/z 591.3 (M+1).

Step 2. (4S)-3-{(2S,3S)-2-[(4'-fluorobiphenyl-4-yl)methoxy]-3-hydroxy-2-methyl-3-[5-(methylsulfinyl)isoxazol-3-yl]propanoyl}-5,5-dimethyl-4-phenyl-1,3-oxazolidin-2-one (C77). A solution of C78 (690 mg, 1.17 mmol) and 3-phenyl-2-(phenylsulfonyl)-1,2-oxaziridine (336 mg, 1.28 mmol) in chloroform (12 mL) was stirred under nitrogen atmosphere at 25° C. for about 18 hours. The reaction mixture was then concentrated onto silica gel and purified by chromatography (gradient: 20:80 ethyl acetate:heptane to 80:20 ethyl acetate:heptane) to provide C77 as a white solid. Yield: 560 mg, 79%. MS (APCI) m/z 607.4 (M+1).

Step 3. Compound 44 was synthesized according to the general procedure for the synthesis of 1 in Example 1 except that C77 was used instead of C8 to provide 44 as a white solid. Yield: 205 mg, 50%. MS (APCI) m/z 449.2 (M+1). $^1$H NMR (400 MHz, DMSO-d$_6$) δ 1.43 (3H, s), 3.04 (3H, s), 4.53 (1H, d, J=12.0 Hz), 4.61 (1H, d, J=12.0 Hz), 5.12 (1H, brs), 6.29 (1H, brs), 6.96 (1H, d, J=3.3 Hz), 7.28 (2H, m), 7.42 (2H, d, J=8.0 Hz), 7.59 (2H, d, J=8.4 Hz), 7.69 (2H, dd, J=8.8, 5.5 Hz), 8.86 (1H, br s), 10.58 (1H, br s).

Example 45

Preparation of (2S,3S)-2-(biphenyl-4-ylmethoxy)-N,3-dihydroxy-2-methyl-3-(1H-pyrazol-3-yl)propanamide (45)

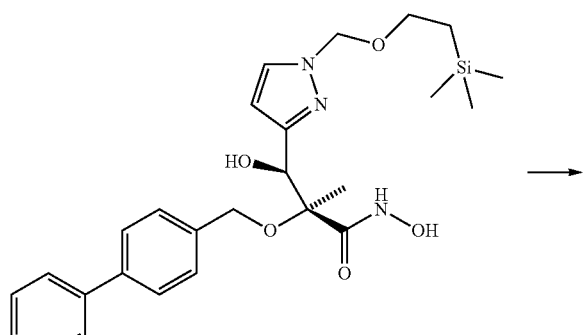

C79

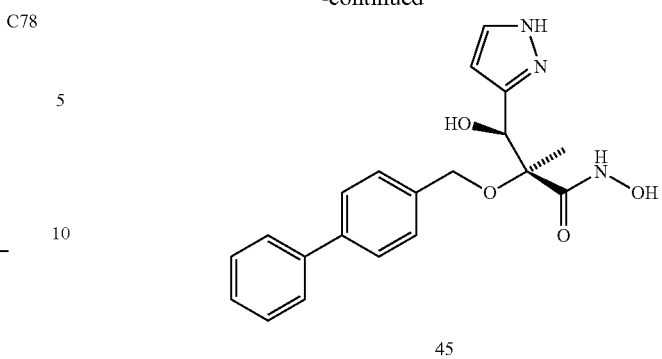

45

Step 1. Preparation of 1-{[2-(trimethylsilyl)ethoxy]methyl}-1H-pyrazole-3-carbaldehyde (C80).

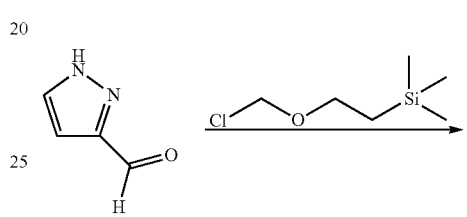

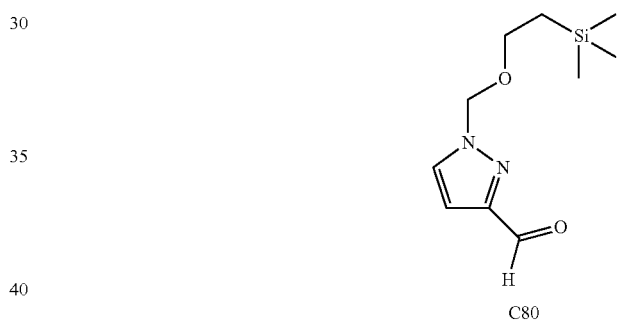

C80

Sodium hydride (60% dispersion in mineral oil, 0.668 g, 16.7 mmol) was added to dimethylformamide (45 mL) at 25° C., and the mixture was stirred for 10 minutes. A solution of 1H-pyrazole-3-carbaldehyde (1.46 g, 15.2 mmol) in dimethylformamide (10 mL) was added to the reaction mixture over 15 minutes, and the reaction was allowed to stir for an additional 15 minutes. The mixture was cooled to 0° C. and treated with 2-(trimethylsilyl)ethoxymethyl chloride (2.96 mL, 15.2 mmol) drop-wise over 10 minutes, after which the solution was warmed to 25° C. and stirred for 2 hours. The reaction mixture was poured into aqueous sodium bicarbonate solution (5% solution, 50 mL) that had been pre-cooled to 0° C., and the resulting mixture was extracted with diethyl ether (3×). The combined organic layers were dried over magnesium sulfate and concentrated; the crude product was purified by silica gel chromatography (gradient: hexanes to 30% ethyl acetate in hexanes) to provide C80 as a clear liquid. Yield: 3.5 g, quantitative as a mixture of regioisomers. MS (APCI) m/z 227.26 (M+1).

Step 2. Preparation of (4S)-3-[(2S,3S)-2-(biphenyl-4-ylmethoxy)-3-hydroxy-2-methyl-3-(1-{[2-(trimethylsilyl)ethoxy]methyl}-1H-pyrazol-3-yl)propanoyl]-5,5-dimethyl-4-phenyl-1,3-oxazolidin-2-one (C81).

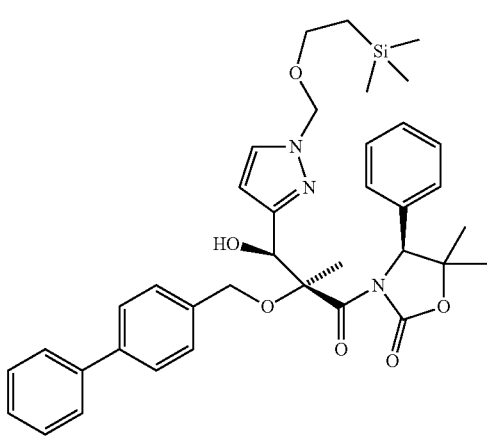

C81

Compound C81 was synthesized according to the general procedure for the synthesis of C8 in Example 1, except that C80 was used instead of propionaldehyde to provide C81 as a clear foam. Yield: 296 mg, 19%. MS (APCI) m/z 656.50 (M+1).

Step 3. Preparation of (2S,3S)-2-(biphenyl-4-ylmethoxy)-N,3-dihydroxy-2-methyl-3-(1-{[2-(trimethylsilyl)ethoxy]methyl}-1H-pyrazol-3-yl)propanamide (C79).

Compound C79 was synthesized according to the general procedure for the synthesis of 16 in Example 16 except that compound C81 was used instead of compound C23 to provide C79 as a clear gum. Yield: 16 mg, 43%. MS (APCI) m/z 498.39 (M+1). ¹H NMR (400 MHz, DMSO-d₆) δ −0.08 (9H, s), 0.78 (2H, m), 1.30 (3H, s), 3.46 (2H, m), 4.34 (1H, d, J=11.5 Hz), 4.41 (1H, d, J=11.5 Hz), 5.10 (1H, d, J=11.1 Hz), 5.16 (1H, bd, J=5.5 Hz), 5.7 (1H, d, J=11.1 Hz), 5.84 (1H, bd, J=5.5 Hz), 6.30 (1H, d, J=1.7 Hz), 7.38 (6H, m), 7.6 (4H, m), 8.84 (1H, br s), 10.7 (1H, v br s).

Step 4. A solution of compound C79 (80 mg, 0.16 mmol) in ethanol (5 mL) was treated with aqueous hydrochloric acid (3 N, 5 mL) and heated at 50° C. for about 18 hours. The reaction mixture was cooled to 25° C., neutralized with aqueous sodium bicarbonate solution, and concentrated onto silica gel. The resultant residue was then purified by chromatography (isocratic: 84:15:1 dichloromethane:methanol:triethylamine) to provide 45 as an off-white residue. Yield: 3.2 mg, 5%. MS (APCI) m/z 368.1 (M+1).

Example 46

Preparation of (2S,3S)-N,3-dihydroxy-3-[5-(hydroxymethyl)-2-furyl]-2-methyl-2-{[4'-(1,3-oxazol-5-yl)biphenyl-4-yl]methoxy}propanamide (46)

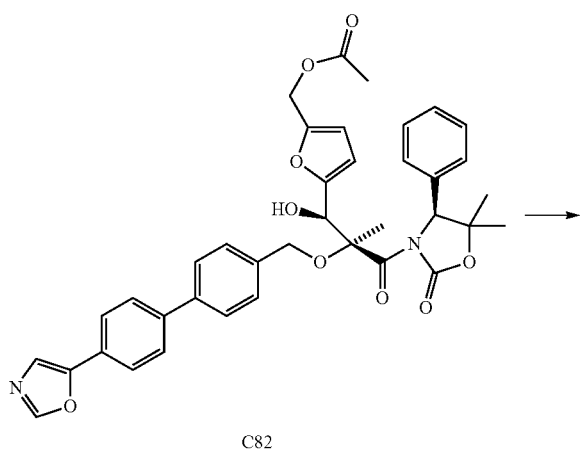

C82

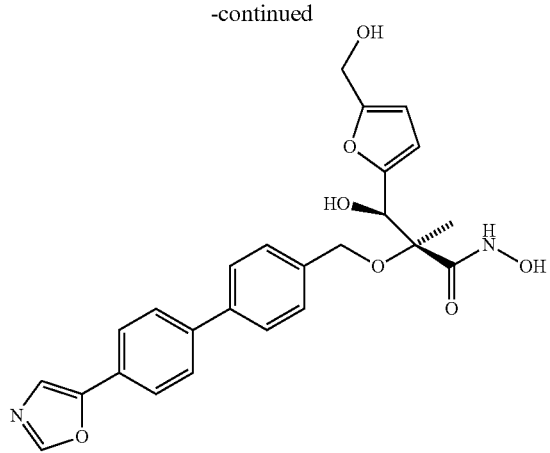

46

Step 1. Preparation of (4S)-5,5-dimethyl-3-[(2S)-2-{[4'-(1,3-oxazol-5-yl)biphenyl-4-yl]methoxy}propanoyl]-4-phenyl-1,3-oxazolidin-2-one (C83). Compound C83 was prepared by the method depicted in Scheme 10 and described in detail below:

Scheme 10

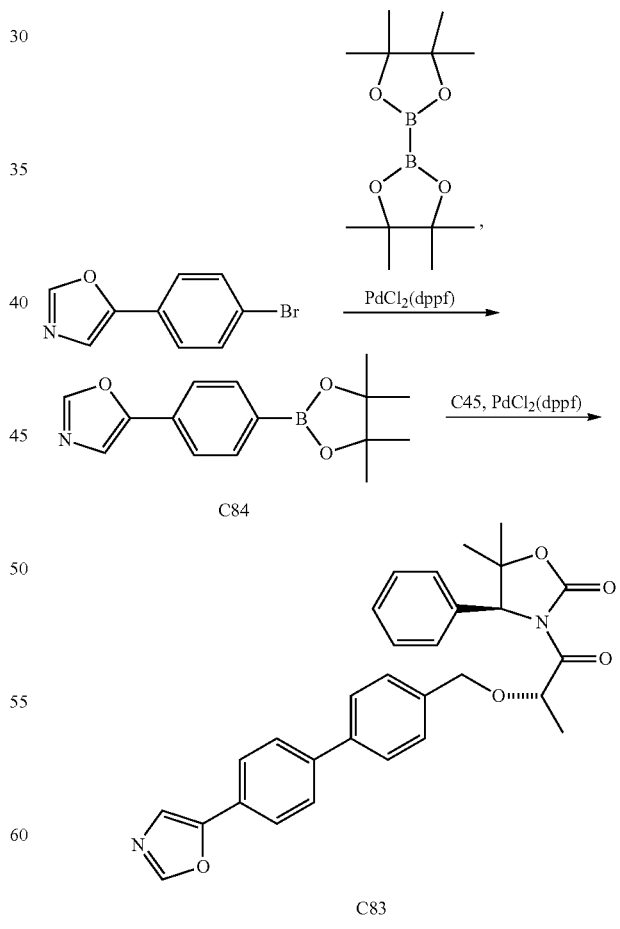

C83

A. Preparation of 5-[4-(4,4,5,5-tetramethyl-1,3,2-dioxaborolan-2-yl)phenyl]-1,3-oxazole (C84). A solution of 5-(4-bromophenyl)-1,3-oxazole (3.0 g, 13.4 mmol), pinacol diborane (4.42 g, 17.4 mmol) and potassium acetate (3.94 g, 40.2 mmol) in anhydrous dioxane (100 mL) was treated with the methylene chloride adduct of 1,1'-[bis(diphenylphosphino) ferrocene]dichloropalladium(II) (PdCl$_2$(dppf).CH$_2$Cl$_2$, 553 mg, 0.67 mmol). The mixture was purged with nitrogen and heated at 90° C. for 2 hours. The reaction mixture was then concentrated onto silica gel, and the resultant residue was purified by chromatography (gradient: 95:5 heptane:ethyl acetate to 80:20 heptane:ethyl acetate) to provide C84 as a white solid. Yield: 3.63 g, 100%. LCMS (APCI) m/z 272.3 (M+1). $^1$H NMR (400 MHz, CDCl$_3$) δ 1.37 (12H, s), 7.42 (1H, s), 7.66 (2H, d, J=8.2 Hz), 7.87 (2H, d, J=8.2 Hz), 7.94 (1H, s).

B. Preparation of compound C83. A mixture of C84 (1.90 g, 4.40 mmol), C45 (1.31 g, 4.83 mmol), potassium acetate (1.29 g, 13.2 mmol), and potassium fluoride (766 mg, 13.2 mmol) in dimethylformamide (20 mL) was purged with nitrogen gas for 2 minutes and treated with the methylene chloride adduct of 1,1'-[bis(diphenylphosphino)ferrocene]dichloropalladium(II) (PdCl$_2$(dppf).CH$_2$Cl$_2$, 363 mg, 0.44 mmol). The mixture was purged with nitrogen for another minute and then heated at 90° C. for about 18 hours. The reaction mixture was then partitioned between ethyl acetate and water, and the organic phase was collected. The aqueous phase was extracted once more with ethyl acetate. The combined organic fractions were washed with water (2×) and saturated aqueous sodium chloride solution (1×) and dried over sodium sulfate. The organics were concentrated onto silica gel, and the resultant residue was purified by chromatography to provide C83 as a white solid. Yield: 1.03 g, 47%. $^1$H NMR (400 MHz, DMSO-d$_6$) δ 0.84 (3H, s), 1.33 (3H, d, J=6.4 Hz), 1.55 (3H, s), 4.36 (2H, br s), 5.19 (2H, br s), 5.70 (2H, s), 7.30 (8H, m), 7.76 (6H, m), 8.42 (1H, br s).

Step 2. Preparation of {5-[(1S,2S)-3-[(4S)-5,5-dimethyl-2-oxo-4-phenyl-1,3-oxazolidin-3-yl]-1-hydroxy-2-methyl-2-{[4'-(1,3-oxazol-5-yl)biphenyl-4-yl]methoxy}-3-oxopropyl]-2-furyl}methyl acetate (C82). A solution of lithium diisopropylamide in heptane/tetrahydrofuran/ethylbenzene (2.0 M, 0.71 mL) was cooled to –78° C. and treated with a cold solution (–78° C.) of compound C83 (500 mg, 1.01 mmol) in tetrahydrofuran (5 mL). The reaction mixture was stirred at –78° C. for an additional 30 minutes and slowly treated with chlorotitanium triisopropoxide (1 M in hexanes, 4.05 mL). The reaction mixture was then stirred at –40° C. for an additional 1 hour. The reaction mixture was cooled to –78° C. and slowly treated with a solution of (5-formylfuran-2-yl)methyl acetate (220 mg, 1.31) in tetrahydrofuran (2 mL). The mixture was then warmed to –40° C. and stirred for an additional 2 hours. The reaction mixture was quenched with saturated aqueous ammonium chloride solution, diluted with tetrahydrofuran (10 mL), stirred with Celite for 1 hour, and filtered. The resultant filtrate was concentrated, and the residue was purified by silica gel chromatography (gradient: 95:5 hexane:ethyl acetate to 65:35 hexane:ethyl acetate) to provide C82 as a white solid. Yield: 51 mg, 8%. MS (APCI) m/z 665.5 (M+1).

Step 3. A suspension of hydroxylamine hydrochloride (21 mg, 0.31 mmol) in methanol (2 mL) was cooled to –20° C. and treated drop-wise with a solution of methylmagnesium bromide in tetrahydrofuran (1.4 M, 0.44 mL). The mixture was then stirred and sonicated until a solution formed. The chilled solution (–20° C.) was then treated drop-wise with stirring with a solution of compound C82 (51 mg, 0.077 mmol) in methanol (2 mL). The reaction mixture was allowed to warm to 25° C. and stirred for an additional 1 hour to allow cleavage of the acetate. The reaction mixture was then diluted with saturated aqueous ammonium chloride solution and concentrated onto silica gel. The resultant residue was purified by chromatography (gradient: dichloromethane to 9:1 dichloromethane:methanol) to provide 46 as a white solid. Yield: 7 mg, 20%. LCMS (APCI) m/z 463.1 (M–1).

Example 47

Preparation of trisodium {3-[(1S,2S)-2-(biphenyl-4-ylmethoxy)-1-hydroxy-2-methyl-3-(oxidoamino)-3-oxopropyl]isoxazol-5-yl}methyl phosphate (47)

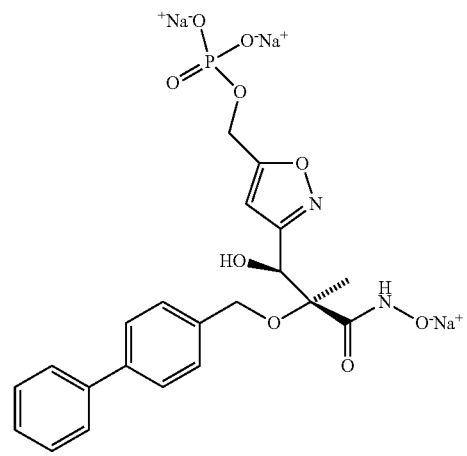

Compound 47 was prepared by the procedure depicted in Schemes 11 and 12 and described in detail below.

Step 1. Synthesis of di-tert-butyl phosphorochloridate (C85). A mixture of CCl$_4$ (22 mL), 20% aqueous sodium hydroxide (22 mL) and benzyltriethylammonium chloride (0.36 g, 1.58 mmol) was treated with a solution of di-tert-butyl phosphonate (7.0 g, 36.08 mmol) in dichloromethane (10 mL) at a rate such that the temperature of the reaction mixture was maintained between 20 and 25° C. The reaction mixture was allowed to stir for 4 hours at 25° C. then treated with dichloromethane (50 mL). The resultant organic phase was collected, washed with water (30 mL×4), dried over sodium sulfate, and concentrated to provide C85 as a thick colorless oil. Yield: 6.2 g, 75%. $^1$H-NMR (400 MHz, CDCl$_3$) δ 1.57 (s, 18H).

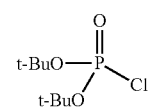

Step 2. Synthesis of (3-{(1S,2S)-2-(biphenyl-4-ylmethoxy)-3-[(4S)-5,5-dimethyl-2-oxo-4-phenyl-1,3-oxazolidin-3-yl]-1-hydroxy-2-methyl-3-oxopropyl}isoxazol-5-yl) methyl di-tert-butyl phosphate (C86). Compound C86 was prepared by the procedure depicted in Scheme 11 below:

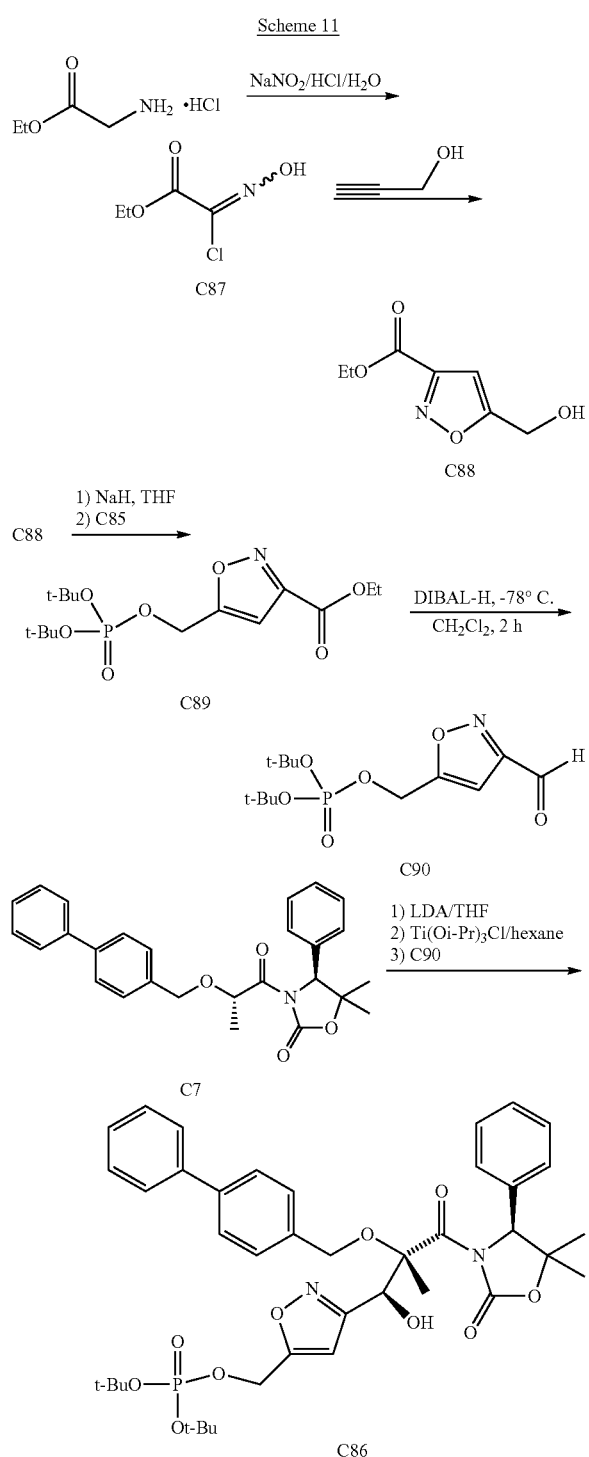

Scheme 11

A. Synthesis of ethyl chloro(hydroxyimino)acetate (C87). Ethyl 2-aminoacetate hydrochloride (40 g, 286.57 mmol) was added to a solution of water (54 mL) and concentrated hydrochloric acid (36 mL) and the reaction was cooled to −5° C. The solution was then treated drop-wise with a solution of sodium nitrite (19.77 g, 286.57 mmol) in water (36 mL) while maintaining the reaction temperature below −5° C. The mixture was stirred for 0.5 h and treated with another portion of concentrated hydrochloric acid (36 mL) followed by the drop-wise addition of a solution of sodium nitrite (19.77 g, 286.57 mmol) in water (36 mL). The reaction was further stirred for 2 h at −5° C. The mixture was then extracted with diethyl ether (400 mL). The resultant organic layer was collected, washed with water (100 mL), saturated aqueous sodium chloride solution (50 mL), dried over sodium sulfate and concentrated. The resultant residue was recrystallized from hexanes to provide C87 as a white solid. Yield: 19.10 g, 44%. $^1$H-NMR (400 MHz, CDCl$_3$) δ 9.76 (1H, br. s), 4.41 (2H, q), 1.40 (3H, t).

B. Synthesis of ethyl 5-(hydroxymethyl)isoxazole-3-carboxylate (C88). A solution of compound C87 (19.00 g, 126.0 mmol) in dichloromethane (200 mL) at 0° C. was treated drop-wise with prop-2-yn-1-ol (7.06 g, 126.0 mmol), followed by the drop-wise addition of triethylamine (12.73 g, 126.0 mmol). The resultant mixture was stirred at 25° C. for about 18 hours. The mixture was then washed with water (50 mL), dried over sodium sulfate and concentrated. The resultant residue was purified by silica gel chromatography (isocratic; eluting with 1:1 ethyl acetate:hexanes) to provide C88 as a light orange oil. Yield: 8.98 g, 42%. $^1$H-NMR (400 MHz, CDCl$_3$) δ 6.63 (1H, s), 4.82 (2H, s), 4.42 (2H, q), 2.79 (1H, br. s), 1.40 (3H, t).

C. Synthesis of ethyl 5-{[(di-tert-butoxyphosphoryl)oxy]methyl}isoxazole-3-carboxylate (C89). A solution of C88 (2.04 g, 11.92 mmol) in tetrahydrofuran (25 mL) at 0° C. was treated with sodium hydride (0.43 g, 17.88 mmol) and stirred for 0.5 h at 25° C. The mixture was treated with C85 (3.81 g, 16.69 mmol) and stirred at 25° C. for about 18 hours. The mixture was then extracted with ethyl acetate (150 mL). The resultant organic phase was collected and washed with water (30 mL), saturated aqueous sodium chloride solution (30 mL), dried over sodium sulfate, and concentrated. The resultant residue was purified by chromatography (silica gel pretreated with Et$_3$N, eluting with 1:1 ethyl acetate:hexanes) to provide C89 as a thick, light golden oil. Yield: 3.90 g, 90%. $^1$H-NMR (400 MHz, CDCl$_3$) δ 6.75 (1H, s), 5.07 (2H, d), 4.43 (2H, q), 1.47 (18H, s), 1.40 (3H, t).

D. Synthesis of di-tert-butyl (3-formylisoxazol-5-yl)methyl phosphate (C90). A solution of C89 (2 g, 5.50 mmol) in dichloromethane (35 mL) was cooled to −78° C. and treated drop-wise with a 1 M solution of diisobutylaluminum hydride (DIBAL-H, 16.50 mL, 16.50 mmol). The mixture was stirred for 2 hours at −78° C. then quenched with water at −78° C. The mixture was then treated with saturated aqueous ammonium chloride solution (50 mL), stirred for 1.5 hour at 25° C., and filtered through Celite. The organic layer was collected, dried over sodium sulfate, and concentrated. The resultant residue was purified by silica gel chromatography (isocratic; eluting with 1:1 Et$_2$O:hexanes) to provide C90 as a thick, light yellow oil. Yield: 1.20 g, 66%. $^1$H-NMR (400 MHz, CDCl$_3$) δ 10.18 (1H, s), 6.74 (1H, s), 5.11 (2H, d), 1.48 (18H, s).

E. A solution of C7 (2.32 g, 5.40 mmol) in tetrahydrofuran (20 mL) was cooled to −78° C., treated drop-wise with a 2M solution of lithium diisopropylamide in heptane/tetrahydrofuran/ethylbenzene (3.10 mL, 6.20 mmol), and stirred for 45 minutes at −78° C. The mixture was held at −78° C. and treated with a 1M solution of chlorotitanium triisopropoxide in hexanes (8.10 mL, 8.10 mmol). The reaction mixture was stirred for 0.5 hours as the temperature was allowed to rise to −50° C. The mixture was then treated with a solution of compound C90 (0.86 g, 2.70 mmol) in tetrahydrofuran (2 mL). The mixture was stirred for 1 hour as the temperature was allowed to rise to 0° C. The mixture was then quenched with saturated aqueous ammonium chloride solution (20 mL), treated with an additional amount of ethyl acetate (100 mL), and filtered through a pad of Celite. The organic layer was collected, washed with saturated aqueous sodium chloride solution (20 mL), dried over sodium sulfate, and concentrated. The resultant residue was purified by column chromatography (silica pre-treated with Et₃N, eluting with 1:1 hexanes:ethyl acetate) to provide C86 as a white foam. Yield: 0.66 g, 33%. ¹H-NMR (400 MHz, CDCl₃) δ 7.57 (4H, m), 7.47-7.32 (8H, m), 7.18 (2H, m), 6.26 (1H, s), 6.00 (1H, d), 5.08 (1H, s), 4.97 (2H, d), 4.83 (1H, d), 4.53 (1H, d), 3.58 (1H, d), 1.84 (3H, s), 1.61 (3H, s), 1.58 (18H, s).

Step 3. Compound C86 was converted to 47 using the procedure depicted in Scheme 12 and described below.

Scheme 12

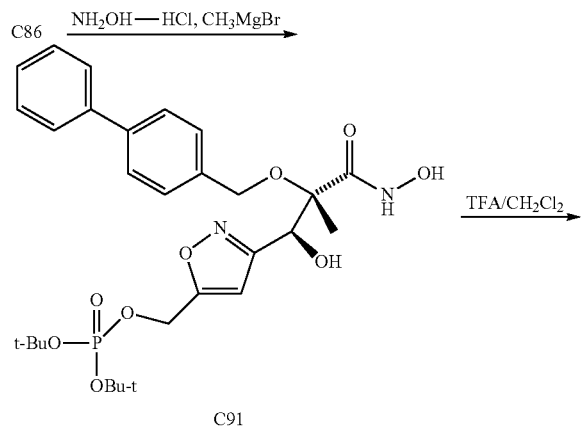

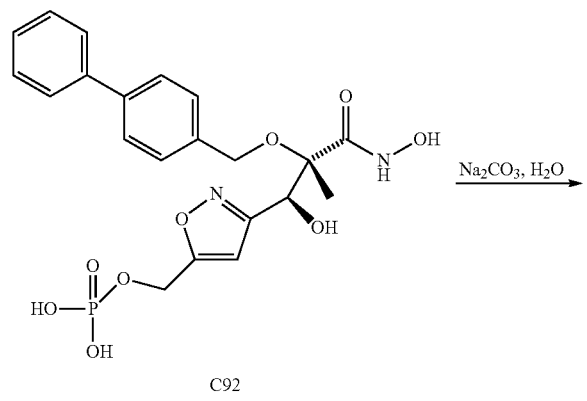

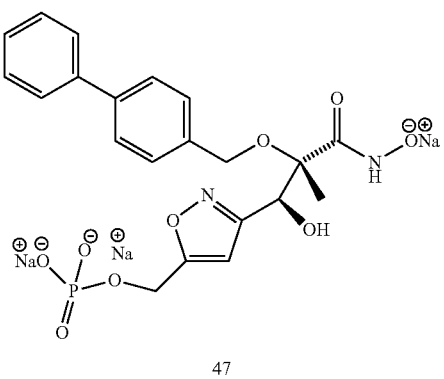

47

A. Synthesis of {3-[(1S,2S)-2-(biphenyl-4-ylmethoxy)-1-hydroxy-3-(hydroxyamino)-2-methyl-3-oxopropyl]isoxazol-5-yl}methyl di-tert-butyl phosphate (C91). A solution of hydroxylamine hydrochloride (0.15 g, 2.20 mmol) in methanol (30 mL) was cooled to 0° C., treated drop-wise with a 3M solution of methylmagnesium bromide in diethyl ether (1.17 mL, 3.52 mmol), and stirred for 15 minutes at 25° C. In a separate flask a solution of C86 (0.66 g, 0.88 mmol) in methanol (10 mL) was cooled to 0° C. and treated drop-wise with the hydroxylamine solution. The mixture was stirred for 3 hours at 0° C. and concentrated. The resultant residue was purified using column chromatography (silica pre-treated with triethylamine, eluting with 3:7 methanol:dichloromethane) to provide C91 as a thick orange gum. Yield: 0.34 g, 65%. ¹H-NMR (400 MHz, CD₃OD) δ 7.59 (4H, m), 7.41 (4H, m), 7.32 (1H, m), 6.50 (1H, s), 5.14 (1H, s), 5.02 (2H, d), 4.77 (1H, d), 4.62 (1H, d), 1.58 (3H, s), 1.43 (18H, s).

B. Synthesis of {3-[(1S,2S)-2-(biphenyl-4-ylmethoxy)-1-hydroxy-3-(hydroxyamino)-2-methyl-3-oxopropyl]isoxazol-5-yl}methyl dihydrogen phosphate (C92). A solution of C91 (0.70 g, 1.18 mmol) in dichloromethane (20 mL) was cooled to 0° C. and treated with trifluoroacetic acid (0.60 mL). The resultant mixture was stirred for 4 hours at 0° C. and concentrated. The resultant residue was loaded onto a reverse-phase silica column (C18, carbon 23%) and eluted with water. Fractions containing the desired product were combined and concentrated under reduced pressure to provide C92 as a thick, light orange oil. Yield: 0.34 g, 60%. ¹H-NMR (400 MHz, CD₃OD) δ 7.59 (4H, m), 7.42 (4H, m), 7.33 (1H, m), 6.52 (1H, s), 5.11 (1H, s), 5.02 (2H, d), 4.78 (1H, d), 4.62 (1H, d), 1.57 (3H, s).

C. A solution of C92 (0.34 g, 0.71 mmol) in water (10 mL) was cooled to 0° C. and slowly treated with sodium carbonate until the pH was in the range of from 8 to 9. The mixture was stirred for 15 minutes and then loaded onto a Dianion HP-20 resin column. The contents of the column were then eluted with water:methanol (gradient: (95:5), (85:15), (70:30) and then (1:1)). The fractions containing product were combined and concentrated by freeze drying to provide 47 as a fluffy white solid. Yield: 0.24 g, 62%. LCMS m/z 477.3 (M−1). ¹H-NMR (400 MHz, CD₃OD) δ 7.58 (4H, m), 7.40 (4H, m), 7.29 (1H, m), 6.46 (1H, s), 5.07 (1H, s), 4.92 (2H, d, J=6.6 Hz), 4.76 (1H, d, J=11.7 Hz), 4.66 (1H, d, J=11.7 Hz), 1.56 (s, 3H).

Example 48

Preparation of 2-(biphenyl-4-ylmethoxy)-N-hydroxy-2-(1-hydroxycyclobutyl)propanamide (48)

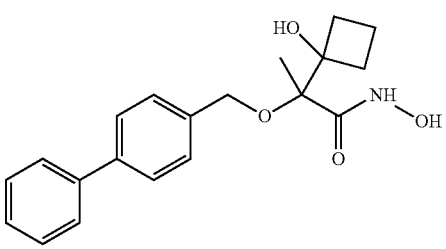

48

Compound 48 was prepared by the procedure depicted in Scheme 13 and described in detail below.

Scheme 13

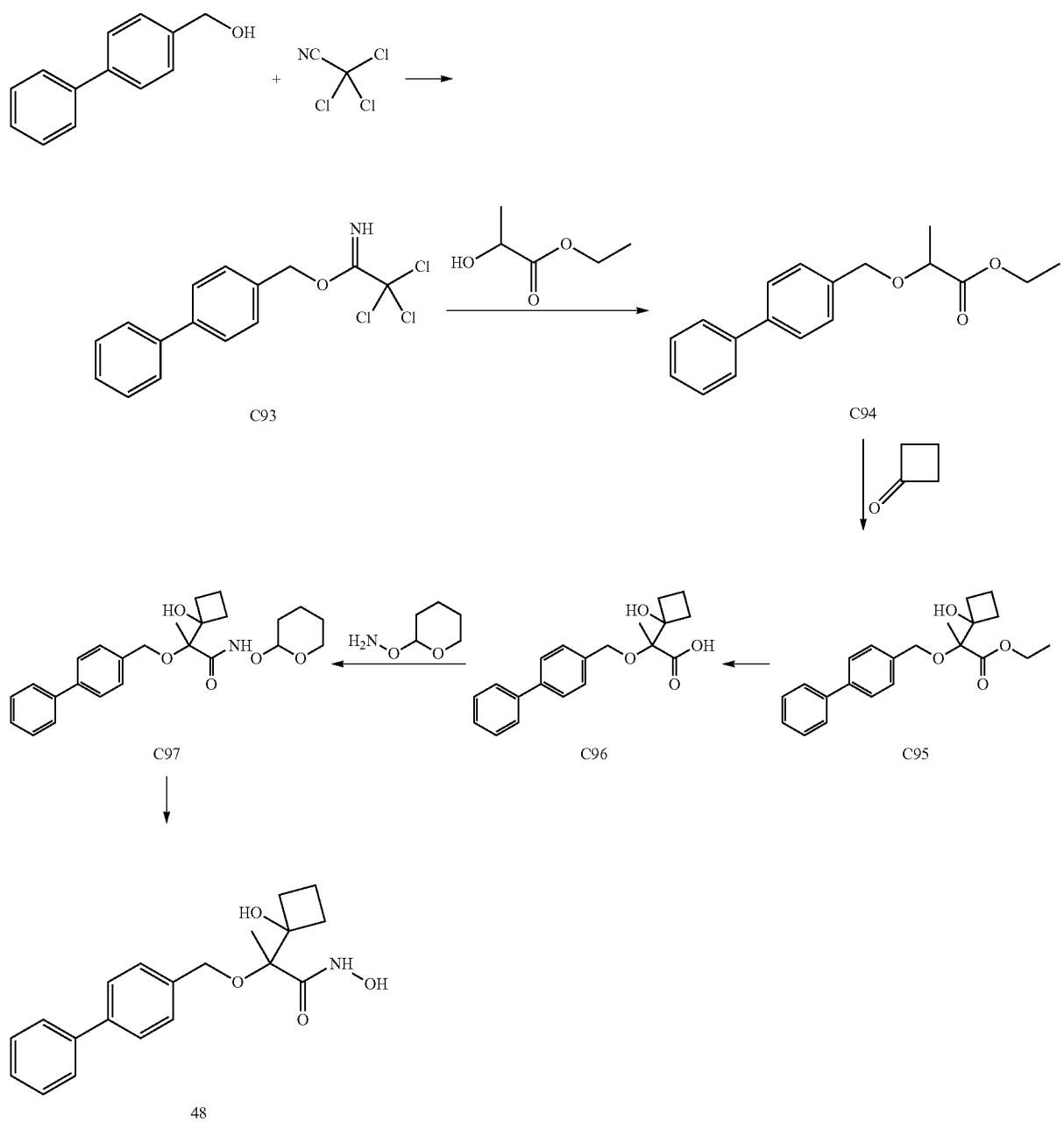

Step 1. Preparation of biphenyl-4-ylmethyl 2,2,2-trichloroethanimidoate (C93). A suspension of biphenyl-4-ylmethanol (36.8 g, 200 mmol) in dichloromethane (240 mL) was treated with 50% aqueous potassium hydroxide solution (160 mL). The reaction mixture was cooled to 0° C., and maintained at 0-10° C. as tetra-n-butylammonium sulfate (1.16 g, 2.0 mmol) was added, followed by a slow addition of trichloroacetonitrile (25.1 mL, 250 mmol) over 10 minutes. The reaction was stirred at 0° C. for an hour, and then stirred at 25° C. for an additional hour, after which the organic layer was filtered through a short pad of Celite on top of a layer of silica gel. The pad was rinsed with additional methylene chloride (1500 mL), and the eluents were concentrated in vacuo to provide C93 as a white solid, which was used in the next step without purification. Yield: 66.1 g, quantitative. LCMS m/z 167.2 ($C_{13}H_{11}^+$). $^1$H NMR (400 MHz, CDCl$_3$) δ 5.40 (s, 2H), 7.37 (m, 1H), 7.46 (m, 2H), 7.52 (d, J=8.7 Hz, 2H), 7.62 (m, 4H), 8.43 (br s, 1H).

Step 2. Preparation of ethyl 2-(biphenyl-4-ylmethoxy)propanoate (C94). Ethyl 2-hydroxypropanoate (17.2 mL, 150 mmol) was added to a solution of C93 (32.9 g, 100 mmol) in dichloromethane (44.4 mL) and heptane (196 mL). Trifluoromethanesulfonic acid (750 mg, 5.0 mmol) was added, and the reaction mixture was stirred at 25° C. for about 18 hours, then filtered through Celite, followed by rinsing with heptane (1.2 L). The filtrate was washed with saturated aqueous sodium bicarbonate solution (900 mL) and water (900 mL), dried over sodium sulfate and filtered. Removal of solvents in vacuo provided a residue, which was purified via chromatography on silica gel (Eluant: 5% ethyl acetate in heptane) to provide C94 as a viscous yellow oil. Yield: 17.1 g, 60.1 mmol, 60%. LCMS m/z 167.2 ($C_{13}H_{11}^+$). $^1$H NMR (400 MHz, CDCl$_3$) δ 1.32 (t, J=7.0 Hz, 3H), 1.48 (d, J=6.6 Hz, 3H), 4.10 (q, J=6.6 Hz, 1H), 4.25 (m, 2H), 4.51 (d, J=11.6 Hz, 1H), 4.76 (d, J=11.6 Hz, 1H), 7.36 (m, 1H), 7.45 (m, 4H), 7.60 (m, 4H).

Step 3. Preparation of ethyl 2-(biphenyl-4-ylmethoxy)-2-(1-hydroxycyclobutyl)propanoate (C95). A solution of C94 (1.03 g, 3.62 mmol) in tetrahydrofuran (10 mL) was added drop-wise to a solution of lithium diisopropylamide (1.8M in heptane/tetrahydrofuran/ethylbenzene [Aldrich], 2.6 mL, 4.7 mmol) in tetrahydrofuran (5 mL) at −78° C. The reaction was allowed to stir for 15 minutes at this temperature, and was then treated with cyclobutanone (0.29 mL, 3.9 mmol). After 30 minutes, the reaction was quenched with water, diluted with diethyl ether, and allowed to warm to 25° C. over about an hour. The layers were separated, and the aqueous layer was extracted with diethyl ether. The combined organic layers were washed with saturated aqueous sodium chloride solution, dried over magnesium sulfate, filtered and concentrated in vacuo to provide the crude product. Purification via silica gel chromatography (Gradient: 5% to 65% ethyl acetate in heptane) provided C95 as a colorless oil. Yield: 1.03 g, 2.91 mmol, 80%. LCMS m/z 372.4 (M+NH$_4$). $^1$H NMR (400 MHz, CDCl$_3$) δ 1.33 (t, J=7.1 Hz, 3H), 1.57 (s, 3H), 1.61 (m, 1-2H), 1.97 (m, 3H), 2.55 (m, 2H), 4.27 (m, 2H), 4.58 (d, J=11.0 Hz, 1H), 4.67 (d, J=11.1 Hz, 1H), 7.36 (m, 1H), 7.47 (m, 4H), 7.60 (m, 4H).

Step 4. Preparation of 2-(biphenyl-4-ylmethoxy)-2-(1-hydroxycyclobutyl)propanoic acid (C96). Lithium hydroxide (43 mg, 1.0 mmol) and C95 (227 mg, 0.638 mmol) were combined in tetrahydrofuran:methanol:water (2:2:1 ratio, 4 mL). The reaction was allowed to stir for about 42 hours, then acidified to pH 2 with 1N hydrochloric acid and partitioned between ethyl acetate and water. The aqueous layer was extracted with ethyl acetate and the combined organic layers were washed with saturated aqueous sodium chloride solution and dried over magnesium sulfate. Filtration and concentration in vacuo provided C96 as a white solid, which was used without purification. Yield: 208 mg, 0.637 mmol, 100%. LCMS m/z 325.4 (M−1).

Step 5. Preparation of 2-(biphenyl-4-ylmethoxy)-2-(1-hydroxycyclobutyl)-N-(tetrahydro-2H-pyran-2-yloxy)propanamide (C97). Compound C96 (208 mg, 0.637 mmol), O-(tetrahydro-2H-pyran-2-yl)hydroxylamine (97 mg, 0.83 mmol), 1-hydroxybenzotriazole monohydrate (157 mg, 1.02 mmol), triethylamine (0.15 mL, 1.08 mmol) and N-[3-(dimethylamino)propyl]-N'-ethylcarbodiimide hydrochloride (170 mg, 0.89 mmol) were combined in dimethylformamide (2 mL) and allowed to react for about 18 hours. The reaction mixture was then partitioned between ethyl acetate and water, and the aqueous layer was extracted with ethyl acetate. The combined organic layers were washed with saturated aqueous sodium chloride solution, dried over magnesium sulfate and filtered. The filtrate was then evaporated onto silica gel and subjected to column chromatography (Gradient: 10% to 100% ethyl acetate in heptane) to provide C97 as a colorless oil. Yield: 118 mg, 0.277 mmol, 43%. LCMS m/z 426.5 (M+1). $^1$H NMR (400 MHz, CDCl$_3$) δ 1.55-2.05 (m, 8H), 1.62 (s, 3H), 2.46 (m, 2H), 3.60 (m, 2H), 3.90 (m, 2H), 4.59 (m, 1H), 4.72 (m, 2H), 4.95 and 5.02 (br singlets, 1H), 7.37 (m, 1H), 7.45 (m, 4H), 7.62 (m, 4H), 9.33 (br s, 1H).

Step 6. Preparation of compound 48. A solution of C97 (115 mg, 0.27 mmol) in methanol (2 mL) was treated with hydrochloric acid (4N in dioxane, 2.0 mL, 8 mmol) and allowed to stir at 25° C. for 1 hour. The reaction mixture was evaporated onto silica gel and purified by chromatography (Gradient: 1% to 10% methanol in dichloromethane), to deliver 48 as a white foam. Yield: 58.1 mg, 0.170 mmol, 63%. LCMS m/z 340.4 (M−1). $^1$H NMR (400 MHz, DMSO-d$_6$) δ 1.32 (s, 3H), 1.49 (m, 1H), 1.77 (m, 3H), 2.39 (m, 1H), 2.68 (m, 1H), 4.49 (AB quartet, J=12.2 Hz, 2H), 7.36 (dd, J=7.5, 7.5 Hz, 1H), 7.48 (m, 4H), 7.65 (m, 4H), 10.24 (br s, 1H).

Example 49

Preparation of N-hydroxy-2-({4'-[3-(hydroxymethyl)isoxazol-5-yl]biphenyl-4-yl}methoxy)-N',2-dimethylmalonamide (49)

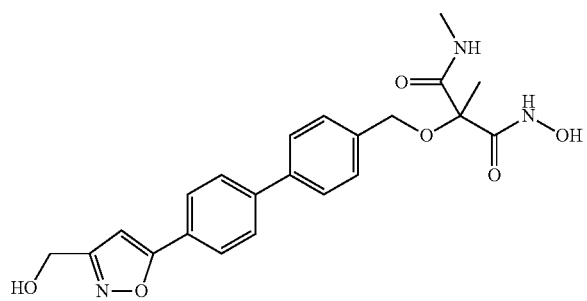

Compound 49 was prepared by the procedures depicted in Scheme 15 and described in detail below.

Step 1. Preparation of methyl 2-[(4-bromobenzyl)oxy]-3-(tert-butyldimethylsilyloxy)-2-methylpropanoate (C101). Compound C101 was prepared by the procedures depicted in Scheme 14 and described in detail below.

Scheme 14

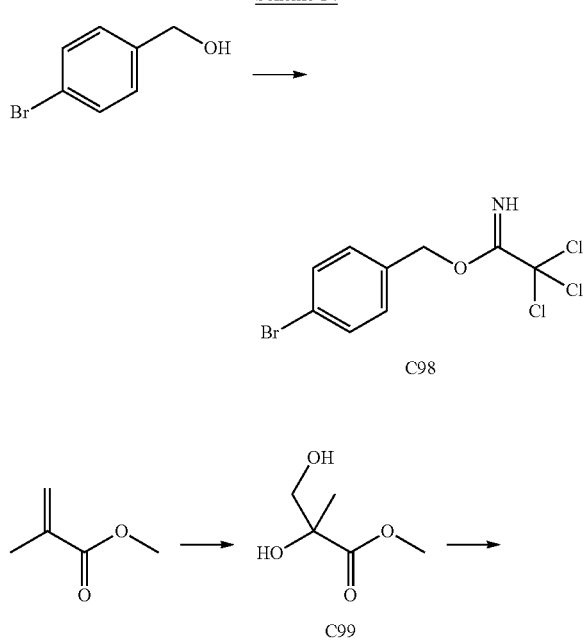

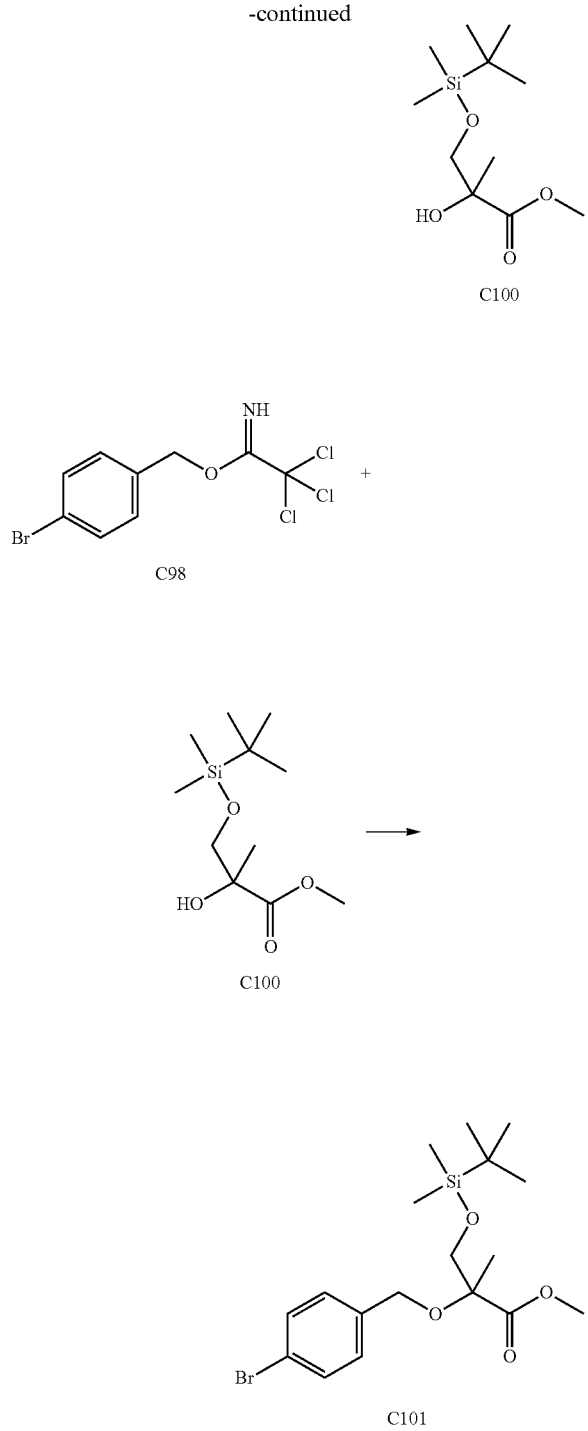

A. Preparation of 4-bromobenzyl 2,2,2-trichloroethanimidoate (C98). A suspension of sodium hydride (60% in mineral oil, 5.35 g, 0.134 mol) in anhydrous tetrahydrofuran (25 mL) was stirred at 25° C. for 5 minutes. A solution of (4-bromophenyl)methanol (25.0 g, 0.134 mol) in anhydrous tetrahydrofuran (250 mL) was slowly added drop-wise. The resulting pale yellow solution was stirred at 25° C. for 15 minutes and then cooled to 0° C. in an ice bath. Trichloroacetonitrile (13.4 mL, 0.13 mol) in anhydrous tetrahydrofuran (25 mL) was added drop-wise and the resulting orange solution was allowed to warm to 25° C. and stirred for 2 hours. The reaction mixture was concentrated in vacuo to afford C98 as a pale brown solid. Yield: 44.10 g, 0.133 mol, 99%. $^1$H NMR (500 MHz, CDCl$_3$) δ 5.29 (s, 2H), 7.31 (m, 2H), 7.51 (m, 2H), 8.41 (s, 1H).

B. Preparation of methyl 3-(tert-butyldimethylsilyloxy)-2-hydroxy-2-methylpropanoate (C100). Preparation of methyl 2,3-dihydroxy-2-methylpropanoate (C99). Osmium tetroxide (2.5% by weight in tert-butanol, 24.7 mL, 2.4 mmol) was added to a solution of N-methylmorpholine N-oxide (46.0 g, 0.39 mol), water (56 mL), acetone (41 mL) and tert-butanol (37 mL). Methyl methacrylate (20 mL, 0.19 mol) in acetone (53 mL) was then added drop-wise, and the reaction was stirred at 25° C. for about 18 hours. The reaction was quenched with a small amount of water and extracted with ethyl acetate. The organic layer was dried over magnesium sulfate and concentrated in vacuo to a brown oil, which was dissolved in 30% ethyl acetate in hexanes and eluted through a plug of silica. Fractions containing the desired product were combined and concentrated to provide C99 as a yellow oil. Yield: 17.7 g, 0.13 mol, 68%. $^1$H-NMR (500 MHz, CDCl$_3$) δ 1.35 (s, 3H), 3.18 (brs, 1H), 3.58 (d, 1H), 3.80 (d, 1H), 3.81 (s, 3H), 3.97 (br s, 1H).

C. A solution of C99 (10.0 g, 74.6 mmol) and imidazole (6.1 g, 90 mmol) in anhydrous dimethylformamide (100 mL) was treated portion-wise with tert-butyldimethylsilyl chloride (13.5 g, 90 mmol). The reaction was stirred at 25° C. for about 18 hours, then diluted with ethyl acetate and washed twice with saturated aqueous sodium bicarbonate solution and then three times with water. The organic layer was dried over anhydrous magnesium sulfate, filtered, and concentrated in vacuo to provide C100 as a pale yellow oil. Yield: 18.5 g, 74.5 mmol, 100%. $^1$H-NMR (500 MHz, CDCl$_3$) δ 0.01 (s, 6H), 0.84 (s, 9H), 1.30 (s, 3H), 3.40 (br s, 1H), 3.48 (d, 1H), 3.72 (s, 3H), 3.82 (d, 1H).

D. To a solution of C98 (43.5 g, 0.131 mol) in anhydrous diethyl ether (800 mL) at 0° C. was rapidly added, in a drop-wise manner, a solution of C100 (32.6 g, 0.131 mol) in anhydrous ether (400 mL). Trifluoromethanesulfonic acid (2.32 mL, 0.026 mol) was then added via syringe, causing the reaction to change from a cloudy deep yellow to an orange solution. The reaction was stirred at 0° C. for 1 hour and then allowed to warm to 25° C. and stir at this temperature for about 18 hours. Additional trifluoromethanesulfonic acid (1.16 mL, 0.013 mol) was added via syringe and the reaction mixture was stirred at 25° C. for an additional 18 hours, at which time it was quenched by addition of saturated aqueous sodium bicarbonate solution (1200 mL). The organic layer was separated and washed with water (800 mL), then dried over magnesium sulfate, filtered and concentrated in vacuo to an orange/brown semi-solid residue. The crude material was purified by silica gel column chromatography (Eluant: hexanes to 0.5% ethyl acetate/hexanes to 1% ethyl acetate/hexanes), providing C101 as a pale yellow oil. Yield: 29.3 g, 70.2 mmol, 54%. $^1$H NMR (500 MHz, CDCl$_3$) δ 0.01 (s, 6H), 0.84 (s, 9H), 1.43 (s, 3H), 3.70 (s, 3H), 3.75 (d, 1H), 3.82 (d, 1H), 4.44 (d, 1H), 4.53 (d, 1H), 7.22 (m, 2H), 7.41 (m, 2H).

Step 2. Preparation of methyl 2-({4'-[3-(hydroxymethyl) isoxazol-5-yl]biphenyl-4-yl}methoxy)-2-methyl-3-(methylamino)-3-oxopropanoate (C106). Compound C106 was prepared according to the method depicted in Scheme 15 and described in detail below.

Scheme 15

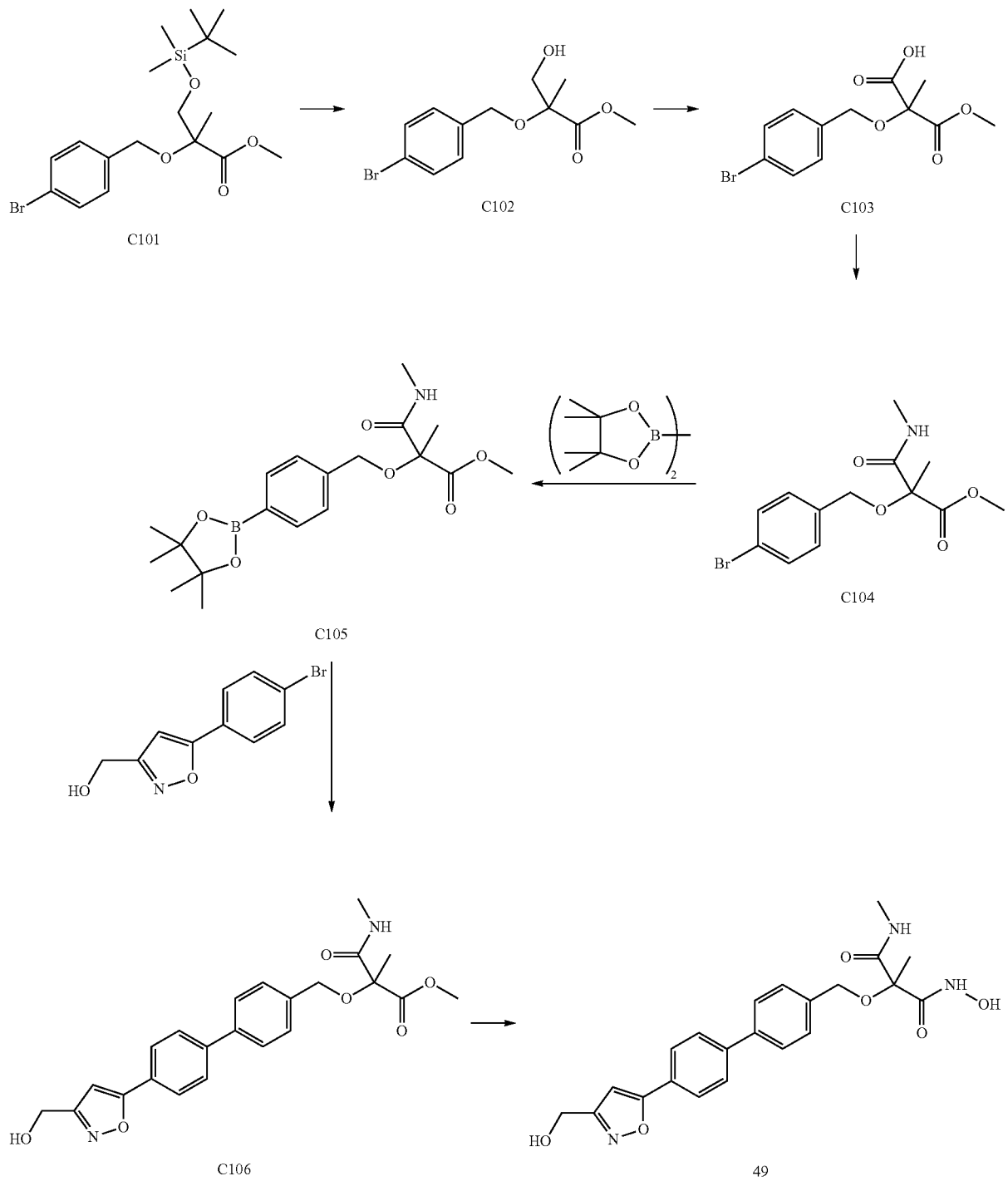

A. Preparation of methyl 2-[(4-bromobenzyl)oxy]-3-hydroxy-2-methylpropanoate (C102). A solution of C101 (27.28 g, 65.39 mmol) in anhydrous tetrahydrofuran (550 mL) was treated with glacial acetic acid (11.23 mL, 0.20 mol) followed by a rapid drop-wise addition of tetra-n-butyl ammonium fluoride (196 mL, 0.20 mol). The solution was stirred under nitrogen at 25° C. for about 18 hours, then subjected to additional glacial acetic acid (2.86 mL, 0.05 mol) followed by tetra-n-butylammonium fluoride (50 mL, 0.05 mol). The mixture was stirred for about 42 hours at 25° C., then concentrated in vacuo, and the crude residue was partitioned between saturated aqueous sodium bicarbonate solution (1500 mL) and ethyl acetate (1500 mL). The organic layer was separated and the aqueous layer (pH 8-9) was extracted with ethyl acetate (3×600 mL). The combined organics were washed with water (800 mL), dried over magnesium sulfate, filtered and concentrated in vacuo to an orange oil. This crude material was purified by silica gel column chromatography (Eluant: hexanes to 5% ethyl acetate/hexanes to 10% ethyl acetate/hexanes) to afford a yellow oil, which was dissolved in tert-butyl methyl ether (500 mL) and washed with 2N hydrochloric acid (2×150 mL) and then water (1×200 mL), followed by removal of solvent in vacuo, to afford C102 as a viscous yellow oil. Yield: 15.20 g, 50.1 mmol, 77%. $^1$H NMR (500 MHz, CDCl$_3$) δ 1.49 (s, 3H), 2.22 (m, 1H), 3.73 (m, 1H), 3.79 (s, 3H), 3.81 (m, 1H), 4.48 (d, 1H), 4.62 (d, 1H), 7.27 (m, 2H), 7.47 (m, 2H). Elemental analysis, calculated for C$_{12}$H$_{15}$BrO$_4$: C, 47.54; H, 4.99; Br: 26.36; Found: C, 47.29; H, 4.87; Br: 26.71.

B. Preparation of 2-[(4-bromobenzyl)oxy]-3-methoxy-2-methyl-3-oxopropanoic acid (C103). Compound C102 (1.00 g, 3.30 mmol), 2,2,6,6-tetramethyl-N-piperidinyloxy, free radical (TEMPO, 25 mg, 0.16 mmol), sodium bicarbonate (650 mg, 7.7 mmol) and tetrabutylammonium bromide (80 mg, 0.25 mmol) were combined with water (5 mL) and dichloromethane (5 mL), and the resulting mixture was cooled in an ice bath. A solution of sodium hypochlorite (0.72 g, 9.7 mmol) and sodium bicarbonate (810 mg, 9.6 mmol) in water (3 mL) was added, and then the yellow mixture was allowed to warm to 25° C. Cautious addition of hydrochloric acid (1N, 30 mL, 30 mmol) was followed by separation of phases, and extraction of the aqueous layer with dichloromethane. The combined organic layers were washed with saturated aqueous sodium chloride solution, dried over magnesium sulfate and concentrated in vacuo. This crude product was purified by silica gel chromatography (Eluant: 1:1 ethyl acetate:hexanes containing 1% acetic acid) to deliver C103. Yield: 0.49 g, 1.55 mmol, 47%. MS (APCI) m/z 315.3 (M−1). $^1$H NMR (400 MHz, CDCl$_3$) δ 1.78 (s, 3H), 3.83 (s, 3H), 4.59 (s, 2H), 7.27 (d, 2H), 7.50 (d, 2H).

C. Preparation of methyl 2-[(4-bromobenzyl)oxy]-2-methyl-3-(methylamino)-3-oxopropanoate (C104). A solution of C103 (2.0 g, 6.3 mmol) in a mixture of dichloromethane (20 mL) and dimethylformamide (10 mL) at 0° C. was treated with methylamine hydrochloride (0.51 g, 7.55 mmol), O-(7-azabenzotriazol-1-yl)-N,N,N'N'-tetramethyluronium hexafluorophosphate (HATU, 2.87 g, 7.55 mmol), and diisopropylethylamine (4.38 mL, 25.1 mmol) drop-wise over 10 minutes. The reaction mixture was allowed to warm to 25° C. and stirred for 12 hours, after which the dichloromethane was removed in vacuo, and the reaction was quenched by the addition of aqueous hydrochloric acid (1N, 20 mL). The mixture was extracted with ethyl acetate (3×20 mL), and the combined organic layers were washed with saturated aqueous sodium chloride solution (30 mL), dried over magnesium sulfate and concentrated in vacuo. The resulting solid was suspended in diethyl ether (10 mL), filtered and washed with diethyl ether (10 mL). The filtrate was concentrated and purified by silica gel chromatography (Gradient: hexanes to 50% ethyl acetate in hexanes) to provide C104 as a gum. Yield: 1.01 g, 3.06 mmol, 49%. MS (APCI) m/z 332.1 (M+1). $^1$H NMR (400 MHz, CDCl$_3$) δ 1.75 (s, 3H), 2.83 (d, J=5.0 Hz, 3H), 3.79 (s, 3H), 4.36 (d, J=10.8 Hz, 1H), 4.50 (d, J=10.7 Hz, 1H), 6.79 (br s, 1H), 7.25 (m, apparent d, J=8.4 Hz, 2H), 7.50 (m, apparent d, J=8.4 Hz, 2H).

D. Preparation of methyl 2-methyl-3-(methylamino)-3-oxo-2-{[4-(4,4,5,5-tetramethyl-1,3,2-dioxaborolan-2-yl)benzyl]oxy}propanoate (C105). A solution of C104 (0.73 g, 2.21 mmol) in dioxane (70 mL) was treated sequentially with pinacol diborane (0.67 g, 2.6 mmol) and potassium acetate (1.08 g, 11.0 mmol). The mixture was degassed and flushed with nitrogen three times, then treated with the methylene chloride adduct of 1,1'-[bis(diphenylphosphino)ferrocene]dichloropalladium(I) (PdCl$_2$(dppf).CH$_2$Cl$_2$, 0.18 g, 0.22 mmol), degassed and flushed with nitrogen three times, and heated to reflux for 3 hours. The reaction mixture was then cooled to 25° C., diluted with dichloromethane (70 mL) and filtered under vacuum. The filtrate was concentrated in vacuo to afford C105 as a brown oil, which was used directly in the next step. MS (APCI) m/z 378.4 (M+1).

E. A solution of C105 from the previous step (assumed 0.83 g, 2.21 mmol) in a mixture of toluene:isopropyl alcohol (2:1, 100 mL) was treated sequentially with [5-(4-bromophenyl)isoxazol-3-yl]methanol. (see A. K. Roy and S. Batra, Synthesis 2003, 2325) (0.67 g, 2.64 mmol) and aqueous cesium carbonate (2.2 M, 5.0 mL, 11 mmol). The mixture was degassed and flushed with nitrogen three times, then treated with the methylene chloride adduct of 1,1'-[bis(diphenylphosphino)ferrocene]dichloropalladium(II) (0.16 g, 0.20 mmol), degassed and flushed with nitrogen three times and heated to reflux for 3 hours. The reaction mixture was cooled to 25° C. and partitioned between ethyl acetate (100 mL) and saturated aqueous sodium chloride solution (100 mL). The aqueous layer was extracted with ethyl acetate (3×100 mL) and the combined organic layers were washed with saturated aqueous sodium chloride solution, dried over magnesium sulfate and concentrated in vacuo. Purification of the residue by silica gel chromatography (Gradient: 0-5% methanol in dichloromethane) provided C106 as a clear gum. Yield: 0.60 g, 1.4 mmol, 63%. LCMS m/z 425.2 (M+1). $^1$H NMR (400 MHz, CDCl$_3$) δ 1.79 (s, 3H), 2.86 (d, J=4.8 Hz, 3H), 3.82 (s, 3H), 4.47 (d, J=10.8 Hz, 1H), 4.62 (d, J=10.8 Hz, 1H), 4.85 (s, 2H), 6.64 (s, 1H), 6.87 (br s, 1H), 7.48 (d, J=7.9 Hz, 2H), 7.65 (d, J=7.9 Hz, 2H), 7.71 (d, J=8.3 Hz, 2H), 7.87 (d, J=8.3 Hz, 2H).

Step 3. Compound 49 was prepared from compound C106 as shown above in Scheme 15. A solution of lithium methoxide (1M in methanol, 28.3 mL, 28.3 mmol) was treated with hydroxylamine hydrochloride (0.982 g, 14.1 mmol) at 25° C. The mixture was stirred for 10 min and then cooled to 0° C. A solution of C106 (0.600 g, 1.41 mmol) in methanol (6 mL) was added to the cold reaction mixture drop-wise, over 10 minutes, and the mixture was stirred at 0° C. for 1 hour and then at 25° C. for 2 hours. The solution was cooled to 0° C. and quenched by the addition of acetic acid (5.0 mL, 87 mmol), after which solvents were removed in vacuo. The crude material was suspended in a mixture of water (15 mL) and acetonitrile (15 mL), and the resulting suspension was heated, then filtered. The solid was washed with a cold solution of water (2 mL) and acetonitrile (2 mL) to provide 49 (0.428 g, 1.01 mmol, 72%) as an orange solid. MS (APCI) m/z 426.3 (M+1). $^1$H NMR (400 MHz, CDCl$_3$) δ 1.55 (s, 3H), 2.65 (br s, 3H), 4.47 (AB quartet, J=12 Hz, 2H), 4.56 (br s, 2H), 5.57 (br s, 1H), 7.05 (s, 1H), 7.57 (d, J=7.6 Hz, 2H), 7.73 (m, 3H), 7.84 (d, J=7.4 Hz, 2H), 7.96 (d, J=7.4 Hz, 2H), 8.98 (br s, 1H), 10.60 (br s, 1H).

Example 50

Preparation of 2-(biphenyl-4-ylmethoxy)-3,3,3-trifluoro-N-hydroxy-2-(hydroxymethyl)propanamide (50)

Compound 50 was prepared by the procedure shown in Scheme 16 and described below.

Scheme 16

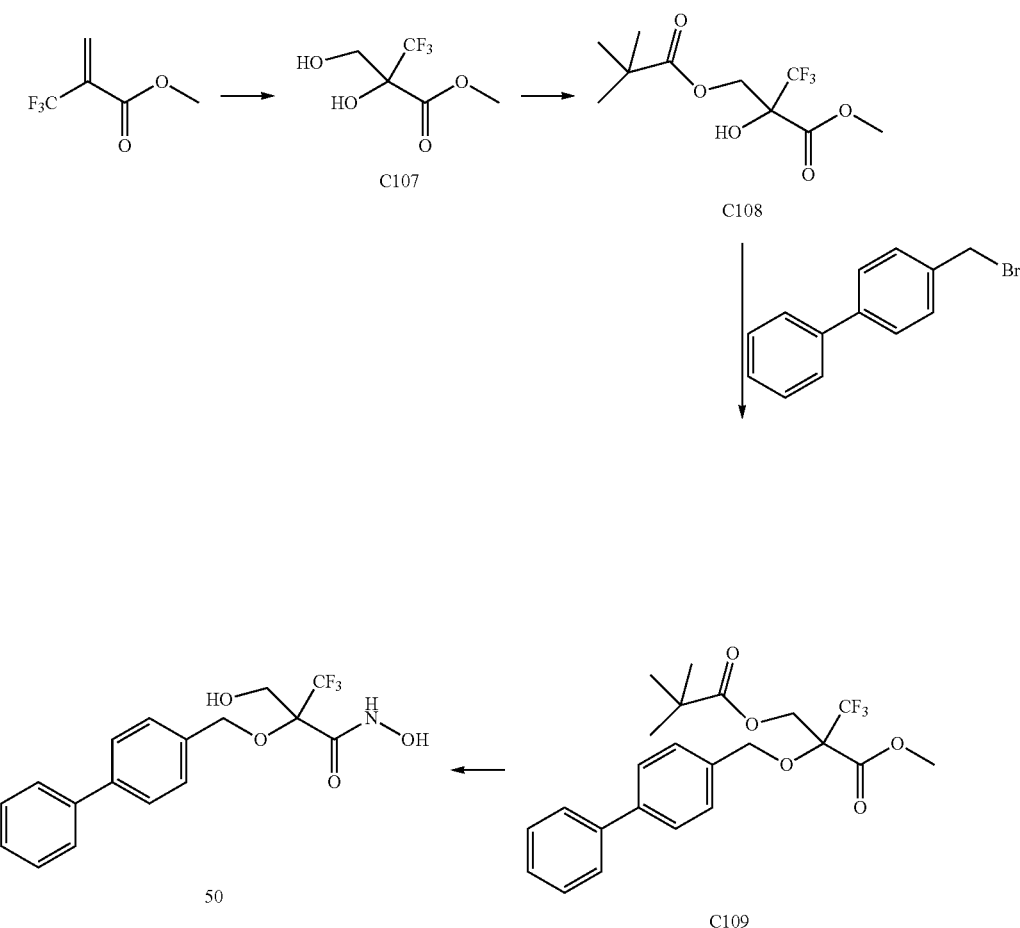

Step 1. Preparation of methyl 3,3,3-trifluoro-2-hydroxy-2-(hydroxymethyl)propanoate (C107). Compound C107 was synthesized according to the general procedure for the synthesis of C99 in Example 49, except that methyl 2-(trifluoromethyl)acrylate was used instead of methyl methacrylate, to provide C107 as a colorless oil. Yield: 3.8 g, 78%. $^1$H NMR (400 MHz, DMSO-$d_6$) δ 3.60 (dd, J=11.2, 5.0 Hz, 1H), 3.70 (s, 3H), 3.77 (dd, J=11.2, 6.34 Hz, 1H), 5.34 (dd, apparent t, J=6 Hz, 1H), 6.85 (s, 1H).

Step 2. Preparation of methyl 2-{[(2,2-dimethylpropanoyl)oxy]methyl}-3,3,3-trifluoro-2-hydroxypropanoate (C108). A solution of C107 (3.8 g, 20 mmol) in pyridine (5 mL) and dichloromethane (5 mL) at 0° C. was treated drop-wise with pivaloyl chloride (3.0 mL, 24 mmol). The reaction was stirred at 0° C. for 30 minutes, warmed to 25° C. and stirred an additional two hours, then diluted with dichloromethane (100 mL) and washed with 1N hydrochloric acid (100 mL). The organic layer was washed with saturated aqueous sodium bicarbonate solution (100 mL), dried over sodium sulfate and concentrated to provide C108 as a colorless oil. Yield: 5.0 g, 91%. LCMS m/z 273.16 (M+1). $^1$H NMR (400 MHz, DMSO-$d_6$) δ 1.12 (s, 9H), 3.78 (s, 3H), 4.35 (AB quartet, J=11.5 Hz, 2H), 7.50 (br s, 1H).

Step 3. Preparation of methyl 2-(biphenyl-4-ylmethoxy)-2-{[(2,2-dimethylpropanoyl)oxy]methyl}-3,3,3-trifluoropropanoate (C109). Compound C109 was synthesized according to the general procedure for the synthesis of C4 in Example 1, except that C108 was used in place of methyl (S)-2-hydroxypropanoate, to afford C109 as a colorless oil. Yield: 1.52 g, 47%. $^1$H NMR (400 MHz, DMSO-$d_6$) δ 1.14 (s, 9H), 3.87 (s, 3H), 4.63 (d, J=12.8 Hz, 1H), 4.77 (m, 3H), 7.37 (m, 1H), 7.47 (m, 4H), 7.67 (m, 4H).

Step 4. Preparation of compound 50. Compound 50 was synthesized according to the general procedure for the synthesis of 49 in Example 49, except that C109 was used in place of C106, and after the acetic acid quench, the reaction mixture was diluted with water to give an oily suspension. On further agitation, a heavy precipitate formed, which was filtered, washed twice with water and dried, to provide 50 as a white solid. Yield: 1.03 g, 84%. LCMS m/z 356.21 (M+1). $^1$H NMR (400 MHz, DMSO-$d_6$) δ 4.06 (d, J=4.8 Hz, 2H), 4.80 (AB quartet, J=11.1 Hz, 2H), 5.47 (t, J=5.2 Hz, 1H), 7.32 (t, J=7.4 Hz, 1H), 7.38-7.51 (m, 4H), 7.61 (m, 4H), 9.05 (s, 1H), 10.82 (s, 1H).

Example 51

Preparation of N,3-dihydroxy-2-(hydroxymethyl)-2-[(4'-propylbiphenyl-4-yl)methoxy]propanamide (51)

Compound 51 was prepared by the procedure shown in Scheme 17 and described below.

Scheme 17

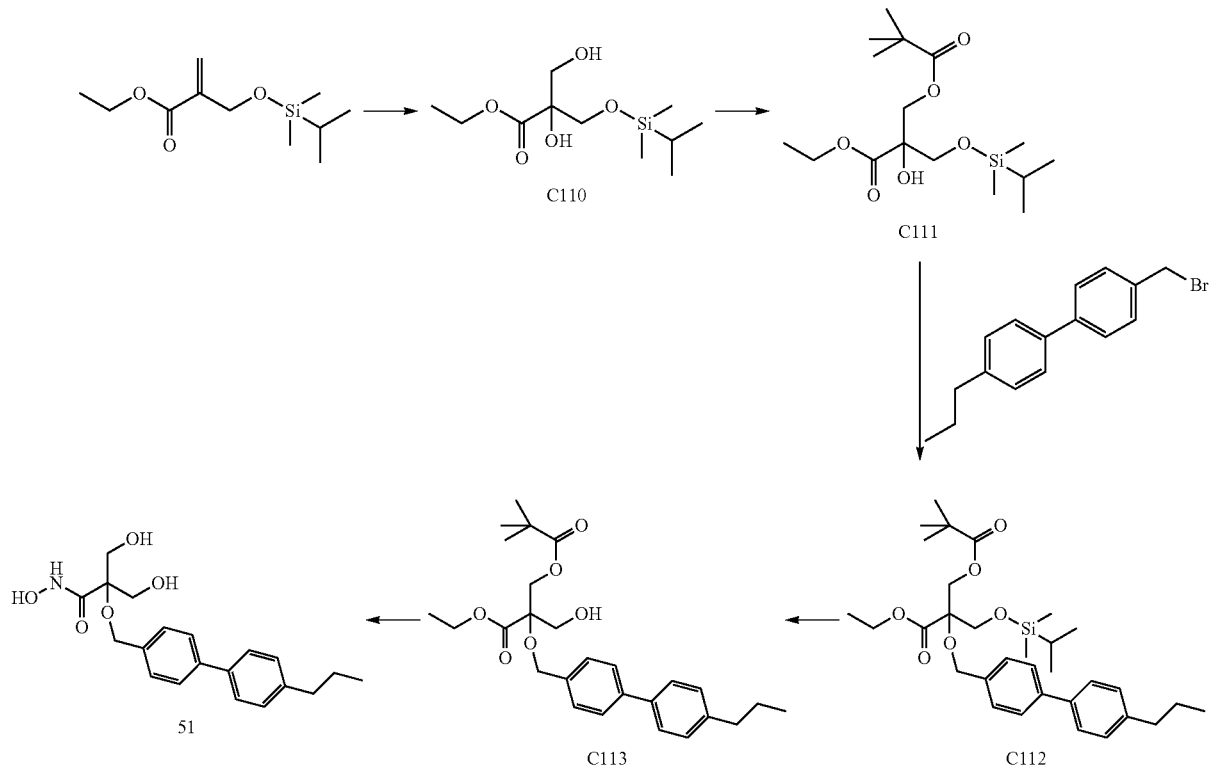

Step 1. Preparation of ethyl 3-(tert-butyldimethylsilyloxy)-2-hydroxy-2-(hydroxymethyl)propanoate (C110). Compound C110 was synthesized according to the general procedure for the synthesis of C99 in Example 49, except that ethyl 2-[(tert-butyldimethylsilyloxy)methyl]acrylate [see J. Robertson et al., Organic Letters 2004, 6, 3857] was used instead of methyl methacrylate, to provide C110 as a brown oil. Yield: 5.3 g, 93%. $^1$H NMR (400 MHz, CDCl$_3$) δ 0.04 (s, 3H), 0.05 (s, 3H), 0.87 (s, 9H), 1.31 (t, J=7.1 Hz, 3H), 2.32 (br s, 1H), 3.62 (br s, 1H), 3.66 (m, 2H), 3.79 (d, J=11.4 Hz, 1H), 3.85 (d, J=10.0 Hz, 1H), 4.26 (q, J=7.1 Hz, 2H). LCMS m/z 279.21 (M+1).

Step 2. Preparation of ethyl 3-(tert-butyldimethylsilyloxy)-2-{[(2,2-dimethylpropanoyl)oxy]methyl}-2-hydroxypropanoate (C111). A solution of C110 (5.3 g, 19 mmol) in pyridine (5 mL) and dichloromethane (5 mL) at 0° C. was treated drop-wise with pivaloyl chloride (2.8 mL, 23 mmol). The reaction was stirred at 0° C. for 1 hour, warmed to 25° C. and stirred an additional three hours, then diluted with dichloromethane (50 mL) and washed with 1N hydrochloric acid (50 mL). The organic layer was washed with saturated aqueous sodium bicarbonate solution (50 mL), dried over sodium sulfate and concentrated in vacuo. The residue was redissolved in diethyl ether (50 mL), washed with additional saturated aqueous sodium bicarbonate solution (50 mL), dried over sodium sulfate and concentrated to provide C111 as a brown oil. Yield: 5.5 g, 80%. LCMS m/z 363.33 (M+1). $^1$H NMR (400 MHz, CDCl$_3$) δ 0.05 (s, 3H), 0.06 (s, 3H), 0.88 (s, 9H), 1.19 (s, 9H), 1.30 (t, J=7.1 Hz, 3H), 3.46 (s, 1H), 3.69 (d, J=9.9 Hz, 1H), 3.86 (d, J=9.9 Hz, 1H). 4.24 (s, 2H), 4.25 (q, J=7.1 Hz, 2H).

Step 3. Preparation of ethyl 3-(tert-butyldimethylsilyloxy)-2-{[(2,2-dimethylpropanoyl)oxy]methyl}-2-[(4'-propylbiphenyl-4-yl)methoxy]propanoate (C112). Compound C112 was synthesized according to the general procedure for the synthesis of C4 in Example 1, except that C111 was used in place of methyl (S)-2-hydroxypropanoate, and 4-(bromomethyl)-4'-propylbiphenyl instead of 4-(bromomethyl)biphenyl, to afford C112 as a colorless oil, which was used in the next reaction without purification. Yield: 0.60 g, 27%.

Step 4. Preparation of ethyl 3-[(2,2-dimethylpropanoyl)oxy]-2-(hydroxymethyl)-2-[(4'-propylbiphenyl-4-yl)methoxy]propanoate (C113). A solution of C112 (0.60 g, 1.05 mmol) in tetrahydrofuran (70 mL) at 25° C. was treated with acetic acid (0.30 mL, 5.5 mmol) followed by tetrabutylammonium fluoride (1.4 g, 5.3 mmol). The reaction was stirred overnight at 25° C., then concentrated in vacuo. The residue was purified by silica gel column chromatography (Gradient: 15%-60% ethyl acetate/hexanes) to provide C113. Yield: 0.36 g, 75%. $^1$H NMR (400 MHz, DMSO-d$_6$) δ 0.91 (t, J=7.3 Hz, 3H), 1.13 (s, 9H), 1.23 (t, J=7.1 Hz, 3H), 1.61 (m, 2H), 2.59 (m, 2H), 3.69 (dd, J=11.2, 6.0 Hz, 1H), 3.77 (dd, J=11.3, 5.7 Hz, 1H), 4.18 (m, 2H), 4.31 (d, J=11.7 Hz, 1H), 4.48 (d, J=11.7 Hz, 1H), 4.56 (s, 2H), 5.21 (dd, apparent t, J=5.9 Hz, 1H), 7.27 (d, J=8.4 Hz, 2H), 7.41 (d, J=8.5 Hz, 2H), 7.56 (d, J=8.3 Hz, 2H), 7.61 (d, J=8.4 Hz, 2H).

Step 5. Preparation of 51. Compound 51 was synthesized according to the general procedure for the synthesis of 50 in Example 50, except that C113 was used in place of C109, to provide 51 as a white solid. Yield: 0.225 g, 79%. LCMS m/z 360.23 (M+1). $^1$H NMR (400 MHz, DMSO-d$_6$) δ 0.92 (t, J=7.3 Hz, 3H), 1.62 (m, 2H), 2.59 (m, 2H), 3.72 (br s, 4H), 4.59 (s, 2H), 4.73 (br s, 2H), 7.27 (d, J=8.4 Hz, 2H), 7.50 (d, J=8.5 Hz, 2H), 7.57 (d, J=8.3 Hz, 2H), 7.60 (d, J=8.4 Hz, 2H), 8.75 (br s, 1H), 10.18 (br s, 1H).

Example 52

Preparation of (2S)-2-(biphenyl-4-ylmethoxy)-N-hydroxy-2-methyl-N'-[(5-methylisoxazol-3-yl)methyl]malonamide (52)

Compound 52 was prepared by the procedure shown in Scheme 18 and described below.

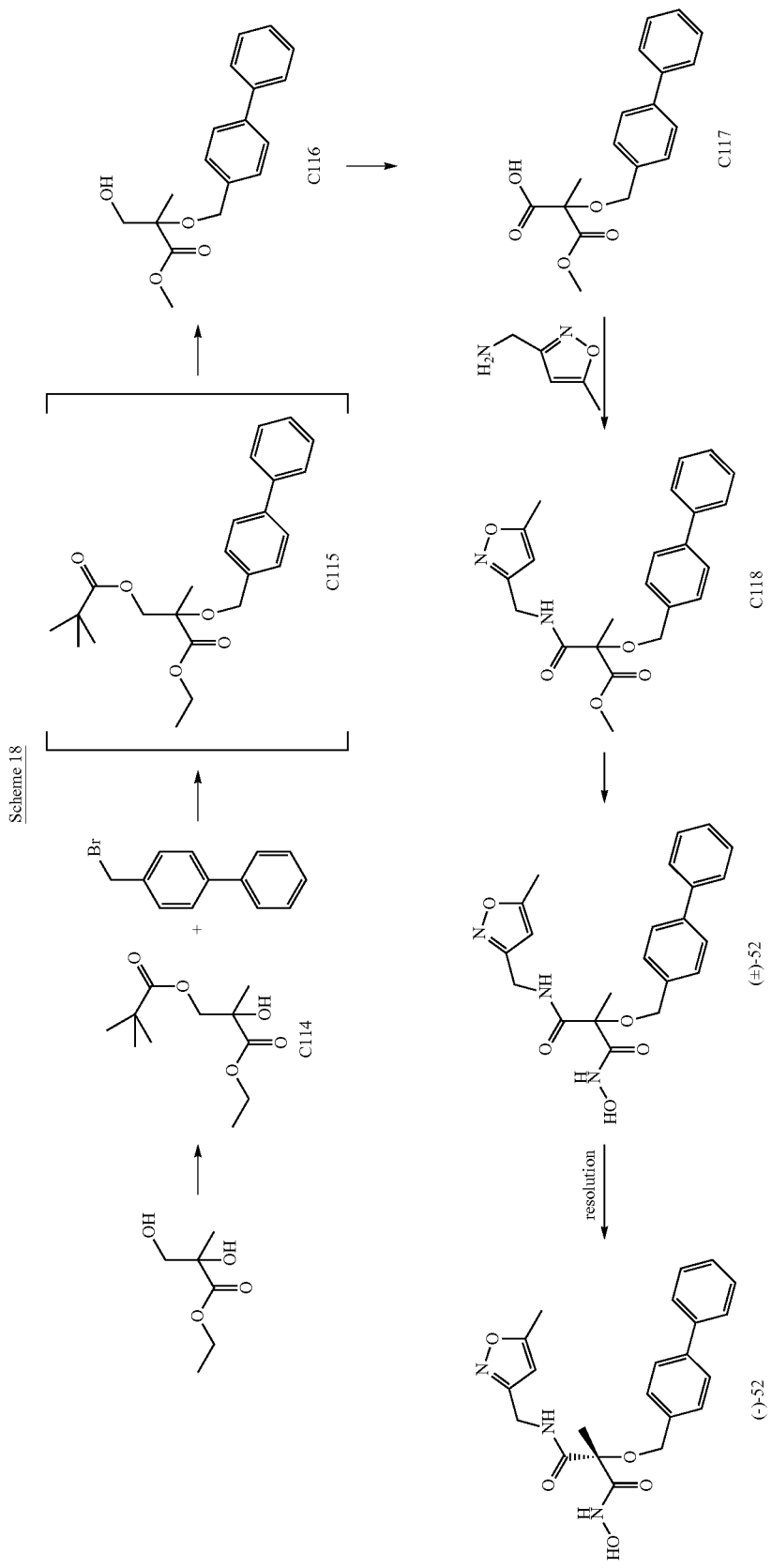

Step 1. Preparation of ethyl 3-[(2,2-dimethylpropanoyl) oxy]-2-hydroxy-2-methylpropanoate (C114). Compound C114 was synthesized according to the general procedure for the synthesis of C108 in Example 50, except that ethyl 2,3-dihydroxy-2-methylpropanoate was used in place of methyl 3,3,3-trifluoro-2-hydroxy-2-(hydroxymethyl)propanoate, to provide C114 as a colorless oil. Yield: 12.3 g, 86%. LCMS m/z 233.18 (M+1). $^1$H NMR (400 MHz, DMSO-d$_6$) δ 1.06 (s, 9H), 1.13 (t, J=6.7 Hz, 3H), 1.24 (s, 3H), 3.89-4.09 (m, 4H).

Step 2. Preparation of methyl 2-(biphenyl-4-ylmethoxy)-3-hydroxy-2-methylpropanoate (C116). Ethyl 2-(biphenyl-4-ylmethoxy)-3-[(2,2-dimethylpropanoyl)oxy]-2-methyl-propanoate (C115) was synthesized according to the general procedure for the synthesis of C4 in Example 1, except that C114 (12.3 g, 53.0 mmol) was used in place of methyl (S)-2-hydroxypropanoate, and the product was not chromatographed, to afford crude C115. Crude compound C115 was dissolved in methanol (5 mL) and added to a solution of lithium methoxide in methanol (1M, 44 mL). The solution was stirred for 30 minutes at 25° C., quenched with acetic acid (45 mL) and concentrated in vacuo. The residue was diluted with water (250 mL) and extracted with ethyl acetate (2×200 mL), and the combined organic layers were dried over sodium sulfate and concentrated in vacuo. Purification of the residue by column chromatography on silica gel (Gradient: 20%-70% ethyl acetate/heptane) provided C116 as a colorless oil. Yield: 7.5 g, 47%. $^1$H NMR (400 MHz, DMSO-d$_6$) δ 1.41 (s, 3H), 3.62 (m, 2H), 3.68 (s, 3H), 4.51 (AB quartet, J=11.1 Hz, 2H), 5.06 (dd, apparent t, J=6 Hz, 1H), 7.36 (m, 1H), 7.46 (m, 4H), 7.64 (m, 4H).

Step 3. Preparation of 2-(biphenyl-4-ylmethoxy)-3-methoxy-2-methyl-3-oxopropanoic acid (C117). Compound C117 was synthesized according to the general procedure for the synthesis of C103 in Example 49, except that C116 was used in place of C102, and 4-acetamido-2,2,6,6-tetramethyl-N-piperidinyloxy free radical (4-acetamido-TEMPO) was used instead of TEMPO, to afford C117 as a yellow oil. Yield: 2.5 g, 48%. $^1$H NMR (400 MHz, DMSO-d$_6$) δ 1.62 (s, 3H), 3.73 (s, 3H), 4.61 (AB quartet, J=11.2 Hz, 2H), 7.36 (m, 1H), 7.47 (m, 4H), 7.65 (m, 4H).

Step 4. Preparation of methyl 2-(biphenyl-4-ylmethoxy)-2-methyl-3-{[(5-methylisoxazol-3-yl)methyl]amino}-3-oxopropanoate (C118). A solution of C117 (0.45 g, 1.43 mmol) in dimethylformamide (5 mL) was treated with O-(7-azabenzotriazol-1-yl)-N,N,N′N′-tetramethyluronium hexafluorophosphate (HATU, 0.82 g, 2.1 mmol) followed by triethylamine (0.60 mL, 4.3 mmol). The reaction was stirred for 10 minutes and 1-(5-methylisoxazol-3-yl)methanamine (0.21 g, 1.9 mmol) was added.

The solution was stirred for 1 hour, diluted with water (50 mL), and extracted with ethyl acetate (3×25 mL). The combined organics were dried over sodium sulfate and concentrated. Purification by column chromatography on silica gel (Gradient: 20%-60% ethyl acetate/heptane) provided C118. Yield: 0.41 g, 70%. LCMS m/z 409.22 (M+1). $^1$H NMR (400 MHz, DMSO-d$_6$) δ 1.63 (s, 3H), 2.36 (d, J=0.9 Hz, 3H), 3.69 (s, 3H), 4.30 (m, 2H), 4.41 (d, J=11.3 Hz, 1H), 4.65 (d, J=11.5 Hz, 1H), 6.03 (d, J=1.0 Hz, 1H), 7.37 (m, 1H), 7.48 (m, 4H), 7.65 (m, 4H), 8.53 (dd, apparent t, J=6 Hz, 1H).

Step 5. Preparation of (2S)-2-(biphenyl-4-ylmethoxy)-N-hydroxy-2-methyl-N'-[(5-methylisoxazol-3-yl)methyl]malonamide ((−)-52). Lithium methoxide (1M solution in methanol, 20 mL) was added to hydroxylamine hydrochloride (0.70 g, 10.0 mmol) and the resulting solution was stirred for 10 minutes at 25° C. A solution of C118 (0.410 g, 1.00 mmol) in methanol (5 mL) was added and the reaction was stirred for 30 minutes. The reaction was quenched with acetic acid (0.86 mL, 15 mmol) and concentrated in vacuo. Purification by reverse phase column chromatography (Gradient: 80%-20% water/acetonitrile) provided (±)-52. Yield: 0.23 g, 56%. LCMS m/z 410.2 (M+1). $^1$H NMR (400 MHz, DMSO-d$_6$) δ 1.58 (s, 3H), 2.35 (s, 3H), 4.31 (m, 2H), 4.48 (br s, 2H), 6.09 (s, 1H), 7.36 (m, 1H), 7.47 (m, 2H), 7.54 (m, 2H), 7.65 (m, 4H), 8.36 (br s, 1H), 9.0 (br s, 1H), 10.4 (br s, 1H). A fraction of (±)-52 (0.20 g) was further purified by chiral supercritical fluid chromatography (methanol with 0.5% iodine, AS-H column). The less retained fraction was concentrated to provide (−)-52 as a glassy solid. Yield: 0.065 g, 32%. $^1$H NMR and MS data were identical to those of the racemic material.

Example 53

Preparation of 2-{[6-(4-fluorophenyl)pyridin-3-yl]methoxy}-N-hydroxy-2-methyl-N'-[(5-methylisoxazol-3-yl)methyl]malonamide (53)

Compound 53 was prepared by the procedure shown in Scheme 19 and described below.

Scheme 19

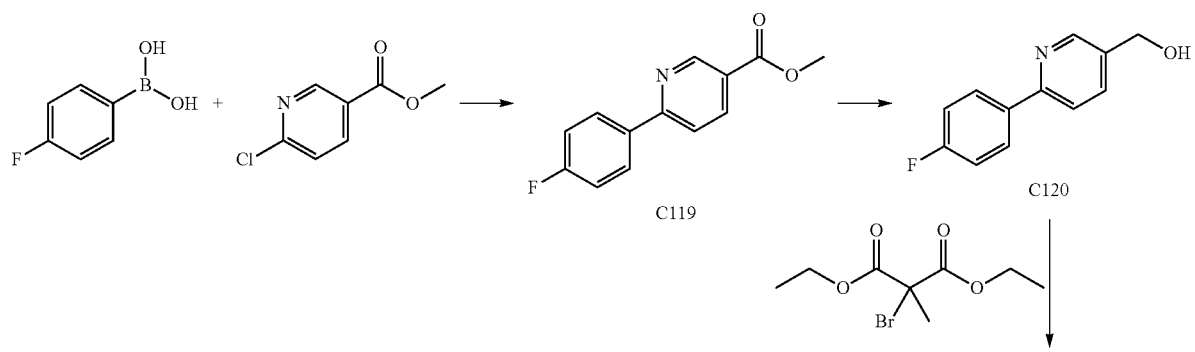

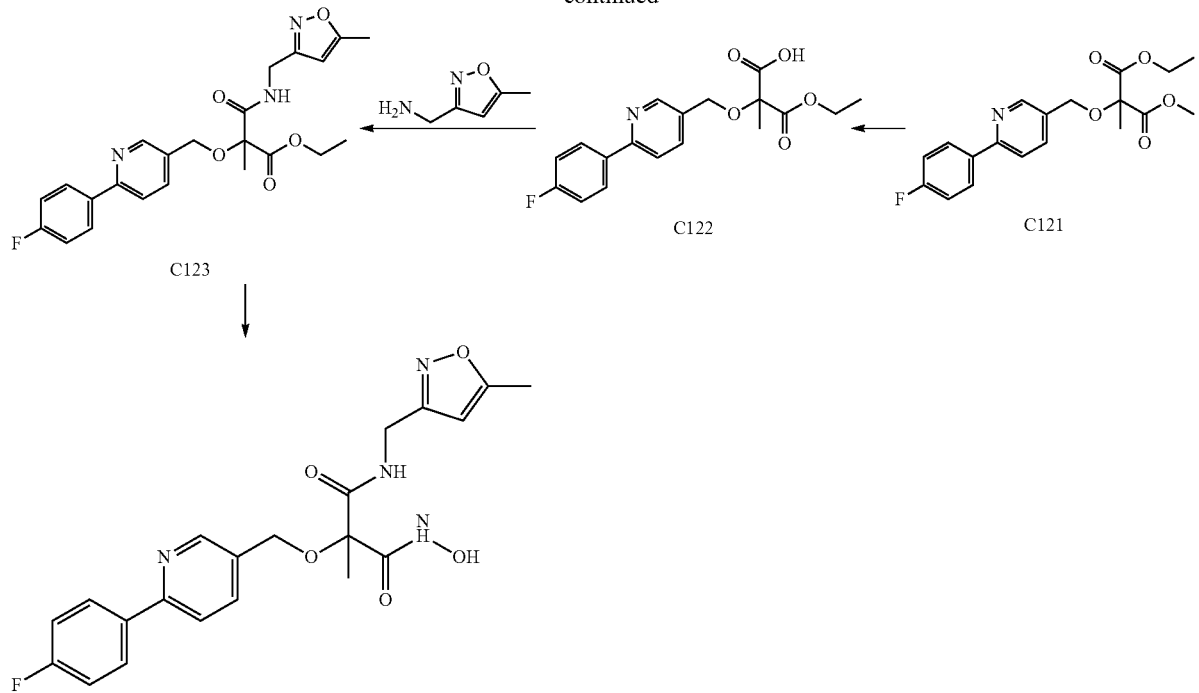

53

Step 1. Preparation of methyl 6-(4-fluorophenyl)nicotinate (C119). To a degassed suspension of methyl 6-chloronicotinate (5.0 g, 29 mmol), 4-fluorophenylboronic acid (4.89 g, 43.7 mmol) and sodium carbonate (7.50 g, as a solution in 35.4 mL of water, 70.8 mmol) in dimethoxyethane (45 mL) was added tetrakis(triphenylphosphine)palladium(O) (1.68 g, 1.46 mmol), and the reaction was stirred and heated to reflux (~80° C.) overnight. The reaction was allowed to cool to 25° C., solvent was removed in vacuo, and the residue was partitioned between ethyl acetate and ice water. The organic layer was washed with water and saturated aqueous sodium chloride solution, dried over magnesium sulfate, filtered and concentrated. The residue was purified by silica gel column chromatography (Gradient: 10:1 hexanes:ethyl acetate to 1:1 hexanes:ethyl acetate) to yield C119. Yield: 6.60 g, 98%. $^1$H NMR (400 MHz, CDCl$_3$) δ 3.94 (s, 3H), 7.15 (m, 2H), 7.73 (dd, J=8.3, 0.9 Hz, 1H), 8.02 (m, 2H), 8.30 (dd, J=8.3, 2.2 Hz, 1H), 9.22 (dd, J=2.2, 0.9 Hz, 1H).

Step 2. Preparation of [6-(4-fluorophenyl)pyridin-3-yl] methanol (C120). A solution of C119 (6.5 g, 28 mmol) in tetrahydrofuran (75 mL) was slowly added to a slurry of lithium aluminum hydride (1.28 g, 33.7 mmol) in dry tetrahydrofuran (125 mL) cooled to 0-5° C. in an ice bath under nitrogen. When the addition was complete, the cooling bath was removed and the mixture was stirred at 25° C. for 5 hrs. The reaction mixture was then cooled to 0° C. in an ice bath and the reaction was carefully quenched with water (1.2 mL), 15% aqueous sodium hydroxide (1.2 mL), and then water (3.38 mL). After being stirred for 30 minutes, the mixture was diluted with ethyl acetate (80-100 mL), filtered through a Celite pad, washed with ethyl acetate, and concentrated under reduced pressure. The isolated material was chromatographed on silica gel, (Gradient: 0%-75% ethyl acetate in hexanes), to yield C120 as a white solid. Yield: 4.36 g, 76%. MS (APCI) m/z 204.18 (M+1).

Step 3. Preparation of diethyl {[6-(4-fluorophenyl)pyridin-3-yl]methoxy}(methyl)malonate (C121). A solution of C120 (4.35 g, 21.4 mmol) in tetrahydrofuran (190 mL) at 0° C. was treated with sodium hydride (60% dispersion in mineral oil, 0.892 g, 22.3 mmol) portion-wise over 10 minutes. The resulting mixture was stirred at 25° C. for 1 hour and then cooled to 0° C. The mixture was treated with diethyl 2-bromo-2-methylmalonate (3.42 mL, 17.8 mmol) in tetrahydrofuran (30 mL) at 0° C. over 10 minutes, then allowed to warm to 25° C. over 30 minutes, and refluxed (~75° C.) for 2 hours. The solution was cooled to 25° C., cautiously treated with saturated aqueous ammonium chloride solution, and extracted with ethyl acetate. The combined organic layers were washed with water, then with saturated aqueous sodium chloride solution, dried over magnesium sulfate, and the solvent was removed in vacuo. The crude material was purified by silica gel chromatography (Gradient: 0%-50% ethyl acetate in hexanes), to give C121 as a clear oil. Yield 3.73 g, 46%. MS (APCI) m/z 376.29 (M+1).

Step 4. Preparation of 3-ethoxy-2-{[6-(4-fluorophenyl)pyridin-3-yl]methoxy}-2-methyl-3-oxopropanoic acid (C122). A solution of C121 (3.65 g, 9.72 mmol) in ethanol (42 mL) was treated with aqueous potassium hydroxide (4N, 3.65 mL, 14.60 mmol) over 10 minutes. The resulting mixture was stirred at 25° C. for 3 hours, and then a solid precipitate was removed by filtration and washed with ethanol. Saturated aqueous ammonium chloride solution was added to the filtrate, followed by water, and the mixture was extracted with ethyl acetate. The combined organic layers were washed with saturated aqueous sodium chloride solution, dried over magnesium sulfate, filtered and concentrated. Ethyl acetate was added, a precipitate was removed by filtration and the filtrate concentrated in vacuo. The isolated material was subjected to silica gel chromatography (Gradient: 0%-15% of [20% methanol in dichloromethane] in dichloromethane) to afford C122. Yield: 2.85 g, 84%. MS (APCI) m/z 348.25 (M+1).

Step 5. Preparation of ethyl 2-{[6-(4-fluorophenyl)pyridin-3-yl]methoxy}-2-methyl-3-{[(5-methylisoxazol-3-yl)methyl]amino}-3-oxopropanoate (C123). A solution of C122 (2.10 g, 6.05 mmol) in a mixture of dichloromethane (20 mL) and dimethylformamide (20 mL) was treated with O-(7-azabenzotriazol-1-yl)-N,N,N'N'-tetramethyluronium hexafluorophosphate (HATU, 2.87 g, 7.56 mmol) followed by diisopropylethylamine (5.27 mL) at 0° C. The mixture was stirred for 15 min at 0° C., then treated with 1-(5-methylisoxazol-3-yl)methanamine (0.847 g, 7.56 mmol). The resulting solution was allowed to warm to about 25° C. and stirring was continued at that temperature for 18 hours. The reaction mixture was quenched by the addition of aqueous 1N hydrochloric acid (20 mL), and extracted with ethyl acetate (3×20 mL). The combined organic layers were washed with saturated aqueous sodium chloride solution (40 mL), dried over magnesium sulfate, and the solvent was removed in vacuo. The isolated material was subjected to silica gel chromatography (Gradient: 0%-15% of [20% methanol in dichloromethane] in dichloromethane), to afford C123. Yield: 2.05 g, 77%. MS (APCI) m/z 442.30 (M+1). $^1$H NMR (400 MHz, CDCl$_3$) δ 1.30 (t, J=7.1 Hz, 3H), 1.79 (s, 3H), 2.38 (s, 3H), 4.27 (q, J=7.1 Hz, 2H), 4.48 (m, 3H), 4.63 (d, J=10.9 Hz, 1H), 5.95 (s, 1H), 7.16 (m, apparent t, J=8.7 Hz, 2H), 7.30 (m, 1H), 7.69 (d, J=8.2 Hz, 1H), 7.78 (dd, J=8.0, 2.0 Hz, 1H), 7.97 (d, J=8.8 Hz, 1H), 7.99 (d, J=8.8 Hz, 1H), 8.63 (br s, 1H).

Step 6. Preparation of compound 53. Lithium methoxide (1M solution in methanol, 47.6 mL, 47.6 mmol) was added to hydroxylamine hydrochloride (1.65 g, 23.7 mmol) in methanol and held for 10 minutes at 25° C. before being cooled in an ice bath. Compound C123 (1.05 g, 2.38 mmol) was dissolved in methanol (15 mL) and added to the reaction solution over several minutes. The resulting solution was stirred at 0° C. for 2 hours then at 25° C. for 1 hour. The reaction was then quenched with acetic acid (3.40 mL) and stirred for 20 minutes, after which the solvent was removed in vacuo, and the residue was taken up in ethyl acetate and washed with saturated aqueous sodium bicarbonate solution. The aqueous layer was extracted with ethyl acetate, and the combined organic layers were washed with saturated aqueous sodium chloride solution, dried over magnesium sulfate, filtered, and concentrated in vacuo. The crude material was dissolved in a minimum quantity of dichloromethane/methanol, and chromatographed on silica gel (Gradient: 0%-60% of [20% methanol in dichloromethane]/dichloromethane). The isolated product was triturated with cold ethanol followed by ethyl acetate/hexanes. The resulting solid was dried overnight to yield 53 as a solid. Yield: 0.640 g, 63%. MS (APCI) m/z 429.26 (M+1). Elemental analysis: Calculated for C$_{21}$H$_{21}$FN$_4$O$_5$: C, 58.87%; H, 4.94%; N, 13.08%; Found: C, 58.68%; H, 4.82%; N, 13.00%.

Example 54

Preparation of 2-(biphenyl-4-ylmethoxy)-N-hydroxypropanamide (54)

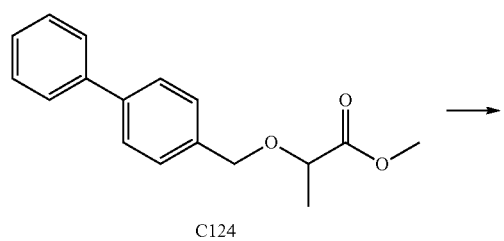

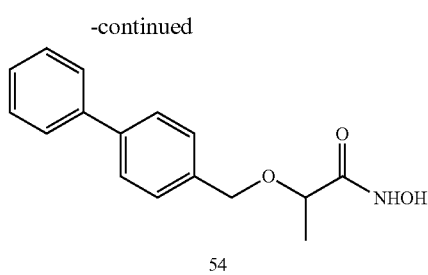

Step 1. Preparation of methyl 2-(biphenyl-4-ylmethoxy)propanoate (C124). To a solution of methyl (S)-2-hydroxypropanoate (0.105 g, 1.01 mmol) in dry tetrahydrofuran (4 mL) was added sodium hydride (60% in oil, 40 mg, 1.0 mmol) and tetrabutylammonium iodide (37 mg, 0.10 mmol). The reaction was stirred for 30 minutes at 25° C., then treated with 4-(bromomethyl)biphenyl (0.25 g, 1.01 mmol) and stirred under nitrogen for about 18 hours. Thin layer chromatographic analysis after this time still showed starting material; the reaction was heated to 90° C. for an additional 5 hours. The reaction was then partitioned between ethyl acetate (30 mL) and water (30 mL), and the organic layer was washed with water, dried over magnesium sulfate and concentrated in vacuo. The crude product was purified by silica gel chromatography (Eluant: ethyl acetate:hexanes mixture), affording C124 as a yellow liquid. Yield: 92 mg, 33% yield.

Step 2. Preparation of compound 54. Lithium methoxide (1M solution in methanol, 22 mL, 22 mmol) was added to a solution of anhydrous methanol (10 mL) and hydroxylamine hydrochloride (0.48 g, 9.61 mmol). The reaction was then treated with a solution of C124 (0.26 g, 0.96 mmol) in methanol (10 mL), and stirred at 25° C. for about 18 hours. The reaction mixture was then diluted with ethyl acetate (50 mL), washed with saturated aqueous ammonium chloride solution (50 mL), dried over magnesium sulfate and concentrated in vacuo, to afford 54 as a solid. Yield: 0.155 g, 60%. Melting point: 120-123° C. Purity by HPLC-MS: 96.12%. $^1$H-NMR (500 MHz, DMSO-d$_6$) δ 1.25 (d, 3H), 3.9 (q, 1H), 4.4-4.58 (AB quartet, 2H), 7.35-7.7 (m, 9H), 8.9 (s, 1H), 10.8 (s, 1H). Elemental analysis: Calculated for C$_{16}$H$_{17}$NO$_3$: C, 70.83%; H, 6.32%; N, 5.16%; Found: C, 70.61%; H, 6.43%; N, 4.75%.

Example 55

Preparation of N,3-dihydroxy-2-methyl-2-({4'-[3-(morpholin-4-ylmethyl)isoxazol-5-yl]biphenyl-4-yl}methoxy)propanamide (55)

Compound 55 was prepared by the procedure depicted in Scheme 20 and described in detail below.

Scheme 20

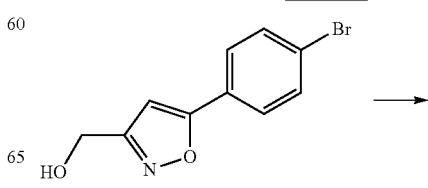

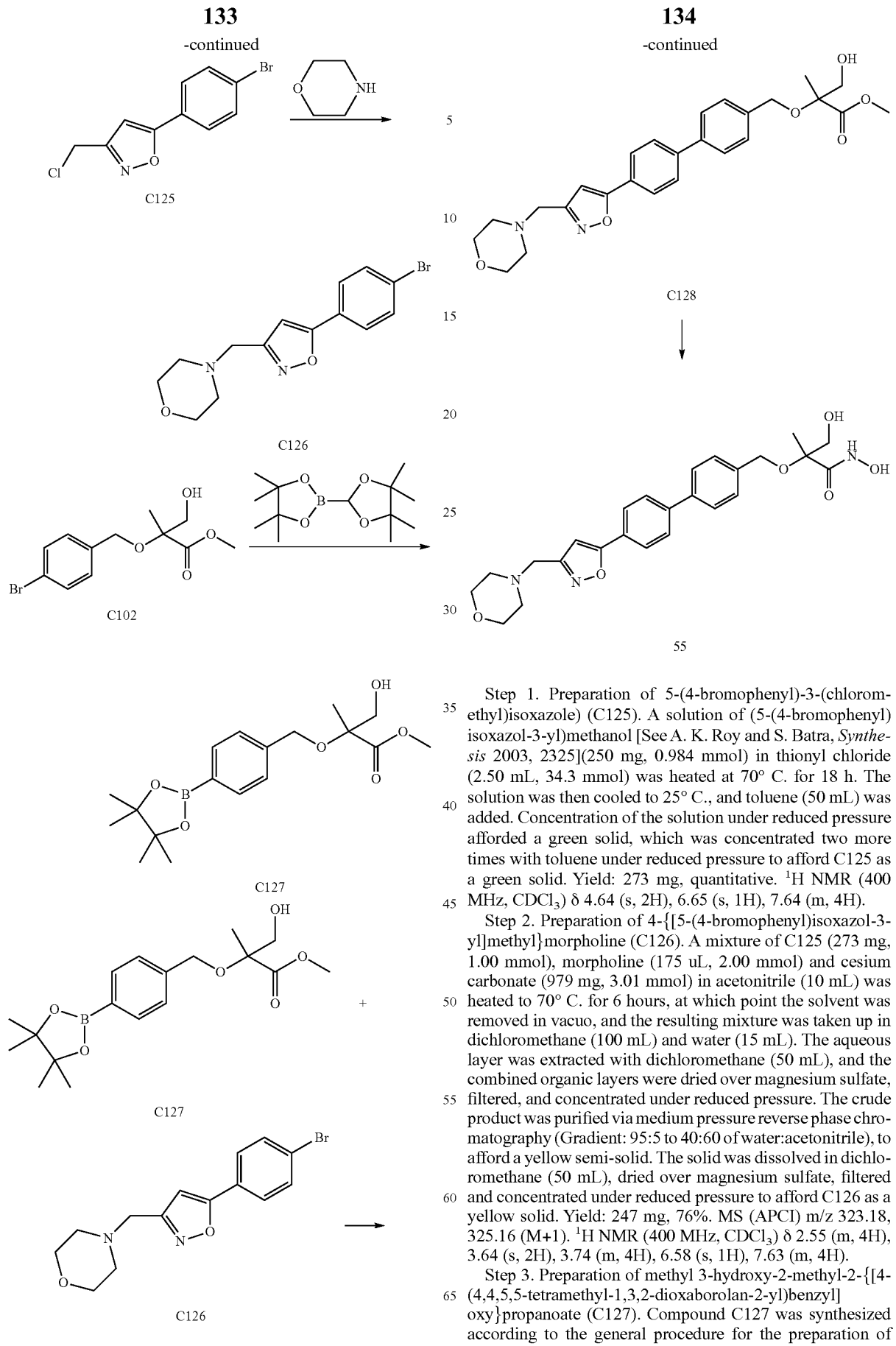

Step 1. Preparation of 5-(4-bromophenyl)-3-(chloromethyl)isoxazole) (C125). A solution of (5-(4-bromophenyl)isoxazol-3-yl)methanol [See A. K. Roy and S. Batra, *Synthesis* 2003, 2325](250 mg, 0.984 mmol) in thionyl chloride (2.50 mL, 34.3 mmol) was heated at 70° C. for 18 h. The solution was then cooled to 25° C., and toluene (50 mL) was added. Concentration of the solution under reduced pressure afforded a green solid, which was concentrated two more times with toluene under reduced pressure to afford C125 as a green solid. Yield: 273 mg, quantitative. $^1$H NMR (400 MHz, CDCl$_3$) δ 4.64 (s, 2H), 6.65 (s, 1H), 7.64 (m, 4H).

Step 2. Preparation of 4-{[5-(4-bromophenyl)isoxazol-3-yl]methyl}morpholine (C126). A mixture of C125 (273 mg, 1.00 mmol), morpholine (175 uL, 2.00 mmol) and cesium carbonate (979 mg, 3.01 mmol) in acetonitrile (10 mL) was heated to 70° C. for 6 hours, at which point the solvent was removed in vacuo, and the resulting mixture was taken up in dichloromethane (100 mL) and water (15 mL). The aqueous layer was extracted with dichloromethane (50 mL), and the combined organic layers were dried over magnesium sulfate, filtered, and concentrated under reduced pressure. The crude product was purified via medium pressure reverse phase chromatography (Gradient: 95:5 to 40:60 of water:acetonitrile), to afford a yellow semi-solid. The solid was dissolved in dichloromethane (50 mL), dried over magnesium sulfate, filtered and concentrated under reduced pressure to afford C126 as a yellow solid. Yield: 247 mg, 76%. MS (APCI) m/z 323.18, 325.16 (M+1). $^1$H NMR (400 MHz, CDCl$_3$) δ 2.55 (m, 4H), 3.64 (s, 2H), 3.74 (m, 4H), 6.58 (s, 1H), 7.63 (m, 4H).

Step 3. Preparation of methyl 3-hydroxy-2-methyl-2-{[4-(4,4,5,5-tetramethyl-1,3,2-dioxaborolan-2-yl)benzyl]oxy}propanoate (C127). Compound C127 was synthesized according to the general procedure for the preparation of C105 in Example 49, except that C102 was used in place of C104. The crude product was taken on to the next step.

Step 4. Preparation of methyl 3-hydroxy-2-methyl-2-({4'-[3-(morpholin-4-ylmethyl)isoxazol-5-yl]biphenyl-4-yl}methoxy)propanoate (C128). Compound C128 was prepared according to the general procedure for the preparation of C106 in Example 49, except that C127 and C126 were used instead of, respectively, C105 and [5-(4-bromophenyl)isoxazol-3-yl]methanol, and the crude C128 was not purified, but taken directly to the next step. MS (M+1), m/z 467.3.

Step 5. Preparation of compound 55. Compound 55 was synthesized according to the general procedure for the preparation of 49 in Example 49, through the quenching of the reaction with acetic acid. The resulting solution was then concentrated under reduced pressure to afford a brown residue, which was triturated several times with ethyl acetate (4×2 mL), with removal of the supernatant each time. The oily residue was then concentrated in vacuo to afford a light brown solid, which was purified via medium pressure reverse phase chromatography (Gradient: 95:5 to 50:50 of water:acetonitrile), to deliver a semi-solid. The semi-solid was lyophilized to yield 55 as a fluffy yellow solid. Yield: 24.5 mg, 31% over three steps. MS (APCI) m/z 468.29 (M+1). $^1$H NMR (400 MHz, DMSO-$d_6$) δ 1.32 (s, 3H), 2.45 (m, 4H), 3.60 (m, 8H), 4.52 (AB quartet, J=11.9 Hz, 2H), 7.06 (s, 1H), 7.53 (d, J=8.4 Hz, 2H), 7.71 (d, J=8.4 Hz, 2H), 7.84 (d, J=8.6 Hz, 2H), 7.96 (d, J=8.6 Hz, 2H).

Example 56

Preparation of 2-(biphenyl-4-ylmethoxy)-N,3-dihydroxy-2-(methoxymethyl)propanamide (56)

Compound 56 was prepared by the procedure shown in Scheme 21 and described below.

Scheme 21

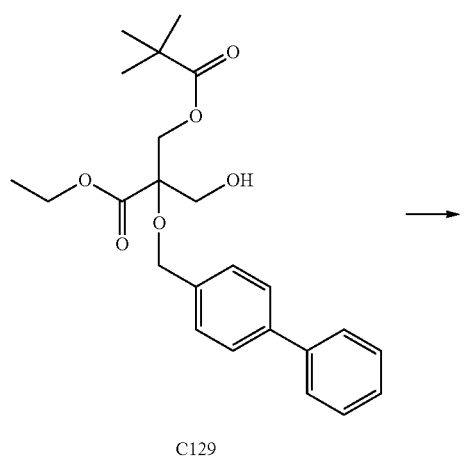

C129

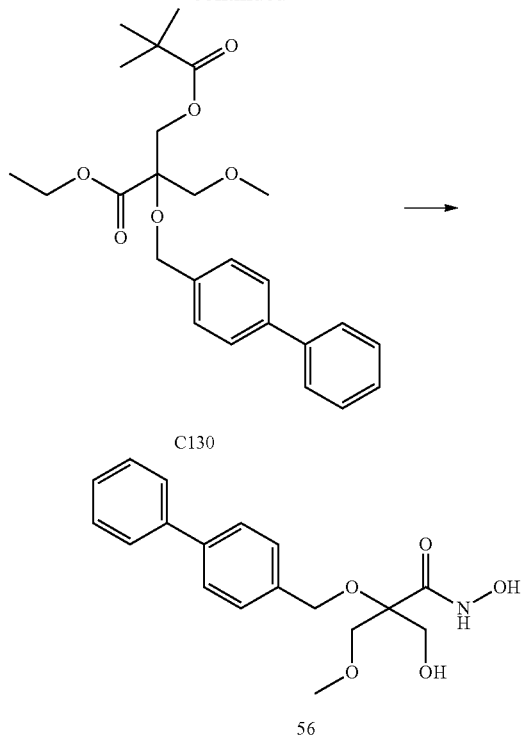

Step 1. Preparation of ethyl 2-(biphenyl-4-ylmethoxy)-3-[(2,2-dimethylpropanoyl)oxy]-2-(hydroxymethyl)propanoate (C129). Compound C129 was synthesized according to the general procedure for the synthesis of C113 in Example 51, except that 4-(bromomethyl)biphenyl was used instead of 4-(bromomethyl)-4'-propylbiphenyl, to provide C129. Yield: 4.3 g, 80%. $^1$H NMR (400 MHz, CDCl$_3$) δ 1.23 (s, 9H), 1.35 (t, J=7.1 Hz, 3H), 2.35 (t, J=6.9 Hz, 1H), 3.90 (d, J=6.8 Hz, 2H), 4.30 (m, 2H), 4.49 (d, J=12.1 Hz, 1H), 4.60 (d, J=12.1 Hz, 1H), 4.65 (d, J=10.6 Hz, 1H), 4.79 (d, J=10.6 Hz, 1H), 7.36 (m, 1H), 7.46 (m, 4H), 7.60 (m, 4H).

Step 2. Preparation of ethyl 2-(biphenyl-4-ylmethoxy)-3-[(2,2-dimethylpropanoyl)oxy]-2-(methoxymethyl)propanoate (C130). 2,6-Di-tert-butyl-4-methylpyridine (1.63 g, 7.96 mmol) was added to a solution of C129 (0.75 g, 1.8 mmol) in dichloromethane (5 mL). Following addition of methyl trifluoromethanesulfonate (1.19 g, 7.24 mmol), the reaction was stirred at 25° C. for 20 hours, filtered, and the filtrate concentrated in vacuo. Purification by silica gel chromatography (Gradient: 5% to 30% ethyl acetate in hexanes) provided C130 as a colorless oil. Yield; 0.33 g, 43%. MS (APCI) m/z 429.26 (M+1). $^1$H NMR (400 MHz, DMSO-$d_6$) δ 1.14 (s, 9H), 1.23 (t, J=7.1 Hz, 3H), 3.30 (s, 3H), 3.66 (d, J=10.1 Hz, 1H), 3.74 (d, J=10.1 Hz, 1H), 4.19 (m, apparent qd, J=7.1, 1.0 Hz, 2H), 4.31 (d, J=11.7 Hz, 1H), 4.45 (d, J=11.7 Hz, 1H), 4.58 (AB quartet, J=11.1 Hz, 2H), 7.36 (m, 1H), 7.45 (m, 4H), 7.65 (m, 4H).

Step 3. Preparation of compound 56. Compound 56 was synthesized according to the general procedure for the synthesis of 50 in Example 50, except that C130 was used in place of C109, to provide 56 as a white solid. Yield 0.205 g, 80%. MS (APCI) m/z 332.24 (M+1). $^1$H NMR (400 MHz, DMSO-$d_6$) δ 3.25 (s, 3H), 3.64 (s, 2H), 3.70 (d, J=5.3 Hz, 2H), 4.59 (s, 2H), 4.85 (t, J=5.4 Hz, 1H), 7.36 (t, J=7.3 Hz, 1H), 7.46 (dd, apparent t, J=7.6 Hz, 2H), 7.50 (d, J=8.2 Hz, 2H), 7.62 (d, J=8.2 Hz, 2H), 7.66 (d, J=7.2 Hz, 2H), 8.79 (s, 1H), 10.27 (s, 1H).

Example 57

Preparation of 2-(biphenyl-4-ylmethoxy)-N-hydroxy-2-methyl-N'-(1H-tetrazol-5-ylmethyl)malonamide (57)

Compound 57 was prepared by the procedure shown in Scheme 22 and described below.

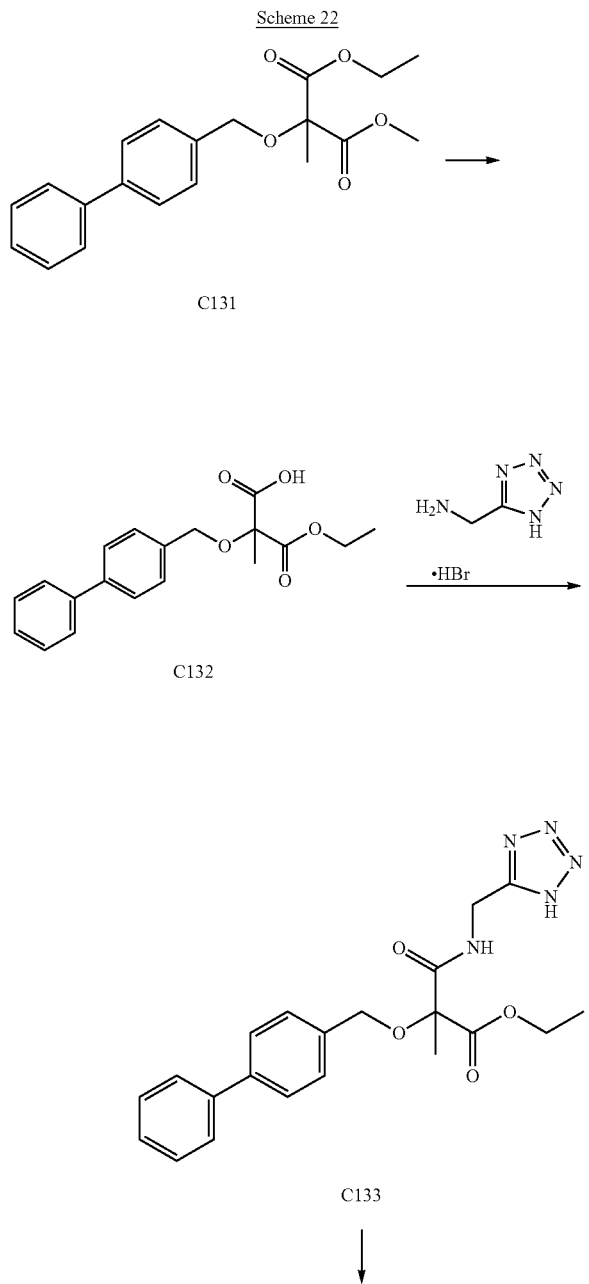

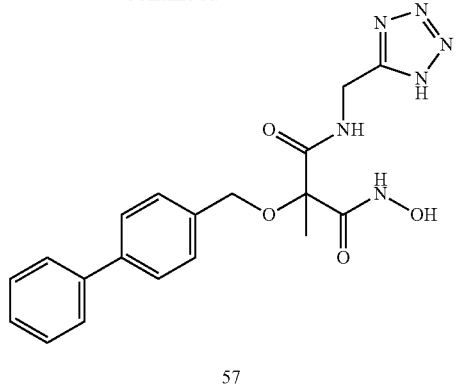

Step 1. Preparation of diethyl (biphenyl-4-ylmethoxy)(methyl)malonate (C131). Compound C131 was prepared according to the general procedure for the synthesis of C121 in Example 53, except that biphenyl-4-ylmethanol was used in place of C120, to provide C131. Yield: 7.64 g, 61%. $^1$H NMR (400 MHz, DMSO-$d_6$) δ 1.21 (t, J=7.1 Hz, 6H), 1.63 (s, 3H), 4.21 (m, 4H), 4.61 (s, 2H), 7.36 (m, 1H), 7.46 (m, 4H), 7.66 (m, 4H).

Step 2. Preparation of 2-(biphenyl-4-ylmethoxy)-3-ethoxy-2-methyl-3-oxopropanoic acid (C132). A solution of C131 (3.05 g, 8.56 mmol) in ethanol (30 mL) was treated with aqueous potassium hydroxide (4N, 3.2 mL, 13 mmol), dropwise over 10 minutes. The reaction was stirred at 25° C. for 3 hours. The resulting suspension was filtered, and the white solid was washed with ethanol (2×5 mL). The filtrate was acidified to pH 2 with 1N hydrochloric acid (about 10 mL), and partitioned between water (20 mL) and ethyl acetate (20 mL). The aqueous layer was extracted with ethyl acetate (3×20 mL), and the combined organic layers were washed with water and dried over magnesium sulfate. Filtration and removal of solvent in vacuo afforded an oil, which was dissolved in a mixture of ethyl acetate (50 mL) and methanol (2 mL) and extracted with 5% aqueous sodium bicarbonate solution (3×20 mL). The basic aqueous layers were acidified to pH 2 with 3N hydrochloric acid (about 15 mL), extracted with ethyl acetate (3×20 mL), and the combined organic extracts were dried over magnesium sulfate, filtered and concentrated to provide C132 as a yellow oil. Yield 2.01 g, 72%. MS (APCI) m/z 327.45 (M−1). $^1$H NMR (400 MHz, DMSO-$d_6$) δ 1.22 (t, J=7.1 Hz, 3H), 1.61 (s, 3H), 4.20 (q, J=7.1 Hz, 2H), 4.62 (AB quartet, J=11.2 Hz, 2H), 7.36 (m, 1H), 7.46 (m, 4H), 7.65 (m, 4H).

Step 3. Preparation of ethyl 2-(biphenyl-4-ylmethoxy)-2-methyl-3-oxo-3-[(1H-tetrazol-5-ylmethyl)amino]propanoate (C133). Compound C133 was synthesized according to the general procedure for preparation of C123 in Example 53, except that C132 was used in place of C122, and 1-(1H-tetrazol-5-yl)methanamine hydrobromide instead of 1-(5-methylisoxazol-3-yl)methanamine, to afford C133 as a pale yellow solid. Yield 1.56 g, 63%. MS (APCI) m/z 410.41 (M+1). $^1$H NMR (400 MHz, DMSO-$d_6$) δ 1.16 (t, J=7.1 Hz, 3H), 1.64 (s, 3H), 4.14 (m, 2H), 4.41 (d, J=11.5 Hz, 1H), 4.54 (dd, J=15.7, 5.7 Hz, 1H), 4.66 (m, 2H), 7.37 (m, 1H), 7.49 (m, 4H), 7.66 (m, 4H), 8.63 (t, J=5.8 Hz, 1H).

Step 4. Preparation of compound 57. Compound 57 was prepared according to the general procedure for synthesis of 49 in Example 49, except that C133 was used instead of C106. At the point after quenching with acetic acid, solvent was removed in vacuo, and the crude material was purified by reverse phase chromatography (C$_{18}$ column, Gradient: 90% to 20% water in acetonitrile), to provide a clear oil. The oil was triturated with a mixture of methanol:dichloromethane: diethyl ether (2:1:10 ratio, 13 mL total volume) to provide 57 as a white solid. Yield 73 mg, 60%. MS (APCI) m/z 397.35 (M+1). $^1$H NMR (400 MHz, DMSO-d$_6$) δ 1.49 (s, 3H), 4.38 (ABX pattern, J=15.1, 5.3 Hz, 2H), 4.50 (AB quartet, J=11.7 Hz, 2H), 7.35 (m, 1H), 7.47 (m, 4H), 7.63 (m, 4H), 8.06 (br t, J=5 Hz, 1H).

Example 58

Preparation of 4-(biphenyl-4-ylmethoxy)-N-hydroxytetrahydro-2H-pyran-4-carboxamide (58)

Compound 58 was prepared by the procedure shown in Scheme 23 and described below.

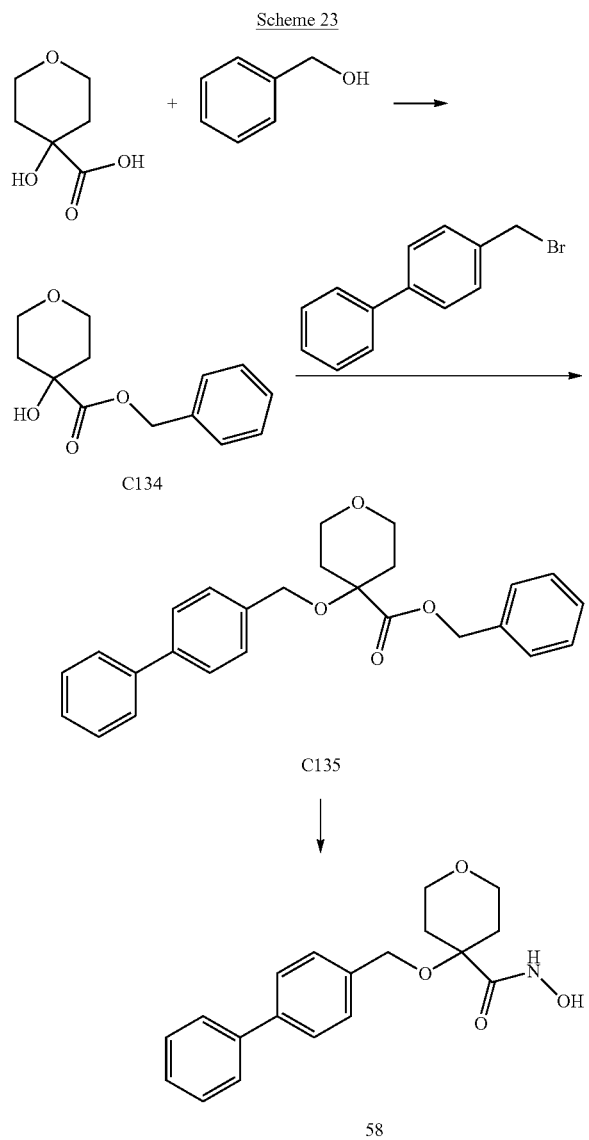

Scheme 23

Step 1. Preparation of benzyl 4-hydroxytetrahydro-2H-pyran-4-carboxylate (C134). 4-Hydroxytetrahydro-2H-pyran-4-carboxylic acid (4.38 g, 30.0 mmol) was treated with toluene (100 mL), phenylmethanol (6.2 mL, 60 mmol) and p-toluenesulfonic acid (0.11 g, 0.6 mmol), and the mixture was heated at reflux for 24 hours with a Dean-Stark trap. Additional phenylmethanol (9.4 mL, 90 mmol) and p-toluenesulfonic acid (0.15 g, 0.9 mmol) were added, and heating was continued for an additional 3 days. The mixture was filtered, and the filtrate was concentrated in vacuo, to provide a residue that was taken up in water (100 mL) and extracted with diethyl ether (100 mL). The organic layer was washed with saturated aqueous sodium chloride solution (50 mL), dried over magnesium sulfate, filtered and concentrated in vacuo. Purification via silica gel chromatography (Gradient: 0% to 30% ethyl acetate in hexanes) afforded C134. Yield 4.00 g, 56%. $^1$H NMR (400 MHz, CDCl$_3$) δ 1.55 (m, 2H), 2.17 (m, 2H), 3.03 (s, 1H), 3.83 (m, 4H), 5.24 (s, 2H), 7.37 (m, 5H).

Step 2. Preparation of benzyl 4-(biphenyl-4-ylmethoxy) tetrahydro-2H-pyran-4-carboxylate (C135). A mixture of C134 (1.0 g, 4.2 mmol), 4-(bromomethyl)biphenyl (3.14 g, 12.7 mmol), tetrabutylammonium iodide (1.56 g, 4.23 mmol) and silver (I) oxide (2.94 g, 12.7 mmol) in dichloromethane (30 mL) was stirred for 4 days at 25° C. while being protected from light. The mixture was filtered, and the filtrate was concentrated in vacuo, to provide a residue that was dissolved in ethyl acetate, washed with saturated aqueous ammonium chloride solution (100 mL), washed with saturated aqueous sodium chloride solution (100 mL), dried over magnesium sulfate and filtered. Removal of solvent in vacuo followed by chromatography on silica gel (Gradient: 0% to 30% ethyl acetate in hexanes) provided a mixture of C135 and the corresponding biphenylmethyl ester (roughly 1:1 by LCMS analysis). Yield 40 mg, 2% yield. This mixture can be used in the next step. $^1$H NMR (400 MHz, CDCl$_3$) δ 2.01 (m, 2H), 2.20 (m, 2H), 3.77 (m, 2H), 3.85 (m, 2H), 4.45 and 4.47 (2 singlets, 2H), 5.24 and 5.28 (2 singlets, 2H), 7.38 (m, about 6H), 7.45 (m, about 4H), 7.57 (m, about 6H).

Step 3. Preparation of compound 58. Compound 58 was prepared according to the general procedure for synthesis of 49 in Example 49, except that C135 was used instead of C106. After the acetic acid quench, the crude product was concentrated onto Celite, and subjected to silica gel chromatography (Gradient: 0% to 8% methanol in dichloromethane), to provide 58. Yield 13 mg, 14%. MS (APCI) m/z 328 (M+1). $^1$H NMR (400 MHz, DMSO-d$_6$) δ 1.84 (m, 2H), 1.94 (m, 2H), 3.63 (m, 4H), 4.38 (s, 2H), 7.36 (m, 1H), 7.48 (m, 4H), 7.66 (m, 4H), 8.84 (br s, 1H), 10.78 (br s, 1H).

General Method A

Preparation of 4-substituted 2-(benzyloxy)-N,3-dihydroxy-2-methylpropanamides

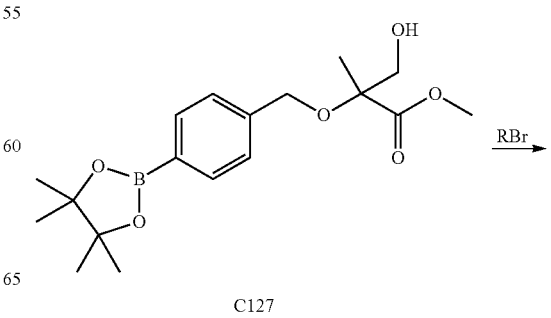

C127

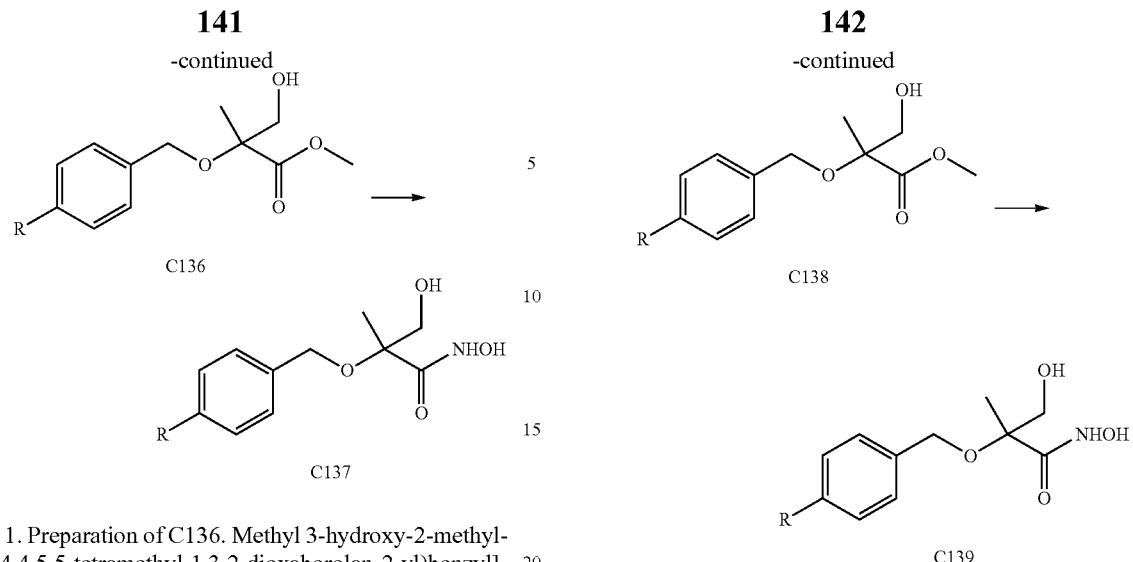

Step 1. Preparation of C136. Methyl 3-hydroxy-2-methyl-2-{[4-(4,4,5,5-tetramethyl-1,3,2-dioxaborolan-2-yl)benzyl]oxy}propanoate (C127) (2 mL of a 0.064 M solution in tetrahydrofuran, 0.128 mmol) was added to the aryl bromide (0.165 mmol), and this mixture was treated with cesium carbonate (0.4 mL of a 1.6 M aqueous solution, 0.64 mmol). The methylene chloride adduct of 1,1'-[bis(diphenylphosphino)ferrocene]dichloropalladium(II) (PdCl$_2$(dppf).CH$_2$Cl$_2$, 10.6 mg, 0.013 mmol) was added, and the reaction mixture was sonicated for several seconds, then shaken in a heated block at 70° C. for 2 hours. After cooling to 25° C., the reaction was partitioned between ethyl acetate (5 mL) and saturated aqueous sodium chloride solution (1 mL). The layers were separated, and the aqueous layer was extracted with ethyl acetate (2 mL). The combined organic layers were dried over magnesium sulfate, filtered and concentrated under reduced pressure. The crude methyl ester C136 was taken on to the next step.

Step 2. Preparation of C137. Compound C136 from the previous step (0.128 mmol) was treated with lithium methoxide and hydroxylamine hydrochloride (2.57 mL of a solution in methanol: 1.0 M in lithium methoxide and 0.5 M in hydroxylamine hydrochloride, respectively 2.57 mmol and 1.29 mmol). The vial was shaken for 2.5 hours at 25° C., treated with acetic acid (74 uL, 1.29 mmol), and shaken for an additional 20 minutes. Removal of solvents in vacuo provided a crude product, which was purified by reverse phase high-pressure liquid chromatography (HPLC) using a Phenomenex Luna C$_{18}$ column [21.2×100 mm, 5 um] (Gradient: water/acetonitrile/n-propanol (92:5:3 to 5:92:3) over 10 minutes at a flow rate of 30 mL/min) to provide compound C137. Purity was determined at 214 nm. The reported percent yield is over two steps General Method B Preparation of 4-substituted 2-(benzyloxy)-N,3-dihydroxy-2-methylpropanamides

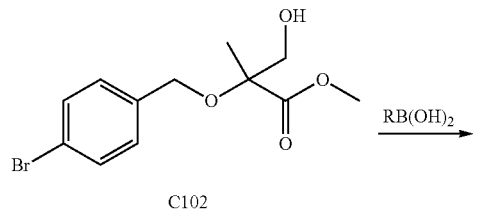

Step 1. Preparation of C138. The boronic acid (0.171 mmol) was treated with methyl 2-[(4-bromobenzyl)oxy]-3-hydroxy-2-methylpropanoate (C102) (2 mL of a 0.066 M solution in tetrahydrofuran, 0.132 mmol), followed by cesium carbonate (0.5 mL of a 1.33 M solution in water, 0.66 mmol). After addition of the methylene chloride adduct of 1,1'-[bis(diphenylphosphino)ferrocene]dichloropalladium (I) (PdCl$_2$(dppf).CH$_2$Cl$_2$, 10.9 mg, 0.0132 mmol), the reaction was carried out and worked up as in Step 1 of General Method A, to provide C138.

Step 2. Preparation of C139. Compound C138 from the previous step (0.132 mmol) was treated with lithium methoxide and hydroxylamine hydrochloride (2.64 mL of a solution in methanol: 1.0 M in lithium methoxide and 0.5 M in hydroxylamine hydrochloride, respectively 2.64 mmol and 132 mmol). The vial was shaken for 3 hours at 25° C., treated with acetic acid (76 uL, 1.32 mmol), and shaken for an additional 30 minutes. Removal of solvents in vacuo provided a crude product, which was purified by reverse phase high-pressure liquid chromatography using a Phenomenex Luna C$_{18}$ column [30×100 mm, 5 um] (Gradient: water/acetonitrile/n-propanol (92:5:3 to 5:92:3) over 10 minutes at a flow rate of 30 mL/min) to provide compound C139. Purity was determined at 214 nm. The reported percent yield is over two steps.

General Method C

Preparation of N'-substituted 2-(biphenyl-4-ylmethoxy)-N-hydroxy-2-methylmalonamides

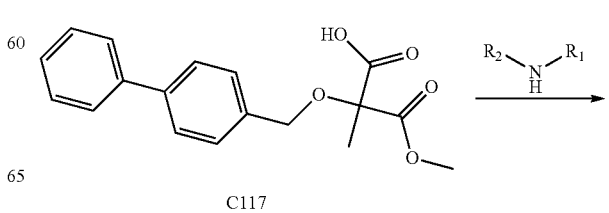

-continued

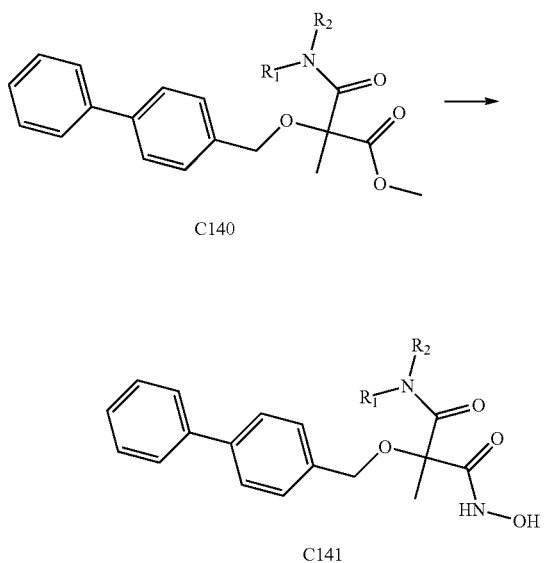

C140

C141

Step 1. Preparation of C140. The amine (0.15 mmol) was treated with O-(7-azabenzotriazol-1-yl)-N,N,N'N'-tetramethyluronium hexafluorophosphate (HATU, 0.5 mL of a 0.41 M solution in dimethylformamide, 0.2 mmol) and 2-(biphenyl-4-ylmethoxy)-3-methoxy-2-methyl-3-oxopropanoic acid (C117, 0.5 mL of a 0.27 M solution in dimethylformamide, 0.14 mmol). After addition of diisopropylethylamine (0.079 mL, 0.45 mmol), the reaction vial was shaken for about 18 hours. Addition of aqueous hydrochloric acid (0.5 N, 5 mL, 0.25 mmol) was followed by extraction with ethyl acetate (2×2 mL). The combined organics were washed with saturated aqueous sodium bicarbonate solution (2 mL), saturated aqueous sodium chloride solution (2 mL) and then dried over magnesium sulfate. Filtration and removal of solid afforded crude C140, which was taken on to the next step.

Step 2. Preparation of C141. Compound C140 (0.14 mmol) was treated with lithium methoxide and hydroxylamine hydrochloride (2.4 mL of a solution in methanol: 1.0 M in lithium methoxide and 0.5 M in hydroxylamine hydrochloride, respectively 2.4 mmol and 1.2 mmol). The vial was sonicated for a short time, then stirred for 3 hours. Acetic acid (0.068 mL, 1.2 mmol) was added, and the reaction was stirred for an additional 20 minutes, after which removal of solvent in vacuo provided a residue. Purification was carried out by reverse phase high-pressure liquid chromatography using a Waters Sunfire $C_{18}$ column ([20×150 mm, 5 uM](Mobile phase A=water+2% n-propanol; mobile phase B=acetonitrile+2% n-propanol; gradient: 2% B to 100% A over 8 min) to provide compound C141. Purity analysis was carried out via reverse phase high-pressure liquid chromatography using a Waters Atlantis $C_{18}$ column [4.6×50 mm, 3.5 uM] (Mobile phase A=water+0.005% formic acid; mobile phase B=acetonitrile+0.005% formic acid. Gradient: 5% B to 98% B over 5 min).

Examples 59-83

Compounds depicted as Examples 59-83 in Table 1 were prepared by the methods described above for Examples 1-58. Table 1 also contains analytical data for these compounds Examples 84-93

Compounds depicted as Examples 84-93 in Table 2 were prepared by the methods described above for Examples 1-58. Table 2 also contains analytical data for these compounds Biological data for Compounds 1-3, 5-17 and 19-93 described above in Examples 1-3, 5-17 and 19-93, respectively, are shown in Table 3.

TABLE 1

Examples 59-83

| Example | Method | IUPAC name | Structure | Yield | Purity | Retention time (min) | Calc. mol. wt. | Observed ion mass spectrum (M + 1) |
|---|---|---|---|---|---|---|---|---|
| 59 | A | N,3-dihydroxy-2-methyl-2-{[4'-(1,2,3-thiadiazol-4-yl)biphenyl-4-yl]methoxy}propanamide | 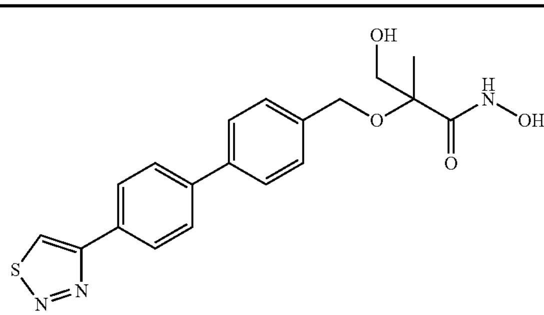 | 3% | 88% | 4.42 | 385.4 | 386.2 |

TABLE 1-continued

Examples 59-83

| Example | Method | IUPAC name | Structure | Yield | Purity | Retention time (min) | Calc. mol. wt. | Observed ion mass spectrum (M + 1) |
|---|---|---|---|---|---|---|---|---|
| 60 | A | N,3-dihydroxy-2-methyl-2-{[4'-(6-oxo-1,4,5,6-tetrahydropyridazin-3-yl)biphenyl-4-yl]methoxy}propanamide | 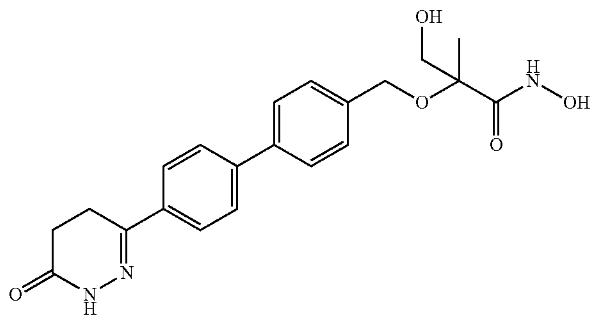 [SMILES: CC(CO)(OCc1ccc(-c2ccc(C3=NNC(=O)CC3)cc2)cc1)C(=O)NO] | 14% | 93% | 3.85 | 397.4 | 398.2 |
| 61 | A | 2-({4'-[(dimethylamino)sulfonyl]biphenyl-4-yl}methoxy)-N,3-dihydroxy-2-methyl-propanamide | 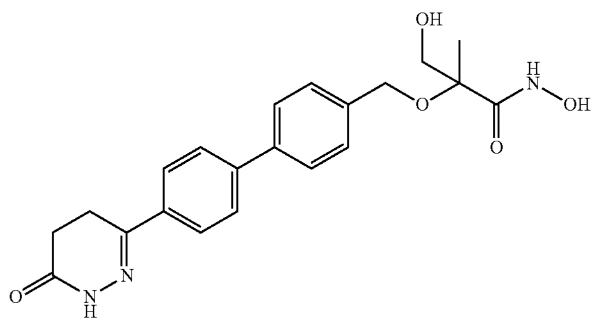 [SMILES: CC(CO)(OCc1ccc(-c2ccc(C3=NNC(=O)CC3)cc2)cc1)C(=O)NO] | 24% | 100% | 4.19 | 408.5 | 409.2 |
| 62 | B | 2-[(4'-chlorobiphenyl-4-yl)methoxy]-N,3-dihydroxy-2-methyl-propanamide | 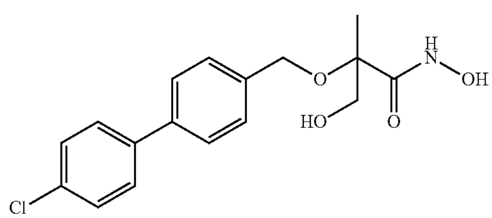 [SMILES: CC(CO)(OCc1ccc(-c2ccc(Cl)cc2)cc1)C(=O)NO] | 11% | 100% | 5.26 | 335.8 | 336.2 |
| 63 | B | 2-[(4'-fluoro-2'-methylbiphenyl-4-yl)methoxy]-N,3-dihydroxy-2-methyl-propanamide | 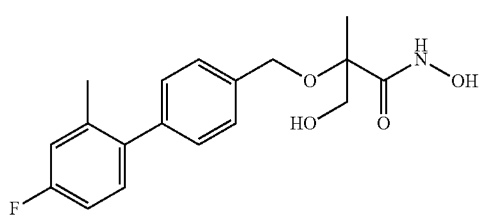 [SMILES: Cc1cc(F)ccc1-c1ccc(COC(C)(CO)C(=O)NO)cc1] | 17% | 100% | 5.09 | 333.4 | 334.2 |
| 64 | B | 2-[(3'-fluorobiphenyl-4-yl)methoxy]-N,3-dihydroxy-2-methyl-propanamide | 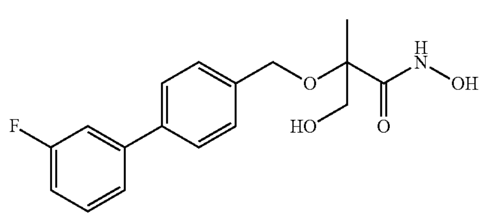 [SMILES: CC(CO)(OCc1ccc(-c2cccc(F)c2)cc1)C(=O)NO] | 15% | 100% | 4.79 | 319.3 | 320.2 |

TABLE 1-continued

Examples 59-83

| Example | Method | IUPAC name | Structure | Yield | Purity | Retention time (min) | Calc. mol. wt. | Observed ion mass spectrum (M + 1) |
|---|---|---|---|---|---|---|---|---|
| 65 | B | 2-[(2'-fluoro-3'-methoxybiphenyl-4-yl)methoxy]-N,3-dihydroxy-2-methyl-propanamide | 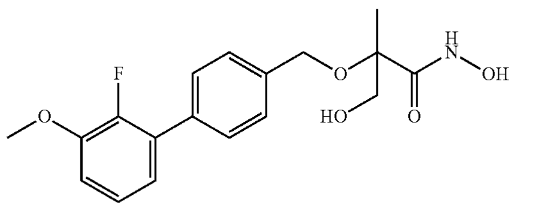 [SMILES: COc1cccc(-c2ccc(COC(C)(CO)C(=O)NO)cc2)c1F] | 17% | 100% | 4.66 | 349.4 | 350.2 |
| 66 | B | 2-[(2',4'-difluoro-biphenyl-4-yl)methoxy]-N,3-dihydroxy-2-methyl-propanamide | 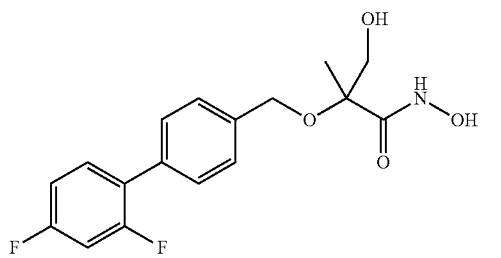 [SMILES: CC(CO)(OCc1ccc(-c2ccc(F)cc2F)cc1)C(=O)NO] | 14% | 100% | 4.89 | 337.3 | 338.2 |
| 67 | C | 2-(biphenyl-4-ylmethoxy)-N-hydroxy-2-methyl-N'-[(5-phenylisoxazol-3-yl)methyl]malonamide | 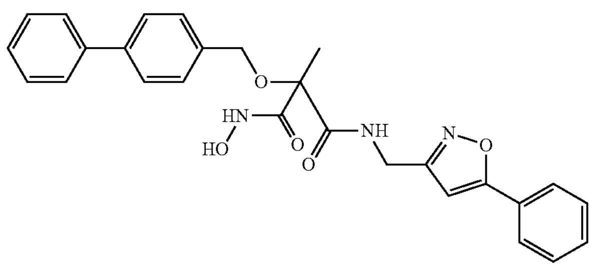 [SMILES: CC(OCc1ccc(-c2ccccc2)cc1)(C(=O)NO)C(=O)NCc1cc(-c2ccccc2)on1] | 42% | 100% | 3.81 | 471.5 | 472.4 |
| 68 | C | 2-(biphenyl-4-ylmethoxy)-N-hydroxy-N'-[(1-hydroxy-cyclopentyl)methyl]-2-methyl-malonamide | 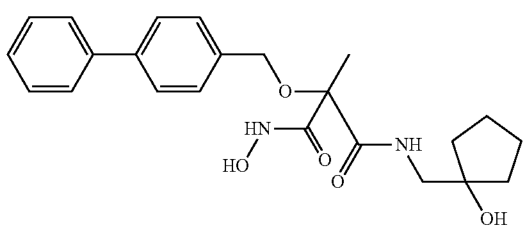 [SMILES: CC(OCc1ccc(-c2ccccc2)cc1)(C(=O)NO)C(=O)NCC1(O)CCCC1] | 34% | 88% | 3.31 | 412.5 | 413.4 |
| 69 | C | 2-(biphenyl-4-ylmethoxy)-N-hydroxy-2-methyl-N'-[(3-phenyl-1,2,4-oxadiazol-5-yl)methyl]malonamide | 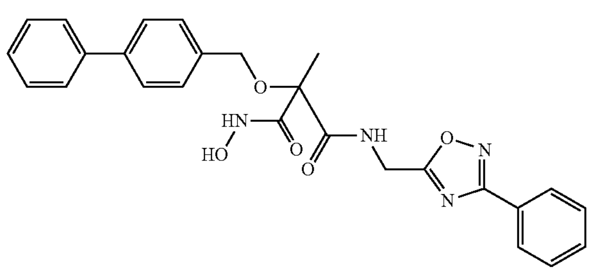 [SMILES: CC(OCc1ccc(-c2ccccc2)cc1)(C(=O)NO)C(=O)NCc1nc(-c2ccccc2)no1] | 37% | 100% | 3.81 | 472.5 | 473.3 |

TABLE 1-continued

Examples 59-83

| Example | Method | IUPAC name | Structure | Yield | Purity | Retention time (min) | Calc. mol. wt. | Observed ion mass spectrum (M + 1) |
|---|---|---|---|---|---|---|---|---|
| 70 | C | 2-(biphenyl-4-ylmethoxy)-N-hydroxy-2-methyl-N'-[2-(3-methylpyridin-2-yl)ethyl]malonamide | 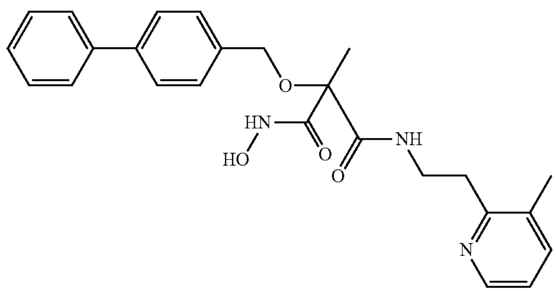 [SMILES: Cc1cccnc1CCNC(=O)C(C)(OCc1ccc(-c2ccccc2)cc1)C(=O)NO] | 14% | 95% | 2.78 | 433.5 | 434.4 |
| 71 | C | 2-(biphenyl-4-ylmethoxy)-N-hydroxy-2-methyl-N'-(pyrimidin-4-ylmethyl)malonamide | 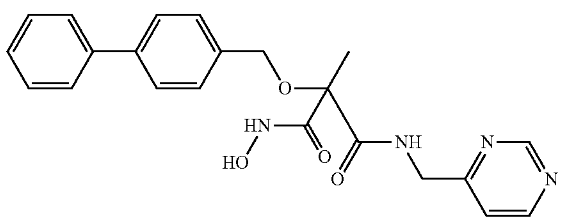 [SMILES: CC(OCc1ccc(-c2ccccc2)cc1)(C(=O)NO)C(=O)NCc1ccncn1] | 24% | 100% | 3.04 | 406.4 | 407.3 |
| 72 | C | 2-(biphenyl-4-ylmethoxy)-N-hydroxy-2-methyl-N'-(4-methylbenzyl)malonamide | 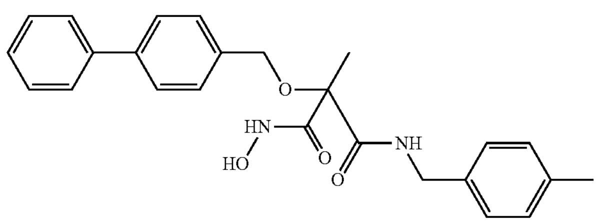 [SMILES: Cc1ccc(CNC(=O)C(C)(OCc2ccc(-c3ccccc3)cc2)C(=O)NO)cc1] | 32% | 100% | 3.84 | 418.5 | 419.4 |
| 73 | C | 2-(biphenyl-4-ylmethoxy)-N-hydroxy-2-methyl-N'-[2-(1-methyl-1H-pyrazol-4-yl)ethyl]malonamide | 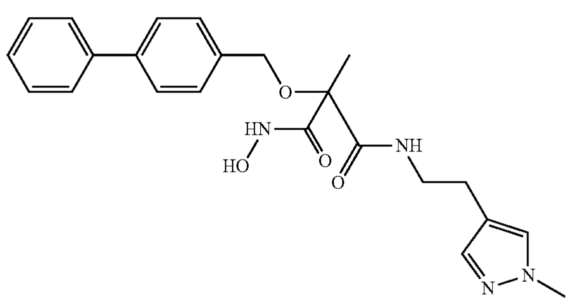 [SMILES: Cn1cc(CCNC(=O)C(C)(OCc2ccc(-c3ccccc3)cc2)C(=O)NO)cn1] | 24% | 90% | 3.14 | 422.5 | 423.4 |
| 74 | C | 2-(biphenyl-4-ylmethoxy)-N-hydroxy-N'-(2-methoxyethyl)-2-methylmalonamide | 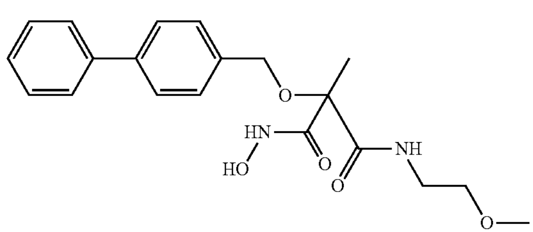 [SMILES: COCCNC(=O)C(C)(OCc1ccc(-c2ccccc2)cc1)C(=O)NO] | 15% | 100% | 3.24 | 372.4 | 373.3 |

TABLE 1-continued

Examples 59-83

| Example | Method | IUPAC name | Structure | Yield | Purity | Retention time (min) | Calc. mol. wt. | Observed ion mass spectrum (M + 1) |
|---|---|---|---|---|---|---|---|---|
| 75 | C | 2-(biphenyl-4-ylmethoxy)-N-hydroxy-2-methyl-N'-[(2S)-tetrahydrofuran-2-ylmethyl]malonamide | 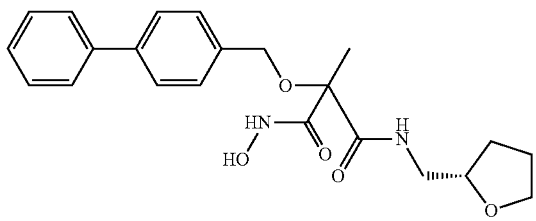 [SMILES: CC(OCc1ccc(-c2ccccc2)cc1)(C(=O)NO)C(=O)NC[C@@H]1CCCO1] | 31% | 98% | 3.34 | 398.5 | 399.3 |
| 76 | C | 2-(biphenyl-4-ylmethoxy)-N-hydroxy-2-methyl-N'-[2-(1,3-thiazol-4-yl)ethyl]malonamide | 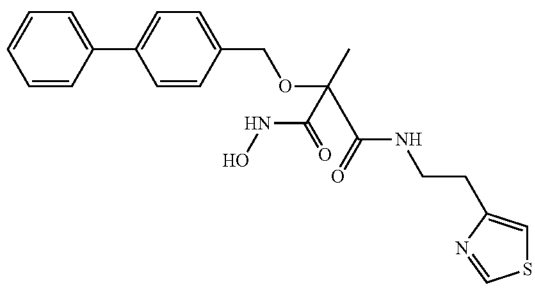 [SMILES: CC(OCc1ccc(-c2ccccc2)cc1)(C(=O)NO)C(=O)NCCc1cscn1] | 21% | 98% | 3.31 | 425.5 | 426.3 |
| 77 | C | N-(2-acetamidoethyl)-2-(biphenyl-4-ylmethoxy)-N'-hydroxy-2-methyl-malonamide | 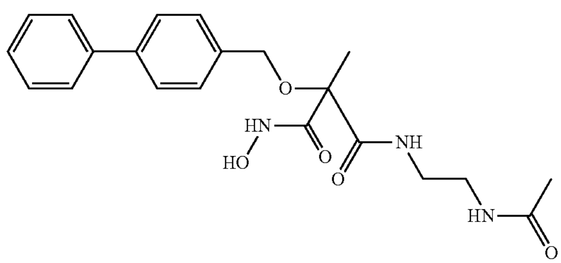 [SMILES: CC(=O)NCCNC(=O)C(C)(OCc1ccc(-c2ccccc2)cc1)C(=O)NO] | 16% | 100% | 2.91 | 399.4 | 400.3 |
| 78 | C | 2-(biphenyl-4-ylmethoxy)-N-[(3,5-dimethyl-1H-pyrazol-4-yl)methyl]-N'-hydroxy-2-methyl-malonamide | 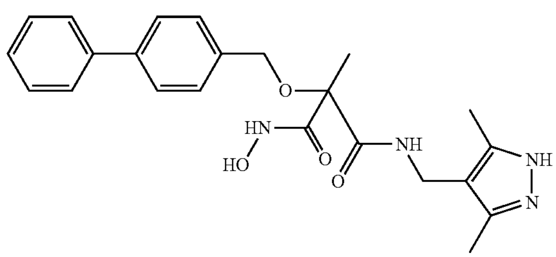 [SMILES: Cc1n[nH]c(C)c1CNC(=O)C(C)(OCc1ccc(-c2ccccc2)cc1)C(=O)NO] | 4% | 98% | 2.98 | 422.5 | 423.4 |
| 79 | C | 2-(biphenyl-4-ylmethoxy)-N-hydroxy-2-methyl-N'-[2-(5-methyl-4H-1,2,4-triazol-3-yl)ethyl]malonamide | 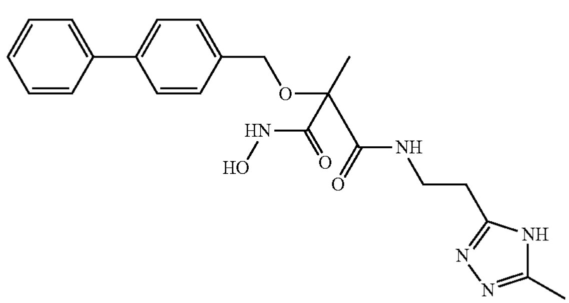 [SMILES: Cc1nnc(CCNC(=O)C(C)(OCc2ccc(-c3ccccc3)cc2)C(=O)NO)[nH]1] | 27% | 100% | 2.84 | 423.5 | 424.3 |

TABLE 1-continued

Examples 59-83

| Example | Method | IUPAC name | Structure | Yield | Purity | Retention time (min) | Calc. mol. wt. | Observed ion mass spectrum (M + 1) |
|---|---|---|---|---|---|---|---|---|
| 80 | C | 2-(biphenyl-4-ylmethoxy)-N-hydroxy-2-methyl-N'-[2-(4-methyl-1,3-thiazol-5-yl)ethyl]malonamide | 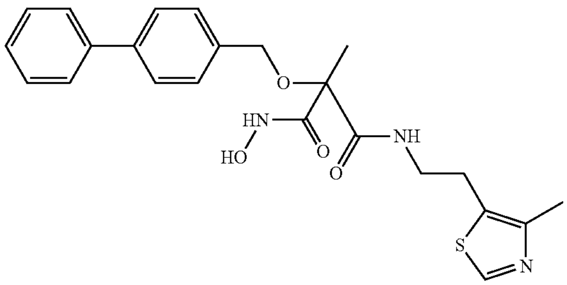 [SMILES: Cc1ncsc1CCNC(=O)C(C)(OCc1ccc(-c2ccccc2)cc1)C(=O)NO] | 21% | 100% | 3.24 | 439.5 | 440.3 |
| 81 | C | 2-(biphenyl-4-ylmethoxy)-N-hydroxy-N'-(2-hydroxyethyl)-2-methyl-malonamide | 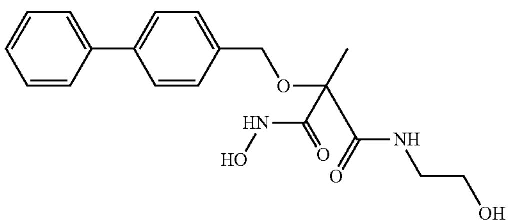 [SMILES: CC(OCc1ccc(-c2ccccc2)cc1)(C(=O)NO)C(=O)NCCO] | 21% | 100% | 2.94 | 358.4 | 359.3 |
| 82 | C | 2-(biphenyl-4-ylmethoxy)-N-[(1-ethyl-5-oxopyrrolidin-3-yl)methyl]-N'-hydroxy-2-methyl-malonamide | 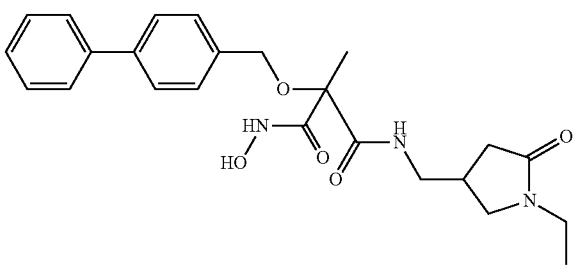 [SMILES: CCN1CC(CNC(=O)C(C)(OCc2ccc(-c3ccccc3)cc2)C(=O)NO)CC1=O] | 25% | 100% | 3.04 | 439.5 | 440.4 |
| 83 | C | 2-(biphenyl-4-ylmethoxy)-N-hydroxy-N'-(imidazo[1,2-a]pyridin-2-ylmethyl)-2-methyl-malonamide | 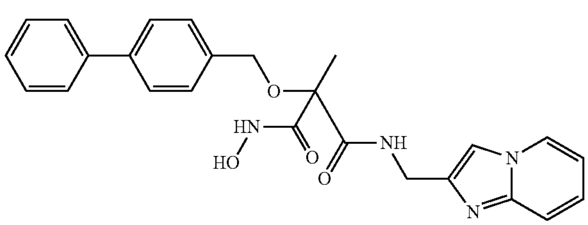 [SMILES: CC(OCc1ccc(-c2ccccc2)cc1)(C(=O)NO)C(=O)NCc1cn2ccccc2n1] | 18% | 94% | 2.54 | 444.5 | 445.4 |

TABLE 2

Examples 84-93

| Example | Method | IUPAC Name | Structure | Analytical |
|---|---|---|---|---|
| 84 | Ex 49, Ex 52 | N-hydroxy-2-({4'-[3-(hydroxymethyl)isoxazol-5-yl]biphenyl-4-yl}methoxy)-2-methyl-N'-[(5-methylisoxazol-3-yl)methyl]malonamide | 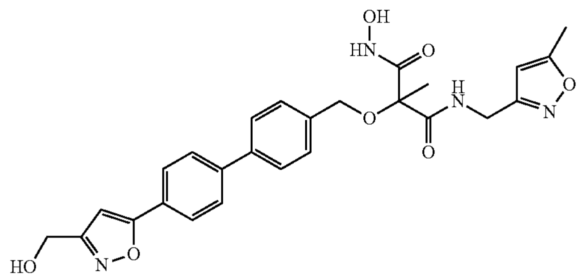 [SMILES: Cc1cc(CNC(=O)C(C)(OCc2ccc(-c3ccc(-c4cc(CO)no4)cc3)cc2)C(=O)NO)no1] | LCMS m/z 507.2 (M + 1); 1H NMR (400 MHz, DMSO-d6) δ 1.58 (s, 3H), 2.36 (d, J = 0.8 Hz, 3H), 4.31 (ABX pattern, J = 15.5, 6 Hz, 2H), 4.50 (apparent br s, 2H), 4.56 (d, J = 5.9 Hz, 2H), 5.55 (t, J = 5.9 Hz, 1H), 6.09 (d, J = 0.9 Hz, 1H), 7.05 (s, 1H), 7.57 (d, J = 8.4 Hz, 2H), 7.73 (d, J = 8.4 Hz, 2H), 7.84 (d, J = 8.7 Hz, 2H), 7.96 (d, J = 8.6 Hz, 2H), 8.38 (br t, J = 6 Hz, 1H), 9.01 (br s, 1H), 10.64 (br s, 1H) |
| 85 | Ex 52 | 2-(biphenyl-4-ylmethoxy)-N-hydroxy-N'-{[5-(methoxymethyl)isoxazol-3-yl]methyl}-2-methylmalonamide | 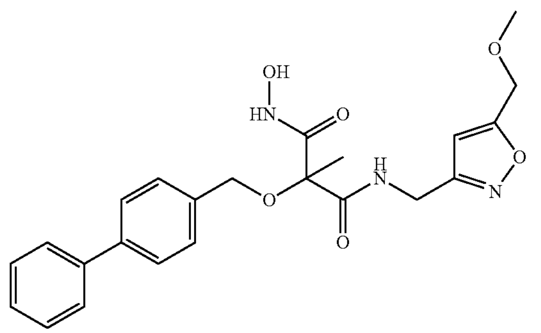 [SMILES: COCc1cc(CNC(=O)C(C)(OCc2ccc(-c3ccccc3)cc2)C(=O)NO)no1] | LCMS m/z 440.3 (M + 1); 1H NMR (400 MHz, DMSO-d6) δ 1.58 (s, 3H), 3.28 (s, 3H), 4.36 (ABX pattern, J = 15.6, 6 Hz, 2H), 4.48 (br s, 2H), 4.50 (s, 2H), 6.37 (s, 1H), 7.36 (m, 1H), 7.47 (m, 2H), 7.54 (d, J = 8.3 Hz, 2H), 7.65 (m, 4H), 8.41 (br t, J = 6 Hz, 1H), 9.01 (br s, 1H), 10.63 (br s, 1H) |
| 86 | Ex 49, Ex 52 | N-hydroxy-2-methyl-N'-[(5-methylisoxazol-3-yl)methyl]-2-{4-(2-methylpyridin-4-yl)benzyl]oxy}malonamide | 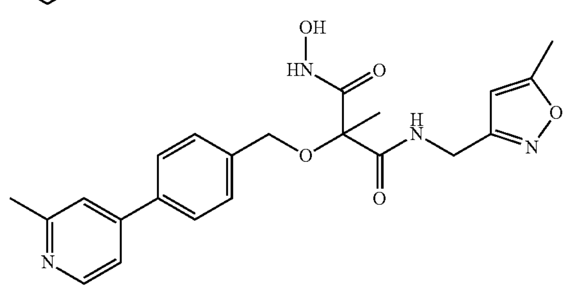 | LCMS m/z 425.3 (M + 1); 1H NMR (400 MHz, DMSO-d6) δ 1.57 (s, 3H), 2.35 (d, J = 0.9 Hz, 3H), 2.53 (s, 3H), 4.31 (ABX pattern, J = 15.6, 6 Hz, 2H), 4.50 (AB quartet, apparent s, 2H), 6.09 (d, J = 0.9 Hz, 1H), 7.50 (dd, J = 5, 1.5 Hz, 1H), 7.58 (m, 1H), 7.59 (d, J = 8.4 Hz, 2H), 7.77 (d, J = 8.4 Hz, 2H), 8.38 (br t, J = 6 Hz, 1H), 8.49 (dd, J = 5.3, 0.5 Hz, 1H), 9.00 (br s, 1H), 10.64 (br s, 1H) |
| 87 | Ex 49, Ex 52 | N-hydroxy-2-methyl-N'-[(5-methylisoxazol-3-yl)methyl]-2-{4-(4-methylpyridin-2-yl)benzyl]oxy}malonamide | 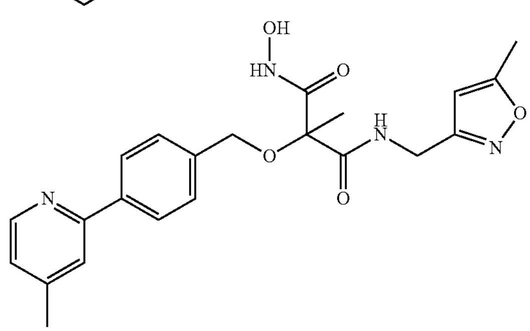 | LCMS m/z 425.3 (M + 1); 1H NMR (400 MHz, DMSO-d6) δ 1.53 (s, 3H), 2.35 (d, J = 0.9 Hz, 3H), 2.39 (s, 3H), 4.30 (ABX pattern, J = 15.5, 6 Hz, 2H), 4.49 (AB quartet, J = 11.7 Hz, 2H), 6.12 (d, J = 0.9 Hz, 1H), 7.17 (m, 1H), 7.53 (d, J = 8.4 Hz, 2H), 7.80 (m, 1H), 8.04 (d, J = 8.5 Hz, 2H), 8.50 (dd, J = 5.0, 0.6 Hz, 1H), 8.55 (br t, J = 6 Hz, 1H) |
| 88 | Ex 49, Ex 52 | 2-{[4-(5-fluoropyridin-2-yl)benzyl]oxy}-N-hydroxy-2-methyl-N'-[(5-methylisoxazol-3-yl)methyl]malonamide | 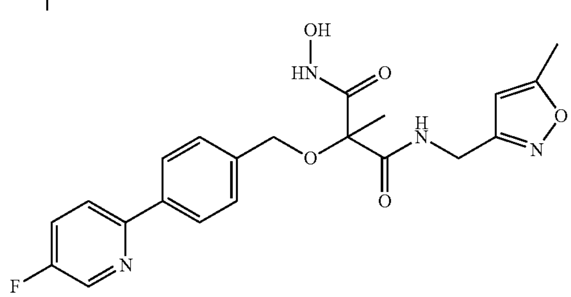 | LCMS m/z 429.3 (M + 1); 1H NMR (400 MHz, DMSO-d6) δ 1.57 (s, 3H), 2.35 (d, J = 0.9 Hz, 3H), 4.31 (ABX pattern, J = 15.5, 6 Hz, 2H), 4.50 (AB quartet, apparent s, 2H), 6.09 (d, J = 0.9 Hz, 1H), 7.56 (d, J = 8.4 Hz, 2H), 7.82 (ddd, apparent td, J = 8.8, 8.8, 3.0 Hz, 1H), 8.03 (d, J = 8.4 Hz, 2H), 8.05 (m, 1H), 8.37 (br t, J = 6 Hz, 1H), 8.65 (d, J = 3.0 Hz, 1H), 9.01 (br s, 1H), 10.64 (br s, 1H) |

TABLE 2-continued

Examples 84-93

| Example | Method | IUPAC Name | Structure | Analytical |
|---|---|---|---|---|
| 89 | Ex 49, Ex 52 | N-hydroxy-2-methyl-N'-[(5-methylisoxazol-3-yl)methyl]-2-{[4-(6-methyl-pyridin-2-yl)benzyl]oxy}malonamide | 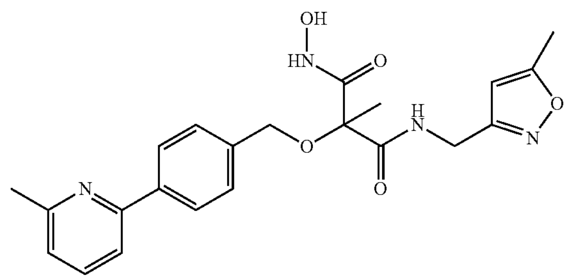 [SMILES: Cc1cccc(-c2ccc(COC(C)(C(=O)NO)C(=O)NCc3cc(C)on3)cc2)n1] | LCMS m/z 425.2 (M + 1); 1H NMR (400 MHz, DMSO-d6) δ 1.58 (s, 3H), 2.35 (d, J = 0.9 Hz, 3H), 2.54 (s, 3H), 4.31 (ABX pattern, J = 15.6, 6 Hz, 2H), 4.49 (AB quartet, apparent s, 2H), 6.09 (d, J = 0.9 Hz, 1H), 7.21 (m, 1H), 7.54 (d, J = 8.5 Hz, 2H), 7.76 (m, 2H), 8.04 (d, J = 8.5 Hz, 2H), 8.37 (br d, J = 6 Hz, 1H), 9.00 (br s, 1H), 10.63 (br s, 1H) |
| 90 | Ex 49, Ex 52 | N-hydroxy-2-methyl-N'-[(5-methylisoxazol-3-yl)methyl]-2-[(4-pyrazin-2-ylbenzyl)oxy]malonamide | 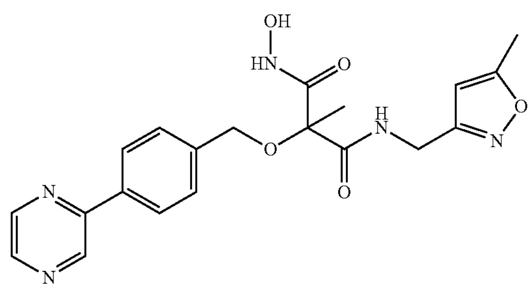 [SMILES: Cc1cc(CNC(=O)C(C)(OCc2ccc(-c3cnccn3)cc2)C(=O)NO)no1] | LCMS m/z 412.3 (M + 1); 1H NMR (400 MHz, DMSO-d6) δ 1.58 (s, 3H), 2.35 (d, J = 0.9 Hz, 3H), 4.31 (ABX pattern, J = 15.5, 6 Hz, 2H), 4.52 (AB quartet, apparent s, 2H), 6.09 (d, J = 0.9 Hz, 1H), 7.62 (d, J = 8.5 Hz, 2H), 8.13 (d, J = 8.4 Hz, 2H), 8.40 (br t, J = 6 Hz, 1H), 8.61 (d, J = 2.4 Hz, 1H), 8.72 (dd, J = 2.4, 1.6 Hz, 1H), 9.00 (br s, 1H), 9.27 (d, J = 1.6 Hz, 1H), 10.66 (br s, 1H) |
| 91 | Ex 51 | 2-(biphenyl-4-ylmethoxy)-N,3-dihydroxy-2-(hydroxymethyl)propanamide | 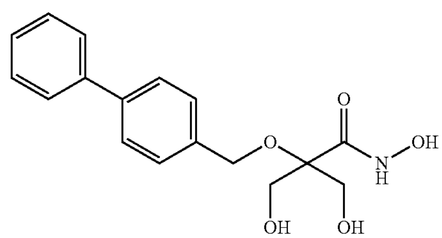 [SMILES: O=C(NO)C(CO)(CO)OCc1ccc(-c2ccccc2)cc1] | LCMS m/z 318.3 (M + 1); 1H NMR (400 MHz, DMSO-d6) δ 3.72 (s, 4H), 4.61 (s, 2H), 4.74 (br s, 2H), 7.36 (m, 1H), 7.46 (m, 2H), 7.52 (d, J = 8.2 Hz, 2H), 7.62 (d, J = 8.2 Hz, 2H), 7.66 (m, 2H), 8.76 (br s, 1H), 10.19 (br s, 1H) |
| 92 | Ex 49, Ex 52 | 2-(biphenyl-4-ylmethoxy)-N,4-dihydroxy-2-(hydroxymethyl)propanamide | 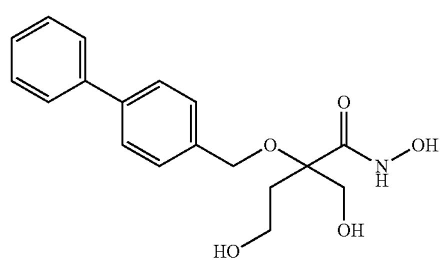 [SMILES: O=C(NO)C(CO)(CCO)OCc1ccc(-c2ccccc2)cc1] | LCMS m/z 332.2 (M + 1); 1H NMR (400 MHz, DMSO-d6) δ 1.93 (m, 2H), 3.44 (m, 2H), 3.70 (ABX pattern, 11.9, 5 Hz, 2H), 4.42 (t, J = 5.2 Hz, 1H), 4.57 (AB quartet, J = 11.6 Hz, 2H), 4.86 (t, J = 5.4 Hz, 1H), 7.36 (m, 1H), 7.47 (m, 2H), 7.52 (d, J = 8.2 Hz, 2H), 7.63 (d, J = 8.2 Hz, 2H), 7.66 (m, 2H), 8.74 (s, 1H), 10.17 (s, 1H) |
| 93 | Ex 52 | 2-(biphenyl-4-ylmethoxy)-N-hydroxy-N',2-dimethyl-malonamide | 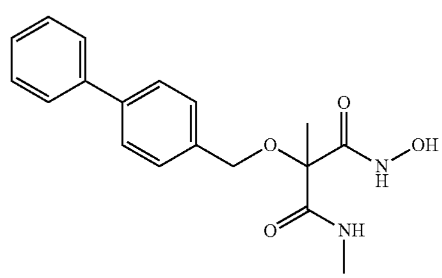 [SMILES: CNC(=O)C(C)(OCc1ccc(-c2ccccc2)cc1)C(=O)NO] | LCMS m/z 329.3 (M + 1); 1H NMR (400 MHz, DMSO-d6) δ 1.54 (s, 3H), 2.64 (d, J = 4.7 Hz, 3H), 4.46 (AB quartet, J = 11.5 Hz, 2H), 7.36 (m, 1H), 7.47 (m, 2H), 7.54 (d, J = 8.2 Hz, 2H), 7.65 (m, 5H), 8.96 (br s, 1H), 10.59 (br s, 1H) |

TABLE 3

Biological data for compounds 1-3, 5-17 and 19-93. [CONFIRM *PSEUDOMONAS* STRAIN NUMBERS WITH KATHERINE]

| Example Number | IC50 (uM) P. aeruginosa LpxC | MIC (ug/mL) P. aeruginosa PAO280 | MIC (ug/mL) P. aeruginosa UI-18 | MIC (ug/mL) A. baumanii/ haemolyticus | MIC (ug/mL) E. aerogenes | MIC (ug/mL) E. coli EC-1 | MIC (ug/mL) K. pneumoniae | MIC (ug/mL) S. aureus ATCC 29213 | MIC (ug/mL) S. marcescens |
|---|---|---|---|---|---|---|---|---|---|
| 1 | 0.00844** | 3* | >64* | >64 | >64 | >64 | >64 | >64* | >64 |
| 2a | 0.00299** | 0.5* | 32* | >64 | >64 | >64 | >64 | >64* | >64 |
| 2b | 0.00435* | 0.75* | 64* | >64 | >64 | >64 | >64 | >64* | >64 |
| 3 | 0.0716** | 32* | >64* | >64 | >64 | >64 | >64 | >64* | >64 |
| 5 | 0.0878 | 16 | >64 | >64 | >64 | >64 | >64 | 64 | >64 |
| 6 | 0.16 | 64 | >64 | >64 | >64 | >64 | >64 | 64 | >64 |
| 7 | 0.00953 | 2 | >64 | >64 | >64 | >64 | >64 | 64 | >64 |
| 8 | 0.0284 | 8 | >64 | >64 | >64 | >64 | >64 | >64 | >64 |
| 9 | 0.00084 | 0.125 | 8 | >64 | >64 | >64 | >64 | >64 | >64 |
| 10 | 0.00246** | 0.19* | 33* | 64* | >64* | 48* | 48* | 48* | 64 |
| 11 | 0.00509** | 8 | >64 | >64 | >64 | >64 | >64 | 32 | >64 |
| 12 | 0.00181 | 0.5 | 32 | >64 | >64 | >64 | >64 | 32 | >64 |
| 13 | 0.00163 | 0.5 | 32 | >32 | >32 | >32 | >32 | >32 | |
| 14 | 0.000582** | 0.5 | 16 | >64 | >64 | >64 | >64 | >64 | |
| 15 | 0.0734 | 32 | >64 | >64 | >64 | >64 | >64 | >64 | |
| 16 | 0.00079 | 0.125 | 8 | >64 | >64 | 64 | >64 | >64 | |
| 17 | 0.0015 | 0.25 | 8 | 32 | >64 | 16 | >64 | >64 | |
| 19 | 0.00256 | 2 | >64 | >64 | >64 | >64 | >64 | >64 | |
| 20 | 0.000726 | 1 | 16 | >64 | >64 | >64 | >64 | >64 | |
| 21 | 0.00823 | 4 | >64 | >64 | >64 | >64 | >64 | >64 | |
| 22 | 0.0105 | 4 | >8 | >8 | >8 | >8 | >8 | >8 | |
| 23 | 0.000376** | 0.015* | 1.75* | 4* | 27* | 4* | 8* | >64* | |
| 24 | 0.00128 | 2 | 32 | >64 | >64 | >64 | >64 | >64 | |
| 25 | 0.00138 | 0.03 | 1.67* | 32* | 16* | 3* | 4* | >64* | |
| 26 | 0.00137 | 2 | 8 | 1 | 8 | 1 | 4 | 32 | |
| 27 | 0.0652 | 16 | >64 | >64 | >64 | >64 | >64 | >64 | |
| 28 | 0.00143 | 4 | 8 | 8 | >16 | 8 | >16 | 16 | |
| 30 | 0.000762** | 1 | 4 | 2 | 16 | 2 | 4 | 32 | |
| 31 | 0.000406 | 0.06 | 6* | 32* | >64* | 16* | 48* | >64* | |
| 32 | 0.000286 | 0.06 | 8* | >64* | >64* | 32* | 64* | >64* | |
| 33 | 0.00323 | 0.25 | 8 | >64 | >64 | 64 | >64 | >64 | |
| 34 | 0.000579** | 0.023* | 1.25* | 64* | >64* | 28* | 64* | >64* | |
| 35 | 0.000695** | 0.03* | 1* | 64* | >64* | 23* | 53* | >64* | |
| 36 | 0.000244 | 0.03 | 1* | 32* | 64* | 4* | 16* | 64* | |
| 37 | 0.000476** | 0.015 | 0.75* | 64* | 64* | 8* | 16* | >64* | |
| 38 | 0.000132 | 0.015 | 1 | 4 | 64 | 2 | 8 | >64 | |
| 39 | 0.000589 | 0.03 | 1 | 4 | 32 | 2 | 4 | >64 | |
| 40 | 0.00081 | 0.125 | 16 | >64 | >64 | >64 | >64 | >64 | |
| 41 | 0.00116 | 0.25 | 32 | >64 | >64 | >64 | >64 | >64 | |
| 42 | 0.000372 | <0.0600 | 2 | 32 | >32 | 16 | >32 | >32 | |
| 43 | 0.000686 | 0.03 | 2 | 64 | 64 | 4 | 16 | 64 | |
| 44 | 0.000283 | 0.015 | 1 | 32 | >64 | 8 | 32 | >64 | |
| 45 | 0.00195 | 0.25 | 16 | >32 | >32 | >32 | >32 | >32 | |
| 46 | 0.000366 | 0.25 | 4 | >8 | >8 | >8 | >8 | >8 | |
| 47 | 0.00565 | | | | | | | | |
| 48 | 0.00623 | <0.0600* | 16* | >64* | >64* | >64* | >64* | >64* | |
| 49 | 0.00175 | 0.045* | 2 | >16 | >16 | 8 | >16 | >16 | |
| 50 | 0.0147** | 1* | 48* | >64 | >64 | >64 | >64 | >64* | >64 |
| 51 | 0.00186 | 1 | >16 | >16 | >16 | >16 | >16 | >16 | |
| 52 | 0.000306 | 0.03 | 2* | 32* | 32* | 3* | 8* | >64* | |
| 53 | 0.0143 | 0.5 | 32 | 64 | >64 | 16 | >64 | >64 | |
| 54 | 0.406** | 32 | >64 | >64 | >64 | >64 | >64 | >64 | >64 |
| 55 | 0.00399 | 0.5 | 32 | >64 | >64 | >64 | >64 | >64 | |
| 56 | 0.0222** | 4* | >64* | >64* | >64* | >64* | >64* | >64* | >64* |
| 57 | 0.00134 | 4 | >64 | >64 | >64 | >64 | >64 | >64 | |
| 58 | 0.0400** | 4 | >64 | >64 | >64 | >64 | >64 | >64 | >64 |
| 59 | 0.00402 | 1 | >64 | | | | | >64 | |
| 60 | 0.0105 | 4 | >64 | | | | | >64 | |
| 61 | 0.0602** | 16 | >64 | | | | | >64 | |
| 62 | 0.00417** | 1* | 32* | >32 | >32 | >32 | >32 | >32* | |
| 63 | 0.0174 | 4 | >64 | | | | | >64 | |
| 64 | 0.00757 | 4 | >64 | | | | | >64 | |
| 65 | 0.00579** | 1 | 64 | | | | | >64 | |
| 66 | 0.00332** | 1.5* | 64* | >64 | >64 | >64 | >64 | >64* | |
| 67 | 0.0032 | 0.5* | 4* | 8 | >16 | 16 | >16 | >16* | |
| 68 | 0.0955 | 4 | >64 | | | | | >64 | |
| 69 | 0.00446 | 0.75* | 12* | 16 | >16 | 16 | >16 | >16* | |
| 70 | 0.00804 | 1* | 32* | 32 | >64 | 16 | >64 | >64* | |
| 71 | 0.00394 | 0.125* | 16* | >64 | >64 | 32 | >64 | >64* | |
| 72 | 0.0307 | 4 | >16 | | | | | >16 | |
| 73 | 0.0156 | 1 | >64 | | | | | >64 | |
| 74 | 0.0139 | 1 | 64 | | | | | >64 | |

TABLE 3-continued

Biological data for compounds 1-3, 5-17 and 19-93. [CONFIRM *PSEUDOMONAS* STRAIN NUMBERS WITH KATHERINE]

| Example Number | IC50 (uM) P. aeruginosa LpxC | MIC (ug/mL) P. aeruginosa PAO280 | MIC (ug/mL) P. aeruginosa UI-18 | MIC (ug/mL) A. baumanii/ haemolyticus | MIC (ug/mL) E. aerogenes | MIC (ug/mL) E. coli EC-1 | MIC (ug/mL) K. pneumoniae | MIC (ug/mL) S. aureus ATCC 29213 | MIC (ug/mL) S. marcescens |
|---|---|---|---|---|---|---|---|---|---|
| 75 | 0.0126 | 1 | 64 | | | | | >64 | |
| 76 | 0.00848 | 0.5 | 64 | | | | | >64 | |
| 77 | 0.00612 | 1 | 64 | | | | | >64 | |
| 78 | 0.0055 | 1 | 64 | | | | | >64 | |
| 79 | 0.00288 | 1 | 64 | | | | | >64 | |
| 80 | 0.00899 | 0.5 | 64 | | | | | >64 | |
| 81 | 0.0261 | 1 | 64 | | | | | >64 | |
| 82 | 0.0486 | 4 | >64 | | | | | >64 | |
| 83 | 0.00218 | 0.125* | 8* | 64 | >64 | 16 | 64 | >32* | |
| 84 | 0.000861 | 0.06 | 2 | >64 | 16 | 1 | 8 | >64 | |
| 85 | 0.00159 | 0.125 | 8 | 64 | >64 | 16 | 32 | 64 | |
| 86 | 0.00681 | 0.25 | 16 | >64 | >64 | >64 | >64 | >64 | |
| 87 | 0.0023 | 0.25 | 32 | >64 | >64 | >64 | >64 | >64 | |
| 88 | 0.00698 | 0.5 | 64 | >64 | >64 | >64 | >64 | >64 | |
| 89 | 0.0135 | 1 | >64 | >64 | >64 | >64 | >64 | >64 | |
| 90 | 0.147 | 4 | >64 | >64 | >64 | >64 | >64 | >64 | |
| 91 | 0.0108** | 1.25* | 43* | >64* | >64* | >64* | >64* | >64* | >64 |
| 92 | 0.0134 | 2 | >64 | >64 | >64 | >64 | >64 | >64 | >64 |
| 93 | 93 | 0.125 | 8 | >64 | >64 | 32 | 64 | >64 | |

*represents 2-6 MIC determinations; arithmetic mean
**average of 2-8 assays

What is claimed is:

1. A compound of formula (I):

$$(R^3-L^4-L^3)_{\overline{m}}-B-A-G \quad (I)$$

or a pharmaceutically acceptable salt thereof, thereof, wherein:

G is a group of formula (II)

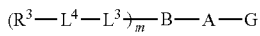

(II)

A is phenyl of formula (III)

(III)

or a 6-membered heteroaryl of formula (IV)

(IV)

wherein said phenyl or said 6-membered heteroaryl of said A is optionally substituted by one to four $R_4$ groups;

B is —$(C_6-C_{10})$aryl or —$(C_1-C_9)$heteroaryl;

$L^1$ is either absent or a linker moiety selected from the group consisting of —C(O)— and —C(O)N($R^7$)—;

$L^2$ is absent or a —$(C_1-C_6)$alkylene- linker moiety; wherein said —$(C_1-C_6)$alkylene- linker moiety of said $L^2$ may optionally be substituted by one to three groups independently selected from the group consisting of -halo, —OH and —N($R^7$)$_2$;

$L^3$ is absent or a linker moiety selected from the group consisting of —C(O)—, —N($R^7$)—, —C(O)N($R^7$)—, —N($R^7$)C(O)—, —S(O)$_j$—, and —S(O)$_j$N($R^7$)—;

$L^4$ is absent or a —$(C_1-C_6)$alkylene- linker moiety; wherein said —$(C_1-C_6)$alkylene- linker moiety of said $L^4$ may optionally be substituted by one to three groups independently selected from the group consisting of -halo, —OH and —N($R^7$)$_2$;

$R^1$ is selected from the group consisting of —OH, -halo, —$(C_1-C_6)$alkyl, -perfluorinated$(C_1-C_6)$alkyl, —O$(C_1-C_6)$alkyl, —$(C_3-C_6)$alkenyl, —$(C_3-C_{10})$cycloalkyl, —$(C_2-C_9)$heterocycloalkyl, —$(C_6-C_{10})$aryl, and —$(C_1-C_9)$heteroaryl; wherein each of said —$(C_1-C_6)$alkyl, —O$(C_1-C_6)$alkyl, —$(C_2-C_6)$alkenyl, —$(C_3-C_{10})$cycloalkyl, —$(C_2-C_9)$heterocycloalkyl, —$(C_6-C_{10})$aryl and —$(C_1-C_9)$heteroaryl of said $R^1$ is optionally substituted with one to three $R^5$ groups;

$R^2$ is selected from the group consisting of —$(C_1-C_6)$alkyl, -perfluorinated$(C_1-C_6)$alkyl, —O$(C_1-C_6)$alkyl, —$(C_2-C_6)$alkenyl, —$(C_3-C_{10})$cycloalkyl, —$(C_2-C_9)$heterocycloalkyl, —$(C_6-C_{10})$aryl, and —$(C_1-C_9)$heteroaryl; wherein each of said —$(C_1-C_6)$alkyl, —O$(C_1-C_6)$alkyl, —($C_2$-$C_6$)alkenyl, —($C_3$-$C_{10}$)cycloalkyl, —($C_2$-$C_9$)heterocycloalkyl, —($C_6$-$C_{10}$)aryl and —($C_2$-$C_9$)heteroaryl of said $R^2$ is optionally substituted with one to three groups selected from the group consisting of —OH, -halo, —N($R^7$)$_2$, —N($R^7$)C(O)$R^9$, —C(O)N($R^7$)$_2$, —S(O)$_j$$R^8$, —N($R^7$)S(O)$_j$$R^8$, —S(O)$_j$N($R^7$)$_2$, -perfluorinated($C_1$-$C_6$)alkyl, —O($C_1$-$C_6$)alkyl, and —O(perfluorinated($C_1$-$C_6$)alkyl); or $R^1$ and $R^2$ together with the carbon atom to which they are attached may form a 3- to 7-membered carbocyclic ring when both $L^1$ and $L^2$ are absent or a 4- to 7-membered heterocyclic ring when both $L^1$ and $L^2$ are absent; wherein each of said 3- to 7-membered carbocyclic ring or a 4- to 7-membered heterocyclic ring formed by the joinder of $R^1$ and $R^2$ is optionally substituted by one to three $R^5$ groups;

each $R^3$ is independently selected from the group consisting of —H, —OH, -halo, —S(O)$_j$$R^8$, —S(O)$_j$N($R^7$)$_2$, —($C_1$-$C_6$)alkyl, —O($C_1$-$C_6$)alkyl, -perfluorinated($C_1$-$C_6$)alkyl, O(perfluorinated($C_1$-$C_6$)alkyl), —($C_2$-$C_6$)alkenyl, —($C_3$-$C_{10}$)cycloalkyl, —($C_2$-$C_9$)heterocycloalkyl, —($C_6$-$C_{10}$)aryl, and —($C_1$-$C_9$)heteroaryl; wherein each of said —($C_1$-$C_6$)alkyl, —O($C_1$-$C_6$)alkyl, —($C_3$-$C_{10}$)cycloalkyl, —($C_2$-$C_9$)heterocycloalkyl, —($C_6$-$C_{10}$)aryl and —($C_1$-$C_9$) heteroaryl of said $R^3$ is optionally independently substituted with one to three $R^6$ groups;

each $R^4$ is independently selected from the group consisting of —OH, -halo, —CN, —C(O)$R^9$, —N($R^7$)$_2$, —N($R^7$)C(O)$R^9$, —C(O)N($R^7$)$_2$, —N($R^7$)S(O)$_j$$R^8$, —S(O)$_j$N($R^7$)$_2$, —OP(O)(OH)$_2$, —($C_1$-$C_6$)alkyl, —($C_1$-$C_6$)alkyl, perfluorinated($C_1$-$C_6$)alkyl, —O($C_1$-$C_6$)alkyl, —O(perfluorinated($C_1$-$C_6$)alkyl), —($C_2$-$C_6$)alkenyl, —($C_3$-$C_{10}$)cycloalkyl, —($C_2$-$C_9$)heterocycloalkyl, —($C_6$-$C_{10}$)aryl and —($C_1$-$C_9$)heteroaryl; wherein each of said —($C_1$-$C_6$)alkyl, —O($C_1$-$C_6$)alkyl, —($C_2$-$C_6$)alkenyl, —($C_3$-$C_{10}$)cycloalkyl, —($C_2$-$C_9$)heterocycloalkyl, —($C_6$-$C_{10}$)aryl and —($C_1$-$C_9$)heteroaryl of said $R^4$ is optionally independently substituted with one to three groups selected from the group consisting of —OH, -halo, —($C_1$-$C_6$)alkyl, —O($C_1$-$C_6$)alkyl, —($C_6$-$C_{10}$)aryl, and —($C_1$-$C_9$)heteroaryl;

each $R^5$ is independently selected from the group consisting of —OH, -halo, —CN, —N($R^7$)$_2$, —N($R^7$)C(O)$R^9$, —C(O)N($R^7$)$_2$, —S(O)$_j$$R^8$, —N($R^7$)S(O)$_j$$R^8$, —S(O)$_j$N($R^7$)$_2$, —OP(O)(OH)$_2$, —($C_1$-$C_6$)alkyl, perfluorinated($C_1$-$C_6$)alkyl, —O($C_1$-$C_6$)alkyl, O(perfluorinated($C_1$-$C_6$)alkyl), —($C_2$-$C_6$)alkenyl, —($C_3$-$C_{10}$)cycloalkyl, —($C_2$-$C_9$)heterocycloalkyl, —($C_6$-$C_{10}$)aryl and —($C_1$-$C_9$)heteroaryl; wherein each of said —($C_1$-$C_6$)alkyl, —O($C_1$-$C_6$)alkyl, —($C_2$-$C_6$)alkenyl, —($C_3$-$C_{10}$)cycloalkyl, —($C_2$-$C_9$)heterocycloalkyl, —($C_6$-$C_{10}$)aryl and —($C_1$-$C_9$)heteroaryl of said $R^5$ is optionally independently substituted with one to three groups selected from the group consisting of —OH, -halo, —($C_1$-$C_6$)alkyl, —O($C_1$-$C_6$)alkyl, —($C_6$-$C_{10}$)aryl, and —($C_1$-$C_9$)heteroaryl ;

each $R^6$ is independently selected from the group consisting of —OH, -halo, —CN, —N($R^7$)$_2$, —N($R^7$)C(O)$R^9$, —C(O)N($R^7$)$_2$, —S(O)$_j$$R^8$, —N($R^7$)S(O)$_j$$R^8$, —S(O)$_j$N($R^7$)$_2$, —CF$_3$, —($C_1$-$C_6$)alkyl, —O($C_1$-$C_6$)alkyl, -perfluorinated($C_1$-$C_6$)alkyl, —O(perfluorinated($C_1$-$C_6$)alkyl), —($C_2$-$C_6$)alkenyl, —($C_3$-$C_{10}$)cycloalkyl, —($C_2$-$C_9$)heterocycloalkyl, —($C_6$-$C_{10}$)aryl, —($C_1$-$C_9$)heteroaryl, —($C_1$-$C_6$)alkylene-OH, —($C_1$-$C_6$)alkylene-halo, —($C_1$-$C_6$)alkylene-N($R^7$)$_2$, —($C_1$-$C_6$)alkylene-N($R^7$)C(O)$R^8$, —($C_1$-$C_6$)alkylene-S(O)$_j$$R^8$, —($C_1$-$C_6$)alkylene-perfluorinated ($C_1$-$C_6$)alkyl, —($C_1$-$C_6$)alkylene-O($C_1$-$C_6$)alkyl, —($C_1$-$C_6$)alkylene-O(perfluorinated($C_1$-$C_6$)alkyl), —($C_1$-$C_6$)alkylene-($C_3$-$C_{10}$)cycloalkyl, —($C_1$-$C_6$)alkylene($C_2$-$C_9$)heterocycloalkyl, —($C_1$-$C_6$)alkylene-($C_1$-$C_6$)alkyl, —($C_1$-$C_6$)alkylene-($C_6$-$C_{10}$)aryl, —($C_1$-$C_6$)alkylene-($C_1$-$C_9$)heteroaryl; wherein each of said —($C_1$-$C_6$)alkyl, —O($C_1$-$C_6$)alkyl, —($C_2$-$C_6$)alkenyl, —($C_3$-$C_{10}$)cycloalkyl, —($C_2$-$C_9$)heterocycloalkyl, —($C_6$-$C_{10}$)aryl and —($C_1$-$C_9$)heteroaryl of said $R^6$ is optionally independently substituted with one to three groups independently selected from the group consisting of —OH, -halo, —($C_1$-$C_6$)alkyl, —O($C_1$-$C_6$)alkyl, —($C_3$-$C_{10}$)cycloalkyl, —($C_2$-$C_9$)heterocycloalkyl, —($C_6$-$C_{10}$) aryl and —($C_1$-$C_9$) heteroaryl;

each $R^7$, $R^8$, and $R^9$ is independently selected from the group consisting of —H, —($C_1$-$C_6$)alkyl, —($C_3$-$C_{10}$)cycloalkyl, —($C_2$-$C_9$)heterocycloalkyl, —($C_6$-$C_{10}$)aryl, and —($C_1$-$C_9$)heteroaryl;

j is 0, 1 or 2; and m is 0, 1 or 2.

2. The compound of claim 1 or a pharmaceutically acceptable salt thereof, wherein A is phenyl of formula (III)

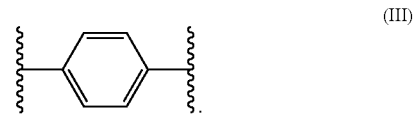

(III)

3. The compound of claim 1 or a pharmaceutically acceptable salt thereof, wherein A is a 6-membered heteroaryl of formula (IV)

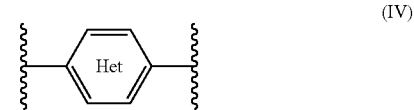

(IV)

selected from the group consisting of -pyridyl, -pyridazinyl, -pyrimidinyl, and -pyrazinyl.

4. The compound of any one of claims 1, 2 and 3, or a pharmaceutically acceptable salt thereof, wherein B is phenyl.

5. The compound of any one of claims 1, 2 and 3, or a pharmaceutically acceptable salt thereof, wherein B is selected from the group consisting of -pyridyl, -pyridazinyl, -pyrimidinyl, and -pyrazinyl.

6. The compound of any one of claims 1, 2 and 3, or a pharmaceutically acceptable salt thereof, wherein $L^2$ is absent.

7. The compound of any one of claims 1, 2 and 3, or a pharmaceutically acceptable salt thereof, wherein $R^1$ is selected from the group consisting of —($C_1$-$C_6$)alkyl, -perfluorinated($C_1$-$C_6$)alkyl, —O($C_1$-$C_6$)alkyl and —($C_2$-$C_6$) alkenyl; wherein each of said —($C_1$-$C_6$)alkyl, —O($C_1$-$C_6$) alkyl, and —($C_2$-$C_6$)alkenyl of said $R^1$ is optionally substituted with one to three $R^5$ groups.

8. The compound of claim 1, or a pharmaceutically acceptable salt thereof, wherein the A is phenyl of formula (III)

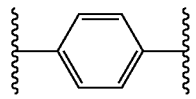

and B is phenyl.

9. The compound of any one of claims 1, 2 and 3, or a pharmaceutically acceptable salt thereof, wherein $L^3$ and $L^4$ are both absent.

10. The compound of any one of claims 1, 2 and 3, or a pharmaceutically acceptable salt thereof, wherein m is 1.

11. The compound of claim 1, or a pharmaceutically acceptable salt thereof wherein G is a group of formula (V):

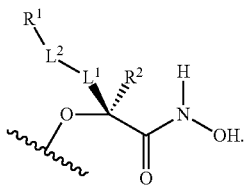

12. The compound of claim 1 selected from the group consisting of:
- (2S,3S)-2-(biphenyl-4-ylmethoxy)-N,3-dihydroxy-2-methylpentanamide;
- (2S,3S)-2-(biphenyl-4-ylmethoxy)-N,3-dihydroxy-2-methylbutanamide;
- (2S,3R)-2-(biphenyl-4-ylmethoxy)-N,3-dihydroxy-2-methylbutanamide;
- (2S,3S)-2-(biphenyl-4-ylmethoxy)-N,3-dihydroxy-2,4-dimethylpentanamide;
- (2S,3S)-2-(biphenyl-4-ylmethoxy)-N,3-dihydroxy-2-methylhexanamide;
- (2S,3S)-2-(biphenyl-4-ylmethoxy)-N,3-dihydroxy-2-methylheptanamide;
- (2S,3S)-2-(biphenyl-4-ylmethoxy)-N,3-dihydroxy-2,5-dimethylhexanamide;
- (2S,3S)-2-(biphenyl-4-ylmethoxy)-N,3-dihydroxy-2-methyl-5,5,5-trifluoropentanamide;
- (2S,3S)-2-(biphenyl-4-ylmethoxy)-5-ethoxy-N,3-dihydroxy-2-methylpentanamide;
- (2S,3)-2-(biphenyl-4-ylmethoxy)-N,3-dihydroxy-3-(1H-imidazol-4-yl)-2-methylpropanamide;
- (2S,3S)-2-(biphenyl-4-ylmethoxy)-N,3-dihydroxy-2-methyl-3-(1-methyl-1-1H-imidazol-2-yl)propanamide;
- (2S,3S)-2-(biphenyl-4-ylmethoxy)-N,3-dihydroxy-2-methyl-3-phenylpropanamide;
- (2S,3S)-2-(biphenyl-4-ylmethoxy)-N,3-dihydroxy-2-methyl-3-pyridin-3-ylpropanamide;
- (2S,3S)-2-(biphenyl-4-ylmethoxy)-3-(2-furyl)-N,3-dihydroxy-2-methylpropanamide;
- (2S,3S)-2-(biphenyl-4-ylmethoxy)-N,3-dihydroxy-3-[5-(hydroxymethyl)-2-furyl]-2-methylpropanamide;
- (2S,3S)-2-(biphenyl-4-ylmethoxy)-3-cyclopropyl-N,3-dihydroxy-2-methylpropanamide;
- (2S,3R)-2-(biphenyl-4-ylmethoxy)-N,3-dihydroxy-3-isoxazol-5-yl-2-methylpropanamide;
- (2S,3S)-2-(biphenyl-4-ylmethoxy)-N,3-dihydroxy-2-methyl-3-pyridin-2-ylpropanamide;
- (2S,3S)-2-(biphenyl-4-ylmethoxy)-N,3-dihydroxy-2-methyl-3-pyrimidin-5-ylpropanamide;
- (2S,3S)-2-(biphenyl-4-ylmethoxy)-N,3-dihydroxy-2-methyl-3-(1-methyl-1H-1,2,3-triazol-5-yl)propanamide;
- (2S,3R)-2-(biphenyl-4-ylmethoxy)-N,3-dihydroxy-2-methyl-3-(1,3-thiazol-2-yl)propanamide;
- (2S,3R)-2-(biphenyl-4-ylmethoxy)-N,3 -dihydroxy-2-methyl-3-(1,3-thiazol-5-yl)propanamide;
- (2S,3S)-2-(biphenyl-4-ylmethoxy)-3-(3-furyl)-N,3-dihydroxy-2-methylpropanamide;
- (2S,3S)-2-(biphenyl-4-ylmethoxy)-N,3-dihydroxy-2-methyl-3-(5-methylisoxazol-3-yl)propanamide;
- (2S,3S)-2-(biphenyl-4-ylmethoxy)-N,3-dihydroxy-3-[5-(methoxymethyl)-2-furyl]-2-methylpropanamide;
- (2R,3S)-2-(biphenyl-4-ylmethoxy)-N,3-dihydroxy-3-imidazo[1,2-a]pyridin-2-yl-2-methylpropanamide;
- (2S,3S)-N,3-dihydroxy-3-imidazo[1,2-a]pyridin-2-yl-2-methyl-2-[(4'-propylbiphenyl-4-yl)methoxy]propanamide;
- (2S,3S)-2-(biphenyl-4-ylmethoxy)-3-(2,5-dimethyl-1,3-oxazol-4-yl)-N,3-dihydroxy-2-methylpropanamide;
- (2S,3S)-2-(biphenyl-4-ylmethoxy)-N,3-dihydroxy-2-methyl-3-(5-phenylisoxazol-3-yl)propanamide;
- (2S,3S)-2-(biphenyl-4-ylmethoxy)-3-[5-(2-furyl)isoxazol-3-yl]-N,3-dihydroxy-2-methylpropanamide;
- (2S,3S)-N,3-dihydroxy-2-methyl-3-(5-methylisoxazol-3-yl)-2-[(4'-propylbiphenyl-4-yl)methoxy]propanamide;
- (2S,3S)-2-(biphenyl-4-ylmethoxy)-N,3-dihydroxy-3-isoxazol-3-yl-2-methylpropanamide;
- (2S,3S)-N,3-dihydroxy-2-methyl-3-(5-methylisoxazol-3-yl)-2-{[4-(5-methylpyridin-2-yl)benzyl]oxy}propanamide;
- (2S,3R)-2-(biphenyl-4-ylmethoxy)-N,3-dihydroxy-2-methyl-3-(1,3-oxazol-2-yl)propanamide;
- (2S,3S)-2-(biphenyl-4-ylmethoxy)-N,3-dihydroxy-3-[5-(hydroxymethyl)isoxazol-3-yl]-2-methylpropanamide;
- (2S,3S)-2-[(4'-fluorobiphenyl-4-yl)methoxy]-N,3-dihydroxy-3-[5-(hydroxymethyl)isoxazol-3-yl]-2-methylpropanamide;
- (2S,3S)-2-[(4'-ethylbiphenyl-4-yl)methoxy]-N,3-dihydroxy-3-[5-(hydroxymethyl)isoxazol-3-yl]-2-methylpropanamide;
- (2S,3S)-N,3-dihydroxy-3-[5-(hydroxymethyl)isoxazol-3-yl]-2-methyl-2-[(4'-methylbiphenyl-4-yl)methoxy]propanamide;
- (2S,3S)-2-[(4'-fluorobiphenyl-4-yl)methoxy]-N,3-dihydroxy-2-methyl-3-(5-methylisoxazol-3-yl)propanamide;
- (2S,3S)-N,3-dihydroxy-2-methyl-2-[(4'-methylbiphenyl-4-yl)methoxy]-3-(5-methylisoxazol-3-yl)propanamide;
- (2S,3S)-N,3-dihydroxy-3-[5-(hydroxymethyl)isoxazol-3-yl]-2-methyl-2-{[(4'-methylpyridin-2-yl)benzyl]oxy}propanamide;
- (2S,3S)-N,3-dihydroxy-3-[5-(hydroxymethyl)isoxazol-3-yl]-2-methyl-2-({4-[5-(trifluoromethyl)pyridine-2-yl]benzyl}oxy)propanamide;
- (2S,3S)-N,3-dihydroxy-3-[5-(hydroxymethyl)isoxazol-3-yl]-2-methyl-2-{[4'-(trifluoromethyl)biphenyl-4-yl]methoxyl}propanamide;
- (2S,3S)-2-(biphenyl-4-ylmethoxy)-N,3-dihydroxy-2-methyl-3-[5-(methylsulfonyl)isoxazol-3-yl]propanamide;
- (2S,3S)-2-[(4'-fluorobiphenyl-4-yl)methoxy]-N,3-dihydroxy-2-methyl-3-[5-(methylsulfinyl)isoxazol-3-yl]propanamide;
- (2S,3S)-2-(biphenyl-4-ylmethoxy)-N,3-dihydroxy-2-methyl-3-(1H-pyrazol-3-yl)propanamide;

(2S,3S)-N,3-dihydroxy-3-[5-(hydroxymethyl)-2-furyl]-2-methyl-2-{[4'-(1,3-oxazol-5-yl)biphenyl-4-yl]methoxy}propanamide;
{3-[(1S,2S)-2-(biphenyl-4-ylmethoxy)-1-hydroxy-2-methyl-3-(oxidoamino)-3-oxopropyl]isoxazol-5-yl}methyl phosphate;
2-(biphenyl-4-ylmethoxy)-N-hydroxy-2-(1-hydroxycyclobutyl)propanamide;
N-hydroxy-2-({4'-[3-(hydroxymethyl)isoxazol-5-yl]biphenyl-4-yl}methoxy)-N',2-dimethyl malonamide;
2-(biphenyl-4-ylmethoxy)-3,3,3-trifluoro-N-hydroxy-2-(hydroxymethyl)propanamide;
N,3-dihydroxy-2-(hydroxymethyl)-2-[(4'-propylbiphenyl-4-yl)methoxy]propanamide;
(2S)-2-(biphenyl-4-ylmethoxy)-N-hydroxy-2-methyl-N'-[(5-methylisoxazol-3-yl)methyl]malonamide;
2-{[6-(4-fluorophenyl)pyridin-3-yl]methoxy}-N-hydroxy-2-methyl-N'-[(5-methylisoxazol-3-yl)methyl]malonamide;
N,3-dihydroxy-2-methyl-2({4'-[3-(morpholin-4-ylmethyl)isoxazol-5-yl]biphenyl-4-yl}methoxy)propanamide;
2-(biphenyl-4-ylmethoxy)-N,3-dihydroxy-2-(methoxymethyl)propanamide;
2-(biphenyl-4-ylmethoxy)-N-hydroxy-2-methyl-N'-(1H-tetrazol-5-ylmethyl)malonamide;
4-(biphenyl-4-ylmethoxy)-N-hydroxytetrahydro-2H-pyran-4-carboxamide;
N,3-dihydroxy-2-methyl-2-{[4'-(1,2,3-thiadiazol-4-yl)biphenyl-4-yl]methoxy}propanamide;
N,3-dihydroxy-2-methyl-2-{[4'-(6-oxo-1,4,5,6-tetrahydropyridazin-3-yl)biphenyl-4-yl]methoxy}propanamide;
2-({4'-[(dimethylamino)sulfonyl]biphenyl-4-yl}methoxy)-N,3-dihydroxy-2-methylpropanamide;
2-[(4'-chlorobiphenyl-4-yl)methoxy]-N,3-dihydroxy-2-methylpropanamide;
2-[(4'-fluoro-2'-methylbiphenyl-4-yl)methoxy]-N,3-dihydroxy-2-methylpropanamide;
2-[(3'-fluorobiphenyl-4-yl)methoxy]-N,3-dihydroxy-2-methylpropanamide;
2-[(2'-fluoro-3'-methoxybiphenyl-4-yl)methoxy]-N,3-dihydroxy-2-methylpropanamide;
2-[(2',4'-difluorobiphenyl-4-yl)methoxy]-N,3-dihydroxy-2-methyl propanamide;
2-(biphenyl-4-ylmethoxy)-N-hydroxy-2-methyl-N'-[(5-phenylisoxazol-3-yl)methyl]malonamide;
2-(biphenyl-4-ylmethoxy)-N-hydroxy-N'-[(1-hydroxycyclopentyl)methyl]-2-methylmalonamide;
2-(biphenyl-4-ylmethoxy)-N-hydroxy-2-methyl-N'-[(3-phenyl-1,2,4-oxadiazol-5-yl)methyl]malonamide;
2-(biphenyl-4-ylmethoxy)-N-hydroxy-2-methyl-N'-[2-(3-methylpyridin-2-yl)ethyl]malonamide;
2-(biphenyl-4-ylmethoxy)-N-hydroxy-2-methyl-N'-(pyrimidin-4-ylmethyl)malonamide;
2-(biphenyl-4-ylmethoxy)-N-hydroxy-2-methyl-N'-(4-methylbenzyl)malonamide;
2-(biphenyl-4-ylmethoxy)-N-hydroxy-2-methyl-N'-[2-(1-methyl-1H-pyrazol-4-yl)ethyl]malonamide;
2-(biphenyl-4-ylmethoxy)-N-hydroxy-N'-(2-methoxyethyl)-2-methylmalonamide;
2-(biphenyl-4-ylmethoxy)-N-hydroxy-2-methyl-N'-[(2S)-tetrahydrofuran-2-ylmethyl]malonamide;
2-(biphenyl-4-ylmethoxy)-N-hydroxy-2-methyl-N'-[2-(1,3-thiazol-4-yl)ethyl]malonamide;
N-(2-acetamidoethyl)-2-(biphenyl-4-ylmethoxy)-N'-hydroxy-2-methyl malonamide;
2-(biphenyl-4-ylmethoxy)-N-[(3,5-dimethyl-1H-pyrazol-4-yl)methyl]-N'-hydroxy-2-methylmalonamide;
2-(biphenyl-4-ylmethoxy)-N-hydroxy-2-methyl-N'-[2-(5-methyl-4H-1,2,4-triazol-3)ethyl]malonamide;
2-(biphenyl-4-ylmethoxy)-N-hydroxy-2-methyl-N'-[2-(4-methyl-1,3-thiazol-5-yl)ethyl]malonamide;
2-(biphenyl-4-ylmethoxy)-N-hydroxy-N'-(2-hydroxyethyl)-2-methylmalonamide;
2-(biphenyl-4-ylmethoxy)-N-[(1-ethyl-5-oxopyrrolidin-3-yl)methyl]-N'-hydroxy-2-methylmalonamide;
2-(biphenyl-4-ylmethoxy)-N-hydroxy-N'-(imidazol-[1,2-a]pyridin-2-ylmethyl)-2-methylmalonamide;
N-hydroxy-2-({4'-[3-(hydroxylmethyl)isoxazol-5-yl]biphenyl-4-yl}methoxy)-2-methyl-N'-[(5-methyl isoxazol-3-yl)methyl]malonamide;
2-(biphenyl-4-ylmethoxy)-N-hydroxy-N'-{[5-(methoxymethyl)isoxazol-3-yl]methyl}-2-methylmalonamide;
N-hydroxy-2-methyl-N'-[(5-methylisoxazol-3-yl)methyl]-2-{[4-(2-methylpyridin-4-yl)benzyl]oxy}malonamide;
N-hydroxy-2-methyl-N'-[(5-methylisoxazol-3-yl)methyl]-2-{[4-(4-methylpyridin-2-yl)benzyl]oxy}malonamide;
2-{[4-(5-fluoropyridin-2-yl)benzyl]oxy}-N-hydroxy-2-methyl-N'-[(5-methylisoxazol-3-yl)methyl]malonamide;
N-hydroxy-2-methyl-N'-[(5-methylisoxazol-3-yl)methyl]-2-{[4-(6-methylpyridin-2-yl)benzyl]oxy}malonamide;
N-hydroxy-2-methyl-N'-[(5-methylisoxazol-3-yl)methyl]-2-[(4-pyrazin-2-ylbenzyl)oxy]malonamide;
2-(biphenyl-4-ylmethoxy)-N,3-dihydroxy-2-(hydroxymethyl)propanamide;
2-(biphenyl-4-ylmethoxy)-N,4-dihydroxy-2-(hydroxyethy)butanamide; and
2-(biphenyl-4-ylmethoxy)-N-hydroxy-N',2-dimethyl malonamide;
or a pharmaceutically acceptable salt thereof.

13. The compound of claim 1 selected from the group consisting of:
(2S,3S)-2-(biphenyl-4-ylmethoxy)-N,3-dihydroxy-2-methylpentanamide;
(2S,3S)-2-(biphenyl-4-ylmethoxy)-N,3-dihydroxy-2-methylbutanamide;
(2S,3R)-2-(biphenyl-4-ylmethoxy)-N,3-dihydroxy-2-methylbutanamide;
(2S,3S)-2-(biphenyl-4-ylmethoxy)-N,3-dihydroxy-2,4-dimethylpentanamide;
(2S,3S)-2-(biphenyl-4-ylmethoxy)-N,3-dihydroxy-2-methylhexanamide;
(2S,3S)-2-(biphenyl-4-ylmethoxy)-N,3-dihydroxy-2-methylheptanamide;
(2S,3S)-2-(biphenyl-4-ylmethoxy)-N,3-dihydroxy-2,5-dimethylhexanamide;
(2S,3S)-2-(biphenyl-4-ylmethoxy)-N,3-dihydroxy-2-methyl-5,5,5-trifluoropentanamide;
(2S,3S)-2-(biphenyl-4-ylmethoxy)-5-ethoxy-N,3-dihydroxy-2-methylpentanamide;
(2S,3S)-2-(biphenyl-4-ylmethoxy)-N,3-dihydroxy-3-(1H-imidazol-4-yl)-2-methylpropanamide;
(2S,3S)-2-(biphenyl-4-ylmethoxy)-N,3-dihydroxy-2-methyl-3-(1-methyl-1H-imidazol-2-ylpropanamide;
(2S,3S)-2-(biphenyl-4-ylmethoxy)-N,3-dihydroxy-2-methyl-3-phenylpropanamide;
(2S,3S)-2-(biphenyl-4-ylmethoxy)-N,3-dihydroxy-2-methyl-3-pyridin-3-ylpropanamide;

(2S,3S)-2-(biphenyl-4-ylmethoxy)-3-(2-furyl)-N,3-dihydroxy-2-methylpropanamide;

(2S,3S)-2-(biphenyl-4-ylmethoxy)-N,3-dihydroxy-3-[5-(hydroxymethyl)-2-furyl]-2-methylpropanamide;

(2S,3S)-2-(biphenyl-4-ylmethoxy)-3-cyclopropyl-N,3-dihydroxy-2-methylpropanamide;

(2S,3R)-2-(biphenyl-4-ylmethoxy)-N,3-dihydroxy-3-isoxazol-5-yl-2-methylpropanamide;

(2S,3S)-2-(biphenyl-4-ylmethoxy)-N,3-dihydroxy-2-methyl-3-pyridin-2-ylpropanamide;

(2S,3S)-2-(biphenyl-4-ylmethoxy)-N,3-dihydroxy-2-methyl-3-pyrimidin-5-ylpropanamide;

(2S,3S)-2-(biphenyl-4-ylmethoxy)-N,3-dihydroxy-2-methyl-3-(1-methyl-1H-1,2,3-triazol-5-yl)propanamide; and (2S,3R)-2-(biphenyl-4-ylmethoxy)-N,3-dihydroxy-2-methyl-3-(1,3-thiazol-2-yl)propanamide;

or a pharmaceutically acceptable salt thereof of each of the foregoing.

14. A pharmaceutical composition comprising a therapeutically effective amount of a compound according to claim 1 or a pharmaceutically acceptable salt thereof, and a pharmaceutically acceptable carrier.

15. A method of treating an bacterial infection in a patient caused by a gram-negative bacteria, the method comprising administering a therapeutically effective amount of a compound according to claim 1 or a pharmaceutically acceptable salt thereof to a patient in need thereof.

16. A method of treating a bacterial infection in a patient caused by a gram-negative bacteria, the method comprising contacting the gram-negative bacteria in the patient with an effective amount of a compound according to claim 12, or a pharmaceutically acceptable salt thereof.

* * * * *